(12) United States Patent
Kaminsky et al.

(10) Patent No.: US 8,151,877 B2
(45) Date of Patent: *Apr. 10, 2012

(54) DOWNHOLE BURNER WELLS FOR IN SITU CONVERSION OF ORGANIC-RICH ROCK FORMATIONS

(75) Inventors: Robert D. Kaminsky, Houston, TX (US); Chad C. Rasmussen, Houston, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 331 days.

This patent is subject to a terminal disclaimer.

(21) Appl. No.: 12/148,414

(22) Filed: Apr. 18, 2008

(65) Prior Publication Data
US 2008/0283241 A1    Nov. 20, 2008

Related U.S. Application Data

(60) Provisional application No. 60/930,311, filed on May 15, 2007, provisional application No. 60/930,308, filed on May 15, 2007.

(51) Int. Cl.
*E21B 43/243* (2006.01)
(52) U.S. Cl. ............. 166/256; 166/260; 166/52; 166/59
(58) Field of Classification Search .................. 166/256, 166/258, 260, 59, 245, 246, 52
See application file for complete search history.

(56) References Cited

U.S. PATENT DOCUMENTS

| | | | |
|---|---|---|---|
| 363,419 A | 5/1887 | Poetsch | |
| 895,612 A | 8/1908 | Baker | |
| 1,342,780 A | 6/1920 | Vedder | |
| 1,422,204 A | 7/1922 | Hoover et al. | |
| 1,666,488 A | 4/1928 | Crawshaw | |
| 1,701,884 A | 2/1929 | Hogle | |

(Continued)

FOREIGN PATENT DOCUMENTS
CA      994694      8/1976
(Continued)

OTHER PUBLICATIONS

Boyer, H. et al. (1985) "Heat-Resistant Materials," *Metals Handbook*, Chap. 16., Amer. Soc. for Metals.

(Continued)

*Primary Examiner* — Brad Harcourt
(74) *Attorney, Agent, or Firm* — ExxonMobil Upstream Research Company-Law Department

(57) ABSTRACT

A method for in situ heating of an organic-rich rock formation is provided. Preferably the organic-rich rock formation comprises kerogen. The method may include the steps of providing a first wellbore extending at least to a depth of the organic-rich rock formation, and providing a second wellbore also extending to a depth of the organic-rich rock formation and intersecting the first wellbore. The method may also include injecting air and a combustible fuel into the first wellbore, and providing a downhole burner in the wellbore so as to cause the air and the combustible fuel to mix and to combust at substantially the depth of the organic-rich rock formation. The method may further include, circulating combustion products into and up the second wellbore such that a pyrolysis zone is created from the first wellbore and second wellbores that provides substantially complete pyrolysis of the organic-rich rock formation between the first wellbore and the second wellbore. Operating conditions may be set or controlled so that the pyrolysis zones surrounding the first and second wellbore mate so to minimize underheated and overheated regions.

58 Claims, 35 Drawing Sheets

U.S. PATENT DOCUMENTS

| | | |
|---|---|---|
| 1,872,906 A | 8/1932 | Doherty |
| 2,033,560 A | 3/1936 | Wells |
| 2,033,561 A | 3/1936 | Wells |
| 2,534,737 A | 12/1950 | Rose |
| 2,584,605 A | 2/1952 | Merriam et al. |
| 2,634,961 A | 4/1953 | Ljungstrom |
| 2,732,195 A | 1/1956 | Ljungstrom |
| 2,777,679 A | 1/1957 | Ljungstrom |
| 2,780,450 A | 2/1957 | Ljungstrom |
| 2,795,279 A | 6/1957 | Sarapuu |
| 2,812,160 A | 11/1957 | West et al. |
| 2,813,583 A | 11/1957 | Marx, J. et al. |
| 2,847,071 A | 8/1958 | De Priester et al. |
| 2,887,160 A | 5/1959 | De Priester |
| 2,895,555 A | 7/1959 | De Priester |
| 2,923,535 A | 2/1960 | Ljungstrom |
| 2,944,803 A | 7/1960 | Hanson |
| 2,952,450 A | 9/1960 | Purre |
| 2,974,937 A | 3/1961 | Kiel |
| 3,004,601 A | 10/1961 | Bodine |
| 3,013,609 A | 12/1961 | Brink |
| 3,095,031 A | 6/1963 | Eurenius et al. |
| 3,106,244 A | 10/1963 | Parker |
| 3,109,482 A | 11/1963 | O'Brien |
| 3,127,936 A | 4/1964 | Eurenius |
| 3,137,347 A | 6/1964 | Parker |
| 3,149,672 A | 9/1964 | Orkiszewski et al. |
| 3,170,815 A | 2/1965 | White |
| 3,180,411 A | 4/1965 | Parker |
| 3,183,675 A | 5/1965 | Schroeder |
| 3,183,971 A | 5/1965 | McEver et al. |
| 3,194,315 A | 7/1965 | Rogers |
| 3,205,942 A | 9/1965 | Sandberg |
| 3,225,829 A | 12/1965 | Chown et al. |
| 3,228,869 A | 1/1966 | Irish |
| 3,241,611 A | 3/1966 | Dougan |
| 3,241,615 A | 3/1966 | Brandt et al. |
| 3,254,721 A | 6/1966 | Smith |
| 3,256,935 A | 6/1966 | Nabor et al. |
| 3,263,211 A | 7/1966 | Heidman |
| 3,267,680 A | 8/1966 | Schlumberger |
| 3,271,962 A | 9/1966 | Dahms et al. |
| 3,284,281 A | 11/1966 | Thomas |
| 3,285,335 A | 11/1966 | Reistle, Jr. |
| 3,288,648 A | 11/1966 | Jones |
| 3,294,167 A | 12/1966 | Vogel |
| 3,295,328 A | 1/1967 | Bishop |
| 3,323,840 A | 6/1967 | Mason et al. |
| 3,358,756 A | 12/1967 | Vogel |
| 3,372,550 A | 3/1968 | Schroeder |
| 3,376,403 A | 4/1968 | Mircea |
| 3,382,922 A | 5/1968 | Needham |
| 3,400,762 A | 9/1968 | Peacock et al. |
| 3,436,919 A | 4/1969 | Shock et al. |
| 3,439,744 A | 4/1969 | Bradley |
| 3,468,376 A | 9/1969 | Slusser et al. |
| 3,500,913 A | 3/1970 | Nordgren et al. |
| 3,501,201 A | 3/1970 | Closmann et al. |
| 3,502,372 A | 3/1970 | Prats |
| 3,513,914 A | 5/1970 | Vogel |
| 3,515,213 A | 6/1970 | Prats |
| 3,516,495 A | 6/1970 | Patton |
| 3,521,709 A | 7/1970 | Needham |
| 3,528,252 A | 9/1970 | Gail |
| 3,528,501 A | 9/1970 | Parker |
| 3,547,193 A | 12/1970 | Gill |
| 3,559,737 A | 2/1971 | Ralstin |
| 3,572,838 A | 3/1971 | Templeton |
| 3,599,714 A | 8/1971 | Messman |
| 3,602,310 A | 8/1971 | Halbert |
| 3,613,785 A | 10/1971 | Closmann et al. |
| 3,620,300 A | 11/1971 | Crowson |
| 3,642,066 A | 2/1972 | Gill |
| 3,661,423 A | 5/1972 | Garret |
| 3,692,111 A | 9/1972 | Breithaupt et al. |
| 3,695,354 A | 10/1972 | Dilgren et al. |
| 3,700,280 A | 10/1972 | Papadopoulos et al. |
| 3,724,225 A | 4/1973 | Mancini et al. |
| 3,729,965 A | 5/1973 | Gartner |
| 3,730,270 A | 5/1973 | Allred |
| 3,739,851 A | 6/1973 | Beard |
| 3,741,306 A | 6/1973 | Papadopoulos et al. |
| 3,759,328 A | 9/1973 | Ueber et al. |
| 3,759,329 A | 9/1973 | Ross |
| 3,759,574 A | 9/1973 | Beard |
| 3,779,601 A | 12/1973 | Beard |
| 3,880,238 A | 4/1975 | Tham et al. |
| 3,882,937 A | 5/1975 | Robinson |
| 3,882,941 A | 5/1975 | Pelofsky |
| 3,888,307 A | 6/1975 | Closmann |
| 3,924,680 A | 12/1975 | Terry |
| 3,943,722 A | 3/1976 | Ross |
| 3,950,029 A | 4/1976 | Timmins |
| 3,958,636 A | 5/1976 | Perkins |
| 3,967,853 A | 7/1976 | Closmann et al. |
| 3,978,920 A | 9/1976 | Bandyopadhyay et al. |
| 3,999,607 A | 12/1976 | Pennington et al. |
| 4,003,432 A | 1/1977 | Paull et al. |
| 4,005,750 A | 2/1977 | Shuck |
| 4,007,786 A | 2/1977 | Schlinger |
| 4,008,762 A | 2/1977 | Fisher et al. |
| 4,008,769 A | 2/1977 | Chang |
| 4,014,575 A | 3/1977 | French et al. |
| 4,030,549 A | 6/1977 | Bouck |
| 4,037,655 A | 7/1977 | Carpenter |
| 4,043,393 A | 8/1977 | Fisher et al. |
| 4,047,760 A | 9/1977 | Ridley |
| 4,057,510 A | 11/1977 | Crouch et al. |
| 4,065,183 A | 12/1977 | Hill et al. |
| 4,067,390 A | 1/1978 | Camacho et al. |
| 4,069,868 A | 1/1978 | Terry |
| 4,071,278 A | 1/1978 | Carpenter et al. |
| 4,093,025 A | 6/1978 | Terry |
| 4,096,034 A | 6/1978 | Anthony |
| 4,125,159 A | 11/1978 | Vann |
| 4,140,180 A | 2/1979 | Bridges et al. |
| 4,149,595 A | 4/1979 | Cha |
| 4,160,479 A | 7/1979 | Richardson et al. |
| 4,163,475 A | 8/1979 | Cha et al. |
| 4,167,291 A | 9/1979 | Ridley |
| 4,169,506 A | 10/1979 | Berry |
| 4,185,693 A | 1/1980 | Crumb et al. |
| 4,186,801 A | 2/1980 | Madgavkar et al. |
| 4,202,168 A | 5/1980 | Acheson et al. |
| 4,239,283 A | 12/1980 | Ridley |
| 4,246,966 A | 1/1981 | Stoddard et al. |
| 4,250,230 A | 2/1981 | Terry |
| 4,265,310 A | 5/1981 | Britton et al. |
| 4,271,905 A | 6/1981 | Redford et al. |
| 4,272,127 A | 6/1981 | Hutchins |
| 4,285,401 A | 8/1981 | Erickson |
| 4,318,723 A | 3/1982 | Holmes et al. |
| 4,319,635 A | 3/1982 | Jones |
| 4,320,801 A | 3/1982 | Rowland et al. |
| 4,324,291 A | 4/1982 | Wong et al. |
| 4,340,934 A | 7/1982 | Segesman |
| 4,344,485 A | 8/1982 | Butler |
| 4,358,222 A | 11/1982 | Landau |
| 4,362,213 A | 12/1982 | Tabor |
| 4,368,921 A | 1/1983 | Hutchins |
| 4,369,842 A | 1/1983 | Cha |
| 4,372,615 A | 2/1983 | Ricketts |
| 4,375,302 A | 3/1983 | Kalmar |
| 4,384,614 A | 5/1983 | Justheim |
| 4,397,502 A | 8/1983 | Hines |
| 4,401,162 A | 8/1983 | Osborne |
| 4,412,585 A | 11/1983 | Bouck |
| 4,417,449 A | 11/1983 | Hegarty et al. |
| 4,473,114 A | 9/1984 | Bell et al. |
| 4,474,238 A | 10/1984 | Gentry et al. |
| 4,483,398 A | 11/1984 | Peters et al. |
| 4,485,869 A | 12/1984 | Sresty et al. |
| 4,487,257 A | 12/1984 | Dauphine |
| 4,487,260 A | 12/1984 | Pittman et al. |
| 4,511,382 A | 4/1985 | Valencia et al. |
| 4,533,372 A | 8/1985 | Valencia et al. |
| 4,537,067 A | 8/1985 | Sharp et al. |

| Patent | Date | Inventor |
|---|---|---|
| 4,545,435 A | 10/1985 | Bridges et al. |
| 4,546,829 A | 10/1985 | Martin et al. |
| 4,550,779 A | 11/1985 | Zakiewicz |
| 4,567,945 A | 2/1986 | Segalman |
| 4,589,491 A | 5/1986 | Perkins |
| 4,589,973 A | 5/1986 | Minden |
| 4,602,144 A | 7/1986 | Vogel |
| 4,607,488 A | 8/1986 | Karinthi et al. |
| 4,626,665 A | 12/1986 | Fort, III |
| 4,633,948 A | 1/1987 | Closmann |
| 4,634,315 A | 1/1987 | Owen et al. |
| 4,637,464 A | 1/1987 | Forgac et al. |
| 4,640,352 A | 2/1987 | Vanmeurs et al. |
| 4,671,863 A | 6/1987 | Tejeda |
| 4,694,907 A | 9/1987 | Stahl et al. |
| 4,704,514 A | 11/1987 | Van Egmond et al. |
| 4,705,108 A | 11/1987 | Little et al. |
| 4,706,751 A | 11/1987 | Gondouin |
| 4,730,671 A | 3/1988 | Perkins |
| 4,737,267 A | 4/1988 | Pao et al. |
| 4,747,642 A | 5/1988 | Gash et al. |
| 4,754,808 A | 7/1988 | Harmon et al. |
| 4,776,638 A | 10/1988 | Hahn |
| 4,779,680 A | 10/1988 | Sydansk |
| 4,815,790 A | 3/1989 | Rosar et al. |
| 4,817,711 A | 4/1989 | Jeambey |
| 4,828,031 A | 5/1989 | Davis |
| 4,860,544 A | 8/1989 | Krieg et al. |
| 4,886,118 A | 12/1989 | Van Meurs et al. |
| 4,923,493 A | 5/1990 | Valencia et al. |
| 4,926,941 A | 5/1990 | Glandt et al. |
| 4,928,765 A | 5/1990 | Nielson |
| 4,929,341 A | 5/1990 | Thirumalachar et al. |
| 4,974,425 A | 12/1990 | Krieg et al. |
| 5,016,709 A | 5/1991 | Combe et al. |
| 5,036,918 A | 8/1991 | Jennings et al. |
| 5,050,386 A | 9/1991 | Krieg et al. |
| 5,055,030 A | 10/1991 | Schirmer |
| 5,055,180 A | 10/1991 | Klaila |
| 5,082,055 A | 1/1992 | Hemsath |
| 5,085,276 A | 2/1992 | Rivas et al. |
| 5,117,908 A | 6/1992 | Hofmann |
| 5,120,338 A | 6/1992 | Potts, Jr. et al. |
| 5,217,076 A | 6/1993 | Masek |
| 5,236,039 A | 8/1993 | Edelstein |
| 5,255,742 A | 10/1993 | Mikus |
| 5,275,063 A | 1/1994 | Steiger et al. |
| 5,297,626 A | 3/1994 | Vinegar et al. |
| 5,305,829 A | 4/1994 | Kumar |
| 5,372,708 A | 12/1994 | Gewertz |
| 5,377,756 A | 1/1995 | Northrop et al. |
| 5,392,854 A | 2/1995 | Vinegar et al. |
| 5,411,089 A | 5/1995 | Vinegar et al. |
| 5,416,257 A | 5/1995 | Peters |
| 5,620,049 A | 4/1997 | Gipson et al. |
| 5,621,844 A | 4/1997 | Bridges |
| 5,661,977 A | 9/1997 | Shnell |
| 5,730,550 A | 3/1998 | Andersland et al. |
| 5,838,634 A | 11/1998 | Jones et al. |
| 5,844,799 A | 12/1998 | Joseph et al. |
| 5,868,202 A | 2/1999 | Hsu |
| 5,899,269 A | 5/1999 | Wellington et al. |
| 5,905,657 A | 5/1999 | Celniker |
| 5,907,662 A | 5/1999 | Buettner |
| 5,956,971 A | 9/1999 | Cole et al. |
| 6,015,015 A | 1/2000 | Luft et al. |
| 6,016,867 A | 1/2000 | Gregoli et al. |
| 6,023,554 A | 2/2000 | Vinegar et al. |
| 6,055,803 A | 5/2000 | Mastronarde et al. |
| 6,056,057 A | 5/2000 | Vinegar et al. |
| 6,079,499 A | 6/2000 | Mikus et al. |
| 6,148,911 A | 11/2000 | Gipson et al. |
| 6,158,517 A | 12/2000 | Hsu |
| 6,246,963 B1 | 6/2001 | Cross et al. |
| 6,247,358 B1 | 6/2001 | Dos Santos |
| 6,328,104 B1 | 12/2001 | Graue |
| 6,434,436 B1 | 8/2002 | Tubel et al. |
| 6,480,790 B1 | 11/2002 | Calvert et al. |
| 6,540,018 B1 | 4/2003 | Vinegar et al. |
| 6,581,684 B2 | 6/2003 | Wellington et al. |
| 6,585,046 B2 | 7/2003 | Neuroth et al. |
| 6,589,303 B1 | 7/2003 | Lokhandwale et al. |
| 6,591,906 B2 | 7/2003 | Wellington et al. |
| 6,607,036 B2 | 8/2003 | Ranson et al. |
| 6,609,761 B1 | 8/2003 | Ramey et al. |
| 6,668,922 B2 | 12/2003 | Ziauddin et al. |
| 6,684,644 B2 | 2/2004 | Mittricker et al. |
| 6,684,948 B1 | 2/2004 | Savage |
| 6,708,758 B2 | 3/2004 | de Rouffignac et al. |
| 6,709,573 B2 | 3/2004 | Smith |
| 6,712,136 B2 | 3/2004 | de Rouffignac et al. |
| 6,715,546 B2 | 4/2004 | Vinegar et al. |
| 6,722,429 B2 | 4/2004 | de Rouffignac et al. |
| 6,742,588 B2 | 6/2004 | Wellington et al. |
| 6,745,831 B2 | 6/2004 | De Rouffignac et al. |
| 6,745,832 B2 | 6/2004 | Wellington et al. |
| 6,752,210 B2 | 6/2004 | de Rouffignac et al. |
| 6,754,588 B2 | 6/2004 | Cross et al. |
| 6,764,108 B2 | 7/2004 | Ernst et al. |
| 6,782,947 B2 | 8/2004 | de Rouffignac et al. |
| 6,796,139 B2 | 9/2004 | Briley et al. |
| 6,820,689 B2 | 11/2004 | Sarada |
| 6,832,485 B2 | 12/2004 | Sugarmen et al. |
| 6,854,929 B2 | 2/2005 | Vinegar et al. |
| 6,858,049 B2 | 2/2005 | Mittricker |
| 6,877,555 B2 | 4/2005 | Karanikas et al. |
| 6,880,633 B2 | 4/2005 | Wellington et al. |
| 6,887,369 B2 | 5/2005 | Moulton et al. |
| 6,896,053 B2 | 5/2005 | Berchenko et al. |
| 6,896,707 B2 | 5/2005 | O'Rear et al. |
| 6,913,078 B2 | 7/2005 | Shahin et al. |
| 6,918,444 B2 | 7/2005 | Passey et al. |
| 6,923,155 B2 | 8/2005 | Vinegar et al. |
| 6,923,258 B2 | 8/2005 | Wellington et al. |
| 6,932,155 B2 | 8/2005 | Vinegar et al. |
| 6,948,562 B2 | 9/2005 | Wellington et al. |
| 6,951,247 B2 | 10/2005 | De Rouffignac et al. |
| 6,953,087 B2 | 10/2005 | de Rouffignac et al. |
| 6,964,300 B2 | 11/2005 | Vinegar et al. |
| 6,969,123 B2 | 11/2005 | Vinegar et al. |
| 6,988,549 B1 | 1/2006 | Babcock |
| 6,994,160 B2 | 2/2006 | Wellington et al. |
| 6,997,518 B2 | 2/2006 | Vinegar et al. |
| 7,001,519 B2 | 2/2006 | Linden et al. |
| 7,004,247 B2 | 2/2006 | Cole et al. |
| 7,004,251 B2 | 2/2006 | Ward et al. |
| 7,011,154 B2 | 3/2006 | Maher et al. |
| 7,032,660 B2 | 4/2006 | Vinegar et al. |
| 7,036,583 B2 | 5/2006 | de Rouffignac et al. |
| 7,048,051 B2 | 5/2006 | McQueen |
| 7,051,807 B2 | 5/2006 | Vinegar et al. |
| 7,055,600 B2 | 6/2006 | Messier et al. |
| 7,063,145 B2 | 6/2006 | Veenstra et al. |
| 7,066,254 B2 | 6/2006 | Vinegar et al. |
| 7,073,578 B2 | 7/2006 | Vinegar et al. |
| 7,077,198 B2 | 7/2006 | Vinegar et al. |
| 7,077,199 B2 | 7/2006 | Vinegar et al. |
| 7,093,655 B2 | 8/2006 | Atkinson |
| 7,096,942 B1 | 8/2006 | de Rouffignac et al. |
| 7,096,953 B2 | 8/2006 | de Rouffignac et al. |
| 7,100,994 B2 | 9/2006 | Vinegar et al. |
| 7,104,319 B2 | 9/2006 | Vinegar et al. |
| 7,121,342 B2 | 10/2006 | Vinegar et al. |
| 7,124,029 B2 | 10/2006 | Jammes et al. |
| 7,165,615 B2 | 1/2007 | Vinegar et al. |
| 7,181,380 B2 | 2/2007 | Dusterhoft et al. |
| 7,198,107 B2 | 4/2007 | Maguire |
| 7,219,734 B2 | 5/2007 | Bai et al. |
| 7,225,866 B2 | 6/2007 | Berchenko et al. |
| 7,243,618 B2 | 7/2007 | Gurevich |
| 7,322,415 B2 | 1/2008 | de St. Remey |
| 7,331,385 B2 | 2/2008 | Symington et al. |
| 7,353,872 B2 | 4/2008 | Sandberg |
| 7,357,180 B2 | 4/2008 | Vinegar et al. |
| 7,441,603 B2 | 10/2008 | Kaminsky et al. |
| 7,461,691 B2 | 12/2008 | Vinegar et al. |
| 7,484,561 B2 | 2/2009 | Bridges |
| 7,516,785 B2 | 4/2009 | Kaminsky |

| | | |
|---|---|---|
| 7,516,786 B2 | 4/2009 | Dallas et al. |
| 7,516,787 B2 | 4/2009 | Kaminsky |
| 7,546,873 B2 | 6/2009 | Kim et al. |
| 7,549,470 B2 | 6/2009 | Vinegar et al. |
| 7,556,095 B2 | 7/2009 | Vinegar |
| 7,617,869 B2 | 11/2009 | Carney |
| 7,631,691 B2 | 12/2009 | Symington et al. |
| 7,644,993 B2 | 1/2010 | Kaminsky et al. |
| 7,647,971 B2 | 1/2010 | Kaminsky |
| 7,654,320 B2 | 2/2010 | Payton |
| 7,669,657 B2 | 3/2010 | Symington et al. |
| 7,647,972 B2 | 6/2010 | Kaminsky |
| 7,743,826 B2 | 6/2010 | Harris et al. |
| 7,798,221 B2 | 9/2010 | Vinegar et al. |
| 7,857,056 B2 | 12/2010 | Kaminsky et al. |
| 7,860,377 B2 | 12/2010 | Vinegar et al. |
| 7,905,288 B2 | 3/2011 | Kinkead |
| 2001/0049342 A1 | 12/2001 | Passey et al. |
| 2002/0013687 A1 | 1/2002 | Ortoleva |
| 2002/0023751 A1 | 2/2002 | Neuroth et al. |
| 2002/0029882 A1 | 3/2002 | Rouffignac et al. |
| 2002/0049360 A1 | 4/2002 | Wellington et al. |
| 2002/0077515 A1 | 6/2002 | Wellington et al. |
| 2002/0099504 A1 | 7/2002 | Cross et al. |
| 2003/0080604 A1 | 5/2003 | Vinegar et al. |
| 2003/0085570 A1 | 5/2003 | Ernst et al. |
| 2003/0111223 A1 | 6/2003 | Rouffignac et al. |
| 2003/0131994 A1 | 7/2003 | Vinegar et al. |
| 2003/0131995 A1 | 7/2003 | de Rouffignac et al. |
| 2003/0178195 A1 | 9/2003 | Agee et al. |
| 2003/0183390 A1 | 10/2003 | Veenstra et al. |
| 2003/0192691 A1 | 10/2003 | Vinegar et al. |
| 2003/0196788 A1 | 10/2003 | Vinegar et al. |
| 2003/0196789 A1 | 10/2003 | Wellington |
| 2003/0209348 A1 | 11/2003 | Ward et al. |
| 2003/0213594 A1 | 11/2003 | Wellington et al. |
| 2004/0020642 A1 | 2/2004 | Vinegar et al. |
| 2004/0140095 A1 | 7/2004 | Vinegar et al. |
| 2004/0198611 A1 | 10/2004 | Atkinson |
| 2004/0211557 A1 | 10/2004 | Cole et al. |
| 2005/0051327 A1 | 3/2005 | Vinegar et al. |
| 2005/0252656 A1 | 11/2005 | Maguire |
| 2005/0252832 A1 | 11/2005 | Doyle et al. |
| 2005/0252833 A1 | 11/2005 | Doyle et al. |
| 2005/0269077 A1 | 12/2005 | Sandberg |
| 2005/0269088 A1 | 12/2005 | Vinegar et al. |
| 2006/0021752 A1 | 2/2006 | de St. Remey |
| 2006/0100837 A1 | 5/2006 | Symington et al. |
| 2006/0213657 A1 | 9/2006 | Berchenko et al. |
| 2007/0000662 A1 | 1/2007 | Symington et al. |
| 2007/0023186 A1 | 2/2007 | Kaminsky et al. |
| 2007/0045265 A1 | 3/2007 | McKinzie, II |
| 2007/0045267 A1 | 3/2007 | Vinegar et al. |
| 2007/0084418 A1 | 4/2007 | Gurevich |
| 2007/0095537 A1 | 5/2007 | Vinegar |
| 2007/0102359 A1 | 5/2007 | Lombardi et al. |
| 2007/0131415 A1 | 6/2007 | Vinegar et al. |
| 2007/0144732 A1 | 6/2007 | Kim et al. |
| 2007/0209799 A1 | 9/2007 | Vinegar et al. |
| 2007/0246994 A1 | 10/2007 | Kaminsky et al. |
| 2008/0087420 A1 | 4/2008 | Kaminsky et al. |
| 2008/0087421 A1 | 4/2008 | Kaminsky |
| 2008/0087426 A1 | 4/2008 | Kaminsky |
| 2008/0087427 A1 | 4/2008 | Kaminsky et al. |
| 2008/0087428 A1 | 4/2008 | Symington et al. |
| 2008/0173443 A1 | 7/2008 | Symington et al. |
| 2008/0185145 A1 | 8/2008 | Carney et al. |
| 2008/0207970 A1 | 8/2008 | Meurer et al. |
| 2008/0230219 A1 | 9/2008 | Kaminsky |
| 2008/0271885 A1 | 11/2008 | Kaminsky |
| 2008/0283241 A1 | 11/2008 | Kaminsky et al. |
| 2008/0289819 A1 | 11/2008 | Kaminsky et al. |
| 2008/0290719 A1 | 11/2008 | Kaminsky et al. |
| 2009/0038795 A1 | 2/2009 | Kaminsky et al. |
| 2009/0050319 A1 | 2/2009 | Kaminsky et al. |
| 2009/0101346 A1 | 4/2009 | Vinegar et al. |
| 2009/0101348 A1 | 4/2009 | Kaminsky |
| 2009/0107679 A1 | 4/2009 | Kaminsky |
| 2009/0133935 A1 | 5/2009 | Kinkead |
| 2009/0145598 A1 | 6/2009 | Symington et al. |
| 2009/0308608 A1 | 12/2009 | Kaminsky et al. |
| 2010/0078169 A1 | 4/2010 | Symington et al. |
| 2010/0089575 A1 | 4/2010 | Kaminsky et al. |
| 2010/0089585 A1 | 4/2010 | Kaminsky |
| 2010/0095742 A1 | 4/2010 | Symington et al. |
| 2010/0101793 A1 | 4/2010 | Symington et al. |
| 2010/0218946 A1 | 9/2010 | Symington et al. |
| 2010/0282460 A1 | 11/2010 | Stone et al. |
| 2010/0319909 A1 | 12/2010 | Symington et al. |

FOREIGN PATENT DOCUMENTS

| | | |
|---|---|---|
| CA | 1288043 | 8/1991 |
| CA | 2560223 | 3/2007 |
| EP | 0387846 | 9/1990 |
| FR | 0866212 | 9/1998 |
| GB | 855408 | 11/1960 |
| GB | 1454324 | 11/1976 |
| GB | 1463444 | 2/1977 |
| GB | 1 478 880 | 7/1977 |
| GB | 1501310 | 2/1978 |
| GB | 1559948 | 1/1980 |
| GB | 1595082 | 8/1981 |
| WO | WO 82/01408 | 4/1982 |
| WO | WO 90/06480 | 6/1990 |
| WO | WO 99/67504 | 12/1999 |
| WO | WO 01/78914 | 10/2001 |
| WO | WO 01/81505 | 11/2001 |
| WO | WO 02/085821 | 10/2002 |
| WO | WO 2005/010320 | 2/2005 |
| WO | WO 2005/045192 | 5/2005 |
| WO | WO 2006/115943 | 11/2006 |
| WO | WO2007/033371 | 3/2007 |
| WO | WO2007/050445 | 5/2007 |
| WO | WO2007/050479 | 5/2007 |
| WO | WO2010/047859 | 4/2010 |

OTHER PUBLICATIONS

Brandt, H. et al. (1965) "Stimulating Heavy Oil Reserves With Downhole Air-Gas Burners," *World Oil*, pp. 91-95.
De Priester, C. et al. (1963) "Well Stimulation by Downhole Gas-Air Burner," *Journal of Petro. Tech.*,, pp. 1297-1302.
EP Search Report No. RS115479 dated Nov. 13, 2007, 3 pages.
International Search Report dated Aug. 21, 2008 for PCT/US08/05008 filed May 15, 2007, 11 pages.
Katz, D.L. et al. (1978) "Predicting phase behavior of condensate/crude-oil systems using methane intereaction coefficients," Journal of Petroleum Technology, pp. 1649-1655.
Salomonsson, G. (1951) "The Ljunstrom In-Situ Method for Shale-Oil Recovery" *Oil Shale and Cannel Coal (vol. 2)*, *Proceedings of the 2$^{nd}$ Oil Shale and Cannel Coal Conference*, Glasgow, Jul. 1951, pp. 260-280.
Sierra, R. et al. (2001) "Promising Progress in Field Application of Reservoir Electrical Heating Methods," *SPE Paper* 69709.
Smith, F. M. (1966) "A Down-Hole Burner—Versatile Tool for Well Heating," *25$^{th}$ Tech. Conf. Petro. Prod.*, Pennsylvania State Univ., pp. 275-285.
Yen, T. F. et al. (1976) *Oil Shale*, Amsterdam, Elsevier, p. 292. (Historical Reference only).
Ali, A.H.A, et al, (2003) "Watching Rocks Change-Mechanical Earth Modeling", *Oilfield Review*, pp. 22-39.
Allred, (1964) "Some Characteristic Properties of Colorado Oil Shale Which May Influence In Situ Processing," *Quarterly Colo. School Of Mines, 1$^{st}$ Symposium Oil Shale*, v.59. No. 3, pp. 47-75.
Asquith, G., et al., (2004) *Basic Well Log Analysis*, Second Ed., Chapter 1, pp. 1-20.
Ball, J.S., et al. (1949) "Composition of Colorado Shale-Oil Naphtha", *Industrial and Engineering Chemistry*, vol. 41, No. 3 pp. 581-587.
Barnes, A. L. et al. (1968) "Quarterly of the Colorado School of Mines" *Fifth Symposium on Oil Shale*, v. 63(4), Oct. 1968, pp. 827-852.
Bastow, T.P., (1998) Sedimentary Processes Involving Aromatic Hydrocarbons>. Thesis (PhD in Applied Chemistry) Curtin University of Technology (Australia), Dec., p. 102.

Baugman, G. L. (1978) *Synthetic Fuels Data Handbook*, Second Edition, Cameron Engineers Inc.

Berry, K. L., et al. (1982) "Modified in situ retorting results of two field retorts", Gary, J. H., ed., 15th Oil Shale Symp., CSM, pp. 385-396.

Blanton, T. L. et al, (1999) "Stress Magnitudes from Logs: Effects of Tectonic Strains and Temperature", *SPE Reservoir Eval. & Eng.* 2, vol. 1, Feb., pp. 62-68.

Brandt, A. R., "Converting Oil Shale to Liquid Fuels: Energy Inputs and Greenhouse Gas Emissions of the Shell in Situ Conversion Process," Environ. Sci. Technol. 2008, 42, pp. 7489-7495.

Brandt, H. et al. (1965) "Stimulating Heavy Oil Reservoirs With Downhole Air-Gas Burners," *World Oil*, (Sep. 1965), pp. 91-95.

Bridges, J. E., et al. (1983) "The ITRI in situ fuel recovery process", *J. Microwave Power*, v. 18, pp. 3-14.

Burnham, A. K. et al. (1983) "High-Pressure Pyrolysis of Green River Oil Shale" in Geochemistry and Chemistry of Oil Shales: ACS Symposium Series.

Burwell, E. L. et al. (1970) "Shale Oil Recovery by In-Situ Retorting—A Pilot Study" Journal of Petroleum Engr., Dec. 1970, pp. 1520-1524.

Charlier, R. et al, (2002) "Numerical Simulation of the Coupled Behavior of Faults During the Depletion of a High-Pressure/High-Temperature Reservoir", *Society of Petroleum Engineers*, SPE 78199, pp. 1-12.

Chute, F. S., and Vermeulen, F. E., (1988) "Present and potential applications of electromagnetic heating in the in situ recovery of oil", AOSTRA J. Res., v. 4, pp. 19-33.

Chute, F. S. And Vermeulen, F.E., (1989) "Electrical heating of reservoirs", Hepler, L., and Hsi, C., eds., AOSTRA Technical Handbook on Oil Sands, Bitumens, and Heavy Oils, Chapt. 13, pp. 339-376.

Cipolla, C.L., et al. (1994), "Practical Application of in-situ Stress Profiles", *Society of Petroleum Engineers*, SPE 28607, pp. 487-499.

Cook, G. L. et al. (1968) "The Composition of Green River Shale Oils" United Nations Symposium of the Development and Utilization of Oil Shale Resources, 23 pgs.

Covell, J. R., et al. (1984) "Indirect in situ retorting of oil shale using the TREE process", Gary, J. H., ed., 17th Oil Shale Symposium Proceedings, Colorado School of Mines, pp. 46-58.

Cummins, J. J. et al. (1972) "Thermal Degradation of Green River Kerogen at 150 to 350C: Rate of Product Formation, Report of Investigation 7620," *US Bureau of Mines*, 1972.

Day, R. L., (1998) "Solution Mining of Colorado Nahcolite, Wyoming State Geological Survey Public Information Circular 40," *Proceedings of the First International Soda Ash Conference*, V.II (Rock Springs, Wyoming, Jun. 10-12) pp. 121-130.

Domine, F. et al. (2002) "Up to What Temperature is Petroleum Stable? New Insights from a 5200 Free Radical Reactions Model", *Organic Chemistry*, 33, pp. 1487-1499.

Dougan, P. M. et al. (1981) "BX *In Situ* Oil Shale Project," *Colorado School of Mines; Fourteenth Oil Shale Symposium Proceedings*, 1981, pp. 118-127.

Dougan, P. M. (1979) "The BX in Situ Oil Shale Project," *Chem. Engr. Progress*, pp. 81-84.

Duncan, D. C., (1967) "Geologic Setting of Oil Shale Deposits and World Prospects," *in Proceedings of the Seventh World Petroleum Congress*, v.3, Elsevier Publishing, pp. 659-667.

Dunks, G. et al. (1983) "Electrochemical Studies of Molten Sodium Carbonate," *Inorg. Chem.*, 22, pp. 2168-2177.

Dusseault, M.B. (1998) "Casing Shear: Causes, Cases, Cures", Society of Petroleum Engineers, SPE 48,864 pp. 337-349.

Dyni, J. R., (1974) "Stratigraphy and Nahcolite Resources of the Saline Facies of the Green River Formation in Northwest Colorado," in D.K. Murray (ed.), *Guidebook to the Energy Resources of the Piceance Creek Basin Colorado, Rocky Mountain Association of Geologists*, Guidebook, pp. 111-122.

Fainberg, V. et al. (1998) "Integrated Oil Shale Processing Into Energy and Chemicals Using Combined-Cycle Technology," Energy Sources, v.20.6, Abstract, 1 page.

Farouq Ali, S. M., (1994), "Redeeming features of in situ combustion", DOE/NIPER *Symposium on in Situ Combustion Practices-Past, Present, and Future Application*, Tulsa, OK, Apr. 21-22, No. ISC 1, p. 3-8.

Fisher, S. T. (1980) "A Comparison of Eleven Processes for Production of Energy from the Solid Fossil Fuels of North America," *SPE* 9098, pp. 1-27.

Fox, J. P, (1980) "Water-related Impacts of In-Situ Oil Shale Processing," *California Univ., Berkeley, Lawrence Berkeley Lab*, Chapters 6-7.

Fredrich, J. T. et al, (1996) "Three-Dimensional Geomechanical Simulation of Reservoir Compaction and Implications for Well Failures in the Belridge Diatomite", *Society of Petroleum Engineers* SPE 36698, pp. 195-210.

Fredrich, J. T. et al, (2000) "Geomechanical Modeling of Reservoir Compaction, Surface Subsidence, and Casing Damage at the Belridge Diatomite Field", *SPE Reservoir Eval. & Eng.*3, vol. 4, Aug., pp. 348-359.

Fredrich, J. T. et al, (2003) "Stress Perturbations Adjacent to Salt Bodies in the Deepwater Gulf of Mexico", *Society of Petroleum Engineers* SPE 84554, pp. 1-14.

Frederiksen, S. et al, (2000) "A Numerical Dynamic Model for the Norwegian-Danish Basin", *Tectonophysics*, 343, 2001, pp. 165-183.

Freund, H. et al., (1989) "Low-Temperature Pyrolysis of Green River Kerogen", *The American Association of Petroleum Geologists Bulletin*, v. 73, No. 8 (Aug.) pp. 1011-1017.

Gatens III, J. M. et al, (1990) "In-Situ Stress Tests and Acoustic Logs Determine Mechanical Properties and Stress Profiles in the Devonian Shales", *SPE Formation Evaluation* SPE 18523, pp. 248-254.

Garthoffner, E. H., (1998), "Combustion front and burned zone growth in successful California ISC projects", SPE 46244, pp. 1-11.

Greaves, M., et al. (1994) "In situ combustion (ISC) processes: 3D studies of vertical and horizontal wells", *Europe Comm. Heavy Oil Technology in a Wider Europe Symposium*, Berlin, Jun. 7-8, p. 89-112.

Hansen, K. S. et al, (1989) "Earth Stress Measurements in the South Belridge Oil Field, Kern County, California", *SPE Formation Evaluation*, Dec. pp. 541-549.

Hansen, K. S. et al, (1993) "Finite-Element Modeling of Depletion-Induced Reservoir Compaction and Surface Subsidence in the South Belridge Oil Field, California", SPE 26074, pp. 437-452.

Hansen, K. S. et al, (1995) "Modeling of Reservoir Compaction and Surface Subsidence at South Belridge", *SPE Production & Facilities*, Aug. pp. 134-143.

Hardy, M. et al. (2003) "Solution Mining of Nahcolite at the American Soda Project, Piceance Creek, Colorado," *SME Annual Mtg.*, Feb. 24-26, Cincinnati, Ohio, Preprint 03-105.

Hardy, M., et al. (2003) "Solution Mining of Nahcolite at American Soda's Yankee Gulch Project," *Mining Engineering*, Oct. 2003, pp. 23-31.

Henderson, W, et al. (1968) "Thermal Alteration as a Contributory Process to the Genesis of Petroleum", *Nature* vol. 219, pp. 1012-1016.

Hilbert, L. B. et al, (1999) "Field-Scale and Wellbore Modeling of Compaction-Induced Casing Failures", *SPE Drill. & Completion*, 14(2), Jun. pp. 92-101.

Hill, G.R. et al. (1967) "The Characteristics of a Low Temperature In Situ Shale Oil," $4^{th}$ *Symposium on Oil Shale, Quarterly of the Colorado School of Mines*, v.62(3), pp. 641-656.

Hill, G. R. et al. (1967) "Direct Production of a Low Pour Point High Gravity Shale Oil", *I&EC Product Research and Development*, 6(1), Mar. pp. 52-59.

Holditch, S. A., (1989) "Pretreatment Formation Evaluation", *Recent Advances in Hydraulic Fracturing*, SPE Monograph vol. 12, Chapter 2 (Henry L. Doherty Series), pp. 39-56.

Holmes, A. S. et al. (1982) "Process Improves Acid Gas Separation," *Hydrocarbon Processing*, pp. 131-136.

Holmes, A. S. et al. (1983) "Pilot Tests Prove Out Cryogenic Acid-Gas/Hydrocarbon Separation Processes," *Oil & Gas Journal*, pp. 85-91.

Humphrey, J. P. (1978) "Energy from in situ processing of Antrim oil shale", *DOE Report* FE-2346-29.

Ingram, L. L. et al. (1983) "Comparative Study of Oil Shales and Shale Oils from the Mahogany Zone, Green River Formation (USA) and Kerosene Creek Seam, Rundle Formation (Australia)," *Chemical Geology*, 38, pp. 185-212.

Ireson, A. T. (1990) "Review of the Soluble Salt Process for In-Situ Recovery of Hydrocarbons from Oil Shale with Emphasis on Leaching and Possible Beneficiation," *23rd Colorado School of Mines Oil Shale Symposium* (Golden, Colorado), 152-161.

Jacobs, H. R. (1983) "Analysis of the Effectiveness of Steam Retorting of Oil Shale", *AIChE Symposium Series—Heat Transfer*—Seattle 1983 pp. 373-382.

Johnson, D. J. (1966) "Decomposition Studies of Oil Shale," *University of Utah*, May 1966.

Kenter, C. J. et al, (2004) "Geomechanics and 4D: Evaluation of Reservoir Characteristics from Timeshifts in the Overburden", *Gulf Rocks 2004, 6th North America Rock Mechanics Symposium (NARMS): Rock Mechanics Across Borders and Disciplines*, Houston, Texas, Jun. 5-9, ARMA/NARMS 04-627.

Kuo, M. C. T. et al (1979) "Inorganics leaching of spent shale from modified in situ processing," J. H. Gary (ed.) *Twelfth Oil Shale Symposium Proceedings*, Colorado School of Mines, Golden CO., Apr. 18-20, pp. 81-93.

Laughrey, C. D. et al. (2003) "Some Applications of Isotope Geochemistry for Determining Sources of Stray Carbon Dioxide Gas," *Environmental Geosciences*, 10(3), pp. 107-122.

Lekas, M. A. et al. (1991) "Initial evaluation of fracturing oil shale with propellants for in situ retorting—Phase 2", DOE Report DOE/MC/11076-3064.

Le Pourhiet, L. et al, (2003) "Initial Crustal Thickness Geometry Controls on the Extension in a Back Arc Domain: Case of the Gulf of Corinth", *Tectonics*, vol. 22, No. 4, pp. 6-1-6-14.

Lundquist, L. (1951) "Refining of Swedish Shale Oil", *Oil Shale Cannel Coal Conference*, vol./Issue: 2, pp 621-627.

Marotta, A. M. et al, (2003) "Numerical Models of Tectonic Deformation at the Baltica-Avalonia Transition Zone During the Paleocene Phase of Inversion", *Tectonophysics*, 373, pp. 25-37.

Miknis, F.P, et al (1985) "Isothermal Decomposition of Colorado Oil Shale", DOE/FE/60177-2288 (DE87009043) May 1985.

Mohammed, Y.A., et al (2001) "A Mathematical Algorithm for Modeling Geomechanical Rock Properties of the Khuff and PreKhuff Reservoirs in Ghawar Field", *Society of Petroleum Engineers* SPE 68194, pp. 1-8.

Molenaar, M. M. et al, (2004) "Applying Geo-Mechanics and 4D: '4D In-Situ Stress' as a Complementary Tool for Optimizing Field Management", *Gulf Rocks 2004, 6th North America Rock Mechanics Symposium (NARMS): Rock Mechanics Across Borders and Disciplines*, Houston, Texas, Jun. 5-9, ARMA/NARMS 04-639, pp. 1-7.

Moschovidis, Z. (1989) "Interwell Communication by Concurrent Fracturing—a New Stimulation Technique", *Journ. of Canadian Petro. Tech.* 28(5), pp. 42-48.

Motzfeldt, K. (1954) "The Thermal Decomposition of Sodium Carbonate by the Effusion Method," *Jml. Phys. Chem.*, v. LIX, pp. 139-147.

Mut, Stephen (2005) "The Potential of Oil Shale," *Shell Oil Presentation at National Academies, Trends in Oil Supply Demand*, in Washington, DC, Oct. 20-21, 2005, 11 pages.

Needham, et al (1976) "Oil Yield and Quality from Simulated In-Situ Retorting of Green River Oil Shale", Society of Petroleum Engineers of American Institute of Mining, Metallurgical and Petroleum Engineers, Inc. SPE 6069.

Newkirk, A. E. et al. (1958) "Drying and Decomposition of Sodium Carbonate," *Anal. Chem.*, 30(5), pp. 982-984.

Nielsen, K. R. (1995) "Colorado Nahcolite: A Low Cost Source of Sodium Chemicals," *7th Annual Canadian Conference on Markets for Industrial Minerals*, (Vancouver, Canada, Oct. 17-18) pp. 1-9.

Nottenburg, R.N. et al. (1979) "Temperature and stress dependence of electrical and mechanical properties of Green River oil shale," *Fuel*, 58, pp. 144-148.

Nowacki, P. (ed.), (1981) *Oil Shale Technical Handbook*, Noyes Data Corp.

Pattillo, P. D. et al, (1998) "Reservoir Compaction and Seafloor Subsidence at Valhall", SPE 47274, 1998, pp. 377-386.

Pattillo, P. D. et al, (2002) "Analysis of Horizontal Casing Integrity in the Valhall Field", SPE 78204, pp. 1-10.

Persoff, P. et al. (1979) "Control strategies for abandoned in situ oil shale retorts," J. H. Gary (ed.), *12th Oil Shale Symposium Proceedings*, Colorado School of Mines, Golden, Co., Apr. 18-20, pp. 72-80.

Peters, G., (1990) "The Beneficiation of Oil Shale by the Solution Mining of Nahcolite," *23rd Colorado School of Mines Oil Shale Symposium* (Golden, Co) pp. 142-151.

Plischke, B., (1994) "Finite Element Analysis of Compaction and Subsidence—Experience Gained from Several Chalk Fields", *Society of Petroleum Engineers*, SPE 28129, 1994, pp. 795-802.

Prats, M. et al. (1975) "The Thermal Conductivity and Diffusivity of Green River Oil Shales", *Journal of Petroleum Technology*, pp. 97-106, Jan. 1975.

Prats, M., et al. (1977) "Soluble-Salt Processes for In-Situ Recovery of Hydrocarbons from Oil Shale," *Journal of Petrol. Technol.*, pp. 1078-1088.

Rajeshwar, K. et al. (1979) "Review: Thermophysical Properties of Oil Shales", *Journal of Materials Science*, v.14, pp. 2025-2052.

Ramey, M. et al. (2004) "The History and Performance of Vertical Well Solution Mining of Nahcolite (NaHCO3) in the Piceance Basin, Northwestern, Colorado, USA," *Solution Mining Research Institute: Fall 2004 Technical Meeting* (Berlin, Germany).

Reade Advanced Materials; 2006 About.com Electrical resistivity of materials. [Retrieved on Oct. 15, 2009] Retrieved from internet: URL: http://www.reade.com/Particle%5FBriefinds/elec%5Fres.html. Entire Document.

Riva, D. et al. (1998) "Suncor down under: the Stuart Oil Shale Project", Annual Meeting of the *Canadian Inst. Of Mining, Metallurgy, and Petroleum*, Montreal, May 3-7.

Rupprecht, R. (1979) "Application of the Ground-Freezing Method to Penetrate a Sequence of Water-Bearing and Dry Formations—Three Construction Cases," *Engineering Geology*, 13, pp. 541-546.

Ruzicka, D.J. et al. (1987) "Modified Method Measures Bromine No. Of Heavy Fuel Oils", *Oil & Gas Journal*, 85(31), Aug. 3, pp. 48-50.

Sahu, D. et al. (1988) "Effect of Benzene and Thiophene on Rate of Coke Formation During Naphtha Pyrolysis", *Canadian Journ. of Chem. Eng.*, 66, Oct. pp. 808-816.

Sandberg, C. R. et al. (1962) "In-Situ Recovery of Oil from Oil Shale—A Review and Summary of Field and Laboratory Studies," RR62.039FR, Nov. 1962.

Siskin, M. et al. (1995) "Detailed Structural Characterization of the Organic Material in Rundel Ramsay Crossing and Green River Oil Shales," *Kluwer Academic Publishers*, pp. 143-158.

Smart, K. J. et al, (2004) "Integrated Structural Analysis and Geomechanical Modeling: an Aid to Reservoir Exploration and Development", *Gulf Rocks 2004, 6th North America Rock Mechanics Symposium (NARMS): Rock Mechanics Across Borders and Disciplines*, Houston, Texas, Jun. 5-9, ARMA/NARMS 04-470.

Sresty, G. C.; et al. (1982) "Kinetics of Low-Temperature Pyrolysis of Oil Shale by the IITRI RF Process," *Colorado School of Mines; Fifteenth Oil Shale Symposium Proceedings*, Aug. 1982, pp. 411-423.

Stevens, A. L., and Zahradnik, R. L. (1983) "Results from the simultaneous processing of modified in situ retorts 7& 8", Gary, J. H., ed., *16th Oil Shale Symp.*, CSM, p. 267-280.

Stoss, K. et al. (1979) "Uses and Limitations of Ground Freezing With Liquid Nitrogen,"*Engineering Geology*, 13, pp. 485-494.

Symington, W.A., et al (2006) ExxonMobil's electrofrac process for in situ oil shale conversion *26th Oil Shale Symposium*, Colorado School of Mines.

Syunyaev, Z.I. et al. (1965) "Change in the Resistivity of Petroleum Coke on Calcination,"Chemistry and Technology of Fuels and Oils, 1(4), pp. 292-295.

Templeton, C. C. (1978) "Pressure-Temperature Relationship for Decomposition of Sodium Bicarbonate from 200 to 600° F," *J. of Chem. And Eng. Data*, 23(1), pp. 7-8.

Thomas, A. M. (1963) "Thermal Decomposition of Sodium Carbonate Solutions," *J. of Chem. And Eng. Data*, 8(1), pp. 51-54.

Thomas, G. W. (1964) "A Simplified Model of Conduction Heating in Systems of Limited Permeability," *Soc.Pet. Engineering Journal*, Dec. 1964, pp. 335-344.

Thomas, G. W. (1966) "Some Effects of Overburden Pressure on Oil Shale During Underground Retorting," *Society of Petroleum Engineers Journal*, pp. 1-8, Mar. 1966.

Tihen, S. S. et al. (1967) "Thermal Conductivity and Thermal Diffusivity of Green River Oil Shale," *Thermal Conductivity: Proceed-* ings of the Seventh Conference (Nov. 13-16, 1967), NBS Special Publication 302, pp. 529-535, 1968.

Tisot, P. R. et al. (1970) "Structural Response of Rich Green River Oil Shales to Heat and Stress and Its Relationship to Induced Permeability," Journal of Chemical Engineering Data, v. 15(3), pp. 425-434.

Tisot, P. R. et al. (1971) "Structural Deformation of Green River Oil Shale as It Relates to in Situ Retorting," US Bureau of Mines Report of Investigations 7576, 1971.

Tisot, P. R. (1975) "Structural Response of Propped Fractures in Green River Oil Shale as It Relates to Underground Retorting," US Bureau of Mines Report of Investigations 8021.

Tissot, B. P., and Welte, D. H. (1984) Petroleum Formation and Occurrence, New York, Springer-Verlag, p. 160-174, 175-198 and 254-266.

Tissot, B. P., and Welte, D. H. (1984) Petroleum Formation and Occurrence, New York, Springer-Verlag, p. 267-289 and 470-492.

Turta, A., (1994), "In situ combustion- from pilot to commercial application", DOE/NIPER Symposium on in Situ Combustion Practices-Past, Present, and Future Application, Tulsa, OK, Apr. 21-22, No. ISC 3, p. 15-39.

Tyner, C. E. et al. (1982) "Sandia/Geokinetics Retort 23: a horizontal in situ retorting experiment", Gary, J. H., ed., 15th Oil Shale Symp., CSM, p. 370-384.

Tzanco, E. T., et al. (1990), "Laboratory Combustion Behavior of Countess B Light Oil", Petroleum Soc. of CIM and SPE, Calgary, Jun. 10-13, No. CIM/SPE 90-63, p. 63.1-63.16.

Veatch, Jr. R.W. and Martinez, S.J., et al. (1990) "Hydraulic Fracturing: Reprint Series No. 28", Soc. of Petroleum Engineers SPE 14085, Part I, Overview.

Warpinski, N. R., (1989) "Elastic and Viscoelastic Calculations of Stresses in Sedimentary Basins", SPE Formation Evaluation, vol. 4, pp. 522-530.

Yoon, E. et al. (1996) "High-Temperature Stabilizers for Jet Fuels and Similar Hydrocarbon Mixtures. 1. Comparative Studies of Hydrogen Donors", Energy & Fuels, 10, pp. 806-811.

Oil & Gas Journal, 1998, "Aussie oil shale project moves to Stage 2", Oct. 26, p. 42.

"Encyclopedia of Chemical Technology" ($4^{th}$ ed), Alkali and Chlorine Products, pp. 1025-1039 (1998).

EP Search Report dated Dec. 29, 2003 (RS 110243, Corresponding to US Pat 7,331,385).

EP Search Report dated Mar. 17, 2004 (RS 110686, Corresponding to U.S. Patent 7,441,603).

EP Search Report, Supplementary dated Apr. 10, 2007 (EP 04 77 9878 Corresponding to U.S. Patent 7,441,603).

EP Search Report dated Apr. 29, 2005 (RS 112183, Corresponding to U.S. Appl. No. 11/250,804, Published as US 2006/0100837 on May 11, 2008).

EP Search Report dated Jun. 2, 2006 (RS113865, corresponding to U.S. Appl. No. 11/726,651).

EP Search Report dated Feb. 16, 2007 (RS 114808, Corresponding to U.S. Appl. No. 11/973,746, Published as US 2008/0087420 on May 17, 2008).

EP Search Report dated Feb. 16, 2007 (RS 114804, Corresponding to U.S. Appl. No. 11/973,750, Published as US 2008/0087427 on Apr. 17, 2008).

EP Search Report dated Mar. 21, 2007 (RS 114890, Corresponding to U.S. Patent 7,516,787).

EP Search Report dated Feb. 16, 2007 (RS 114807, Corresponding to U.S. Patent 7,669,657).

EP Search Report dated Nov. 13, 2007 (RS 115479, Corresponding to U.S. Patent Application 12/148414).

EP Search Report dated Aug. 29, 2007 (No. RS115553, Corresponding to U.S. Appl. No. 12/148,388).

EP Search Report dated Jul. 4, 2007 ( RS 115341 Corresponding to U.S. Appl. No. 12/074,899).

EP Search Report dated Jul. 5, 2007 (RS 115432 Corresponding to U.S. Appl. No. 12/075,087).

EP Search Report dated Mar. 12, 2009 (EP 08 00 3956,-Corresponding to U.S. Appl. No. 12/271,521).

EP Search Report dated Aug. 29, 2007 (RS 1155554, Corresponding to U.S. Appl. No. 12/154,238).

EP Search Report dated Aug. 28, 2007 (RS 1155555, Corresponding to U.S. Appl. No. 12/154,256).

International Search Report for PCT/US01/09247 Jun. 20, 2001.
International Search Report for PCT/US04/11508, Jan. 5, 2005.
International Search Report for PCT/US08/88045, Feb. 12, 2009.
International Search Report for PCT/US04/24947 Mar. 10, 2005.
International Search Report for PCT/US07/07133, Jan. 4, 2008.
International Search Report for PCT/US07/21673 Jun. 24, 2008.
International Search Report for PCT/US07/21668 Apr. 29, 2008.
International Search Report for PCT/US07/21666 Apr. 4, 2008.
International Search Report for PCT/US07/21669, Apr. 29, 2008.
International Search Report for PCT/US07/21660 Apr. 4, 2008.
International Search Report for PCT/US07/021968, May 14, 2008.
International Search Report for PCT/US07/021968, May 21, 2008.
International Search Report for PCT/US08/005008, Aug. 29, 2008.
International Search Report for PCT/US08/05056, Aug. 25, 2008.
International Search Report for PCT/US/08/003069, Jun. 25, 2008.
International Search Report for PCT/US08/003043, Jul. 2, 2008.
International Search Report for PCT/US08/083815, Mar. 20, 2009.
International Search Report for PCT/US08/006462 Sep. 22, 2008.
International Search Report for PCT/US08/006463 Aug. 22, 2008.
International Search Report for PCT/US07/21645 Apr. 21, 2008.
International Search Report for PCT/US09/037419 Jul. 7, 2009.
International Search Report for PCT/US09/055403, Oct. 22, 2009.
International Search Report for PCT/US10/20342 Feb. 26, 2010.
International Search Report for PCT/US10/031910 Aug. 3, 2010.
International Search Report for PCT/US10/057204 Jan. 27, 2011.
U.S. Appl. No. 12/630,636 Office Action mailed Oct. 27, 2010.
U.S. Appl. No. 11/250,804 Office Action mailed Oct. 16, 2008.
U.S. Appl. No. 11/250,804 Office Action mailed Jun. 11, 2009.
U.S. Appl. No. 11/973,746 Office Action mailed Jun. 25, 2009.
U.S. Appl. No. 11/973,746 Office Action mailed Nov. 8, 2010.
U.S. Appl. No. 11/973,750 Office Action mailed Dec. 4, 2008.
U.S. Appl. No. 11/973,750 Office Action mailed Jul. 22, 2009.
U.S. Appl. No. 12/638,630 Office Action mailed Mar. 16, 2011.
U.S. Appl. No. 12/712,904 Office Action mailed Nov. 10, 2010.
U.S. Appl. No. 12/148,414 Office Action mailed May 19, 2010.
U.S. Appl. No. 12/148,414 Office Action mailed Oct. 22, 2010.
U.S. Appl. No. 12/148,388 Office Action mailed Jun. 10, 2010.
U.S. Appl. No. 12/148,388 Office Action mailed Nov. 19, 2010.
U.S. Appl. No. 12/074,899 Office Action mailed Dec. 16, 2009.
U.S. Appl. No. 12/074,899 Office Action mailed Jul. 26, 2010.
U.S. Appl. No. 12/074,899 Office Action mailed Jan. 4, 2011.
U.S. Appl. No. 12/075,087 Office Action mailed Oct. 12, 2010.
U.S. Appl. No. 12/075,087 Office Action mailed Mar. 7, 2011.
U.S. Appl. No. 12/271,521 Office Action mailed Nov. 2, 2010.
U.S. Appl. No. 11/973,898 Office Action mailed May 6, 2010.
U.S. Appl. No. 11/973,898 Office Action mailed Dec. 20, 2010.
U.S. Appl. No. 12/405,901 Office Action mailed Feb. 14, 2011.
U.S. Appl. No. 12/154,238 Office Action mailed Apr. 22, 2011.
U.S. Appl. No. 12/154,256 Office Action mailed May 9, 2011.
U.S. Appl. No. 12/148,414 Office Action mailed May 17, 2011.
U.S. Appl. No. 12/443,680 Office Action mailed Jun. 23, 2011.
U.S. Pat No. 6,918,444—Office Action mailed Sep. 16, 2004.
US Pat No. 7,331,385—Office Action mailed Jul. 12, 2007.
U.S. Pat No. 7,631,691—Office Action mailed Mar. 18, 2009.
U.S. Pat No. 7,441,603—Office Action mailed Feb. 25, 2008.
U.S. Pat No. 7,857,056—Office Action mailed Mar. 19, 2010.
US Pat No. 7,516,785—Office Action mailed Apr. 2, 2008.
US Pat No. 7,516,787—Office Action mailed Apr. 3, 2008.
U.S. Pat No. 7,647,972—Office Action mailed May 19, 2009.
U.S. Pat No. 7,647,971—Office Action mailed May 21, 2009.
U.S. Pat No. 7,669,657—Office Action mailed Jun. 26, 2008.
U.S. Pat No. 7,669,657—Office Action mailed Dec. 15, 2008.
U.S. Pat No. 7,669,657—Office Action mailed Sep. 15, 2009.
U.S. Pat No. 7,644,993—Office Action mailed Jun. 24, 2009.

DOWNHOLE BURNER WELLS FOR IN SITU CONVERSION OF ORGANIC-RICH ROCK FORMATIONS

CROSS-REFERENCE TO RELATED APPLICATIONS

This application claims the benefit of U.S. Provisional Patent Application Ser. No. 60/930,311, filed May 15, 2007. That application is titled "Downhole Burner Wells for In Situ Conversion of Organic-Rich Rock Formations," and is incorporated herein in its entirety by reference.

This application is related to co-pending, concurrently filed, and commonly assigned U.S. patent application Ser. No. 12/148,388 entitled "Downhole Burners for In Situ Conversion of Organic-Rich Rock Formations", which claims the benefit of U.S. Provisional Patent Application Ser. No. 60/930,308, filed May 15, 2007, the disclosures of which are hereby incorporated herein in their entirety by reference.

BACKGROUND OF THE INVENTION

1. Field of the Invention

The present invention relates to the field of hydrocarbon recovery from subsurface formations. More specifically, the present invention relates to the in situ recovery of hydrocarbon fluids from organic-rich rock formations including, for example, oil shale formations, coal formations and tar sands formations. The present invention also relates to methods for heating a subsurface formation using combustion fuel.

2. Background of the Invention

Certain geological formations are known to contain an organic matter known as "kerogen." Kerogen is a solid, carbonaceous material. When kerogen is imbedded in rock formations, the mixture is referred to as oil shale. This is true whether or not the mineral is, in fact, technically shale, that is, a rock formed from compacted clay.

Kerogen is subject to decomposing upon exposure to heat over a period of time. Upon heating, kerogen molecularly decomposes to produce oil, gas, and carbonaceous coke. Small amounts of water may also be generated. The oil, gas and water fluids become mobile within the rock matrix, while the carbonaceous coke remains essentially immobile.

Oil shale formations are found in various areas worldwide, including the United States. Such formations are notably found in Wyoming, Colorado, and Utah. Oil shale formations tend to reside at relatively shallow depths and are often characterized by limited permeability. Some consider oil shale formations to be hydrocarbon deposits which have not yet experienced the years of heat and pressure thought to be required to create conventional oil and gas reserves.

The decomposition rate of kerogen to produce mobile hydrocarbons is temperature dependent. Temperatures generally in excess of 270° C. (518° F.) over the course of many months may be required for substantial conversion. At higher temperatures substantial conversion may occur within shorter times. When kerogen is heated to the necessary temperature, chemical reactions break the larger molecules forming the solid kerogen into smaller molecules of oil and gas. The thermal conversion process is referred to as pyrolysis or retorting.

Attempts have been made for many years to extract oil from oil shale formations. Near-surface oil shales have been mined and retorted at the surface for over a century. In 1862, James Young began processing Scottish oil shales. The industry lasted for about 100 years. Commercial oil shale retorting through surface mining has been conducted in other countries as well such as Australia, Brazil, China, Estonia, France, Russia, South Africa, Spain, and Sweden. However, the practice has been mostly discontinued in recent years because it proved to be uneconomical or because of environmental constraints on spent shale disposal. (See T. F. Yen, and G. V. Chilingarian, "*Oil Shale*," Amsterdam, Elsevier, p. 292, the entire disclosure of which is incorporated herein by reference.) Further, surface retorting requires mining of the oil shale, which limits application to very shallow formations.

In the United States, the existence of oil shale deposits in northwestern Colorado has been known since the early 1900's. While research projects have been conducted in this area from time to time, no serious commercial development has been undertaken. Most research on oil shale production has been carried out in the latter half of the 1900's. The majority of this research was on oil shale geology, geochemistry, and retorting in surface facilities.

In 1947, U.S. Pat. No. 2,732,195 issued to Ljungstrom. That patent, entitled "Method of Treating Oil Shale and Recovery of Oil and Other Mineral Products Therefrom," proposed the application of heat at high temperatures to the oil shale formation in situ. The purpose of such in situ heating was to distill hydrocarbons and produce them to the surface. The '195 Ljungstrom patent is incorporated herein by reference.

Ljungstrom coined the phrase "heat supply channels" to describe bore holes drilled into the formation. The bore holes received an electrical heat conductor which transferred heat to the surrounding oil shale. Thus, the heat supply channels served as early heat injection wells. The electrical heating elements in the heat injection wells were placed within sand or cement or other heat-conductive material to permit the heat injection wells to transmit heat into the surrounding oil shale while preventing the inflow of fluid. According to Ljungstrom, the "aggregate" was heated to between 500° and 1,000° C. in some applications.

Along with the heat injection wells, fluid producing wells were also completed in near proximity to the heat injection wells. As kerogen was pyrolyzed upon heat conduction into the rock matrix, the resulting oil and gas would be recovered through the adjacent production wells.

Ljungstrom applied his approach of thermal conduction from heated wellbores through the Swedish Shale Oil Company. A full scale plant was developed that operated from 1944 into the 1950's. (See G. Salamonsson, "The Ljungstrom In Situ Method for Shale-Oil Recovery," $2^{nd}$ Oil Shale and Cannel Coal Conference, v. 2, Glasgow, Scotland, Institute of Petroleum, London, p. 260-280 (1951), the entire disclosure of which is incorporated herein by reference.)

Additional in situ methods have been proposed. These methods generally involve the injection of heat and/or solvent into a subsurface oil shale formation. Heat may be in the form of heated methane (see U.S. Pat. No. 3,241,611 to J. L. Dougan), flue gas, or superheated steam (see U.S. Pat. No. 3,400,762 to D. W. Peacock). Heat may also be in the form of electric resistive heating, dielectric heating, radio frequency (RF) heating (U.S. Pat. No. 4,140,180, assigned to the ITT Research Institute in Chicago, Ill.) or oxidant injection to support in situ combustion. In some instances, artificial permeability has been created in the matrix to aid the movement of pyrolyzed fluids. Permeability generation methods include mining, rubblization, hydraulic fracturing (see U.S. Pat. No. 3,468,376 to M. L. Slusser and U.S. Pat. No. 3,513,914 to J. V. Vogel), explosive fracturing (see U.S. Pat. No. 1,422,204 to W. W. Hoover, et al.), heat fracturing (see U.S. Pat. No. 3,284,281 to R. W. Thomas), and steam fracturing (see U.S. Pat. No. 2,952,450 to H. Purre).

In 1989, U.S. Pat. No. 4,886,118 issued to Shell Oil Company, the entire disclosure of which is incorporated herein by reference. That patent, entitled "Conductively Heating a Subterranean Oil Shale to Create Permeability and Subsequently Produce Oil," declared that "[c]ontrary to the implications of . . . prior teachings and beliefs . . . the presently described conductive heating process is economically feasible for use even in a substantially impermeable subterranean oil shale." (col. 6, ln. 50-54). Despite this declaration, it is noted that few, if any, commercial in situ shale oil operations have occurred other than Ljungstrom's enterprise. The '118 patent proposed controlling the rate of heat conduction within the rock surrounding each heat injection well to provide a uniform heat front.

Additional history behind oil shale retorting and shale oil recovery can be found in co-owned patent publication WO 2005/010320 entitled "Methods of Treating a Subterranean Formation to Convert Organic Matter into Producible Hydrocarbons," and in patent publication WO 2005/045192 entitled "Hydrocarbon Recovery from Impermeable Oil Shales." The Background and technical disclosures of these two patent publications are incorporated herein by reference.

A need exists for improved processes for the production of shale oil. In addition, a need exists for improved downhole burners for converting an organic-rich formation into hydrocarbon fluids.

SUMMARY OF THE INVENTION

In one embodiment, the invention includes a method for in situ heating of an organic-rich rock formation. The method includes providing a first wellbore extending at least to a depth of the organic-rich rock formation, and providing a second wellbore intersecting the first wellbore. The method further includes injecting an oxidant and a first combustible fuel into the first wellbore and providing hardware in the first wellbore so as to cause the oxidant and the first combustible fuel to mix and to combust at substantially the depth of the organic-rich rock formation. In this way, first combustion products are formed. The method further includes flowing the first combustion products into and up the second wellbore such that (1) a first heat profile is created from the first wellbore, and (2) a second heat profile is created from the second wellbore. After flowing the first combustion products for a period of time, the first heat profile mates with the second heat profile. At the time of mating, this provides a substantially continuous pyrolysis zone of formation hydrocarbons located within a substantial portion of the organic-rich rock formation between the first and second wellbores.

In one aspect, the formation hydrocarbons comprise heavy hydrocarbons. Preferably, the organic-rich rock formation is an oil shale formation and the formation hydrocarbons comprise oil shale.

It is preferred that the combustion products are above a pyrolysis temperature in the second wellbore at or just below the approximate depth of the hardware in the first wellbore. Alternatively or in addition, the combustion products fall below a pyrolysis temperature in the second wellbore at or just above the proximate depth of the hardware in the first wellbore. In one aspect, at or near the end of flowing, the combustion products in the second wellbore are at a temperature of between 270° C. and 360° C. at a depth proximate to that of an upper depth of the hardware in the first wellbore.

The method may further include the steps of providing a casing string within the first wellbore, and providing a casing string within the second wellbore.

In an alternate embodiment, the invention includes a method for in situ heating of a targeted organic-rich rock formation. The method may include providing a first wellbore extending at least to a depth of the targeted organic-rich rock formation, with the first wellbore having a lower end. The method may further include providing a second wellbore also having a lower end, the lower end of the second wellbore intersecting with the lower end of the first wellbore to create fluid communication therebetween. The method may further include selecting a distance between the first wellbore and the second wellbore. The method may further include providing a burner in the first wellbore, and injecting an oxidant and a combustible fuel into the first wellbore and to the burner so as to combust the combustible fuel. The method may further include circulating flue gas generated from the burner in the first wellbore through the second wellbore and to the surface. This serves to form (1) a first pyrolysis zone around the first wellbore, and (2) a second pyrolysis zone around the second wellbore. The first pyrolysis zone mates with the second pyrolysis zone upon circulating the flue gas for a period of time.

In an alternate embodiment, the invention includes a heater well for the in situ heating of a targeted organic-rich rock formation. The heater well may include a first wellbore extending at least to a depth of the targeted organic-rich rock formation. The first wellbore has a substantially vertical portion and a deviated portion defining a heel and a toe. The heater well may further include a substantially vertical second wellbore having a lower end, the lower end of the second wellbore intersecting with the toe of the first wellbore to create fluid communication therebetween. The heater well may further include at least one downhole combustion burner within either the first or the second wellbore. A spacing is provided between the first wellbore and the second wellbore so that following the circulation of heated flue gas through the heater well for a period of time, a first pyrolysis zone from the first wellbore mates with a second pyrolysis zone from the second wellbore in such a manner that (i) a substantially continuous pyrolysis zone of formation hydrocarbons is formed within a substantial portion of the organic-rich rock formation between the first and second wellbores, and (ii) the combustion products are above a pyrolysis temperature in the second wellbore at or just below the approximate depth of the at least one combustion burner in the first wellbore, and fall below a pyrolysis temperature in the second wellbore at or just above the approximate depth of the at least one combustion burner in the first wellbore.

In an alternate embodiment, the invention includes a method of producing a hydrocarbon fluid. The method may include heating an organic-rich rock formation in situ using a heater well, and producing a hydrocarbon fluid from the organic-rich rock formation. The hydrocarbon fluid has been at least partially generated as a result of pyrolysis of formation hydrocarbons located in the organic-rich rock formation. The heater well may include a first wellbore extending at least to a depth of the targeted organic-rich rock formation. The first wellbore has a substantially vertical portion, and a lower deviated portion defining a heel and a toe. The heater well may further include a substantially vertical second wellbore having a lower end, the lower end of the second wellbore intersecting with the toe of the first wellbore to create fluid communication therebetween. The heater well may also include at least one downhole combustion burner within either the first or the second wellbore.

An alternate method of producing a hydrocarbon fluid is disclosed herein. The method may include providing a first wellbore extending at least to a depth of the organic-rich rock formation, and providing a second wellbore intersecting the first wellbore. The method may further include injecting an oxidant and a first combustible fuel into the first wellbore, and providing hardware in the first wellbore so as to cause the oxidant and the first combustible fuel to mix and to combust at substantially the depth of the organic-rich rock formation. In this way first combustion products are formed. The method may further include flowing the first combustion products into and up the second wellbore. A first heat profile is created from the first wellbore, and a second heat profile is created from the second wellbore. The first and second wellbores are spaced and configured so that following the circulation of heated flue gas for a period of time, a first pyrolysis zone from the first wellbore mates with a second pyrolysis zone from the second wellbore in such a manner that (i) a substantially continuous pyrolysis zone of formation hydrocarbons is formed within a substantial portion of the organic-rich rock formation between the first and second wellbores, and (ii) the combustion products are above a pyrolysis temperature in the second wellbore at or just below the approximate depth of the at least one combustion burner in the first wellbore, and fall below a pyrolysis temperature in the second wellbore at or just above the approximate depth of the at least one combustion burner in the first wellbore. The method may further include producing a hydrocarbon fluid from the organic-rich rock formation, where the hydrocarbon fluid has been at least partially generated as a result of pyrolysis of formation hydrocarbons located in the organic-rich rock formation.

BRIEF DESCRIPTION OF THE DRAWINGS

So that the present invention can be better understood, certain drawings, graphs and flow charts are appended hereto. It is to be noted, however, that the drawings illustrate only selected embodiments of the inventions and are therefore not to be considered limiting of scope, for the inventions may admit to other equally effective embodiments and applications.

DETAILED DESCRIPTION OF CERTAIN EMBODIMENTS

Definitions

Figure 1:
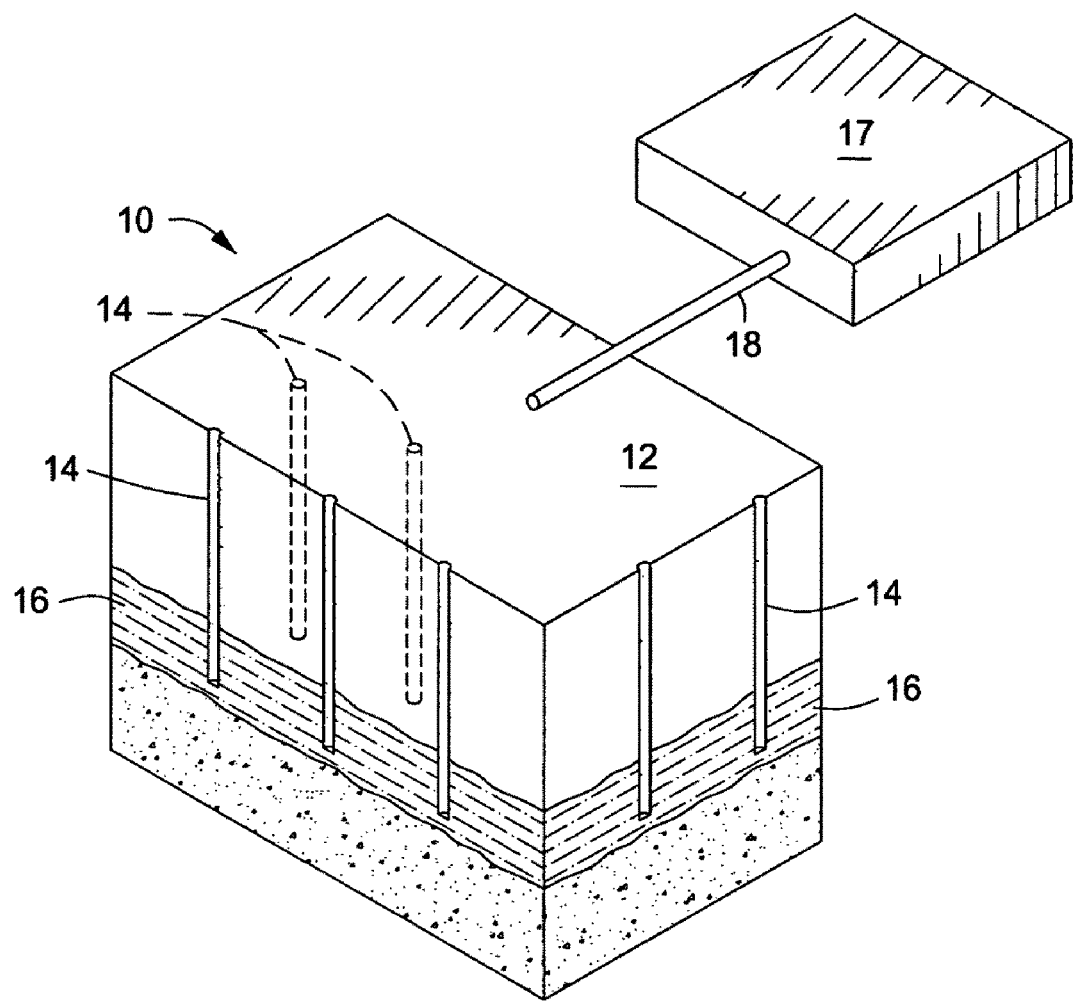
FIG. 1 is a cross-sectional isometric view of an illustrative subsurface area. The subsurface area includes an organic-rich rock matrix that defines a subsurface formation.

As used herein, the term "hydrocarbon(s)" refers to organic material with molecular structures containing carbon bonded to hydrogen. Hydrocarbons may also include other elements, such as, but not limited to, halogens, metallic elements, nitrogen, oxygen, and/or sulfur.

As used herein, the term "hydrocarbon fluids" refers to a hydrocarbon or mixtures of hydrocarbons that are gases or liquids. For example, hydrocarbon fluids may include a hydrocarbon or mixtures of hydrocarbons that are gases or liquids at formation conditions, at processing conditions or at ambient conditions (15° C. and 1 atm pressure). Hydrocarbon fluids may include, for example, oil, natural gas, coal bed methane, shale oil, pyrolysis oil, pyrolysis gas, a pyrolysis product of coal, and other hydrocarbons that are in a gaseous or liquid state.

As used herein, the terms "produced fluids" and "production fluids" refer to liquids and/or gases removed from a subsurface formation, including, for example, an organic-rich rock formation. Produced fluids may include both hydrocarbon fluids and non-hydrocarbon fluids. Production fluids may include, but are not limited to, pyrolyzed shale oil, synthesis gas, a pyrolysis product of coal, carbon dioxide, hydrogen sulfide and water (including steam). Produced fluids may include both hydrocarbon fluids and non-hydrocarbon fluids.

As used herein, the term "condensable hydrocarbons" means those hydrocarbons that condense at 25° C. and one atmosphere absolute pressure. Condensable hydrocarbons may include a mixture of hydrocarbons having carbon numbers greater than 4.

As used herein, the term "non-condensable hydrocarbons" means those hydrocarbons that do not condense at 25° C. and one atmosphere absolute pressure. Non-condensable hydrocarbons may include hydrocarbons having carbon numbers less than 5.

As used herein, the term "heavy hydrocarbons" refers to hydrocarbon fluids that are highly viscous at ambient conditions (15° C. and 1 atm pressure). Heavy hydrocarbons may include highly viscous hydrocarbon fluids such as heavy oil, tar, and/or asphalt. Heavy hydrocarbons may include carbon and hydrogen, as well as smaller concentrations of sulfur, oxygen, and nitrogen. Additional elements may also be present in heavy hydrocarbons in trace amounts. Heavy hydrocarbons may be classified by API gravity. Heavy hydrocarbons generally have an API gravity below about 20 degrees. Heavy oil, for example, generally has an API gravity of about 10-20 degrees, whereas tar generally has an API gravity below about 10 degrees. The viscosity of heavy hydrocarbons is generally greater than about 100 centipoise at 15° C.

As used herein, the term "solid hydrocarbons" refers to any hydrocarbon material that is found naturally in substantially solid form at formation conditions. Non-limiting examples include kerogen, coal, shungites, asphaltites, and natural mineral waxes.

As used herein, the term "formation hydrocarbons" refers to both heavy hydrocarbons and solid hydrocarbons that are contained in an organic-rich rock formation. Formation hydrocarbons may be, but are not limited to, kerogen, oil shale, coal, bitumen, tar, natural mineral waxes, and asphaltites.

As used herein, the term "tar" refers to a viscous hydrocarbon that generally has a viscosity greater than about 10,000 centipoise at 15° C. The specific gravity of tar generally is greater than 1.000. Tar may have an API gravity less than 10 degrees. "Tar sands" refers to a formation that has tar in it.

As used herein, the term "kerogen" refers to a solid, insoluble hydrocarbon that principally contains carbon, hydrogen, nitrogen, oxygen, and sulfur. Oil shale contains kerogen.

As used herein, the term "bitumen" refers to a non-crystalline solid or viscous hydrocarbon material that is substantially soluble in carbon disulfide.

As used herein, the term "oil" refers to a hydrocarbon fluid containing a mixture of condensable hydrocarbons.

As used herein, the term "subsurface" refers to geologic strata occurring below the earth's surface.

As used herein, the term "hydrocarbon-rich formation" refers to any formation that contains more than trace amounts of hydrocarbons. For example, a hydrocarbon-rich formation may include portions that contain hydrocarbons at a level of greater than 5 volume percent. The hydrocarbons located in a hydrocarbon-rich formation may include, for example, oil, natural gas, heavy hydrocarbons, and solid hydrocarbons.

As used herein, the term "organic-rich rock" refers to any rock matrix holding solid hydrocarbons and/or heavy hydrocarbons. Rock matrices may include, but are not limited to, sedimentary rocks, shales, siltstones, sands, silicilytes, carbonates, and diatomites.

As used herein, the term "formation" refers to any finite subsurface region. The formation may contain one or more hydrocarbon-containing layers, one or more non-hydrocarbon containing layers, an overburden, and/or an underburden of any subsurface geologic formation. An "overburden" and/or an "underburden" is geological material above or below the formation of interest. An overburden or underburden may include one or more different types of substantially impermeable materials. For example, overburden and/or underburden may include rock, shale, mudstone, or wet/tight carbonate (i.e., an impermeable carbonate without hydrocarbons). An overburden and/or an underburden may include a hydrocarbon-containing layer that is relatively impermeable. In some cases, the overburden and/or underburden may be permeable.

As used herein, the term "organic-rich rock formation" refers to any formation containing organic-rich rock. Organic-rich rock formations include, for example, oil shale formations, coal formations, and tar sands formations.

As used herein, the term "pyrolysis" refers to the breaking of chemical bonds through the application of heat. For example, pyrolysis may include transforming a compound into one or more other substances by heat alone or by heat in combination with an oxidant. Pyrolysis may include modifying the nature of the compound by addition of hydrogen atoms which may be obtained from molecular hydrogen, water, carbon dioxide, or carbon monoxide. Heat may be transferred to a section of the formation to cause pyrolysis.

As used herein, the term "water-soluble minerals" refers to minerals that are soluble in water. Water-soluble minerals include, for example, nahcolite (sodium bicarbonate), soda ash (sodium carbonate), dawsonite ($NaAl(CO_3)(OH)_2$), or combinations thereof. Substantial solubility may require heated water and/or a non-neutral pH solution.

As used herein, the term "formation water-soluble minerals" refers to water-soluble minerals that are found naturally in a formation.

As used herein, the term "migratory contaminant species" refers to species that are both soluble or moveable in water or an aqueous fluid, and are considered to be potentially harmful or of concern to human health or the environment. Migratory contaminant species may include inorganic and organic contaminants. Organic contaminants may include saturated hydrocarbons, aromatic hydrocarbons, and oxygenated hydrocarbons. Inorganic contaminants may include metal contaminants, and ionic contaminants of various types that may significantly alter pH or the formation fluid chemistry. Aromatic hydrocarbons may include, for example, benzene, toluene, xylene, ethylbenzene, and tri-methylbenzene, and various types of polyaromatic hydrocarbons such as anthracenes, naphthalenes, chrysenes and pyrenes. Oxygenated hydrocarbons may include, for example, alcohols, ketones, phenols, and organic acids such as carboxylic acid. Metal contaminants may include, for example, arsenic, boron, chromium, cobalt, molybdenum, mercury, selenium, lead, vanadium, nickel or zinc. Ionic contaminants include, for example, sulfides, sulfates, chlorides, fluorides, ammonia, nitrates, calcium, iron, magnesium, potassium, lithium, boron, and strontium.

As used herein, the term "sequestration" refers to the storing of a fluid that is a by-product of a process rather than discharging the fluid to the atmosphere or open environment.

As used herein, the term "subsidence" refers to a downward movement of a surface relative to an initial elevation of the surface.

As used herein, the term "thickness" of a layer refers to the distance between the upper and lower boundaries of a cross section of a layer, wherein the distance is measured normal to the average tilt of the cross section.

As used herein, the term "thermal fracture" refers to fractures created in a formation caused directly or indirectly by expansion or contraction of a portion of the formation and/or fluids within the formation, which in turn is caused by increasing/decreasing the temperature of the formation and/or fluids within the formation, and/or by increasing/decreasing a pressure of fluids within the formation due to heating. Thermal fractures may propagate into or form in neighboring regions significantly cooler than the heated zone.

As used herein, the term "hydraulic fracture" refers to a fracture at least partially propagated into a formation, wherein the fracture is created through injection of pressurized fluids into the formation. The fracture may be artificially held open by injection of a proppant material. Hydraulic fractures may be substantially horizontal in orientation, substantially vertical in orientation, or oriented along any other plane.

As used herein, the term "wellbore" refers to a hole in the subsurface made by drilling or insertion of a conduit into the subsurface. A wellbore may have a substantially circular cross section, or other cross-sectional shapes (e.g., circles, ovals, squares, rectangles, triangles, slits, or other regular or irregular shapes). As used herein, the term "well", when referring to an opening in the formation, may be used interchangeably with the term "wellbore."

As used herein, the term "cowl" means a tubular body of any material or construction having perforations or vents therein.

As used herein, the term "targeted organic-rich rock formation" means a portion of an organic-rich rock formation that has been chosen for heating. The chosen portion may be defined according to a given depth or range of depths, a given horizontal distance, or both.

As used herein with respect to temperature and downhole burners, the term "substantially uniform" means that the temperature remains within a desired temperature range over a selected portion of an organic-rich rock formation.

As used herein, the terms "heat profile" means a region of a formation adjacent a source of heat that has been heated to greater than a specified temperature. For example, the specified temperature may be a minimum temperature at which pyrolysis begins to occur at a minimum desired rate.

The term "pyrolysis zone" means an area within a subsurface formation that has reached a temperature wherein pyrolysis of formation hydrocarbons begins to occur. A pyrolysis zone is associated with a heat profile.

As used herein, the term "mating" or "mates" means that a first heat profile expands in such a way as to meet a second heat profile so that at the time of first merging, substantial portions of both the first and second heat profiles have reached a pyrolysis temperature.

DESCRIPTION OF SPECIFIC EMBODIMENTS

The inventions are described herein in connection with certain specific embodiments. However, to the extent that the following detailed description is specific to a particular embodiment or a particular use, this is intended to be illustrative only, and is not to be construed as limiting the scope of the invention.

As discussed herein, some embodiments of the invention include or have application related to an in situ method of recovering natural resources. The natural resources may be recovered from an organic-rich rock formation, including, for example, an oil shale formation. The organic-rich rock formation may include formation hydrocarbons, including, for example, kerogen, coal, and heavy hydrocarbons. In some embodiments of the invention the natural resources may include hydrocarbon fluids, including, for example, products of the pyrolysis of formation hydrocarbons such as shale oil. In some embodiments of the invention the natural resources may also include water-soluble minerals, including, for example, nahcolite (sodium bicarbonate, or $2NaHCO_3$), soda ash (sodium carbonate, or $Na_2CO_3$) and dawsonite ($NaAl(CO_3)(OH)_2$).

FIG. 1 presents a perspective view of an illustrative oil shale development area 10. A surface 12 of the development area 10 is indicated. Below the surface is an organic-rich rock formation 16. The illustrative subsurface formation 16 contains formation hydrocarbons (such as, for example, kerogen) and possibly valuable water-soluble minerals (such as, for example, nahcolite). It is understood that the representative formation 16 may be any organic-rich rock formation, including a rock matrix containing coal or tar sands, for example. In addition, the rock matrix making up the formation 16 may be permeable, semi-permeable or non-permeable. The present inventions are particularly advantageous in oil shale development areas initially having very limited or effectively no fluid permeability.

In order to access formation 16 and recover natural resources therefrom, a plurality of wellbores is formed. Wellbores are shown at 14 in FIG. 1. The representative wellbores 14 are essentially vertical in orientation relative to the surface 12. However, it is understood that some or all of the wellbores 14 could deviate into an obtuse or even horizontal orientation. In the arrangement of FIG. 1, each of the wellbores 14 is completed in the oil shale formation 16. The completions may be either open or cased hole. The well completions may also include propped or unpropped hydraulic fractures emanating therefrom.

In the view of FIG. 1, only seven wellbores 14 are shown. However, it is understood that in an oil shale development project, numerous additional wellbores 14 will most likely be drilled. The wellbores 14 may be located in relatively close proximity, being from 10 feet to up to 300 feet in separation. In some embodiments, a well spacing of 15 to 25 feet is provided. Typically, the wellbores 14 are also completed at shallow depths, being from 200 to 5,000 feet at total depth. In some embodiments the oil shale formation targeted for in situ retorting is at a depth greater than 200 feet below the surface or alternatively 400 feet below the surface. Alternatively, conversion and production of an oil shale formation occurs at depths between 500 and 2,500 feet.

The wellbores 14 will be selected for certain functions and may be designated as heat injection wells, water injection wells, oil production wells and/or water-soluble mineral solution production wells. In one aspect, the wellbores 14 are dimensioned to serve two, three, or all four of these purposes. Suitable tools and equipment may be sequentially run into and removed from the wellbores 14 to serve the various purposes.

A fluid processing facility 17 is also shown schematically. The fluid processing facility 17 is equipped to receive fluids produced from the organic-rich rock formation 16 through one or more pipelines or flow lines 18. The fluid processing facility 17 may include equipment suitable for receiving and separating oil, gas, and water produced from the heated formation. The fluid processing facility 17 may further include equipment for separating out dissolved water-soluble minerals and/or migratory contaminant species, including, for example, dissolved organic contaminants, metal contaminants, or ionic contaminants in the produced water recovered from the organic-rich rock formation 16. The contaminants may include, for example, aromatic hydrocarbons such as benzene, toluene, xylene, and tri-methylbenzene. The contaminants may also include polyaromatic hydrocarbons such as anthracene, naphthalene, chrysene and pyrene. Metal contaminants may include species containing arsenic, boron, chromium, mercury, selenium, lead, vanadium, nickel, cobalt, molybdenum, or zinc. Ionic contaminant species may include, for example, sulfates, chlorides, fluorides, lithium, potassium, aluminum, ammonia, and nitrates.

Figure 2:
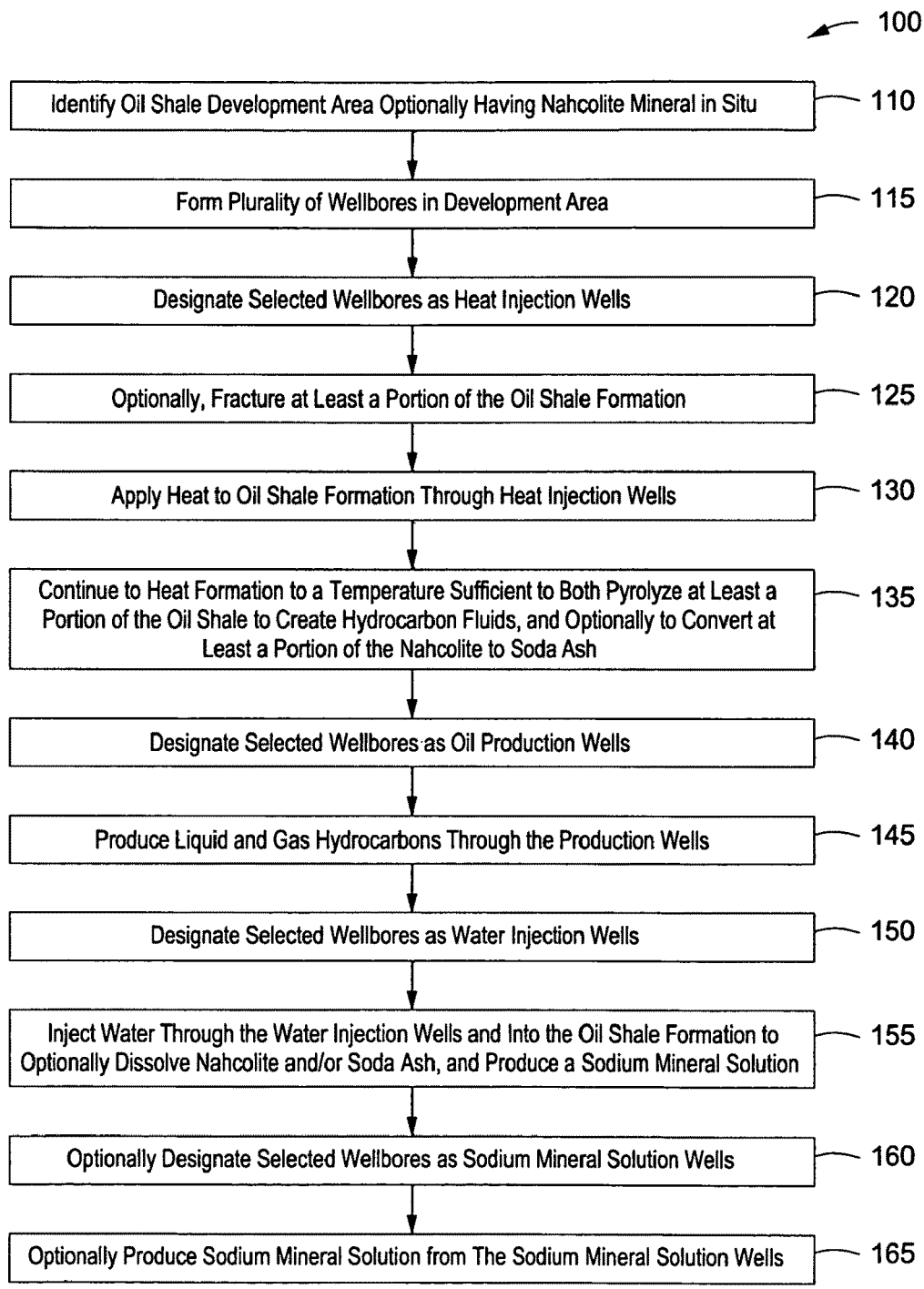
FIG. 2 is a flow chart demonstrating a general method of in situ thermal recovery of oil and gas from an organic-rich rock formation, in one embodiment.

In order to recover oil, gas, and sodium (or other) water-soluble minerals, a series of steps may be undertaken. FIG. 2 presents a flow chart demonstrating a method of in situ thermal recovery of oil and gas from an organic-rich rock formation 100, in one embodiment. It is understood that the order of some of the steps from FIG. 2 may be changed, and that the sequence of steps is merely for illustration.

First, the oil shale (or other organic-rich rock) formation 16 is identified within the development area 10. This step is shown in box 110. Optionally, the oil shale formation may contain nahcolite or other sodium minerals. The targeted development area within the oil shale formation may be identified by measuring or modeling the depth, thickness and organic richness of the oil shale as well as evaluating the position of the organic-rich rock formation relative to other rock types, structural features (e.g. faults, anticlines or synclines), or hydrogeological units (i.e. aquifers). This is accomplished by creating and interpreting maps and/or models of depth, thickness, organic richness and other data from available tests and sources. This may involve performing geological surface surveys, studying outcrops, performing seismic surveys, and/or drilling boreholes to obtain core samples from subsurface rock. Rock samples may be analyzed to assess kerogen content and hydrocarbon fluid generating capability.

The kerogen content of the organic-rich rock formation may be ascertained from outcrop or core samples using a variety of data. Such data may include organic carbon content, hydrogen index, and modified Fischer assay analyses. Subsurface permeability may also be assessed via rock samples, outcrops, or studies of ground water flow. Furthermore the connectivity of the development area to ground water sources may be assessed.

Next, a plurality of wellbores 14 is formed across the targeted development area 10. This step is shown schematically in box 115. The purposes of the wellbores 14 are set forth above and need not be repeated. However, it is noted that for purposes of the wellbore formation step of box 115, only a portion of the wells need be completed initially. For instance, at the beginning of the project heat injection wells are needed, while a majority of the hydrocarbon production wells are not yet needed. Production wells may be brought in once conversion begins, such as after 4 to 12 months of heating.

It is understood that petroleum engineers will develop a strategy for the best depth and arrangement for the wellbores 14, depending upon anticipated reservoir characteristics, economic constraints, and work scheduling constraints. In addition, engineering staff will determine what wellbores 14 shall be used for initial formation 16 heating. This selection step is represented by box 120.

Concerning heat injection wells, there are various methods for applying heat to the organic-rich rock formation 16. The present methods are not limited to the heating technique employed unless specifically so stated in the claims. The heating step is represented generally by box 130. Preferably, for in situ processes the heating of a production zone takes place over a period of months, or even four or more years.

The formation 16 is heated to a temperature sufficient to pyrolyze at least a portion of the oil shale in order to convert the kerogen to hydrocarbon fluids. The bulk of the target zone of the formation may be heated to between 270° C. to 800° C. Alternatively, the targeted volume of the organic-rich formation is heated to at least 350° C. to create production fluids. The conversion step is represented in FIG. 2 by box 135. The resulting liquids and hydrocarbon gases may be refined into products which resemble common commercial petroleum products. Such liquid products include transportation fuels such as diesel, jet fuel and naphtha. Generated gases include light alkanes, light alkenes, $H_2$, $CO_2$, CO, and $NH_3$.

Conversion of the oil shale will create permeability in the oil shale section in rocks that were originally impermeable. Preferably, the heating and conversion processes of boxes 130 and 135, occur over a lengthy period of time. In one aspect, the heating period is from three months to four or more years. Also as an optional part of box 135, the formation 16 may be heated to a temperature sufficient to convert at least a portion of nahcolite, if present, to soda ash. Heat applied to mature the oil shale and recover oil and gas will also convert nahcolite to sodium carbonate (soda ash), a related sodium mineral. The process of converting nahcolite (sodium bicarbonate) to soda ash (sodium carbonate) is described herein.

In connection with the heating step 130, the rock formation 16 may optionally be fractured to aid heat transfer or later hydrocarbon fluid production. The optional fracturing step is shown in box 125. Fracturing may be accomplished by creating thermal fractures within the formation through application of heat. By heating the organic-rich rock and transforming the kerogen to oil and gas, the permeability is increased via thermal fracture formation and subsequent production of a portion of the hydrocarbon fluids generated from the kerogen. Alternatively, a process known as hydraulic fracturing may be used. Hydraulic fracturing is a process known in the art of oil and gas recovery where a fracture fluid is pressurized within the wellbore above the fracture pressure of the formation, thus developing fracture planes within the formation to relieve the pressure generated within the wellbore. Hydraulic fractures may be used to create additional permeability in portions of the formation and/or be used to provide a planar source for heating. The WO 2005/010320 patent publication incorporated above describes one use of hydraulic fracturing.

As part of the hydrocarbon fluid production process 100, certain wells 14 may be designated as oil and gas production wells. This step is depicted by box 140. Oil and gas production might not be initiated until it is determined that the kerogen has been sufficiently retorted to allow maximum recovery of oil and gas from the formation 16. In some instances, dedicated production wells are not drilled until after heat injection wells (box 130) have been in operation for a period of several weeks or months. Thus, box 140 may include the formation of additional wellbores 14. In other instances, selected heater wells are converted to production wells.

After certain wellbores 14 have been designated as oil and gas production wells, oil and/or gas is produced from the wellbores 14. The oil and/or gas production process is shown at box 145. At this stage (box 145), any water-soluble minerals, such as nahcolite and converted soda ash may remain substantially trapped in the rock formation 16 as finely disseminated crystals or nodules within the oil shale beds, and are not produced. However, some nahcolite and/or soda ash may be dissolved in the water created during heat conversion (box 135) within the formation.

Box 150 presents an optional next step in the oil and gas recovery method 100. Here, certain wellbores 14 are designated as water or aqueous fluid injection wells. Aqueous fluids are solutions of water with other species. The water may constitute "brine," and may include dissolved inorganic salts of chloride, sulfates and carbonates of Group I and II elements of The Periodic Table of Elements. Organic salts can also be present in the aqueous fluid. The water may alternatively be fresh water containing other species. The other species may be present to alter the pH. Alternatively, the other species may reflect the availability of brackish water not saturated in the species wished to be leached from the subsurface. Preferably, the water injection wells are selected from some or all of the wellbores used for heat injection or for oil and/or gas production. However, the scope of the step of box 150 may include the drilling of yet additional wellbores 14 for use as dedicated water injection wells. In this respect, it may be desirable to complete water injection wells along a periphery of the development area 10 in order to create a boundary of high pressure.

Next, optionally water or an aqueous fluid is injected through the water injection wells and into the oil shale formation 16. This step is shown at box 155. The water may be in the form of steam or pressurized hot water. Alternatively the injected water may be cool and becomes heated as it contacts the previously heated formation. The injection process may further induce fracturing. This process may create fingered caverns and brecciated zones in the nahcolite-bearing intervals some distance, for example up to 200 feet out, from the water injection wellbores. In one aspect, a gas cap, such as nitrogen, may be maintained at the top of each "cavern" to prevent vertical growth.

Along with the designation of certain wellbores 14 as water injection wells, the design engineers may also designate certain wellbores 14 as water or water-soluble mineral solution production wells. This step is shown in box 160. These wells may be the same as wells used to previously produce hydrocarbons or inject heat. These recovery wells may be used to produce an aqueous solution of dissolved water-soluble minerals and other species, including, for example, migratory contaminant species. For example, the solution may be one primarily of dissolved soda ash. This step is shown in box 165. Alternatively, single wellbores may be used to both inject water and then to recover a sodium mineral solution. Thus, box 165 includes the option of using the same wellbores 14 for both water injection and solution production (box 165).

Temporary control of the migration of the migratory contaminant species, especially during the pyrolysis process, can be obtained via placement of the injection and production wells 14 such that fluid flow out of the heated zone is minimized. Typically, this involves placing injection wells at the periphery of the heated zone so as to cause pressure gradients which prevent flow inside the heated zone from leaving the zone.

Figure 3:
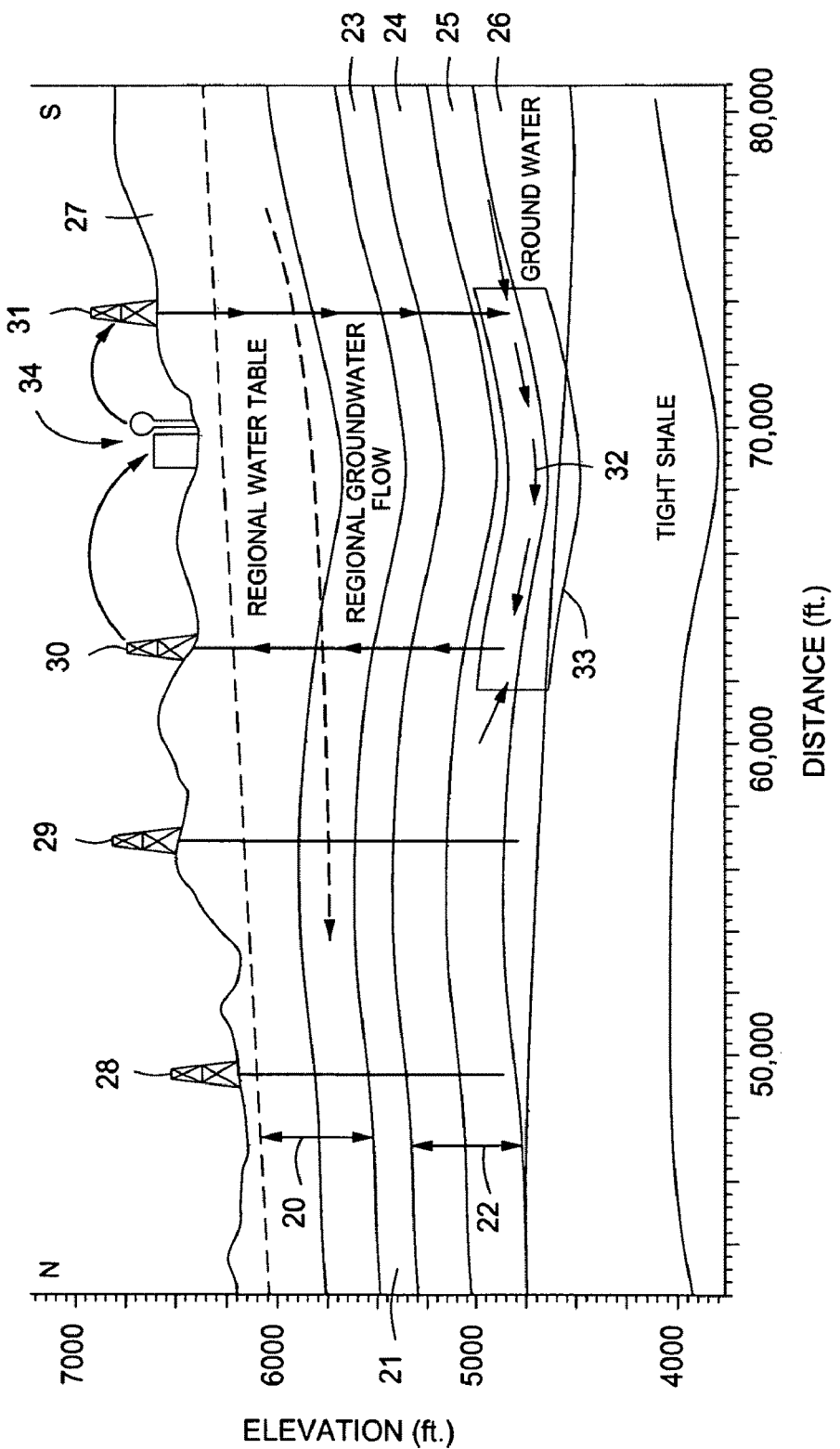
FIG. 3 is a cross-sectional view of an illustrative oil shale formation that is within or connected to groundwater aquifers and a formation leaching operation.

FIG. 3 is a cross-sectional view of an illustrative oil shale formation that is within or connected to ground water aquifers and a formation leaching operation. Four separate oil shale formation zones are depicted (23, 24, 25 and 26) within the oil shale formation. The water aquifers are below the ground surface 27, and are categorized as an upper aquifer 20 and a lower aquifer 22. Intermediate the upper and lower aquifers is an aquitard 21. It can be seen that certain zones of the formation are both aquifers or aquitards and oil shale zones. A plurality of wells (28, 29, 30 and 31) is shown traversing vertically downward through the aquifers. One of the wells is serving as a water injection well 31, while another is serving as a water production well 30. In this way, water is circulated 32 through at least the lower aquifer 22.

FIG. 3 shows diagrammatically water circulating 32 through an oil shale volume that was heated 33, that resides within or is connected to an aquifer 22, and from which hydrocarbon fluids were previously recovered. Introduction of water via the water injection well 31 forces water into the previously heated oil shale 33 so that water-soluble minerals and migratory contaminants species are swept to the water production well 30. The water may then processed in a facility 34 wherein the water-soluble minerals (e.g., nahcolite or soda ash) and the migratory contaminants may be substantially removed from the water stream. Water is then re-injected into the oil shale volume 33 and the formation leaching is repeated. This leaching with water is intended to continue until levels of migratory contaminant species are at environmentally acceptable levels within the previously heated oil shale zone 33. This may require 1 cycle, 2 cycles, 5 cycles 10 cycles or more cycles of formation leaching, where a single cycle indicates injection and production of approximately one pore volume of water. It is understood that there may be numerous water injection and water production wells in an actual oil shale development. Moreover, the system may include monitoring wells (28 and 29) which can be utilized during the oil shale heating phase, the shale oil production phase, the leaching phase, or during any combination of these phases to monitor for migratory contaminant species and/or water-soluble minerals.

In some fields, formation hydrocarbons, such as oil shale, may exist in more than one subsurface formation. In some instances, the organic-rich rock formations may be separated by rock layers that are hydrocarbon-free or that otherwise have little or no commercial value. Therefore, it may be desirable for the operator of a field under hydrocarbon development to undertake an analysis as to which of the subsurface, organic-rich rock formations to target or in which order they should be developed.

The organic-rich rock formation may be selected for development based on various factors. One such factor is the thickness of the hydrocarbon containing layer within the formation. Greater pay zone thickness may indicate a greater potential volumetric production of hydrocarbon fluids. Each of the hydrocarbon containing layers may have a thickness that varies depending on, for example, conditions under which the formation hydrocarbon containing layer was formed. Therefore, an organic-rich rock formation will typically be selected for treatment if that formation includes at least one formation hydrocarbon-containing layer having a thickness sufficient for economical production of produced fluids.

An organic-rich rock formation may also be chosen if the thickness of several layers that are closely spaced together is sufficient for economical production of produced fluids. For example, an in situ conversion process for formation hydrocarbons may include selecting and treating a layer within an organic-rich rock formation having a thickness of greater than about 5 meters, 10 meters, 50 meters, or even 100 meters. In this manner, heat losses (as a fraction of total injected heat) to layers formed above and below an organic-rich rock formation may be less than such heat losses from a thin layer of formation hydrocarbons. A process as described herein, however, may also include selecting and treating layers that may include layers substantially free of formation hydrocarbons or thin layers of formation hydrocarbons.

The richness of one or more organic-rich rock formations may also be considered. Richness may depend on many factors including the conditions under which the formation hydrocarbon containing layer was formed, an amount of formation hydrocarbons in the layer, and/or a composition of formation hydrocarbons in the layer. A thin and rich formation hydrocarbon layer may be able to produce significantly more valuable hydrocarbons than a much thicker, less rich formation hydrocarbon layer. Of course, producing hydrocarbons from a formation that is both thick and rich is desirable.

The kerogen content of an organic-rich rock formation may be ascertained from outcrop or core samples using a variety of data. Such data may include organic carbon content, hydrogen index, and modified Fischer assay analyses. The Fischer Assay is a standard method which involves heating a sample of a formation hydrocarbon containing layer to approximately 500° C. in one hour, collecting fluids produced from the heated sample, and quantifying the amount of fluids produced.

Subsurface formation permeability may also be assessed via rock samples, outcrops, or studies of ground water flow. Furthermore the connectivity of the development area to ground water sources may be assessed. Thus, an organic-rich rock formation may be chosen for development based on the permeability or porosity of the formation matrix even if the thickness of the formation is relatively thin.

Other factors known to petroleum engineers may be taken into consideration when selecting a formation for development. Such factors include depth of the perceived pay zone, stratigraphic proximity of fresh ground water to kerogen-containing zones, continuity of thickness, and other factors. For instance, the assessed fluid production content within a formation will also effect eventual volumetric production.

In producing hydrocarbon fluids from an oil shale field, it may be desirable to control the migration of pyrolyzed fluids. In some instances, this includes the use of injection wells, particularly around the periphery of the field. Such wells may inject water, steam, $CO_2$, heated methane, or other fluids to drive cracked kerogen fluids inwardly towards production wells. In some embodiments, physical barriers may be placed around the area of the organic-rich rock formation under development. One example of a physical barrier involves the creation of freeze walls. Freeze walls are formed by circulating refrigerant through peripheral wells to substantially reduce the temperature of the rock formation. This, in turn, prevents the pyrolyzation of kerogen present at the periphery of the field and the outward migration of oil and gas. Freeze walls will also cause native water in the formation along the periphery to freeze.

The use of subsurface freezing to stabilize poorly consolidated soils or to provide a barrier to fluid flow is known in the art. Shell Exploration and Production Company has discussed the use of freeze walls for oil shale production in several patents, including U.S. Pat. No. 6,880,633 and U.S. Pat. No. 7,032,660. Shell's '660 patent uses subsurface freezing to protect against groundwater flow and groundwater contamination during in situ shale oil production. Additional patents that disclose the use of so-called freeze walls are U.S. Pat. Nos. 3,528,252, 3,943,722, 3,729,965, 4,358,222, 4,607,488, and WO Pat. No. 98996480.

As noted above, several different types of wells may be used in the development of an organic-rich rock formation, including, for example, an oil shale field. For example, the heating of the organic-rich rock formation may be accomplished through the use of heater wells. The heater wells may include, for example, electrical resistance heating elements. The production of hydrocarbon fluids from the formation may be accomplished through the use of wells completed for the production of fluids. The injection of an aqueous fluid may be accomplished through the use of injection wells. Finally, the production of an aqueous solution may be accomplished through use of solution production wells.

The different wells listed above may be used for more than one purpose. Stated another way, wells initially completed for one purpose may later be used for another purpose, thereby lowering project costs and/or decreasing the time required to perform certain tasks. For example, one or more of the production wells may also be used as injection wells for later injecting water into the organic-rich rock formation. Alternatively, one or more of the production wells may also be used as solution production wells for later producing an aqueous solution from the organic-rich rock formation.

In other aspects, production wells (and in some circumstances heater wells) may initially be used as dewatering wells (e.g., before heating is begun and/or when heating is initially started). In addition, in some circumstances dewatering wells can later be used as production wells (and in some circumstances heater wells). As such, the dewatering wells may be placed and/or designed so that such wells can be later used as production wells and/or heater wells. The heater wells may be placed and/or designed so that such wells can be later used as production wells and/or dewatering wells. The production wells may be placed and/or designed so that such wells can be later used as dewatering wells and/or heater wells. Similarly, injection wells may be wells that initially were used for other purposes (e.g., heating, production, dewatering, monitoring, etc.), and injection wells may later be used for other purposes. Similarly, monitoring wells may be wells that initially were used for other purposes (e.g., heating, production, dewatering, injection, etc.). Finally, monitoring wells may later be used for other purposes such as water production.

The wellbores for the various wells may be located in relatively close proximity, being from 10 feet to up to 300 feet in separation. Alternatively, the wellbores may be spaced from 30 to 200 feet, or 50 to 100 feet. Typically, the wellbores are also completed at shallow depths, being from 200 to 5,000 feet at total depth. Alternatively, the wellbores may be completed at depths from 1,000 to 4,000 feet, or 1,500 to 3,500 feet. In some embodiments, the oil shale formation targeted for in situ retorting is at a depth greater than 200 feet below the surface. In alternative embodiments, the oil shale formation targeted for in situ retorting is at a depth greater than 500, 1,000, or 1,500 feet below the surface. In alternative embodiments, the oil shale formation targeted for in situ retorting is at a depth between 200 and 5,000 feet, alternatively between 1,000 and 4,000 feet, 1,200 and 3,700 feet, or 1,500 and 3,500 feet below the surface.

It is desirable to arrange the various wells for an oil shale field in a pre-planned pattern. For instance, heater wells may be arranged in a variety of patterns including, but not limited to triangles, squares, hexagons, and other polygons. The pattern may include a regular polygon to promote uniform heating through at least the portion of the formation in which the heater wells are placed. The pattern may also be a line drive pattern. A line drive pattern generally includes a first linear array of heater wells, a second linear array of heater wells, and a production well or a linear array of production wells between the first and second linear array of heater wells. Interspersed among the heater wells are typically one or more production wells. The injection wells may likewise be disposed within a repetitive pattern of units, which may be similar to or different from that used for the heater wells.

One method to reduce the number of wells is to use a single well as both a heater well and a production well. Reduction of the number of wells by using single wells for sequential purposes can reduce project costs. One or more monitoring wells may be disposed at selected points in the field. The monitoring wells may be configured with one or more devices that measure a temperature, a pressure, and/or a property of a fluid in the wellbore. In some instances, a heater well may also serve as a monitoring well, or otherwise be instrumented.

Another method for reducing the number of heater wells is to use well patterns. Regular patterns of heater wells equidistantly spaced from a production well may be used. The patterns may form equilateral triangular arrays, hexagonal arrays, or other array patterns. The arrays of heater wells may be disposed such that a distance between each heater well is less than about 70 feet (21 meters). A portion of the formation may be heated with heater wells disposed substantially parallel to a boundary of the hydrocarbon formation.

In alternative embodiments, the array of heater wells may be disposed such that a distance between each heater well may be less than about 100 feet, or 50 feet, or 30 feet. Regardless of the arrangement of or distance between the heater wells, in certain embodiments, a ratio of heater wells to production wells disposed within a organic-rich rock formation may be greater than about 5, 8, 10, 20, or more.

In one embodiment, individual production wells are surrounded by at most one layer of heater wells. This may include arrangements such as 5-spot, 7-spot, or 9-spot arrays, with alternating rows of production and heater wells. In another embodiment, two layers of heater wells may surround a production well, but with the heater wells staggered so that a clear pathway exists for the majority of flow away from the further heater wells. Flow and reservoir simulations may be employed to assess the pathways and temperature history of hydrocarbon fluids generated in situ as they migrate from their points of origin to production wells.

Figure 4:
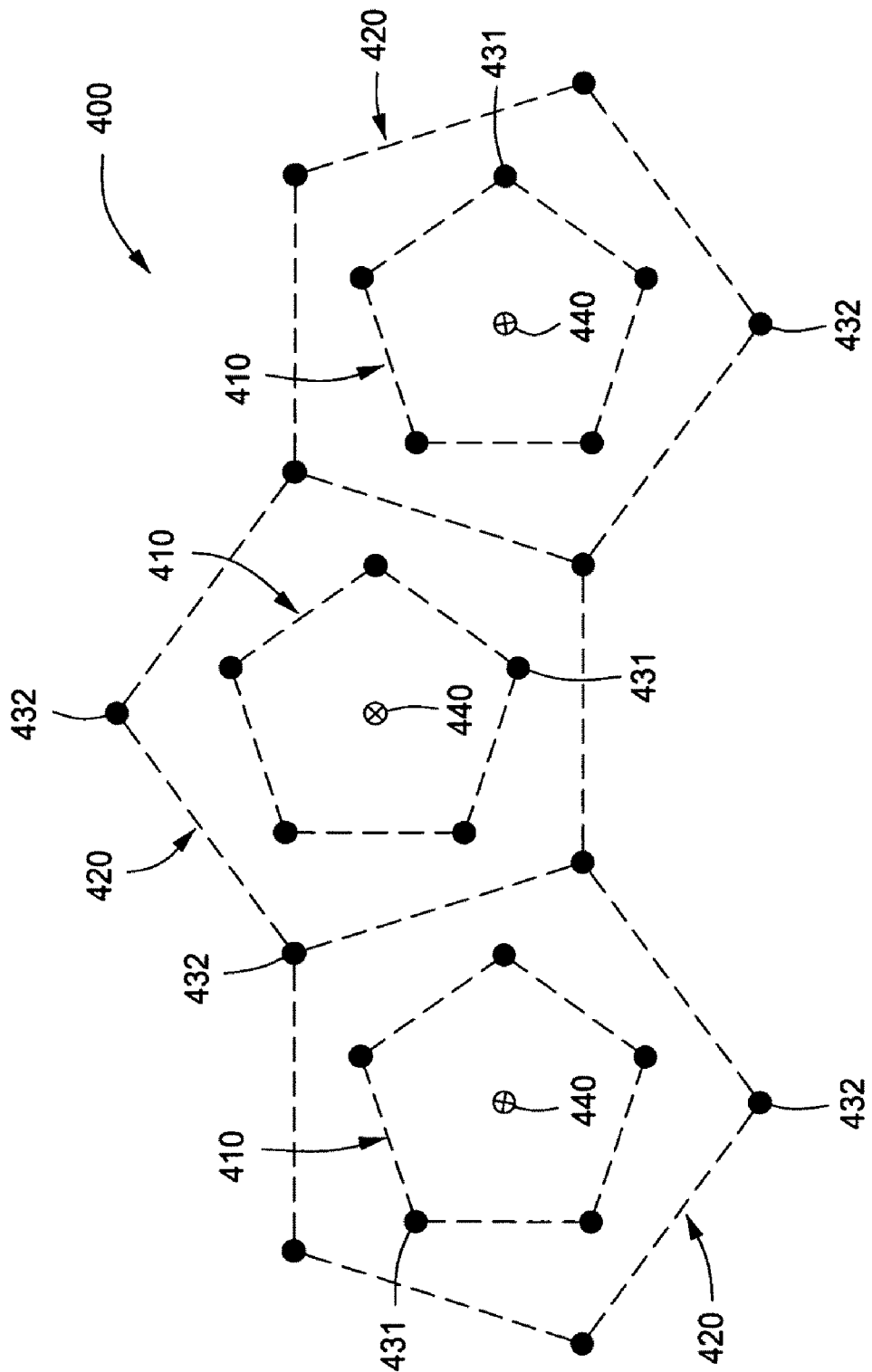
FIG. 4 is a plan view of an illustrative heater well pattern, around a production well. Two layers of heater wells are shown.

FIG. 4 provides a plan view of an illustrative heater well arrangement using more than one layer of heater wells. The heater well arrangement is used in connection with the production of hydrocarbons from a shale oil development area 400. In FIG. 4, the heater well arrangement employs a first layer of heater wells 410, surrounded by a second layer of heater wells 420. The heater wells in the first layer 410 are referenced at 431, while the heater wells in the second layer 420 are referenced at 432.

A production well 440 is shown central to the well layers 410 and 420. It is noted that the heater wells 432 in the second layer 420 of wells are offset from the heater wells 431 in the first layer 410 of wells, relative to the production well 440. The purpose is to provide a flowpath for converted hydrocarbons that minimizes travel near a heater well in the first layer 410 of heater wells. This, in turn, minimizes secondary cracking of hydrocarbons converted from kerogen as hydrocarbons flow from the second layer of wells 420 to the production wells 440.

In the illustrative arrangement of FIG. 4, the first layer 410 and the second layer 420 each defines a 5-spot pattern. However, it is understood that other patterns may be employed, such as 3-spot or 6-spot patterns. In any instance, a plurality of heater wells 431 comprising a first layer of heater wells 410 is placed around a production well 440, with a second plurality of heater wells 432 comprising a second layer of heater wells 420 placed around the first layer 410.

The heater wells in the two layers also may be arranged such that the majority of hydrocarbons generated by heat from each heater well 432 in the second layer 420 are able to migrate to a production well 440 without passing substantially near a heater well 431 in the first layer 410. The heater wells 431, 432 in the two layers 410, 420 further may be arranged such that the majority of hydrocarbons generated by heat from each heater well 432 in the second layer 420 are able to migrate to the production well 440 without passing through a zone of substantially increasing formation temperature.

Another method for reducing the number of heater wells is to use well patterns that are elongated in a particular direction, particularly in a direction determined to provide the most efficient thermal conductivity. Heat convection may be affected by various factors such as bedding planes and stresses within the formation. For instance, heat convection may be more efficient in the direction perpendicular to the least horizontal principal stress on the formation. In some instanced, heat convection may be more efficient in the direction parallel to the least horizontal principal stress.

In connection with the development of a shale oil field, it may be desirable that the progression of heat through the subsurface in accordance with steps 130 and 135 be uniform. However, for various reasons the heating and maturation of formation hydrocarbons in a subsurface formation may not proceed uniformly despite a regular arrangement of heater and production wells. Heterogeneities in the oil shale properties and formation structure may cause certain local areas to be more or less productive. Moreover, formation fracturing which occurs due to the heating and maturation of the oil shale can lead to an uneven distribution of preferred pathways and, thus, increase flow to certain production wells and reduce flow to others. Uneven fluid maturation may be an undesirable condition since certain subsurface regions may receive more heat energy than necessary where other regions receive less than desired. This, in turn, leads to the uneven flow and recovery of production fluids. Produced oil quality, overall production rate, and/or ultimate recoveries may be reduced.

To detect uneven flow conditions, production and heater wells may be instrumented with sensors. Sensors may include equipment to measure temperature, pressure, flow rates, and/or compositional information. Data from these sensors can be processed via simple rules or input to detailed simulations to reach decisions on how to adjust heater and production wells to improve subsurface performance. Production well performance may be adjusted by controlling backpressure or throttling on the well. Heater well performance may also be adjusted by controlling energy input. Sensor readings may also sometimes imply mechanical problems with a well or downhole equipment which requires repair, replacement, or abandonment.

In one embodiment, flow rate, compositional, temperature and/or pressure data are utilized from two or more wells as inputs to a computer algorithm to control heating rate and/or production rates. Unmeasured conditions at or in the neighborhood of the well are then estimated and used to control the well. For example, in situ fracturing behavior and kerogen maturation are estimated based on thermal, flow, and compositional data from a set of wells. In another example, well integrity is evaluated based on pressure data, well temperature data, and estimated in situ stresses. In a related embodiment the number of sensors is reduced by equipping only a subset of the wells with instruments, and using the results to interpolate, calculate, or estimate conditions at uninstrumented wells. Certain wells may have only a limited set of sensors (e.g., wellhead temperature and pressure only) where others have a much larger set of sensors (e.g., wellhead temperature and pressure, bottomhole temperature and pressure, production composition, flow rate, electrical signature, casing strain, etc.).

As noted above, there are various methods for applying heat to an organic-rich rock formation. For example, one method may include electrical resistance heaters disposed in a wellbore or outside of a wellbore. One such method involves the use of electrical resistive heating elements in a cased or uncased wellbore. Electrical resistance heating involves directly passing electricity through a conductive material such that resistive losses cause it to heat the conductive material. Other heating methods include the use of downhole combustors, in situ combustion, radio-frequency (RF) electrical energy, or microwave energy. Still others include injecting a hot fluid into the oil shale formation to directly heat it. The hot fluid may or may not be circulated.

One method for formation heating involves the use of electrical resistors in which an electrical current is passed through a resistive material which dissipates the electrical energy as heat. This method is distinguished from dielectric heating in which a high-frequency oscillating electric current induces electrical currents in nearby materials and causes them to heat. The electric heater may include an insulated conductor, an elongated member disposed in the opening, and/or a conductor disposed in a conduit. An early patent disclosing the use of electrical resistance heaters to produce oil shale in situ is U.S. Pat. No. 1,666,488. The '488 patent issued to Crawshaw in 1928. Since 1928, various designs for downhole electrical heaters have been proposed. Illustrative designs are presented in U.S. Pat. Nos. 1,701,884, 3,376,403, 4,626,665, 4,704,514, and 6,023,554.

A review of application of electrical heating methods for heavy oil reservoirs is given by R. Sierra and S. M. Farouq Ali, "Promising Progress in Field Application of Reservoir Electrical Heating Methods", Society of Petroleum Engineers Paper 69709, 2001. The entire disclosure of this reference is hereby incorporated by reference.

Certain previous designs for in situ electrical resistance heaters utilized solid, continuous heating elements (e.g., metal wires or strips). However, such elements may lack the necessary robustness for long-term, high temperature applications such as oil shale maturation. As the formation heats and the oil shale matures, significant expansion of the rock occurs. This leads to high stresses on wells intersecting the formation. These stresses can lead to bending and stretching of the wellbore pipe and internal components. Cementing (e.g., U.S. Pat. No. 4,886,118) or packing (e.g., U.S. Pat. No. 2,732,195) a heating element in place may provide some protection against stresses, but some stresses may still be transmitted to the heating element.

As an alternative, international patent publication WO 2005/010320 teaches the use of electrically conductive fractures to heat the oil shale. A heating element is constructed by forming wellbores and then hydraulically fracturing the oil shale formation around the wellbores. The fractures are filled with an electrically conductive material which forms the heating element. Calcined petroleum coke is an exemplary suitable conductant material. Preferably, the fractures are created in a vertical orientation extending from horizontal wellbores. Electricity may be conducted through the conductive fractures from the heel to the toe of each well. The electrical circuit may be completed by an additional horizontal well that intersects one or more of the vertical fractures near the toe to supply the opposite electrical polarity. The WO 2005/010320 process creates an "in situ toaster" that artificially matures oil shale through the application of electric heat. Thermal conduction heats the oil shale to conversion temperatures in excess of 300° C., causing artificial maturation.

International patent publication WO 2005/045192 teaches an alternative heating means that employs the circulation of a heated fluid within an oil shale formation. In the process of WO 2005/045192, supercritical heated naphtha may be circulated through fractures in the formation. This means that the oil shale is heated by circulating a dense, hot hydrocarbon vapor through sets of closely-spaced hydraulic fractures. In one aspect, the fractures are horizontally formed and conventionally propped. Fracture temperatures of 320°-400° C. are maintained for up to five to ten years. Vaporized naphtha may be the preferred heating medium due to its high volumetric heat capacity, ready availability and relatively low degradation rate at the heating temperature. In the WO 2005/045192 process, as the kerogen matures, fluid pressure will drive the generated oil to the heated fractures where it will be produced with the cycling hydrocarbon vapor.

The purpose for heating the organic-rich rock formation is to pyrolyze at least a portion of the solid formation hydrocarbons to create hydrocarbon fluids. The solid formation hydrocarbons may be pyrolyzed in situ by raising the organic-rich rock formation, (or zones within the formation), to a pyrolyzation temperature. In certain embodiments, the temperature of the formation may be slowly raised through the pyrolysis temperature range. For example, an in situ conversion process may include heating at least a portion of the organic-rich rock formation to raise the average temperature of the zone above about 270° C. at a rate less than a selected amount (e.g., about 10° C., 5° C.; 3° C., 1° C., 0.5° C., or 0.1° C.) per day. In a further embodiment, the portion may be heated such that an average temperature of the selected zone may be less than about 375° C. or, in some embodiments, less than about 400° C. The formation may be heated such that a temperature within the formation reaches (at least) an initial pyrolyzation temperature (e.g., a temperature at the lower end of the temperature range where pyrolyzation begins to occur).

The pyrolysis temperature range may vary depending on the types of formation hydrocarbons within the formation, the heating methodology, and the distribution of heating sources. For example, a pyrolysis temperature range may include temperatures between about 270° C. and about 900° C. Alternatively, the bulk of the target zone of the formation may be heated to between 300° to 600° C. In an alternative embodiment, a pyrolysis temperature range may include temperatures between about 270° C. to about 500° C.

Preferably, for in situ processes the heating of a production zone takes place over a period of months, or even four or more years. Alternatively, the formation may be heated for one to fifteen years, alternatively, 3 to 10 years, 1.5 to 7 years, or 2 to 5 years. The bulk of the target zone of the formation may be heated to between 270° to 800° C. Preferably, the bulk of the target zone of the formation is heated to between 300° to 600° C. Alternatively, the bulk of the target zone is ultimately heated to a temperature below 400° C. (752° F.).

In certain embodiments of the methods of the present invention, downhole burners may be used to heat a targeted organic-rich rock formation. Downhole burners of various designs have been discussed in the patent literature for use in oil shale and other largely solid hydrocarbon deposits. Examples include, in numerical order, U.S. Pat. Nos. 2,887,160; 2,847,071; 2,895,555; 3,095,031; 3,109,482; 3,127,936; 3,225,829; 3,241,615; 3,254,721; 5,255,742; and 5,899,269.

Downhole burners operate through the transport of a combustible fuel (typically natural gas) and an oxidant (typically air) to a subsurface position in a wellbore. The fuel and oxidant react downhole to generate heat. The combustion gases are removed (typically by transport to the surface, but possibly via injection into the formation). Downhole burners may utilize pipe-in-pipe arrangements to separately transport fuel and an oxidant downhole, and then to remove the flue gas back up to the surface. Some downhole burners generate a flame, while others may not.

In the context of heavy oil recovery, downhole burners have been used for steam generation. In downhole steam generation, a combustor in the well is used to boil co-injected water. The water is then released into the formation.

The use of downhole burners is an alternative to other downhole heating methods such as electrical resistance heating and radio-frequency heating. In principle, downhole heating methods can be more efficient than these electrical methods since the energy losses (typically about 50%) associated with generating electricity from combustible fuels are avoided. Downhole burners also reduce infrastructure cost. In this respect, there is no need for an expensive electrical power plant and distribution system.

Downhole heating can also be more efficient than the circulation of surface-heated fluids. This is especially true for deep targets since heat losses to the overburden can be largely avoided.

Applications of downhole heat technology have been described in F. M. Smith, "A Down-Hole Burner—Versatile Tool for Well Heating," 25$^{th}$ Technical Conference on Petroleum Production, Pennsylvania State University, pp 275-285 (Oct. 19-21, 1966); H. Brandt, W. G. Poynter, and J. D. Hummell, "Stimulating Heavy Oil Reservoirs with Downhole Air-Gas Burners," World Oil, pp. 91-95 (September 1965); and C. I. DePriester and A. J. Pantaleo, "Well Stimulation by Downhole Gas-Air Burner," Journal of Petroleum Technology, pp. 1297-1302 (December 1963).

Various challenges are presented by the use of downhole burners for heating a formation. As a result, there have been few major field applications of downhole burners. Key design issues include temperature control and metallurgy limitations. In this respect, the flame temperature in a burner can overheat the tubular and burner hardware, causing them to fail via melting, thermal stresses, loss of tensile strength, or creep. Certain stainless steels, typically with high chromium content, can tolerate temperatures up to about 700° C. for extended periods. (See, for example, H. E. Boyer and T. L. Gall (eds.), *Metals Handbook*, Chapter 16: "Heat-Resistant Material", American Society for Metals, (1985.)) Another drawback is that the flames generated by the downhole burner can cause hot spots within the burner and in the formation surrounding the burner. This is due to radiant heat transfer from the luminous portion of the flame. A typical gas flame can produce temperatures up to about 1,650° C. Therefore, materials of construction for the burners must be sufficient to withstand the temperatures of these hot spots. Use of refractory metals or ceramics can help solve these problems, but typically at a higher cost. Ceramic materials with acceptable strength at temperatures in excess of 900° C. are preferred. These would include high alumina content ceramics. Other ceramics that may be useful include chrome oxide, zirconia oxide, and magnesium oxide-based ceramics.

Additionally, the flue gases generated by the downhole burner can be corrosive due to $CO_2$ and water content. This is particularly true if the water condenses. Use of alloy metals such as stainless steels can be used to reduce this potential problem.

Heat transfer in a pipe-in-pipe arrangement for a downhole burner can also lead to difficulties. The down-going fuel and air will heat exchange with the up-going hot flue gases. In a well there is minimal room for a high degree of insulation and, hence, significant heat transfer is possible. This cross heat-exchange can cause significant heating of the air and fuel prior to entering the burner. This, in turn, can lead to significantly higher-than-expected flame temperatures. Cross heat-exchange can also heat the flue gas moving up past the burner. If the burner is near the top of the target formation, the flue gas thus transports otherwise useful heat into the overburden where it is neither needed nor desired. Additionally, the cross heat-exchange can limit the transport of heat downstream of the burner since the hot flue gases may rapidly lose heat energy to the rising cooler flue gases.

For downhole burner applications, heat transfer can occur in one of several ways. These include conduction, convection, and radiative methods. Radiative heat transfer can be particularly strong for an open flame. Therefore, it is desirable to provide a heater well having a downhole burner that harnesses the heat of the burner and more uniformly distributes heat across a zone of interest. Further, it is desirable to provide a heater well arrangement that minimizes cross heat-exchange. Still further, it is desirable to provide an array of heater wells that create a more uniform heat distribution across a selected subsurface formation.

In one embodiment the invention includes a method for in situ heating of an organic-rich rock formation. The method may include providing a first wellbore extending at least to a depth of the organic-rich rock formation, and providing a second wellbore intersecting the first wellbore. A wellbore circuit is thereby formed that is suitable for providing fluid communication between the first wellbore and the second wellbore. In some embodiments, the first wellbore may extend to a depth below the organic-rich rock formation. The method may include injecting an oxidant, for example air, and a first combustible fuel, for example a light hydrocarbon gas, into the first wellbore, and providing hardware in the first wellbore so as to cause the oxidant and the first combustible fuel to mix and to combust at substantially the depth of the organic-rich rock formation The combustion forms combustion products. The method may further include flowing the combustion products into and up the second wellbore. In this way, (1) a first heat profile is created from the first wellbore, and (2) a second heat profile is created from the second wellbore. The combustion products flow for a period of time, causing the first heat profile to substantially mate with the second heat profile. Pyrolysis of formation hydrocarbons located within the organic-rich rock formation between the first and second wellbores takes place. The formation hydrocarbons located in the organic-rich rock formation may include heavy hydrocarbons and/or solid hydrocarbons. Particular examples include coal, tar sands, or oil shale.

In one embodiment, the combustion products are at a temperature above a pyrolysis temperature, for example 270° C., in the second wellbore at or just below the approximate depth of the hardware in the first wellbore. Thereafter, the combustion products may fall below a pyrolysis temperature in the second wellbore at or just above the approximate depth of the hardware in the first wellbore. In some embodiments, the method may include monitoring the temperature of the combustion products in the second wellbore. In some embodiments, the method may include monitoring the temperature of the combustion products at a point in the casing string within the second wellbore at approximately the depth of the first burner.

In one embodiment both the first and second wellbores include a casing string within the respective wellbores. In some embodiments the first wellbore and the second wellbore are spaced apart from about 20 feet to 100 feet. Alternatively, the first wellbore and the second wellbore are spaced apart from about 20 feet to 50 feet. In some embodiments, the first wellbore is completed horizontally, thereby defining a heel and a toe. In some embodiments, the second wellbore is completed substantially vertically. In some embodiments, the second wellbore intersects the first wellbore at about the toe of the first wellbore.

As used herein, the term "heat profile" means the region of the formation surrounding a source of heat that has been heated to greater than a specified temperature. For example, the specified temperature may be a minimum temperature at which pyrolysis occurs at a minimum desired heating rate. In some embodiments, there is a first heat profile created from the first wellbore, and a second heat profile created from the second wellbore. The first heat profile may include a first region of the organic-rich rock formation around the first wellbore having a temperature greater than 270° C. while the second heat profile may include a second region of the organic-rich rock formation around the second wellbore having a temperature greater than 270° C., for example. For example, the first heat profile and second heat profile may each have a temperature between about 300° C. and 900° C. Still further, the first heat profile and second heat profile may have a temperature between about 400° C. and 700° C. In these instances, the heat profiles create pyrolysis zones.

The method may include mating the first heat profile with the second heat profile. Preferably, the method further includes mating a first pyrolysis zone associated with the first heat profile with a second pyrolysis zone associated with the second heat profile. This may be accomplished by selecting specific operational parameters such as burner intensity, combustion fuel composition, oxidant injection rate, combustion fuel injection rate, well separation between the first wellbore and the second wellbore, or combinations thereof.

The concept of "mating" the heat profiles means that a first heat profile expands in such a way as to meet a second heat profile so that at the time of first meeting, substantial portions of both the first and second heat profiles have reached a pyrolysis temperature. In this way, a substantial portion of organic-rich rock in the formation is pyrolyzed. Designing the heater well to accommodate mating provides various benefits to a pyrolysis operation. For example, over time a more uniform temperature is created within the formation that is above a pyrolysis temperature. This avoids areas within a plane defined between the two wellbores that experience significant overheating or underheating. Preferably, a temperature variance within this plane of less than 350° C. is avoided.

As another benefit, convective heat loss to the overburden is minimized by having the temperature of the combustion gases in the upward-flowing second wellbore be at a minimum practical pyrolysis temperature at the time such gases reach a depth approximately equal to that of the burner in the first wellbore. Preferably, the flue gases traveling in the second wellbore maintain a temperature in the second wellbore at the depth of the first burner that is between 260° C. and 360° C. or, more preferably, that is between 275° C. and 325° C.

In some embodiments, the hardware may include a tubular member residing within the casing string within the first wellbore and extending to a selected portion of the organic-rich rock formation. The tubular member forms an annular region with the surrounding casing. The hardware may further include a first burner connected to the tubular member at a first depth within the organic-rich rock formation. The first burner may be placed near the top of a targeted zone within the organic-rich rock formation. For example, the first burner may be placed within 50 meters of the top of a targeted zone within the organic-rich rock formation. Alternatively, the first burner may be placed within 20 meters of the top of the organic-rich rock formation. The first burner may be ignited using electric resistive heating elements. Alternatively, the first burner may be ignited using a removable electrical heated element. Still further, the first burner may be ignited by injecting a pyrophoric substance, for example triethylborane, into the first and second tubular members. In some embodiments, the first burner supplies about 50 to 250 kW of thermal energy. In alternate embodiments, the first burner provides 0.5 to 3.0 kW per meter of well length in a zone within the organic-rich rock formation targeted for pyrolysis. In other embodiments, the hardware may further include a tubular cowl located immediately below the burner. In some embodiments, the hardware may include at least one fuel line for delivering the injected combustible fuel to the burners. In cases that employ casing and a tubular member, the method may include injecting the first combustible fuel into the tubular member and injecting the oxidant into the annular space around the tubular member. Alternatively, the locations of injection may be reversed.

As a result of practicing certain of the methods, combustion products will be generated and circulated through the second wellbore. In this instance, embodiments of the methods may include collecting the combustion products and reusing such collected combustion products as a portion of the fuel or oxidant for the same or a different heater well arrangement. For example, the method may include collecting the combustion products from the second wellbore at the surface and separating the combustion products in order to reclaim at least a part of the first combustible fuel. Further, the method may include delivering the reclaimed combustible fuel to a tank and thereafter delivering the reclaimed combustible fuel from the tank back into the first wellbore. Alternatively, and particularly in instances where combustion products contain oxygen, the method may include collecting the combustion products from the second wellbore at the surface and compressing the oxygen. The compressed oxygen is mixed with compressed air; and the mixture thereafter delivered into the first wellbore as a portion of the injected oxidant.

Whether the combustion products are collected and reused as a portion of the oxidant or as a portion of the combustible fuel, such collected combustion products may be used in a different well than the well from which they were collected. This process may be completed in yet additional heater wells. Alternatively, the method may include venting the combustion products to the atmosphere. Before the combustion products are vented to the atmosphere, they may be treated to remove $NO_x$ components. In any of these cases, the combustion products may be monitored for the presence of combustible species and/or excess air, thereby assessing whether the burner is firing properly. In some embodiments, the combustible species may include at least one of methane, ethane, hydrogen ($H_2$), and carbon monoxide.

In the various embodiments, the oxidant and the combustible fuel may be delivered to the burner in different ratios and at different rates. In one embodiment, the oxidant may be injected in stoichiometric combustion excess at a mass rate of 1.25 to 6.0 times the stoichiometric combustion amount. In some embodiments, the oxidant is $O_2$-enriched air. In some embodiments, the oxidant may be injected at a rate of about 10,000 to 50,000 kg/day or alternatively the oxidant may be injected at a rate of about 10,000 to 25,000 kg/day. In some embodiments, the oxidant may be injected under a pressure of about 50 to 250 psia. In some embodiments, the combustible fuel may injected under a pressure of greater than about 200 psia; alternatively, the combustible fuel may injected under a pressure of greater than about 600 psia. In some embodiments, at least a portion of the combustible fuel is derived from the gaseous portion of hydrocarbon fluids produced from pyrolyzed oil shale. Alternatively, at least a portion of the combustible fuel is comprised of a pipeline fuel gas. In either case, the combustible fuel may include inert components or inert components. For example, carbon dioxide ($CO_2$) or nitrogen ($N_2$) may be added to the combustible fuel to adjust the composition of the combustible fuel.

In the various described embodiments, the fluid flows within and the roles of the first and second wellbores may be reversed. For example, the inlet and outlet roles of the first and second wellbores may be reversed after the targeted organic-rich rock formation has been heated adjacent the first wellbore above the heel and towards the toe of the first wellbore. Thereafter, a second burner and tubular member may be provided in the second wellbore and a second oxidant and a second combustible fuel may be injected into the second wellbore and through the second burner so as to combust the second combustible fuel and to further heat the targeted organic-rich rock formation adjacent the second wellbore and towards the heel of the first wellbore. Flue gas or combustible products generated from the second burner in the second wellbore may then be circulated through the first wellbore and to the surface.

In the various embodiments, multiple heater well arrangements may be provided to heat larger portions of the organic-rich rock formation. For example, the first wellbore, the second wellbore, and the burner may be thought of as defining a first heater well. Further additional heater wells, each of which also comprises a first wellbore, a second wellbore, and a burner within the first wellbore, may be provided and arranged such that the respective first wellbores and the respective second wellbores are in alternating relation, thereby alternating the portion of each heater well arrangement that contains the burner.

Figure 29A:
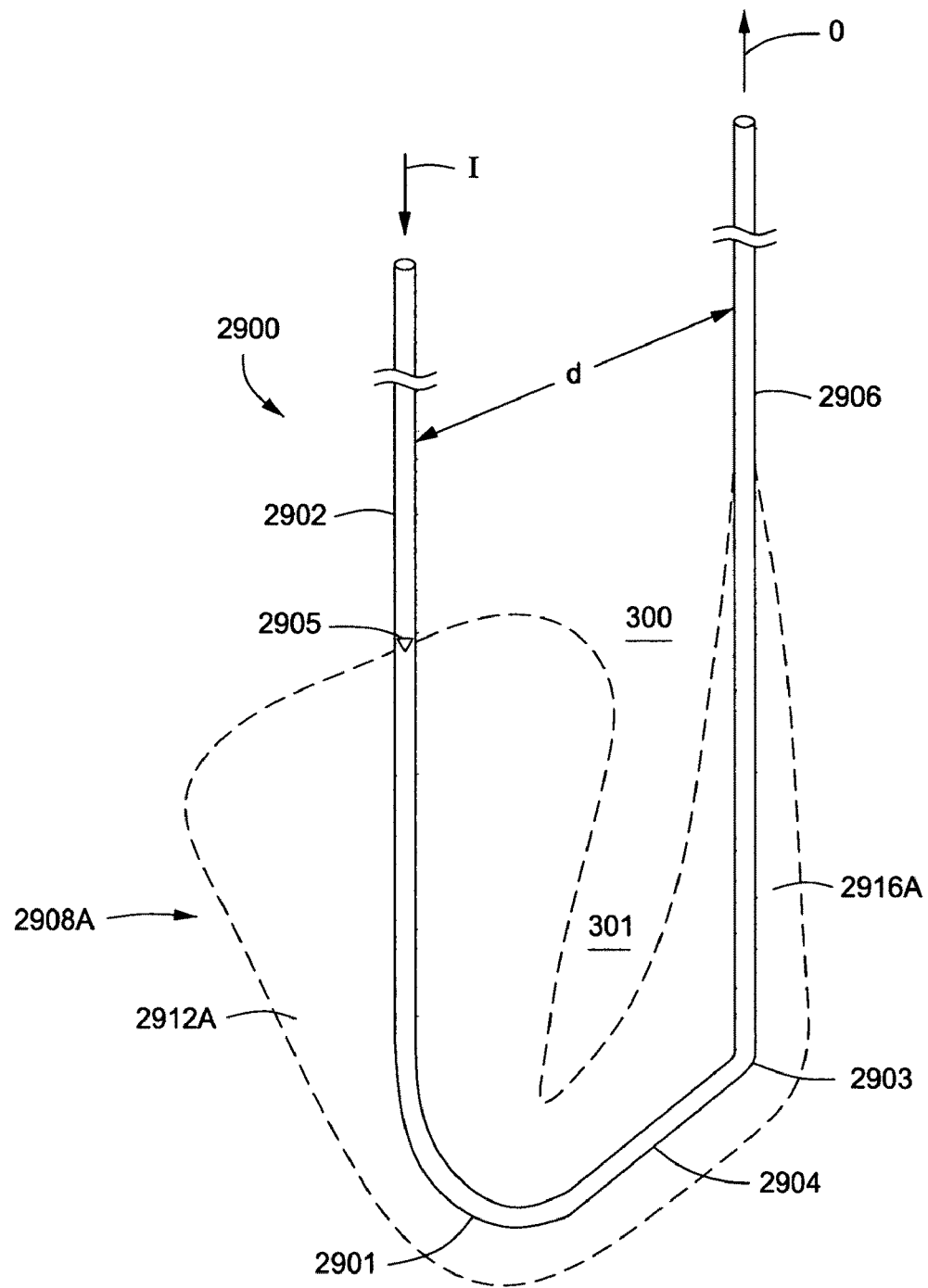
FIG. 29A is a perspective view of a heater well of the present invention, in one embodiment. The heater well includes at least one downhole burner. A profile of a pyrolysis zone around the heater well is indicated.

FIG. 29A is a perspective view of a heater well 2900 of the present invention, in one embodiment. The heater well 2900 generally comprises a first wellbore 2902 that serves as a gas input wellbore, and a second wellbore 2906 that serves as a gas output wellbore. One of the wellbores 2902 or 2906 has a horizontal portion 2904. In the illustrative embodiment of FIG. 29A, the first wellbore 2902 is deviated to provide the horizontal portion 2904. However, it is within the scope of the present disclosure for the second wellbore 2906 to be horizontally deviated instead of the first wellbore 2902. Alternatively, the two wellbores 2902, 2906 may be connected in a manner where each wellbore has a deviated section and where neither deviated section is fully horizontal.

The first wellbore 2902 has a lower end that is shown at 2901. The lower end 2901 defines a "heel" for the horizontal portion 2904 of the wellbore 2902. The first wellbore 2902 also has a "toe" 2903. The toe 2903 represents the end of the horizontal portion 2904 within the targeted formation 300. The second wellbore 2906 also has a lower end. The lower end intersects the toe 2903 of the first wellbore 2902. In this way, fluid communication between the first 2902 and second 2906 wellbores is established.

Arrows "I" (for "input") and "O" (for "output") are indicated for the movement of gases through the wellbores 2902, 2906. In the embodiment of FIG. 29A, the first wellbore 2902 receives an oxidant and a combustible fuel gas (together "I,"), while the second wellbore 2906 delivers combustion products ("O"). However, this role again may be reversed.

The purpose of the heater well 2900 is to generate a substantially continuous pyrolysis zone 2908A within a substantial portion of a targeted organic-rich rock formation 300. More specifically, the purpose is to heat a portion of the formation 300 to a temperature that is sufficient to pyrolyze solid hydrocarbons such as kerogen into hydrocarbon fluids. In the present invention, this is done through the use of combustive heat that is conductively transferred to the formation 300. Air (or other oxidant) and a combustible fuel are injected into the first wellbore 2902. The air and combustible fuel are mixed at a downhole burner 2905, where the fuel combusts and forms into a flame. Flue gases, which may contain excess air or fuel, flow beyond the burner 2905, down the first wellbore 2902, through the horizontal portion 2904, and back up to the surface via the second wellbore 2906. The flue gases (including any excess air or fuel) represent combustion products.

The formation 300 in FIG. 29A represents an organic-rich rock formation. The organic-rich rock formation may comprise tar sands, coal, oil shale, or other rock containing solid hydrocarbons. Preferably, the organic-rich rock formation 300 is an oil shale formation containing kerogen. The burner 2905 is positioned to provide heat to a selected subsurface region that comprises the kerogen.

It is desirable that the heater well 2900 uniformly distributes heat across a zone of interest downhole. The heating of regions above the desired temperature as might be done for rapid pyrolysis reflects an inefficient use of heating energy. Reciprocally, heating more slowly means that regions of the formation 300 will not reach the temperature needed for pyrolysis in a reasonable amount of time, representing both an inefficient use of heating energy and a lost resource opportunity. This presents a challenge with downhole burners because of the intense heat generated immediately at the depth of the burner 2905, followed by rapid cooling as combustion products are circulated in the well. Stated another way, the hot flue gases reduce in temperature as they travel from the burner and along the well, giving up heat to the formation. Moreover, the conventional pipe-in-pipe downhole burner creates undesirable cross heat-exchange above the burner 2905. The heater well 2900 seeks to overcome these challenges to create a uniform pyrolysis zone 2908A within the formation 300.

FIG. 29A shows a snapshot of the pyrolysis zone 2908A around the heater well 2900 at a specific time during formation heating. The pyrolysis zone 2908A may be defined as the region having a temperature greater than a specific value required for reasonably rapid pyrolysis. For example, the value may be 250° C., 270° C., 300° C., 350° C., or some higher value. It can be seen that the pyrolysis zone 2908A expands away from the first wellbore 2902 faster at depths closer to the burner 2905. The pyrolysis zone 2908A expands slower further down the well as the combustion products move through the deviated portion 2904 and into the second wellbore 2906. However, thermal conduction continues to take place into the formation 300 even from the second wellbore 2906.

The utility of circulating a heated gas through the wellbores 2902, 2906 is the ability to create a "mate" or "fit" between heat profiles emanating from the first 2902 and second 2906 wellbores. The illustrative pyrolysis zone 2908A of FIG. 29A provides a good "fit" because the faster heat front emanating from the first wellbore 2902 meets the slower heat front emanating from the second wellbore 2906 roughly simultaneously. This means that there are few if any areas of significant overheating or underheating within the formation 300 at the end of the heating process. In FIG. 29A, only a small area of underheating 301 exists in the pyrolysis zone 2908A. Even this area 301 should be closed off over a modest amount of time as thermal conduction continues.

It is also noted from FIG. 29A that the pyrolysis zone 2908A is formed by heat profiles emanating from the first 2902 and second 2906 wellbores. Heat from combustion products flowing through the first wellbore 2902 creates a first heat profile 2912A, while heat from combustion products flowing through the second wellbore 2906 creates a second heat profile 2916A. The second heat profile 2916A terminates, that is, no longer comprises a pyrolysis temperature, up to an approximate depth of the burner 2905 in the first wellbore. In this way, excess combustion fuel is not employed.

Figure 29B:
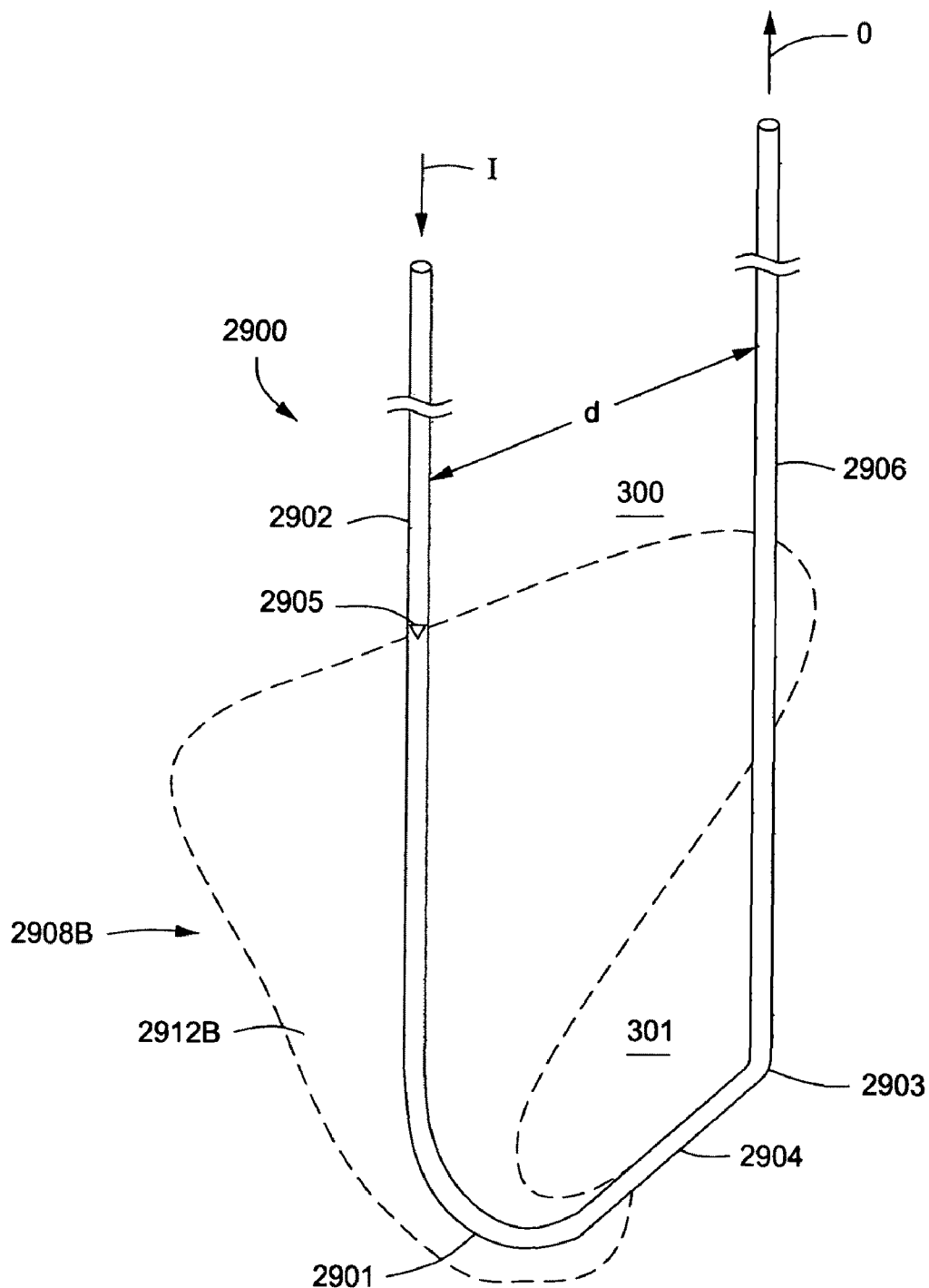
FIG. 29B is a perspective view of the heater well of FIG. 29A. Here, the pyrolysis zone is modified to demonstrate an undesirable heat profile.
Figure 29C:
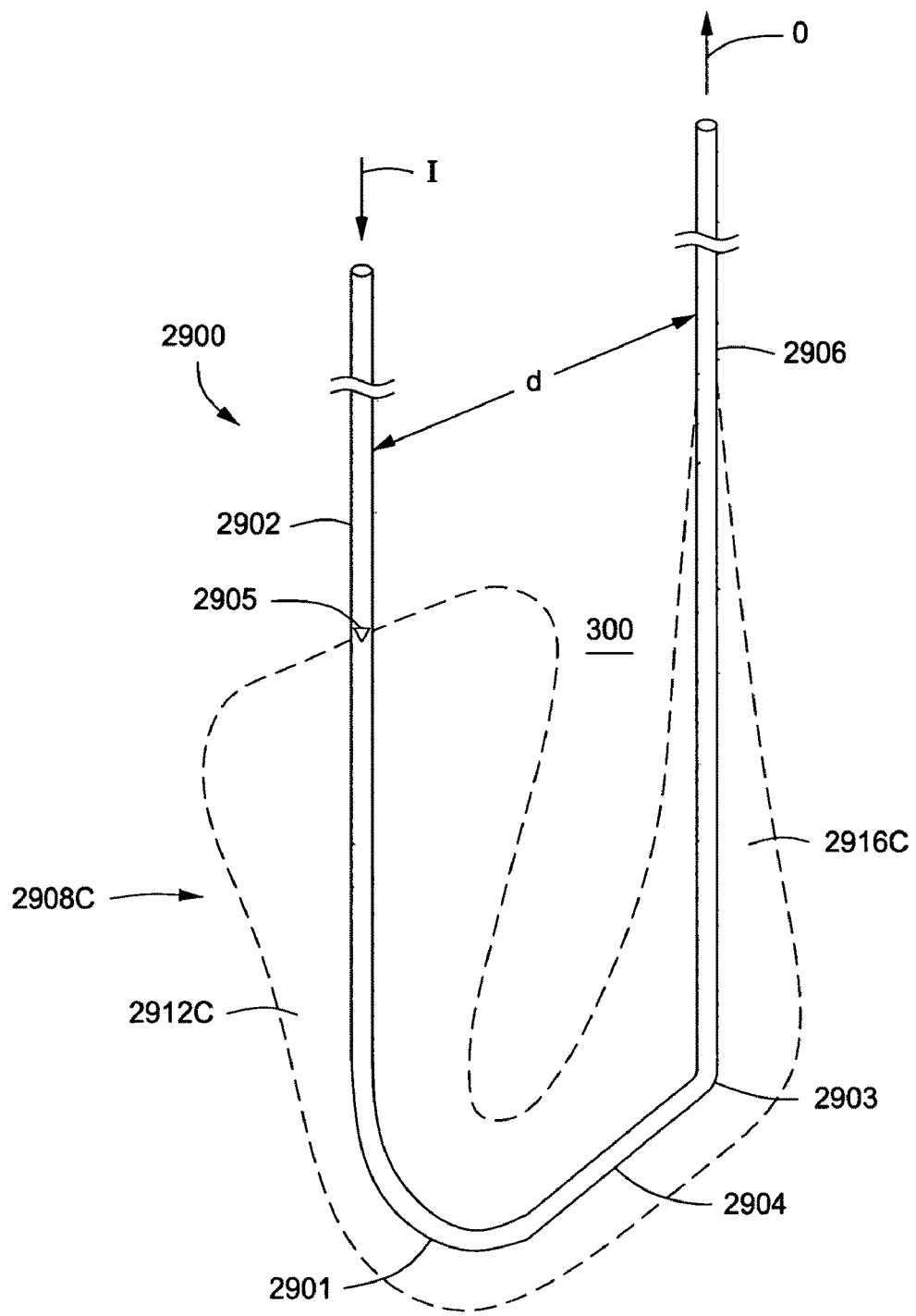
FIG. 29C is another perspective view of the heater well of FIG. 29A. Here, the pyrolysis zone is modified to demonstrate a different undesirable heat profile.

FIGS. 29B and 29C provide contrasts to FIG. 29A. Each of FIGS. 29B and 29C show the heater well 2900 of FIG. 29A. However, a different pyrolysis zone 2908B or 2908C is generated from the first 2902 and second 2906 wellbores.

Concerning FIG. 29B, in pyrolysis zone 2908B heat emanates from the first wellbore 2902 too aggressively due to rapid heating immediately below the burner 2905. At the same time, insufficient heat emanates from the second wellbore 2906 due to excess cooling of the flue gases as they travel into the deviated portion 2904 of the first wellbore 2902. Thus, the pyrolysis zone 2908B does not form a good fit for the heater well 2900 resulting in uneven heating within the formation 300. Further, a large area of underheating 301 exists.

It is seen in FIG. 29B that the pyrolysis zone 2908B is formed by a heat profile emanating solely from the first wellbore 2902. Heat from combustion products flowing through the first wellbore 2902 creates a first heat profile 2912B. However, heat from combustion products flowing through the second wellbore 2906 does not create a true heat profile as pyrolysis temperatures are not reached within the formation 300. This undesirable scenario may be the product of a variety of factors. These include a mass flow rate of oxidant and/or combustible fuel that is too low, a separation between the first 2902 and second 2904 burner wells that is too great, a burner intensity that is too low, a burner position that is too high relative to the horizontal portion 2904 of the first wellbore 2902, or a fuel composition too heavily concentrated with light hydrocarbons.

Concerning FIG. 29C, in pyrolysis zone 2908C heat emanates from the first wellbore 2902 as a first heat profile 2912C, and from the second wellbore 2906 as a second heat profile 2916C. However, the second heat profile 2916C extends too high, that is, it continues above the depth of the burner 2905 in the first wellbore 2902. As a result, the pyrolysis zone 2908C does not form a good fit for the heater well 2900, causing heating outside of the formation 300. While continued heating should prevent any significant areas of underheating in the formation 300, excess heating is taking place at depths higher than the formation 300.

It is also noted from FIG. 29C that the pyrolysis zone 2908C is formed by the heat profiles 2912C, 2916C emanating from the first 2902 and second 2906 wellbores. Heat from combustion products flowing through the first wellbore 2902 creates the first heat profile 2912C, while heat from combustion products flowing through the second wellbore 2906 creates the second heat profile 2916C. Of concern, however, excess heating is taking place at depths along the second wellbore 2906 higher than the depth of the burner 2905 in the first wellbore 2902. This undesirable scenario may be the product of a variety of factors including a mass flow rate of oxidant and/or combustible fuel that is too high, a separation between the first 2902 and second 2904 burner wells that is too small, a burner intensity that is too high, a burner position that is too low relative to the horizontal portion 2904 of the first wellbore 2902, or a fuel composition too lightly concentrated with light hydrocarbons.

In order to correct the poor fit of pyrolysis zones 2908B or 2908C and form the more appropriate fit of pyrolysis zone 2908A, various factors may be taken into account when designing the wellbore 2900. Such factors may include the distance "d" between the two wellbores 2902, 2906, the intensity of the burner 2905, the position or depth of the burner 2905 within the first wellbore 2902, fuel composition, amount of excess air or fuel injected, and formation thermal conductivity.

To provide a best fit for the pyrolysis zone, that is, to make the pyrolysis zone look more like zone 2908A, it is desirable that the combustion products (represented by "O") in the second wellbore 2906 be above a pyrolysis temperature up to an approximate depth of the hardware 2905 in the first wellbore 2902. It is also desirable that the combustion products "O" in the second wellbore 2906 fall below a pyrolysis temperature at or just above the depth of the hardware 2905 in the first wellbore 2902. It is also preferred that the spacing "d" between the two wellbores 2902, 2906 be far enough away to prevent overheating of the formation 300, but close enough to prevent underheating. In one aspect, the spacing is approximately 20 to 100 feet (about 6 to 30 meters). More preferably, the spacing "d" between the two wellbores 2902, 2906 is approximately 30 to 80 feet (about 9 to 24 meters).

Figure 30:
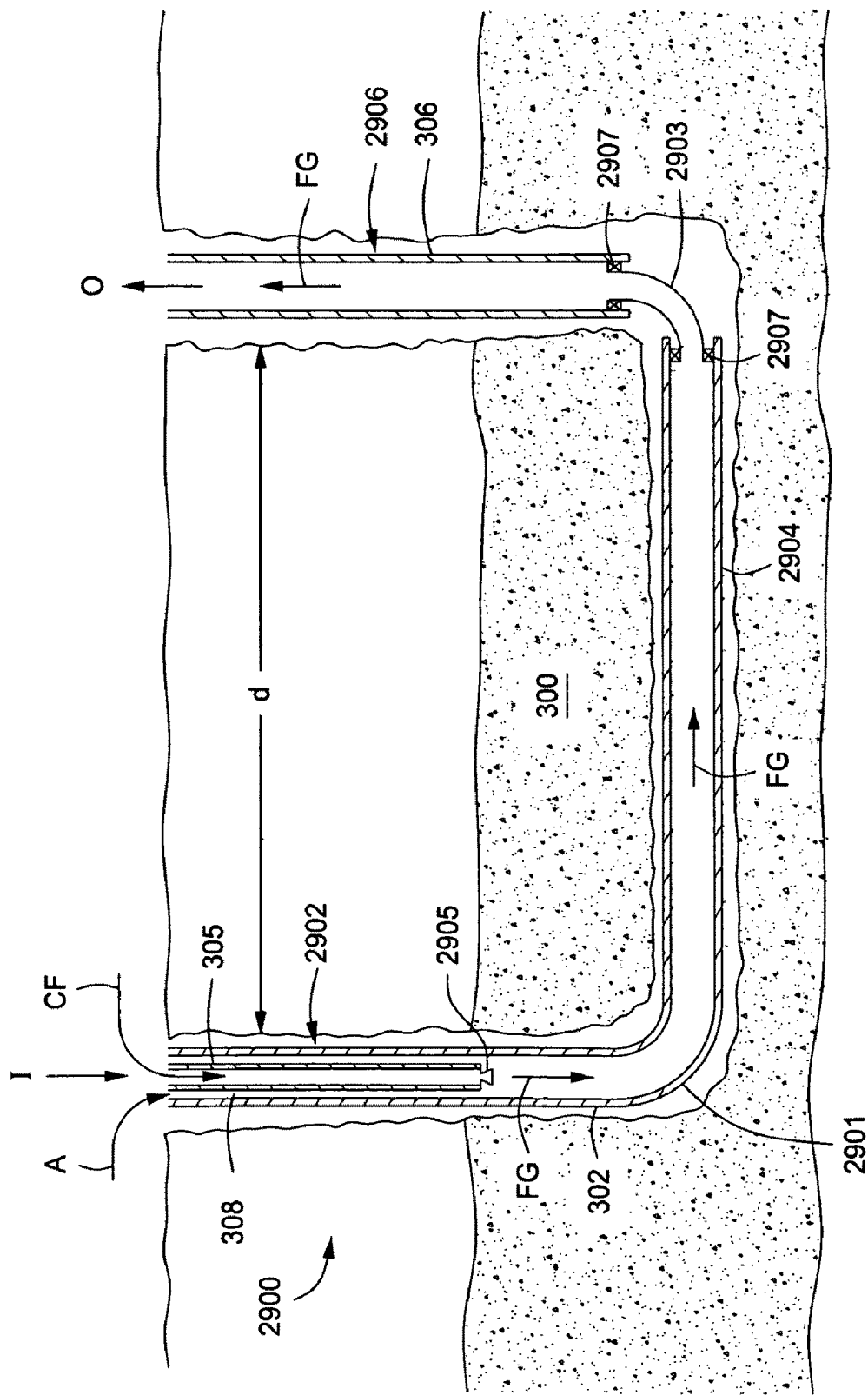
FIG. 30 is an enlarged cross-sectional view of the heater well of FIG. 29A.

FIG. 30 provides an enlarged side view of the heater well 2900 of FIG. 29A. Once again, the first wellbore 2902 and the second wellbore 2906 are seen. The intermediate horizontal portion 2904 of the first wellbore 2902 is also provided. Each of the wellbores 2902 and 2906 is preferably cased. The exception is at the toe 2903 where the connection between the wellbore 2902, 2906 is made. In that instance, an arrangement of packers 2907 is preferably provided to seal the toe 2903 region. Casing strings 302, 306 are provided for the first 2902 and second 2906 wellbores, respectively.

In order to generate heat through the downhole burner 2905, air as indicated by arrow "A" and a combustible fuel, indicated by arrow "CF," are injected into the first wellbore 2902. A tubular member 305 is provided internal to the casing 302 in the first wellbore 2902. An annulus 308 is formed between the tubing 305 and the surrounding casing 302. In one aspect, air "A" is injected into the annulus 308, while combustible fuel "CF" is injected into the tubing 305. In another aspect, fuel "CF" is injected into the annulus 308, while air "A" is injected into the tubing 305.

Various ways may be provided for igniting the combustible fuel "CF". For instance, the burner 2905 may be ignited using electrically resistive heating elements in the wellbore 2902. In one aspect, the resistive heating elements are removable electrical heating elements which can be selectively inserted into the first wellbore 2902. In another aspect, the burner 2905 is ignited by injecting a pyrophoric substance into the tubing 305. The pyrophoric substance may be either a liquid or a solid substance.

Once the combustible fuel "CF" is ignited and a flame is generated, hot flue gases as indicated by arrow "FG are pushed down the first wellbore 2902 and through the horizontal portion 2904. This causes the formation 300 around the first wellbore 2902 and its horizontal portion 2904 to be heated by thermal conduction. The formation 300 around the second wellbore 2906 is also heated by thermal conduction as flue gases "FG" are circulated through the heater well 2900.

The flue gases "FG" " may include air "A." The excess air "A", if any, is pushed through the second wellbore 2906, and exits to the surface as indicated by arrow "O." The heated mixture of air "A" and combustible fuel "CF" is together indicated by arrow "FG," but may also be generally referred to as "combustion products."

Returning to FIG. 29A, it is again noted that a thermal profile, or "pyrolysis zone" 2908A is shown. The pyrolysis zone 2908A represents the extent of heating provided into the targeted organic-rich rock formation 300 by the combustion of fuel "CF" and the circulation of hot flue gas "FG." The profile 2908A extends further out into the formation 300 proximate the burner 2905, and gradually diminishes as the flue gas "FG" travels through the horizontal portion 2904 and up the second wellbore 2906.

Since the purpose of the heating exercise is to pyrolyze solid hydrocarbons within the formation 300, it is desirable that a temperature in excess of 270° C. be provided to the formation 300 between the first 2902 and the second 2906 wellbores. Thus, the pyrolysis zone 2908A represents heat being conducted from the first 2902 and second 2906 wellbores and into the formation 300 for the purposes of pyrolyzing rock in the formation 300 into hydrocarbon fluids. As noted, the pyrolysis zone 2908A has an underheated region 301, but this area 301 should close as well as additional heating takes place over time.

FIG. 29B shows a poor distribution of heat resulting in a substantial underheated region 301. In order to avoid the creation of the underheated region 301, several approaches may be taken. A first approach is to reduce the distance "d" between the first 2902 and second 2906 wellbores. Preferably, the distance "d" is at least 10 meters to 30 meters. However, reducing the distance "d" means that more heater wells 2900 are required. Moreover, reducing well spacing may cause a significant volume to become needlessly overheated due to overlapping of the pyrolysis zones from the two wellbores 2902, 2906. Therefore, it is desired that the heat fronts emanating from the wellbores 2902, 2906 be controlled so that they fit together well or mate when they approach each other.

A second approach is to reverse the direction of gas input as between the first 2902 and the second 2906 wellbores after a period of time. This enables the heat profiles (such as 2912A and 2916A of FIG. 29A) to be reversed, meaning that the pyrolysis zone 2908A becomes larger from the second wellbore 2906 than from the first wellbore 2902. In this way the entire formation 300 is more evenly heated. In connection with this second approach, it is possible to reverse the direction of gas input "I" more than once. However, reversing the direction of gas input "I" typically requires that the burner 2905 be pulled and the injection equipment be moved from the first wellbore 2902 to the second wellbore 2906 each time.

Another approach is to move the burner 2905 incrementally down the first wellbore 2902. In one aspect, the burner 2905 is initially near the top of the formation 300. The burner may then be moved to a position just above the heel 2901 of the wellbore 2902. Subsequently, the burner 2905 may be moved beyond the heel 2901 into the horizontal portion 2904 of the first wellbore 2902. In this way, different portions of the formation 300 receive the higher thermal energy afforded by proximity to the burner 2905. However, this again requires the periodic movement of the burner 2905.

Figure 31:
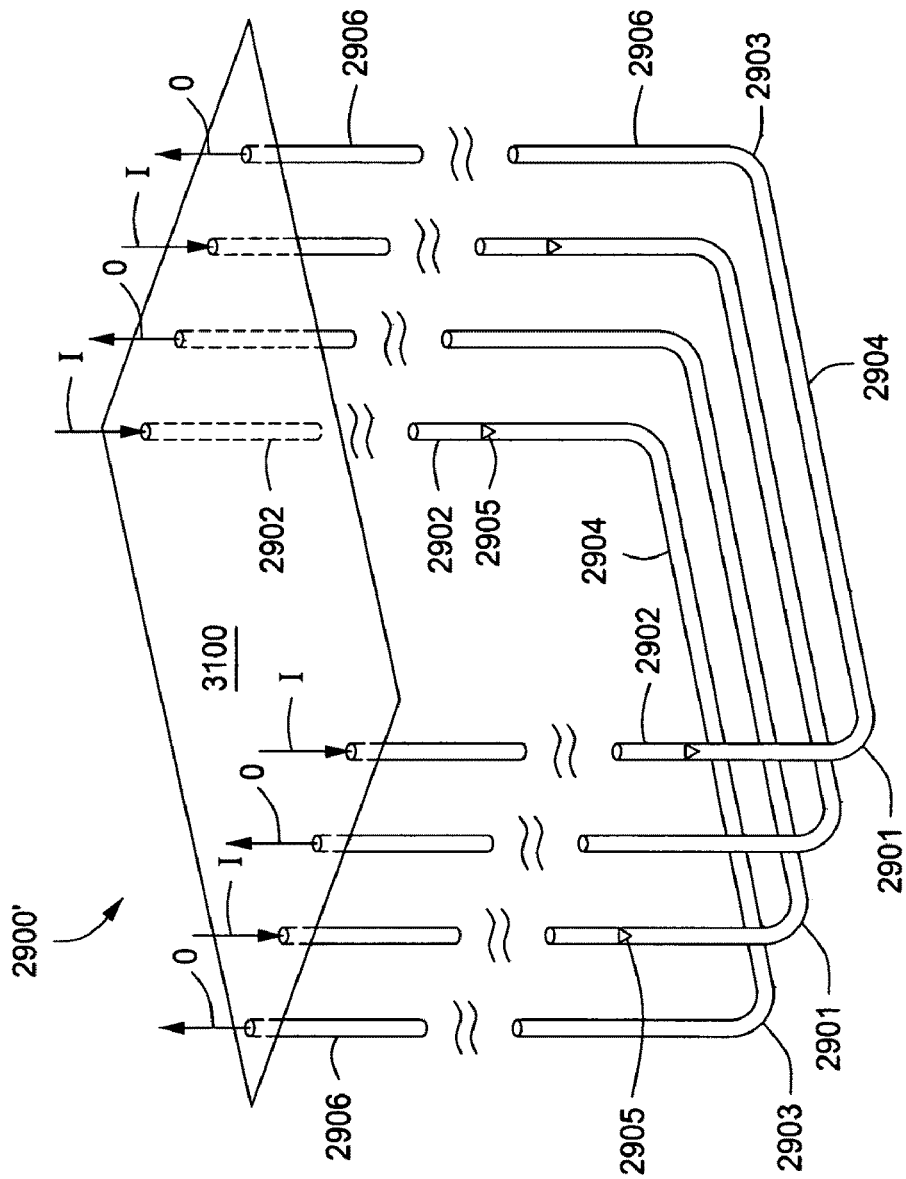
FIG. 31 is a perspective view of a plurality of heater wells of FIG. 29A within a hydrocarbon development area.

A fourth approach is to set up a plurality of adjacent heater wells 2900. FIG. 31 provides a perspective view of a plurality of heater wells 2900 of FIG. 29A within a hydrocarbon development area 3100. An array 2900' of heater wells 2900 is provided. In the array 2900', the heater wells 2900 are aligned side-by-side. However, they are turned in 180° relation to one another. This is indicated in FIG. 31 by the arrows "I" and "O," which are seen to be alternating.

It is noted from the array 2900' that the burners 2905 are also alternating. The result is that a heat front (not shown) originates more aggressively from the respective first wellbores 2902 than from the adjacent second wellbores 2906. A fit or "mating" of the heat fronts thus not only takes place between wellbores 2902, 2906 associated with each respective heater well 2900, but also between wellbores 2902, 2906 in adjoining heater wells 2900.

In establishing an array of heater wells 2900', the same design considerations as listed above must be taken into account. These include the distance between the two wellbores 2902, 2906, the intensity of the burners 2905, the position or depth of the burners 2905 within the first wellbore 2902, fuel composition, amount of excess air or fuel injected, and formation thermal conductivity. In addition, consideration should be given as to the spacing between wellbores 2902, 2906 associated with adjacent heater wells 2900. This is demonstrated in FIGS. 32A and 32B.

Figure 32A:
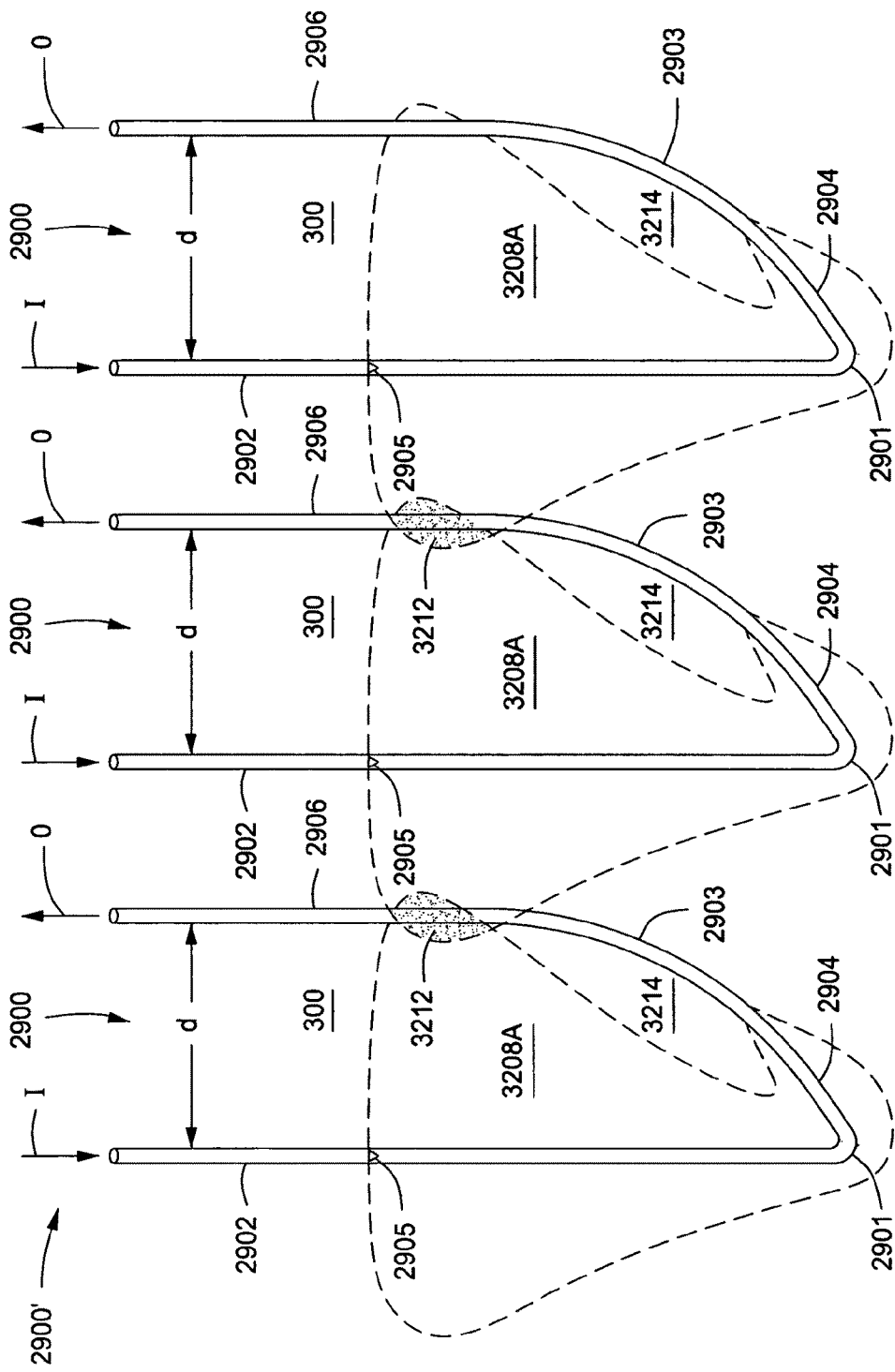
FIG. 32A is a side view of a row of three heater well arrangements from FIG. 29A, disposed in a plane. The three heater wells are placed generally end-to-end in order to heat a formation along a desired direction. A poor pyrolysis zone is shown formed around the heater wells.

FIG. 32A is a side view of three co-planar heater wells 2900 from FIG. 29A. The three heater wells 2900 are placed generally end-to-end in order to heat a formation 300 along a desired direction. This is different from the array 2900' of FIG. 31 where the heater wells 2900 are side-by-side. Of course, in operation the field designer will create an array that places heater wells 2900 both side-by-side and end-to-end.

In the wells 2900 of FIG. 32A, a burner 2905 is seen within each of the first wellbores 2902. The burners 2905 are used to cause heat to emanate from the wells 2900, thereby conductively forming a pyrolysis zone. A pyrolysis zone is seen at 3208A.

A profile of the pyrolysis zone 3208A is seen around each heater well 2900. This is a "snapshot" of the zone 3208A taken as a result of a heating process. It can be seen that the pyrolysis zone 3208A creates a poor heat front across the formation 300. The pyrolysis zone 3208A includes undesirable regions of overheating and underheating. Regions of overheating are shown at 3212, while regions of underheating are shown at 3214. The overheated 3212 and underheated 3214 regions are a result of a placement of the burners 2905 too high in the first wellbore 2902, and/or placing the wells 2900 too closely together, and/or having a burner intensity that is too high.

It is acknowledged that as heating continues in the formation 300, the regions of underheating 3214 will eventually be heated and pyrolysis of formation hydrocarbons within the formation 300 will occur. However, at the same time the regions of overheating 3212 will undesirably grow. Thus, a poor fit of heat profiles will still result.

Figure 32B:
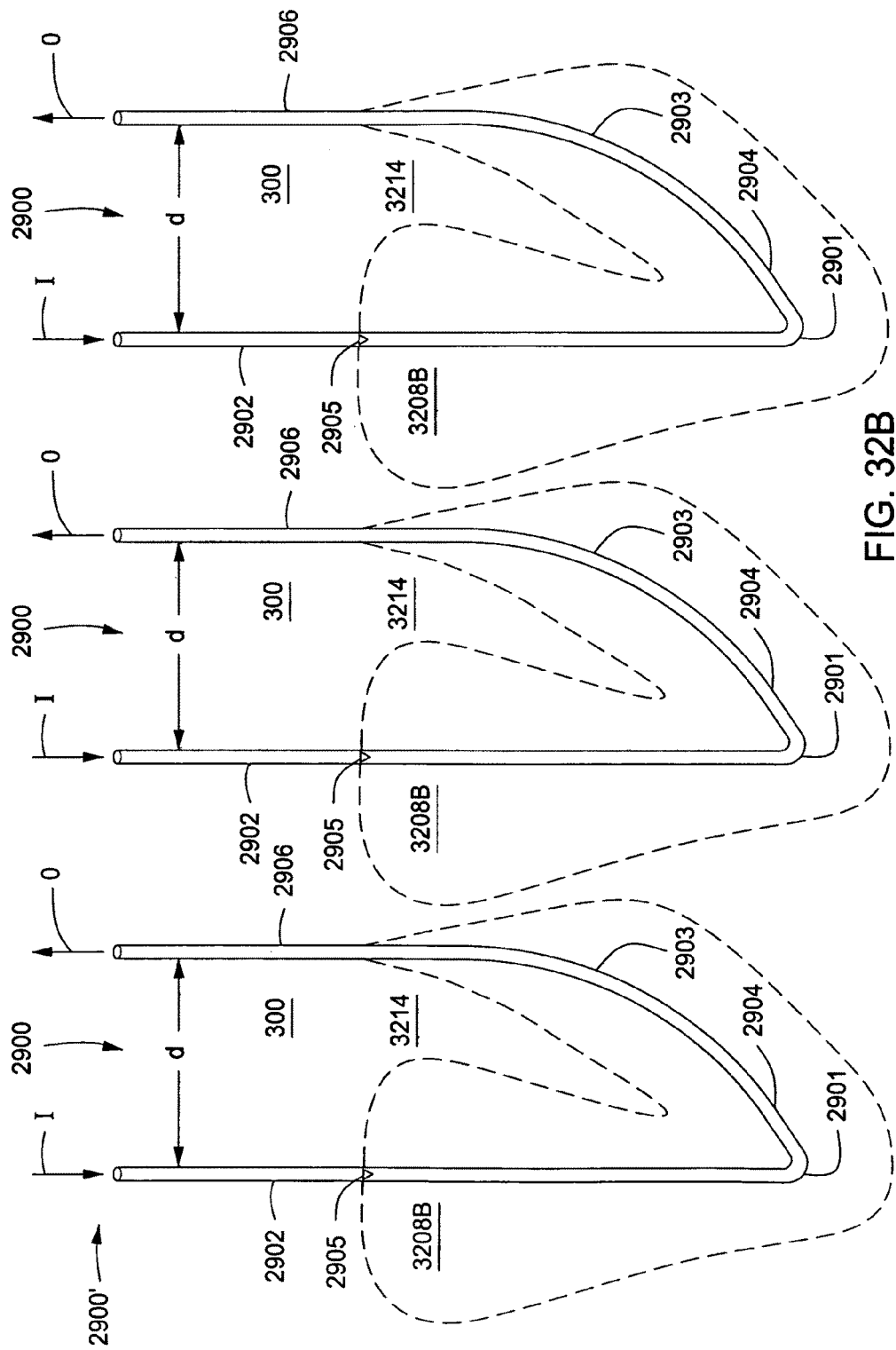
FIG. 32B is another side view of a row of heater wells of FIG. 29A, disposed in a plane. Here, a better pyrolysis zone is shown formed. The better pyrolysis zone produces smaller regions of underheating in comparison to the pyrolysis zone of FIG. 32A.

FIG. 32B is another side view of a series of co-planar heater wells 2900 of FIG. 29A. Here, a pyrolysis zone 3208B is formed as a result of heating from downhole burners 3205. In this instance a more uniform heat front is formed across the formation 300. There is no region of overheating 3212 as seen in FIG. 32A. Only a very small region of underheating 3214 is left between the wellbores 2902, 2906. Further, these regions 3214 will smoothly close off as heating continues. This beneficial pyrolysis zone 3208B is produced because the two wellbores 2902, 2906 in each heater well 2900 are properly spaced. In addition, the burners 2905 are at the right depth or location within the first wellbore 2902. In addition, the burners 2905 are at the correct intensity based upon the air "A" and fuel "CF" injection rates and compositions.

It is noted that the same illustration of heat profile generation demonstrated in FIGS. 32A and 32B where the heater wells 2900 are in end-to-end relation could be made in connection with heater wells 2900 that are in side-by-side relation. In addition, these concepts could be combined in a full array of heater wells 2900 that are in both end-to-end and side-to-side relation. This is demonstrated in FIG. 33.

Figure 33:
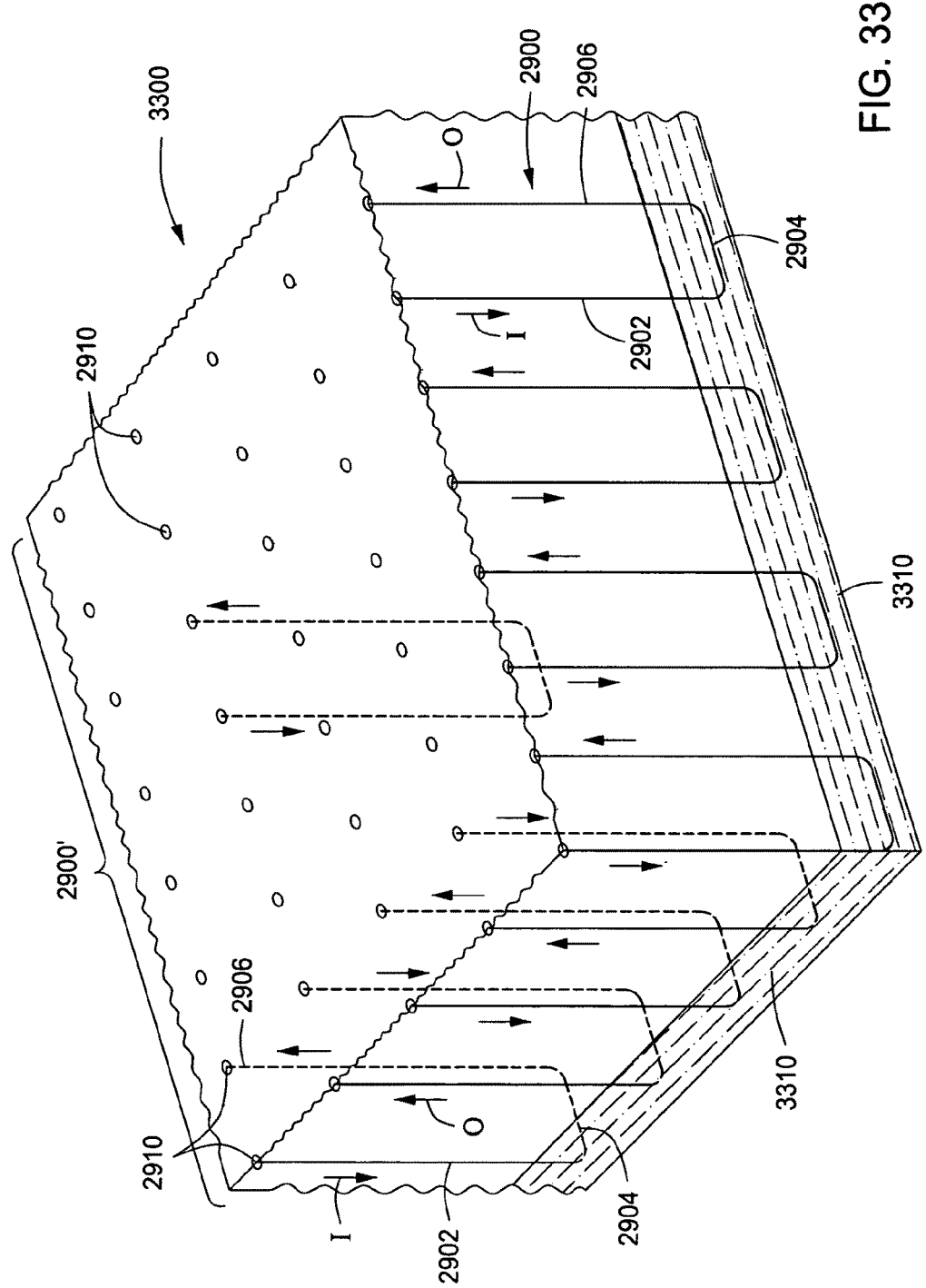
FIG. 33 is another perspective view of a plurality of heater wells of FIG. 29A. The heater wells are in a large array within a hydrocarbon development area.

FIG. 33 provides a perspective view of a plurality of heater wells 2900 of FIG. 29A. The wells 2900 make up a large array 2900' comprised of rows and columns. The array 2900' is provided within a hydrocarbon development area 3300. The hydrocarbon development area 3300 is for the purpose of extracting pyrolyzed hydrocarbon fluids from an organic-rich rock formation 3310.

In FIG. 33, some of the heater wells 2900 are seen in phantom. In some instances only wellheads 2910 are shown. However, it is understood that each heater well 2900 will have hardware for injecting a combustible fuel and an oxidant into a first wellbore 2902, a burner (shown at 2905 in FIG. 29A) proximate the subsurface formation 3310, and a second wellbore 2906. In addition, a horizontal portion 2904 of each of the first wellbores 2902 provides fluid communication with respective second wellbores 2906.

It can be seen from FIG. 33 that the heater wells 2900 are aligned both in side-by-side relation and in end-to-end relation. In each instance, the relationship of first wellbores 2902 to second wellbores 2906 is alternating. This is indicated by the arrows "I" and "O," which are seen to be alternating. A spacing between each of the first 2902 and second 2906 wellbores is selected so that following the circulation of heated flue gas through the respective heater wells 2900 for a period of time, a first pyrolysis zone from the first wellbore 2902 mates with a second pyrolysis zone from the second wellbore 2906 in such a manner that (i) a substantially continuous pyrolysis zone of formation hydrocarbons is formed within a substantial portion of the organic-rich rock formation 3310 between the first 2902 and second 2906 wellbores. In one aspect, as a result of circulation, (ii) the combustion products are above a pyrolysis temperature in each of the respective second wellbores 2906 at or just below the approximate depth of the at least one combustion burner 2905 in corresponding first wellbores 2902, and fall below a pyrolysis temperature in each of the respective second wellbores 2906 at or just above the approximate depth of the at least one combustion burner in the corresponding first wellbores 2902.

Returning to FIG. 29A, those of ordinary skill in the art will appreciate that the flame generated from hardware such as a downhole combustion burner 2905 generates a flame that can be extremely hot. As noted above, this creates a point of very high heat which then quickly diminishes as the flue gas "FG" is circulated through the heater well 2900. To mitigate this effect, it is proposed in some embodiments to use cowls at or below the burner 2905.

Figure 34:
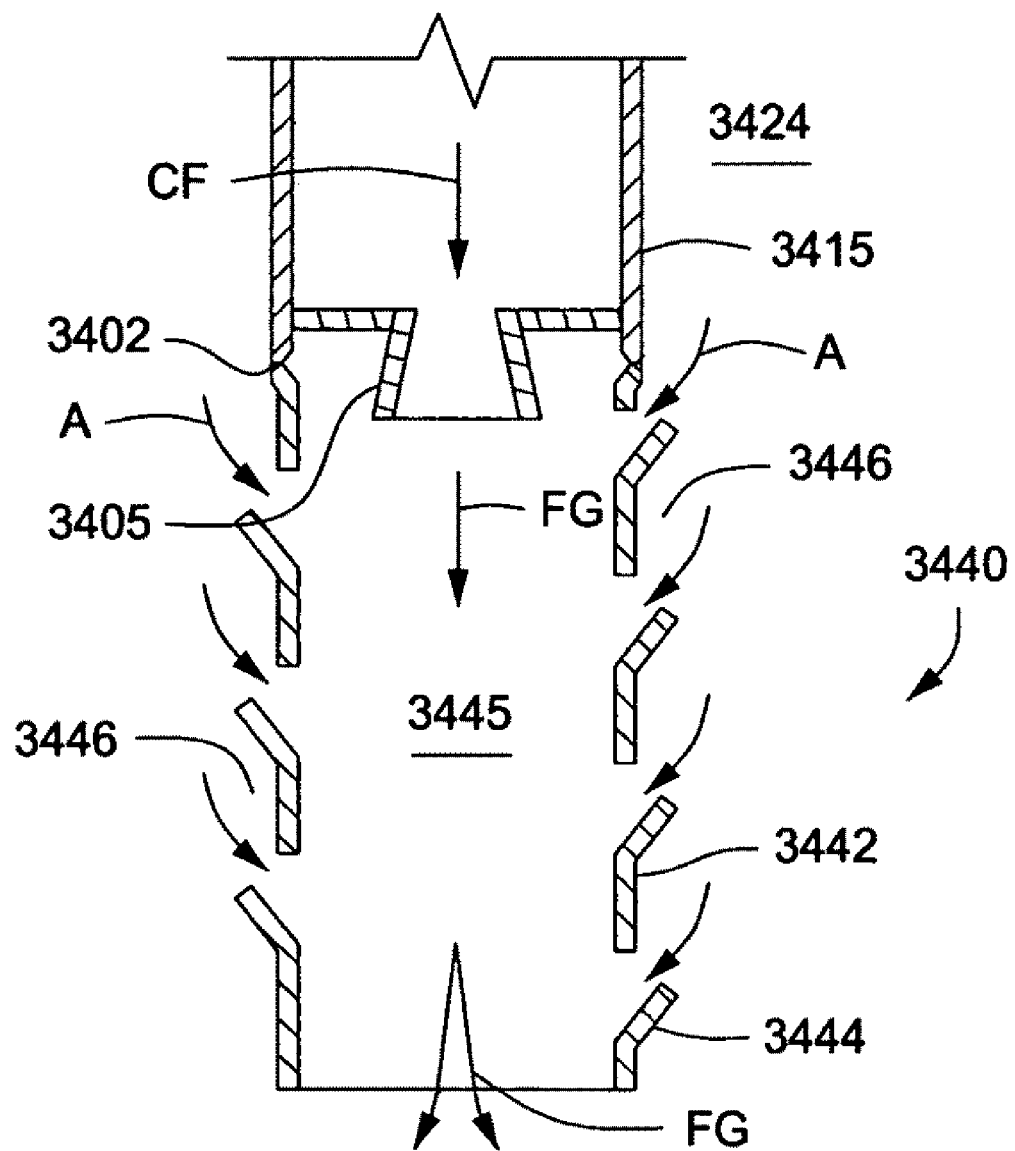
FIG. 34 is a cross-sectional side view of a burner at the end of a tubular member. A cowl is seen adjacent the burner for mitigating heat.

FIG. 34 shows a side view of a burner 3405 disposed at the bottom 3402 of an elongated tubular member 3415. A cowl 3440 is positioned immediately below the burner 3405. The cowl 3440 is preferably fabricated from a heat-resistant material such as ceramic, a tempered steel, or a refractory metal.

The cowl 3440 is a tubular body having a wall 3442 and a bore 3445 therein. The wall 3442 has a plurality of perforations or vents 3446 that provide fluid communication between an inner bore 3445 of the cowl 3440 and a surrounding outer region or annulus 3424. In the illustrative cowl 3440 of FIG. 34, flanges 3444 extend outwardly from the wall 3442 to create vents 3446. The vents 3446 receive air, indicated at arrow "A," from the annulus 3424. The air "A," in turn, mixes with combustible fuel, shown at arrow "CF," to enable the burner 3405 to create a flame. Although not depicted in FIG. 34, the arrangement of the air "A" and combustible fuel "CF" may be reversed such that the vents 3446 receive combustible fuel from the surrounding annulus 3424 which mixes with air from the burner 3405 orifice within the inner bore 3445 to enable the burner 3405 to create a flame.

The use of cowls 3440 helps to contain radiant heat from the burner 3405 and to cool the hot flue gases "FG" with air "A." In this respect, the cowls 3440 employ an elongated body 3442 which insulates the surrounding casing from immediate contact with the flames. The elongated body 3442 provides for a more uniform heat distribution from the flames to the surrounding casing (not shown) and, ultimately, the organic-rich rock formation 300. Because of the thermally insulative effect of the cowl 3440, only the cowl 3440 and, perhaps, a relatively short length of the surrounding casing need be constructed from a highly temperature-resistant material.

Additional approaches may be taken to provide for a more uniform heat distribution from the flames to the surrounding casing string (such as casing 302 of FIG. 30) and, ultimately, the organic-rich rock formation 300. In one aspect, the relative volume of air "A" injected into the annulus 3424 may be increased. For example, the air "A" may be injected at about 1.25 to 6.0 times the stoichiometric combustion amount.

In connection with the heater well 2900 and FIGS. 29A and 32B, various methods for in situ heating of a targeted organic-rich rock formation 300 are provided. In these methods, the organic-rich rock formation 300 preferably comprises oil shale. In one embodiment, the method includes the step of providing a first wellbore 2902 extending to the targeted organic-rich rock formation 300. The first wellbore 2902 has a lower end 2901. The method also includes providing a second wellbore 2906 also having a lower end 2903. The lower end of the second wellbore 2906 intersects with the lower end 2901 of the first wellbore 2902 through a deviated portion 2904. In this way, fluid communication between the first 2902 and second 2906 wellbores is created.

The method also includes providing a burner 2905 along the first wellbore 2902. The burner 2905 is preferably disposed above the lower end 2901 of the first wellbore 2902. The method also includes the step of injecting air "A" and a combustible fuel "CF" into the first wellbore 2902 and through the burner 2905 so as to combust the combustible fuel "CF." The air "A" and the combustible fuel "CF" combust at substantially the depth of the organic-rich rock formation 300 to form hot flue gas "FG." The flue gas "FG" generated from the burner 2905 is circulated through the deviated portion 2904 and the second wellbore 2906.

The first wellbore 2902 is preferably completed horizontally, thereby defining a heel 2901 and a toe 2903. The second wellbore 2906 is preferably completed substantially vertically. In any arrangement, the combustion products are circulated into and up the second wellbore 2906. A heat profile is created from the first wellbore 2902 and second wellbore 2906 that provides substantially complete pyrolysis of the organic-rich rock formation between the first wellbore 2902 and the second wellbore 2906. Preferably, the heat profile defines a pyrolysis zone 2908A that is substantially uniform.

Igniting the burner 2905 creates a flame. In one aspect, the flame and the circulation of heated air "A" through the heater well 2900 cause the targeted organic-rich rock formation 300 to be heated to between about 300° C. and 700° C. between the heel 2901 and the toe 2903.

Preferably, the flue gas "FG" or combustion products in the second wellbore 2906 are above a pyrolysis temperature up to an approximate depth of the hardware 2905 in the first wellbore 2902. Alternatively, the flue gas "FG" or combustion products in the second wellbore 2906 fall below a pyrolysis temperature at or just above the depth of the hardware 2905 in the first wellbore 2902.

In one embodiment, the method further includes heating oil shale in the formation 300 in order to pyrolyze at least a portion of the oil shale into hydrocarbon fluids. The hydrocarbon fluids may include gas. The gas is produced and then used as part of the combustible fuel "CF." In this instance, the method preferably further includes treating the hydrocarbon fluids in order to substantially remove $H_2S$ from the gas before injecting the gas into the first wellbore 2902. In one aspect, the combustible fuel "CF" is a fuel gas. The method may then further include controlling the intensity of the burner 2905 by adjusting the composition of the fuel gas "CF."

As noted, the flue gas "FG" is circulated to the surface. The flue gas "FG" may be vented to the atmosphere. In this instance, the method may further include the step of treating the flue gas "FG" to remove $NO_x$ components prior to venting the received flue gas "FG" to the atmosphere. Alternatively, if the flue gas "FG" still has significant oxygen content or significant fuel content, the flue gas "FG" may be redirected to be used as an oxidant or fuel supply for another well or surface combustor.

In certain embodiments, excess air "A" is injected to cool the flame, reduce $NO_x$, and improve transfer of heat away from the burner 2905. In other embodiments, excess fuel "CF" is injected. Use of excess fuel can reduce compression costs since typically fuel is available at pressure whereas air "A" is only available at atmospheric conditions. However, when using excess fuel "CF" it is generally desirable to insure that no uncombusted fuel is vented to the environment with the combustion products.

When excess air "A" is used, the flue gas "FG" may be collected and, optionally, compressed. The flue gas "FG" containing oxygen, preferably >10 mol %, may be mixed with compressed air "A." The mixture may then be delivered back into the first wellbore 2902 (or into another input "I" wellbore) as air "A." Recapturing the flue gas "FG" allows the step of injecting the air "A" to use the pressure from the flue gas "FG," thereby reducing compression needs at the heater well 2900. In certain cases, the flue gas "FG" may be useable without mixing with compressed air.

In another aspect, the collected flue gas "FG" is compressed. The flue gas "FG" containing combustible gases, preferably >25 mol %, may then be mixed with compressed fuel. The mixture may then be delivered back into the tubular member 2902 together as combustible fuel "CF." The combustible fuel "CF" is preferably injected into the first wellbore 2902 under pressure. In one aspect, the combustible fuel "CF" is injected under a pressure of greater than about 200 psia. In another aspect, the combustible fuel "CF" is injected under a pressure of greater than about 600 psia. In still another aspect, the combustible fuel "CF" is injected under a pressure of only about to 200 psia. In certain cases, the flue gas may be useable without mixing with compressed fuel.

When excess fuel "CF" is used, the collected flue gas "FG" may alternatively be directed to another well as a fuel stream. In such a case, the flue gas "FG" still has combustible components in it. The flue gas "FG" may be first treated to remove free water prior to reuse. The flue gas "FG" may also be recompressed. Alternatively, the flue gas "FG" may be used at the surface to fire turbines or to generate steam. If the fuel components in the flue gas "FG" are in low concentration, catalytic burners may be used to improve combustion performance of these low BTU mixtures.

When excess fuel "CF" is used, it may be desirable to switch the air "A" and fuel "CF" flow. This means that air "A" will flow through the inner tubular 305 and fuel through the annulus 308. A flame generated by this method is a so-called "reverse diffusion" flame and can lead to lower $NO_x$ generation in certain cases.

In another aspect, the flue gas "FG" is again collected from the heater well 2900 at the surface. The method may then include the step of monitoring the collected flue gas "FG" for the presence of combustible species to assess whether the burner 2905 is firing properly. The combustible species may comprise at least one of methane, ethane, hydrogen ($H_2$), and carbon monoxide.

In one embodiment, the method further comprises reversing the inlet and outlet functions of the two wellbores 2902 and 2906 after the targeted organic-rich rock formation 300 has been heated for a period of time. For example, heating may take place for a period of time sufficient to begin pyrolyzing kerogen existing in the formation adjacent the first wellbore 2902 both above the heel 2901 and towards the toe 2903. Thereafter, air "A" and the combustible fuel "CF" are injected into the second wellbore 2906 and through a burner in the second wellbore 2906 so as to combust the combustible fuel "CF" and to further heat the targeted organic-rich rock formation 300 adjacent the second wellbore 2906 and towards the heel 2901 of the first wellbore 2902. Flue gas "FG" generated from the burner 2905 is circulated through the first wellbore 2902 and to the surface. The burner (not shown) in the second wellbore 2906 may be placed during initial instillation of the well or when the reversal occurs. The burner 2905 in the first wellbore 2902 may be left in place or removed when the reversal occurs.

Different sizes of burners 2905 may be employed in the heater well 2900. The size will depend on the length of the portion of the formation to be heated. For example, the burner

2905 may supply about 0.5 to 3 kW of thermal energy per meter of formation to be heated, or more preferably 1.0 to 2.5 kW/m of thermal energy.

It is desirable to control the heat conducted into the formation 300. Thus, in one embodiment the position of the burner 2905, the rate of injecting the combustible fuel "CF," the rate of injecting the air "A," or combinations thereof, are controlled so that the temperature of the flue gas "FG" traveling into the second wellbore 2906 is about 300° C. to 700° C. across a majority of the organic-rich rock formation 300. The rate of injecting the combustible fuel "CF" may be reduced over time.

In one embodiment, the combustible fuel "CF" is a fuel gas such as natural gas. The intensity of the burner 2905 is then controlled by adjusting the composition of the fuel gas. For instance, natural gas may be used as the fuel gas and diluted with added inert components. The added inert components may comprise at least one of carbon dioxide ($CO_2$) or nitrogen ($N_2$). Reducing flame intensity can lead to reduced $NO_x$ generation.

Another method for heating a subsurface formation is provided which uses a plurality 2900' of heater wells 2900. In this embodiment, the first wellbore 2902, the second wellbore 2906, and the burner 2905 define a first heater well 2900. A plurality 2900' of additional heater wells 2900 is then provided, each of which also comprises a first wellbore 2902, a second wellbore 2906, and a burner 2905 within the first wellbore 2902. The method further includes arranging the first heater well 2900 and the plurality 2900' of additional heater wells 2900 such that the respective first wellbores 2902 and the respective second wellbores 2906 are in alternating relation. Air "A" and a combustible fuel "CF" are injected into the first wellbore 2902 and through the burner 2905 of each of the respective plurality 2900' of additional heater wells 2900 so as to combust the combustible fuel "CF" within the plurality 2900' of additional heater wells 2900. Flue gas "FG" generated from each of the burners 2905 is circulated through the respective second wellbores 2906 of the plurality 2900' of additional heater wells 2900 and to the surface.

Certain features of the present inventions relate to improving the performance of downhole burners for heating organic-rich rock formations by extending the region of heating and providing for more uniform heating. In addition, certain features of the present inventions relate to reducing or mitigating maximum temperatures. Reducing maximum temperatures reduces the needs for using costly temperature-resistant materials in the well construction. Reducing maximum temperatures also avoids certain problems posed by high temperatures in a heater well. For example, the presence of very high temperatures can lead to inefficient heating of the subsurface, causing certain areas to become much hotter than required for pyrolysis to occur, or causing pyrolysis to take place at an undesirably high rate in certain regions of a formation. Reducing the temperature also allows $NO_x$ emissions to be reduced. By circulating heated flue gas through adjacent wellbores and conducting thermal energy from each wellbore into the selected organic-rich rock formation, a more uniform heating is achieved over a subsurface region.

Wobbe Index (WI) is often used as a key measure of fuel quality. WI is equal to the ratio of the lower heating value to the square root of the gas specific gravity. Fuel quality control may be useful for shale oil developments where the produced gas composition may change over the life of the field and where the gas typically has significant amounts of $CO_2$, CO, and $H_2$ in addition to light hydrocarbons. Commercial scale oil shale retorting is expected to produce a gas composition that changes with time.

Achieving a certain hydrogen content for low-BTU fuels may be desirable to achieve appropriate burn properties. In certain embodiments of the processes herein, the $H_2$ content of the fuel gas is adjusted via separation or addition in the surface facilities to optimize burner performance. Adjustment of $H_2$ content in non-shale oil surface facilities utilizing low BTU fuels has been discussed in the patent literature (e.g., U.S. Pat. No. 6,684,644 and U.S. Pat. No. 6,858,049, the entire disclosures of which are hereby incorporated by reference).

The process of heating formation hydrocarbons within an organic-rich rock formation, for example, by pyrolysis, may generate fluids. The heat-generated fluids may include water which is vaporized within the formation. In addition, the action of heating kerogen produces pyrolysis fluids which tend to expand upon heating. The produced pyrolysis fluids may include not only water, but also, for example, hydrocarbons, oxides of carbon, ammonia, molecular nitrogen, and molecular hydrogen. Therefore, as temperatures within a heated portion of the formation increase, a pressure within the heated portion may also increase as a result of increased fluid generation, molecular expansion, and vaporization of water. Thus, some corollary exists between subsurface pressure in an oil shale formation and the fluid pressure generated during pyrolysis. This, in turn, indicates that formation pressure may be monitored to detect the progress of a kerogen conversion process.

The pressure within a heated portion of an organic-rich rock formation depends on other reservoir characteristics. These may include, for example, formation depth, distance from a heater well, a richness of the formation hydrocarbons within the organic-rich rock formation, the degree of heating, and/or a distance from a producer well.

It may be desirable for the developer of an oil shale field to monitor formation pressure during development. Pressure within a formation may be determined at a number of different locations. Such locations may include, but may not be limited to, at a wellhead and at varying depths within a wellbore. In some embodiments, pressure may be measured at a producer well. In an alternate embodiment, pressure may be measured at a heater well. In still another embodiment, pressure may be measured downhole of a dedicated monitoring well.

The process of heating an organic-rich rock formation to a pyrolysis temperature range not only will increase formation pressure, but will also increase formation permeability. The pyrolysis temperature range should be reached before substantial permeability has been generated within the organic-rich rock formation. An initial lack of permeability may prevent the transport of generated fluids from a pyrolysis zone within the formation. In this manner, as heat is initially transferred from a heater well to an organic-rich rock formation, a fluid pressure within the organic-rich rock formation may increase proximate to that heater well. Such an increase in fluid pressure may be caused by, for example, the generation of fluids during pyrolysis of at least some formation hydrocarbons in the formation.

Alternatively, pressure generated by expansion of pyrolysis fluids or other fluids generated in the formation may be allowed to increase. This assumes that an open path to a production well or other pressure sink does not yet exist in the formation. In one aspect, a fluid pressure may be allowed to increase to or above a lithostatic stress. In this instance, fractures in the hydrocarbon containing formation may form when the fluid pressure equals or exceeds the lithostatic stress. For example, fractures may form from a heater well to a production well. The generation of fractures within the heated portion may reduce pressure within the portion due to the production of produced fluids through a production well.

Once pyrolysis has begun within an organic-rich rock formation, fluid pressure may vary depending upon various factors. These include, for example, thermal expansion of hydrocarbons, generation of pyrolysis fluids, rate of conversion, and withdrawal of generated fluids from the formation. For example, as fluids are generated within the formation, fluid pressure within the pores may increase. Removal of generated fluids from the formation may then decrease the fluid pressure within the near wellbore region of the formation.

In certain embodiments, a mass of at least a portion of an organic-rich rock formation may be reduced due, for example, to pyrolysis of formation hydrocarbons and the production of hydrocarbon fluids from the formation. As such, the permeability and porosity of at least a portion of the formation may increase. Any in situ method that effectively produces oil and gas from oil shale will create permeability in what was originally a very low permeability rock. The extent to which this will occur is illustrated by the large amount of expansion that must be accommodated if fluids generated from kerogen are unable to flow. The concept is illustrated in FIG. 5.

Figure 5:
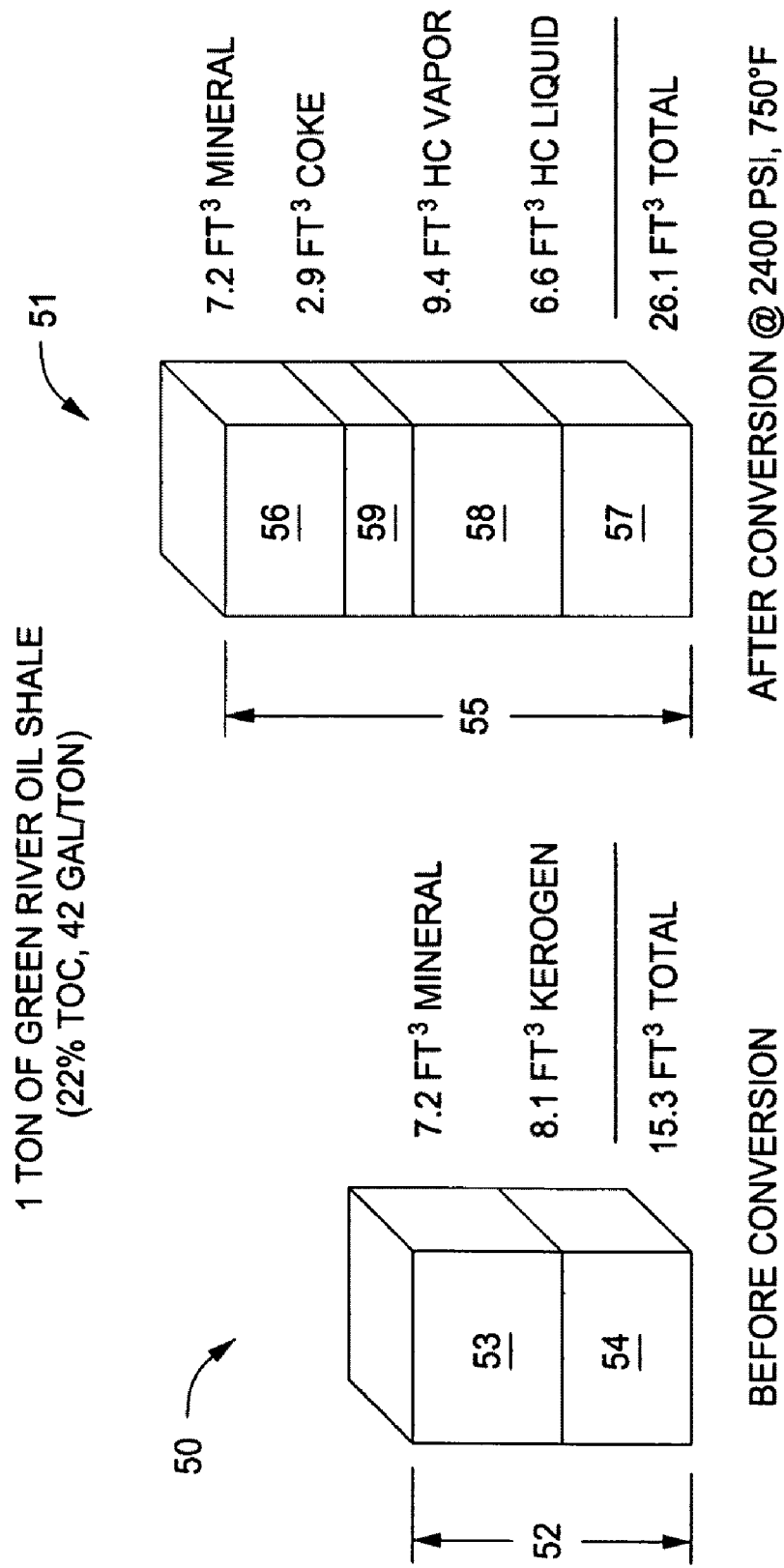
FIG. 5 is a bar chart comparing one ton of Green River oil shale before and after a simulated in situ, retorting process.

FIG. 5 provides a bar chart comparing one ton of Green River oil shale before 50 and after 51 a simulated in situ, retorting process. The simulated process was carried out at 2,400 psi and 750° F. on oil shale having a total organic carbon content of 22 wt. % and a Fisher assay of 42 gallons/ton. Before the conversion, a total of 15.3 ft$^3$ of rock matrix 52 existed. This matrix comprised 7.2 ft$^3$ of mineral 53, i.e., dolomite, limestone, etc., and 8.1 ft$^3$ of kerogen 54 imbedded within the shale. As a result of the conversion the material expanded to 26.1 ft$^3$ 55. This represented 7.2 ft$^3$ of mineral 56 (the same number as before the conversion), 6.6 ft$^3$ of hydrocarbon liquid 57, 9.4 ft$^3$ of hydrocarbon vapor 58, and 2.9 ft$^3$ of coke 59. It can be seen that substantial volume expansion occurred during the conversion process. This, in turn, increases permeability of the rock structure.

In an embodiment, heating a portion of an organic-rich rock formation in situ to a pyrolysis temperature may increase permeability of the heated portion. For example, permeability may increase due to formation of thermal fractures within the heated portion caused by application of heat. As the temperature of the heated portion increases, water may be removed due to vaporization. The vaporized water may escape and/or be removed from the formation. In addition, permeability of the heated portion may also increase as a result of production of hydrocarbon fluids from pyrolysis of at least some of the formation hydrocarbons within the heated portion on a macroscopic scale.

Certain systems and methods described herein may be used to treat formation hydrocarbons in at least a portion of a relatively low permeability formation (e.g., in "tight" formations that contain formation hydrocarbons). Such formation hydrocarbons may be heated to pyrolyze at least some of the formation hydrocarbons in a selected zone of the formation. Heating may also increase the permeability of at least a portion of the selected zone. Hydrocarbon fluids generated from pyrolysis may be produced from the formation, thereby further increasing the formation permeability.

Permeability of a selected zone within the heated portion of the organic-rich rock formation may also rapidly increase while the selected zone is heated by conduction. For example, permeability of an impermeable organic-rich rock formation may be less than about 0.1 millidarcy before heating. In some embodiments, pyrolyzing at least a portion of organic-rich rock formation may increase permeability within a selected zone of the portion to greater than about 10 millidarcies, 100 millidarcies, 1 Darcy, 10 Darcies, 20 Darcies, or 50 Darcies. Therefore, a permeability of a selected zone of the portion may increase by a factor of more than about 10, 100, 1,000, 10,000, or 100,000. In one embodiment, the organic-rich rock formation has an initial total permeability less than 1 millidarcy, alternatively less than 0.1 or 0.01 millidarcies, before heating the organic-rich rock formation. In one embodiment, the organic-rich rock formation has a post heating total permeability of greater than 1 millidarcy, alternatively, greater than 10, 50 or 100 millidarcies, after heating the organic-rich rock formation.

In connection with heating the organic-rich rock formation, the organic-rich rock formation may optionally be fractured to aid heat transfer or hydrocarbon fluid production. In one instance, fracturing may be accomplished naturally by creating thermal fractures within the formation through application of heat. Thermal fracture formation is caused by thermal expansion of the rock and fluids and by chemical expansion of kerogen transforming into oil and gas. Thermal fracturing can occur both in the immediate region undergoing heating, and in cooler neighboring regions. The thermal fracturing in the neighboring regions is due to propagation of fractures and tension stresses developed due to the expansion in the hotter zones. Thus, by both heating the organic-rich rock and transforming the kerogen to oil and gas, the permeability is increased not only from fluid formation and vaporization, but also via thermal fracture formation. The increased permeability aids fluid flow within the formation and production of the hydrocarbon fluids generated from the kerogen.

In addition, a process known as hydraulic fracturing may be used. Hydraulic fracturing is a process known in the art of oil and gas recovery where a fracture fluid is pressurized within the wellbore above the fracture pressure of the formation, thus developing fracture planes within the formation to relieve the pressure generated within the wellbore. Hydraulic fractures may be used to create additional permeability and/or be used to provide an extended geometry for a heater well. The WO 2005/010320 patent publication incorporated above describes one such method.

In connection with the production of hydrocarbons from a rock matrix, particularly those of shallow depth, a concern may exist with respect to earth subsidence. This is particularly true in the in situ heating of organic-rich rock where a portion of the matrix itself is thermally converted and removed. Initially, the formation may contain formation hydrocarbons in solid form, such as, for example, kerogen. The formation may also initially contain water-soluble minerals. Initially, the formation may also be substantially impermeable to fluid flow.

The in situ heating of the matrix pyrolyzes at least a portion of the formation hydrocarbons to create hydrocarbon fluids. This, in turn, creates permeability within a matured (pyrolyzed) organic-rich rock zone in the organic-rich rock formation. The combination of pyrolyzation and increased permeability permits hydrocarbon fluids to be produced from the formation. At the same time, the loss of supporting matrix material also creates the potential for subsidence relative to the earth surface.

In some instances, subsidence is sought to be minimized in order to avoid environmental or hydrogeological impact. In this respect, changing the contour and relief of the earth surface, even by a few inches, can change runoff patterns, affect vegetation patterns, and impact watersheds. In addition, subsidence has the potential of damaging production or heater wells formed in a production area. Such subsidence can create damaging hoop and compressional stresses on wellbore casings, cement jobs, and equipment downhole.

In order to avoid or minimize subsidence, it is proposed to leave selected portions of the formation hydrocarbons substantially unpyrolyzed. This serves to preserve one or more unmatured, organic-rich rock zones. In some embodiments, the unmatured organic-rich rock zones may be shaped as substantially vertical pillars extending through a substantial portion of the thickness of the organic-rich rock formation.

The heating rate and distribution of heat within the formation may be designed and implemented to leave sufficient unmatured pillars to prevent subsidence. In one aspect, heat injection wellbores are formed in a pattern such that untreated pillars of oil shale are left therebetween to support the overburden and prevent subsidence.

It is preferred that thermal recovery of oil and gas be conducted before any solution mining of nahcolite or other water-soluble minerals present in the formation. Solution mining can generate large voids in a rock formation and collapse breccias in an oil shale development area. These voids and brecciated zones may pose problems for in situ and mining recovery of oil shale, further increasing the utility of supporting pillars.

In some embodiments, compositions and properties of the hydrocarbon fluids produced by an in situ conversion process may vary depending on, for example, conditions within an organic-rich rock formation. Controlling heat and/or heating rates of a selected section in an organic-rich rock formation may increase or decrease production of selected produced fluids.

In some embodiments, a heater well may be turned down and/or off after an average temperature in a formation may have reached a selected temperature. Turning down and/or off the heater well may reduce input energy costs, substantially inhibit overheating of the formation, and allow heat to substantially transfer into colder regions of the formation.

Temperature (and average temperatures) within a heated organic-rich rock formation may vary, depending on, for example, proximity to a heater well, thermal conductivity and thermal diffusivity of the formation, type of reaction occurring, type of formation hydrocarbon, and the presence of water within the organic-rich rock formation. At points in the field where monitoring wells are established, temperature measurements may be taken directly in the wellbore. Further, at heater wells the temperature of the immediately surrounding formation is fairly well understood. However, it is desirable to interpolate temperatures to points in the formation intermediate temperature sensors and heater wells.

In accordance with one aspect of the production processes of the present inventions, a temperature distribution within the organic-rich rock formation may be computed using a numerical simulation model. The numerical simulation model may calculate a subsurface temperature distribution through interpolation of known data points and assumptions of formation conductivity. In addition, the numerical simulation model may be used to determine other properties of the formation under the assessed temperature distribution. For example, the various properties of the formation may include, but are not limited to, permeability of the formation. In a simpler context, temperature sensors may be placed along the wellbores 2902, 2904, 2906.

The numerical simulation model may also include assessing various properties of a fluid formed within an organic-rich rock formation under the assessed temperature distribution. For example, the various properties of a formed fluid may include, but are not limited to, a cumulative volume of a fluid formed in the formation, fluid viscosity, fluid density, and a composition of the fluid formed in the formation. Such a simulation may be used to assess the performance of a commercial-scale operation or small-scale field experiment. For example, a performance of a commercial-scale development may be assessed based on, but not limited to, a total volume of product that may be produced from a research-scale operation.

Some embodiments include producing at least a portion of the hydrocarbon fluids from the organic-rich rock formation. The hydrocarbon fluids may be produced through production wells. Production wells may be cased or uncased wells and drilled and completed through methods known in the art.

Some embodiments further include producing a production fluid from the organic-rich rock formation where the production fluid contains the hydrocarbon fluids and an aqueous fluid. The aqueous fluid may contain water-soluble minerals and/or migratory contaminant species. In such case, the production fluid may be separated into a hydrocarbon stream and an aqueous stream at a surface facility. Thereafter the water-soluble minerals and/or migratory contaminant species may be recovered from the aqueous stream. This embodiment may be combined with any of the other aspects of the invention discussed herein.

The produced hydrocarbon fluids may include a pyrolysis oil component (or condensable component) and a pyrolysis gas component (or non-condensable component). Condensable hydrocarbons produced from the formation will typically include paraffins, cycloalkanes, mono-aromatics, and di-aromatics as components. Such condensable hydrocarbons may also include other components such as tri-aromatics and other hydrocarbon species.

In certain embodiments, a majority of the hydrocarbons in the produced fluid may have a carbon number of less than approximately 25. Alternatively, less than about 15 weight % of the hydrocarbons in the fluid may have a carbon number greater than approximately 25. The non-condensable hydrocarbons may include, but are not limited to, hydrocarbons having carbon numbers less than 5.

In certain embodiments, the API gravity of the condensable hydrocarbons in the produced fluid may be approximately 20 or above (e.g., 25, 30, 40, 50, etc.). In certain embodiments, the hydrogen to carbon atomic ratio in produced fluid may be at least approximately 1.7 (e.g., 1.8, 1.9, etc.).

One embodiment of the invention includes an in situ method of producing hydrocarbon fluids with improved properties from an organic-rich rock formation. Applicants have surprisingly discovered that the quality of the hydrocarbon fluids produced from in situ heating and pyrolysis of an organic-rich rock formation may be improved by selecting sections of the organic-rich rock formation with higher lithostatic stress for in situ heating and pyrolysis.

The method may include in situ heating of a section of the organic-rich rock formation that has a high lithostatic stress to form hydrocarbon fluids with improved properties. The method may include creating the hydrocarbon fluid by pyrolysis of a solid hydrocarbon and/or a heavy hydrocarbon present in the organic-rich rock formation. Embodiments may include the hydrocarbon fluid being partially, predominantly or substantially completely created by pyrolysis of the solid hydrocarbon and/or heavy hydrocarbon present in the organic-rich rock formation. The method may include heating the section of the organic-rich rock formation by any method, including any of the methods described herein. For example, the method may include heating the section of the organic-rich rock formation by electrical resistance heating. Further, the method may include heating the section of the organic-rich rock formation through use of a heated heat transfer fluid. The method may include heating the section of the organic-rich rock formation to above 270° C. Alternatively, the method may include heating the section of the organic-rich rock formation between 270° C. and 500° C.

The method may include heating in situ a section of the organic-rich rock formation having a lithostatic stress greater than 200 psi and producing a hydrocarbon fluid from the heated section of the organic-rich rock formation. In alternative embodiments, the heated section of the organic-rich rock formation may have a lithostatic stress greater than 400 psi. In alternative embodiments, the heated section of the organic-rich rock formation may have a lithostatic stress greater than 800 psi, greater than 1,000 psi, greater than 1,200 psi, greater than 1,500 psi or greater than 2,000 psi. Applicants have found that in situ heating and pyrolysis of organic-rich rock formations with increasing amounts of stress lead to the production of hydrocarbon fluids with improved properties.

The lithostatic stress of a section of an organic-rich formation can normally be estimated by recognizing that it will generally be equal to the weight of the rocks overlying the formation. The density of the overlying rocks can be expressed in units of psi/ft. Generally, this value will fall between 0.8 and 1.1 psi/ft and can often be approximated as 0.9 psi/ft. As a result the lithostatic stress of a section of an organic-rich formation can be estimated by multiplying the depth of the organic-rich rock formation interval by 0.9 psi/ft. Thus the lithostatic stress of a section of an organic-rich formation occurring at about 1,000 ft can be estimated to be about (0.9 psi/ft) multiplied by (1,000 ft) or about 900 psi. If a more precise estimate of lithostatic stress is desired the density of overlying rocks can be measured using wireline logging techniques or by making laboratory measurements on samples recovered from coreholes. The method may include heating a section of the organic-rich rock formation that is located at a depth greater than 200 ft below the earth's surface. Alternatively, the method may include heating a section of the organic-rich rock formation that is located at a depth greater than 500 ft below the earth's surface, greater than 1,000 ft below the earth's surface, greater than 1,200 ft below the earth's surface, greater than 1,500 ft below the earth's surface, or greater than 2,000 ft below the earth's surface.

The organic-rich rock formation may be, for example, a heavy hydrocarbon formation or a solid hydrocarbon formation. Particular examples of such formations may include an oil shale formation, a tar sands formation or a coal formation. Particular formation hydrocarbons present in such formations may include oil shale, kerogen, coal, and/or bitumen.

The hydrocarbon fluid produced from the organic-rich rock formation may include both a condensable hydrocarbon portion (e.g. liquid) and a non-condensable hydrocarbon portion (e.g. gas). The hydrocarbon fluid may additionally be produced together with non-hydrocarbon fluids. Exemplary non-hydrocarbon fluids include, for example, water, carbon dioxide, hydrogen sulfide, hydrogen, ammonia, and/or carbon monoxide.

The condensable hydrocarbon portion of the hydrocarbon fluid may be a fluid present within different locations associated with an organic-rich rock development project. For example, the condensable hydrocarbon portion of the hydrocarbon fluid may be a fluid present within a production well that is in fluid communication with the organic-rich rock formation. The production well may serve as a device for withdrawing the produced hydrocarbon fluids from the organic-rich rock formation. Alternatively, the condensable hydrocarbon portion may be a fluid present within processing equipment adapted to process hydrocarbon fluids produced from the organic-rich rock formation. Exemplary processing equipment is described herein. Alternatively, the condensable hydrocarbon portion may be a fluid present within a fluid storage vessel. Fluid storage vessels may include, for example, fluid storage tanks with fixed or floating roofs, knock-out vessels, and other intermediate, temporary or product storage vessels. Alternatively, the condensable hydrocarbon portion may be a fluid present within a fluid transportation pipeline. A fluid transportation pipeline may include, for example, piping from production wells to processing equipment or fluid storage vessels, piping from processing equipment to fluid storage vessels, or pipelines associated with collection or transportation of fluids to or from intermediate or centralized storage locations.

The following discussion of FIGS. 7-16 concerns data obtained in Examples 1-5 which are discussed below in the section labeled "Experiments". The data was obtained through experimental procedures, gas and liquid sample collection procedures, hydrocarbon gas sample gas chromatography (GC) analysis methodology, gas sample GC peak integration methodology, gas sample GC peak identification methodology, whole oil gas chromatography (WOGC) analysis methodology, whole oil gas chromatography (WOGC) peak integration methodology, whole oil gas chromatography (WOGC) peak identification methodology, and pseudo component analysis methodology discussed in the Experiments section. For clarity, when referring to gas chromatography chromatograms of hydrocarbon gas samples, graphical data is provided for one unstressed experiment through Example 1, two 400 psi stressed experiments through Examples 2 and 3, and two 1,000 psi stressed experiments through Examples 4 and 5. When referring to whole oil gas chromatography (WOGC) chromatograms of liquid hydrocarbon samples, graphical data is provided for one unstressed experiment through Example 1, one 400 psi stressed experiments through Example 3, and one 1,000 psi stressed experiment through Example 4.

Figure 7:
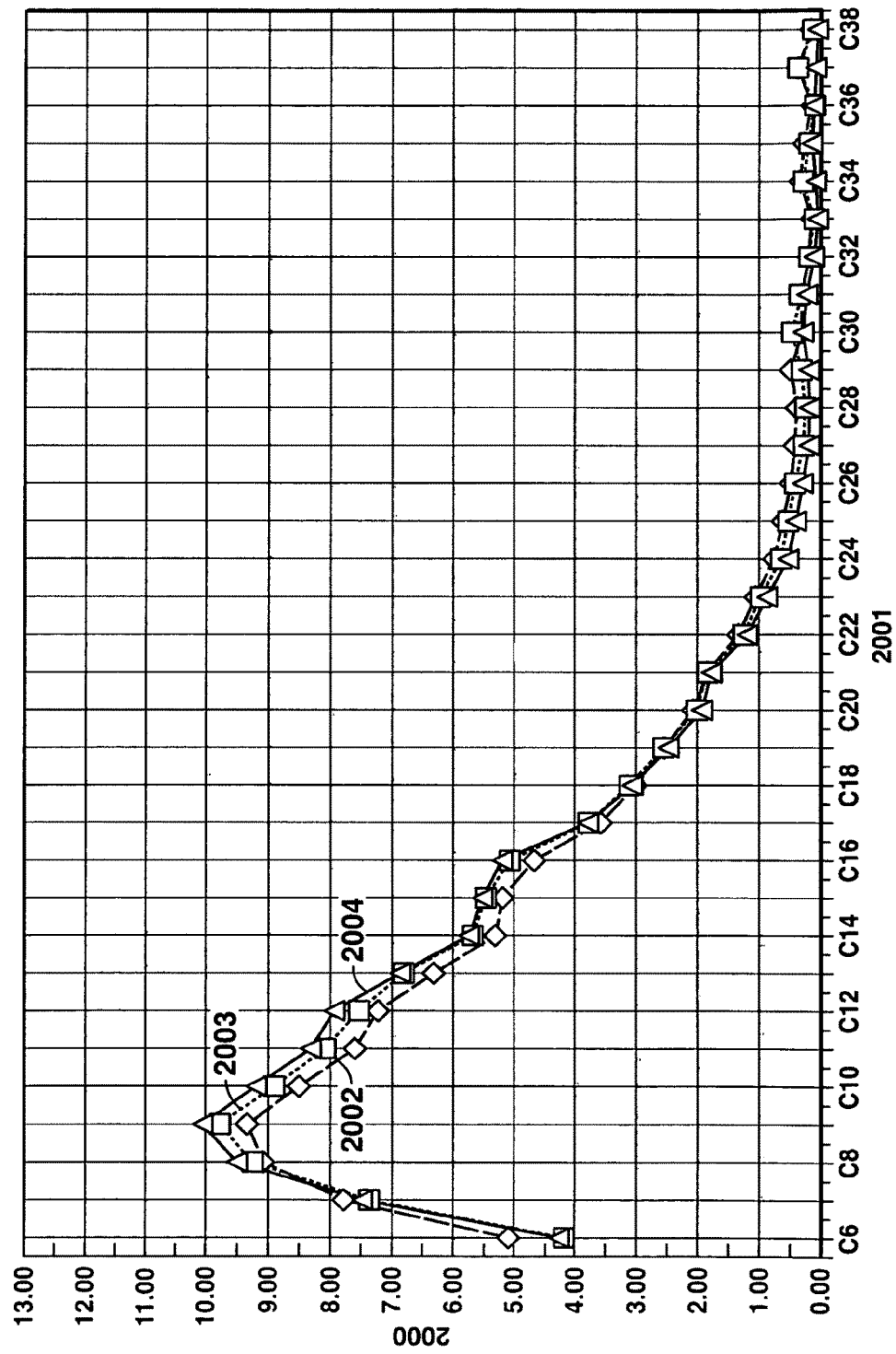
FIG. 7 is a graph of the weight percent of each carbon number pseudo component occurring from C6 to C38 for laboratory experiments conducted at three different stress levels.

FIG. 7 is a graph of the weight percent of each carbon number pseudo component occurring from C6 to C38 for each of the three stress levels tested and analyzed in the laboratory experiments discussed herein. The pseudo component weight percentages were obtained through the experimental procedures, liquid sample collection procedures, whole oil gas chromatography (WOGC) analysis methodology, whole oil gas chromatography (WOGC) peak identification and integration methodology, and pseudo component analysis methodology discussed in the Experiments section. For clarity, the pseudo component weight percentages are taken as a percentage of the entire C3 to pseudo C38 whole oil gas chromatography areas and calculated weights. Thus the graphed C6 to C38 weight percentages do not include the weight contribution of the associated gas phase product from any of the experiments which was separately treated. Further, the graphed weight percentages do not include the weight contribution of any liquid hydrocarbon compounds heavier than (i.e. having a longer retention time than) the C38 pseudo component. The y-axis 2000 represents the concentration in terms of weight percent of each C6 to C38 pseudo component in the liquid phase. The x-axis 2001 contains the identity of each hydrocarbon pseudo component from C6 to C38. The data points occurring on line 2002 represent the weight percent of each C6 to C38 pseudo component for the unstressed experiment of Example 1. The data points occurring on line 2003 represent the weight percent of each C6 to C38 pseudo component for the 400 psi stressed experiment of Example 3. While the data points occurring on line 2004 represent the weight percent of each C6 to C38 pseudo component for the 1,000 psi stressed experiment of Example 4. From FIG. 7 it can be seen that the hydrocarbon liquid produced in the unstressed experiment, represented by data points on line 2002, contains a lower weight percentage of lighter hydrocarbon components in the C8 to C17 pseudo component range and a greater weight percentage of heavier hydrocarbon components in the C20 to C29 pseudo component range, both as compared to the 400 psi stress experiment hydrocarbon liquid and the 1,000 psi stress experiment hydrocarbon liquid. Looking now at the data points occurring on line 2003, it is apparent that the intermediate level 400 psi stress experiment produced a hydrocarbon liquid having C8 to C17 pseudo component concentrations between the unstressed experiment represented by line 2002 and the 1,000 psi stressed experiment represented by line 2004. It is noted that the C17 pseudo component data for both the 400 psi and 1,000 psi stressed experiments are about equal. Further, it is apparent that the weight percentage of heavier hydrocarbon components in the C20 to C29 pseudo component range for the intermediate stress level experiment represented by line 2003 falls between the unstressed experiment (Line 2002) hydrocarbon liquid and the 1,000 psi stress experiment (Line 2004) hydrocarbon liquid. Lastly, it is apparent that the high level 1,000 psi stress experiment produced a hydrocarbon liquid having C8 to C17 pseudo component concentrations greater than both the unstressed experiment represented by line 2002 and the 400 psi stressed experiment represented by line 2003. Further, it is apparent that the weight percentage of heavier hydrocarbon components in the C20 to C29 pseudo component range for the high level stress experiment represented by line 2004 are less than both the unstressed experiment (Line 2002) hydrocarbon liquid and the 400 psi stress experiment (Line 2003) hydrocarbon liquid. Thus pyrolyzing oil shale under increasing levels of lithostatic stress appears to produce hydrocarbon liquids having increasingly lighter carbon number distributions.

Figure 8:
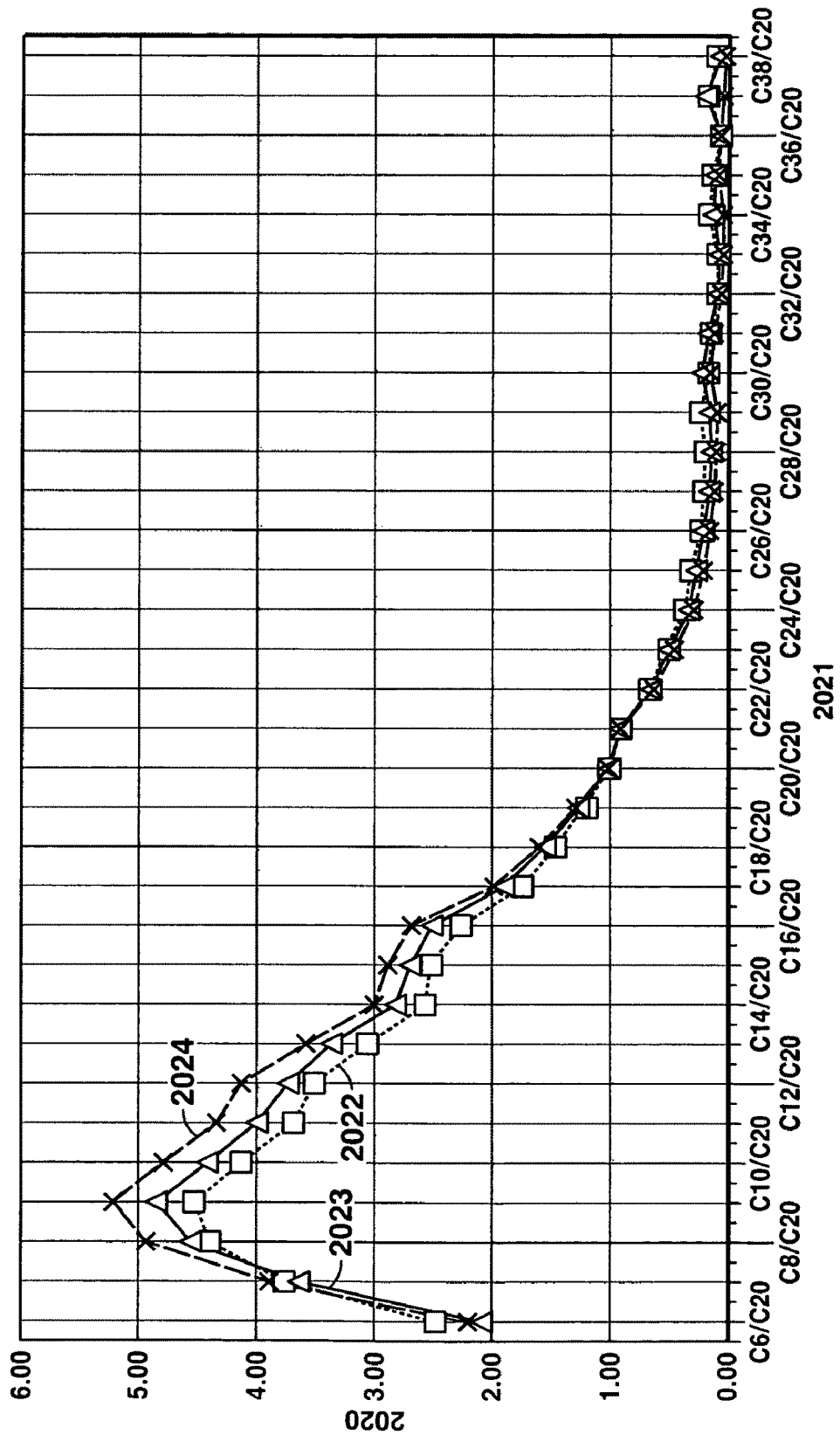
FIG. 8 is a graph of the weight percent ratios of each carbon number pseudo component occurring from C6 to C38 as compared to the C20 pseudo component for laboratory experiments conducted at three different stress levels.

FIG. 8 is a graph of the weight percent ratios of each carbon number pseudo component occurring from C6 to C38 as compared to the C20 pseudo component for each of the three stress levels tested and analyzed in the laboratory experiments discussed herein. The pseudo component weight percentages were obtained as described for FIG. 7. The y-axis 2020 represents the weight ratio of each C6 to C38 pseudo component compared to the C20 pseudo component in the liquid phase. The x-axis 2021 contains the identity of each hydrocarbon pseudo component ratio from C6/C20 to C38/C20. The data points occurring on line 2022 represent the weight ratio of each C6 to C38 pseudo component to C20 pseudo component for the unstressed experiment of Example 1. The data points occurring on line 2023 represent the weight ratio of each C6 to C38 pseudo component to C20 pseudo component for the 400 psi stressed experiment of Example 3. While the data points occurring on line 2024 represent the weight ratio of each C6 to C38 pseudo component to C20 pseudo component for the 1,000 psi stressed experiment of Example 4. From FIG. 8 it can be seen that the hydrocarbon liquid produced in the unstressed experiment, represented by data points on line 2022, contains a lower weight percentage of lighter hydrocarbon components in the C8 to C18 pseudo component range as compared to the C20 pseudo component and a greater weight percentage of heavier hydrocarbon components in the C22 to C29 pseudo component range as compared to the C20 pseudo component, both as compared to the 400 psi stress experiment hydrocarbon liquid and the 1,000 psi stress experiment hydrocarbon liquid. Looking now at the data points occurring on line 2023, it is apparent that the intermediate level 400 psi stress experiment produced a hydrocarbon liquid having C8 to C18 pseudo component concentrations as compared to the C20 pseudo component between the unstressed experiment represented by line 2022 and the 1,000 psi stressed experiment represented by line 2024. Further, it is apparent that the weight percentage of heavier hydrocarbon components in the C22 to C29 pseudo component range as compared to the C20 pseudo component for the intermediate stress level experiment represented by line 2023 falls between the unstressed experiment (Line 2022) hydrocarbon liquid and the 1,000 psi stress experiment (Line 2024) hydrocarbon liquid. Lastly, it is apparent that the high level 1,000 psi stress experiment produced a hydrocarbon liquid having C8 to C18 pseudo component concentrations as compared to the C20 pseudo component greater than both the unstressed experiment represented by line 2022 and the 400 psi stressed experiment represented by line 2023. Further, it is apparent that the weight percentage of heavier hydrocarbon components in the C22 to C29 pseudo component range as compared to the C20 pseudo component for the high level stress experiment represented by line 2024 are less than both the unstressed experiment (Line 2022) hydrocarbon liquid and the 400 psi stress experiment (Line 2023) hydrocarbon liquid. This analysis further supports the relationship that pyrolyzing oil shale under increasing levels of lithostatic stress produces hydrocarbon liquids having increasingly lighter carbon number distributions.

Figure 9:
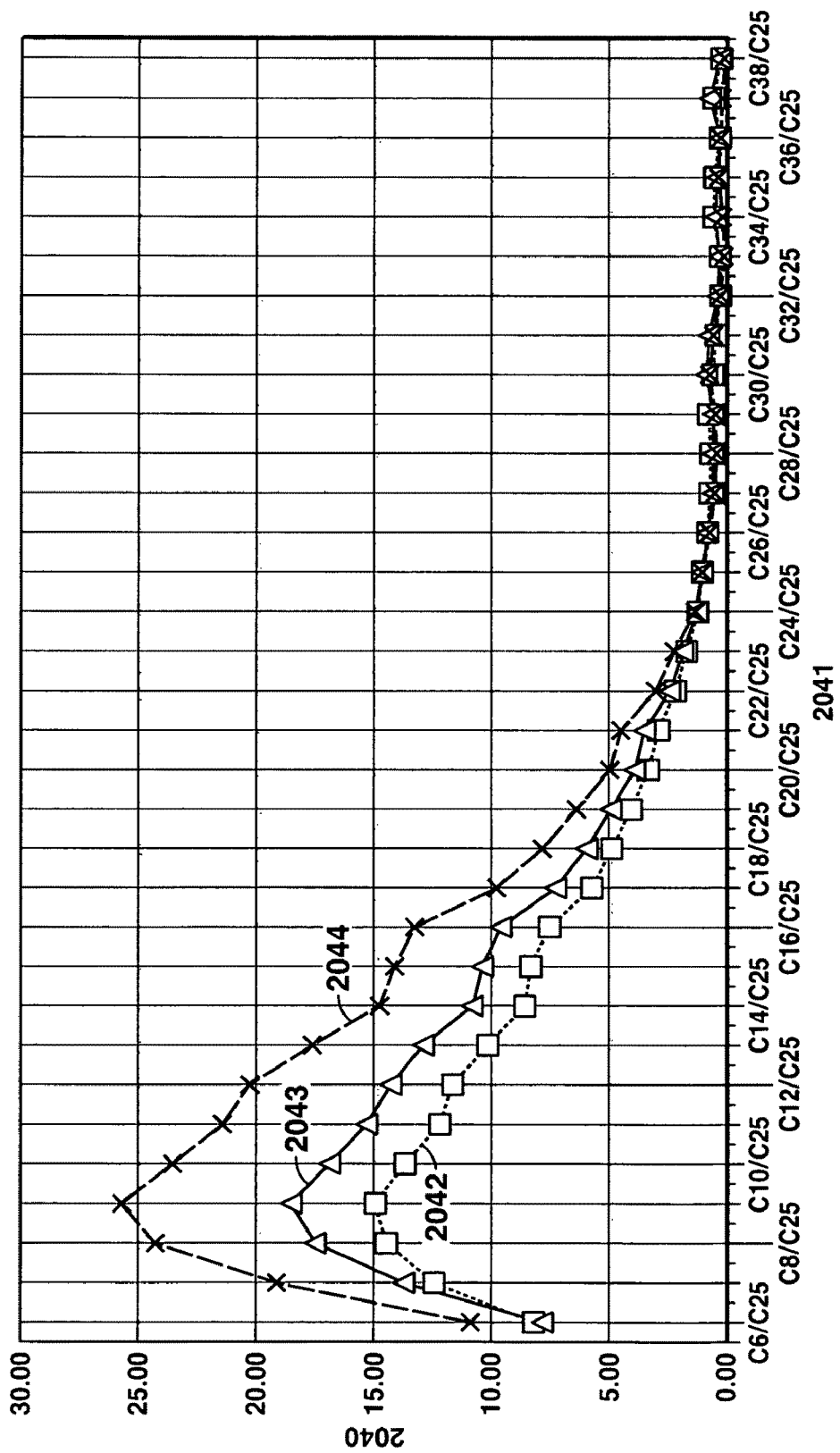
FIG. 9 is a graph of the weight percent ratios of each carbon number pseudo component occurring from C6 to C38 as compared to the C25 pseudo component for laboratory experiments conducted at three different stress levels.

FIG. 9 is a graph of the weight percent ratios of each carbon number pseudo component occurring from C6 to C38 as compared to the C25 pseudo component for each of the three stress levels tested and analyzed in the laboratory experiments discussed herein. The pseudo component weight percentages were obtained as described for FIG. 7. The y-axis 2040 represents the weight ratio of each C6 to C38 pseudo component compared to the C25 pseudo component in the liquid phase. The x-axis 2041 contains the identity of each hydrocarbon pseudo component ratio from C6/C25 to C38/C25. The data points occurring on line 2042 represent the weight ratio of each C6 to C38 pseudo component to C25 pseudo component for the unstressed experiment of Example 1. The data points occurring on line 2043 represent the weight ratio of each C6 to C38 pseudo component to C25 pseudo component for the 400 psi stressed experiment of Example 3. While the data points occurring on line 2044 represent the weight ratio of each C6 to C38 pseudo component to C25 pseudo component for the 1,000 psi stressed experiment of Example 4. From FIG. 9 it can be seen that the hydrocarbon liquid produced in the unstressed experiment, represented by data points on line 2042, contains a lower weight percentage of lighter hydrocarbon components in the C7 to C24 pseudo component range as compared to the C25 pseudo component and a greater weight percentage of heavier hydrocarbon components in the C26 to C29 pseudo component range as compared to the C25 pseudo component, both as compared to the 400 psi stress experiment hydrocarbon liquid and the 1,000 psi stress experiment hydrocarbon liquid. Looking now at the data points occurring on line 2043, it is apparent that the intermediate level 400 psi stress experiment produced a hydrocarbon liquid having C7 to C24 pseudo component concentrations as compared to the C25 pseudo component between the unstressed experiment represented by line 2042 and the 1,000 psi stressed experiment represented by line 2044. Further, it is apparent that the weight percentage of heavier hydrocarbon components in the C26 to C29 pseudo component range as compared to the C25 pseudo component for the intermediate stress level experiment represented by line 2043 falls between the unstressed experiment (Line 2042) hydrocarbon liquid and the 1,000 psi stress experiment (Line 2044) hydrocarbon liquid. Lastly, it is apparent that the high level 1,000 psi stress experiment produced a hydrocarbon liquid having C7 to C24 pseudo component concentrations as compared to the C25 pseudo component greater than both the unstressed experiment represented by line 2042 and the 400 psi stressed experiment represented by line 2043. Further, it is apparent that the weight percentage of heavier hydrocarbon components in the C26 to C29 pseudo component range as compared to the C25 pseudo component for the high level stress experiment represented by line 2044 are less than both the unstressed experiment (Line 2042) hydrocarbon liquid and the 400 psi stress experiment (Line 2043) hydrocarbon liquid. This analysis further supports the relationship that pyrolyzing oil shale under increasing levels of lithostatic stress produces hydrocarbon liquids having increasingly lighter carbon number distributions.

Figure 10:
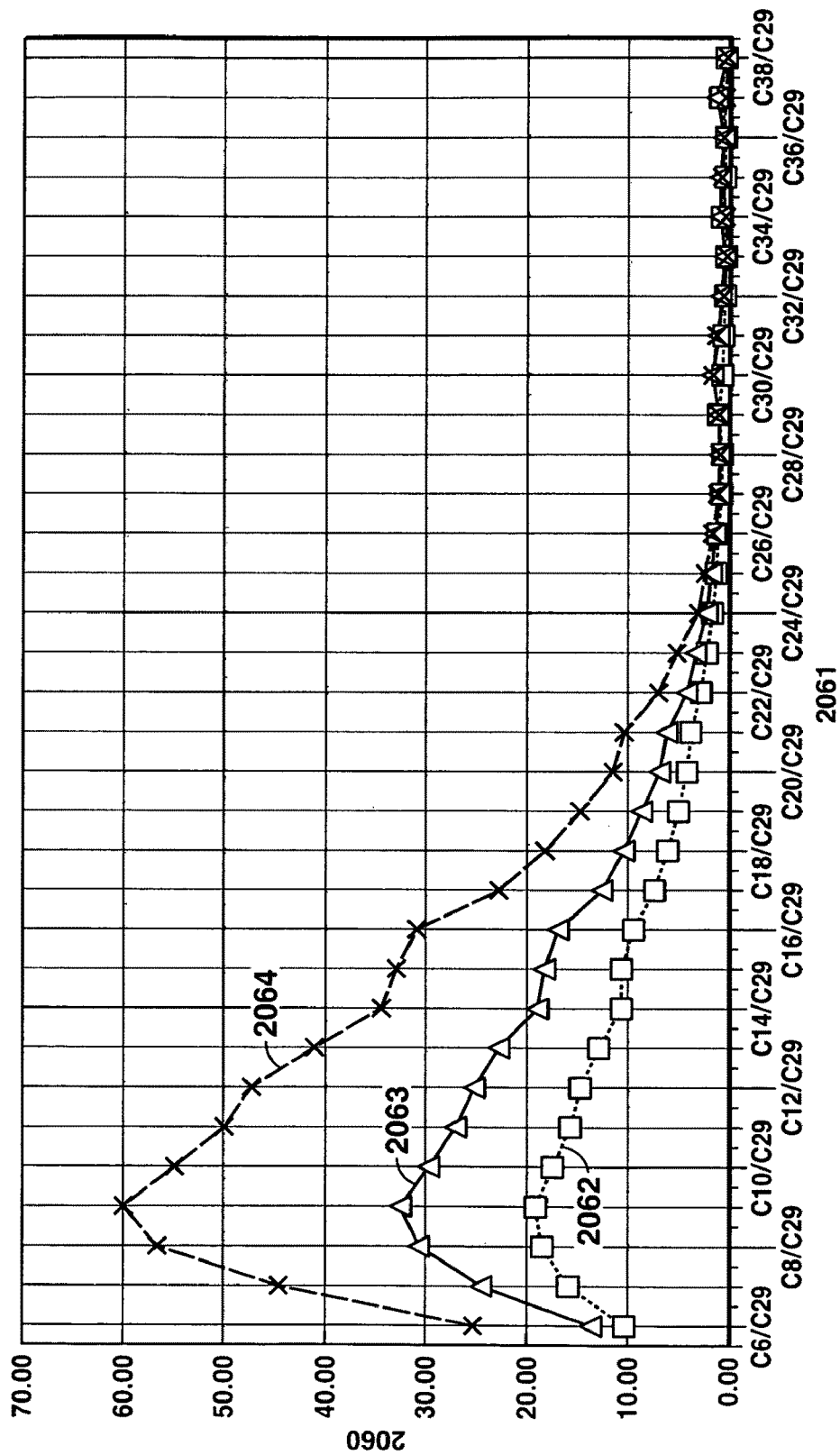
FIG. 10 is a graph of the weight percent ratios of each carbon number pseudo component occurring from C6 to C38 as compared to the C29 pseudo component for laboratory experiments conducted at three different stress levels.

FIG. 10 is a graph of the weight percent ratios of each carbon number pseudo component occurring from C6 to C38 as compared to the C29 pseudo component for each of the three stress levels tested and analyzed in the laboratory experiments discussed herein. The pseudo component weight percentages were obtained as described for FIG. 7. The y-axis 2060 represents the weight ratio of each C6 to C38 pseudo component compared to the C29 pseudo component in the liquid phase. The x-axis 2061 contains the identity of each hydrocarbon pseudo component ratio from C6/C29 to C38/C29. The data points occurring on line 2062 represent the weight ratio of each C6 to C38 pseudo component to C29 pseudo component for the unstressed experiment of Example 1. The data points occurring on line 2063 represent the weight ratio of each C6 to C38 pseudo component to C29 pseudo component for the 400 psi stressed experiment of Example 3. While the data points occurring on line 2064 represent the weight ratio of each C6 to C38 pseudo component to C29 pseudo component for the 1,000 psi stressed experiment of Example 4. From FIG. 10 it can be seen that the hydrocarbon liquid produced in the unstressed experiment, represented by data points on line 2062, contains a lower weight percentage of lighter hydrocarbon components in the C6 to C28 pseudo component range as compared to the C29 pseudo component, both as compared to the 400 psi stress experiment hydrocarbon liquid and the 1,000 psi stress experiment hydrocarbon liquid. Looking now at the data points occurring on line 2063, it is apparent that the intermediate level 400 psi stress experiment produced a hydrocarbon liquid having C6 to C28 pseudo component concentrations as compared to the C29 pseudo component between the unstressed experiment represented y line 2062 and the 1,000 psi stressed experiment represented by line 2064. Lastly, it is apparent that the high level 1,000 psi stress experiment produced a hydrocarbon liquid having C6 to C28 pseudo component concentrations as compared to the C29 pseudo component greater than both the unstressed experiment represented by line 2062 and the 400 psi stressed experiment represented by line 2063. This analysis further supports the relationship that pyrolyzing oil shale under increasing levels of lithostatic stress produces hydrocarbon liquids having increasingly lighter carbon number distributions.

Figure 11:
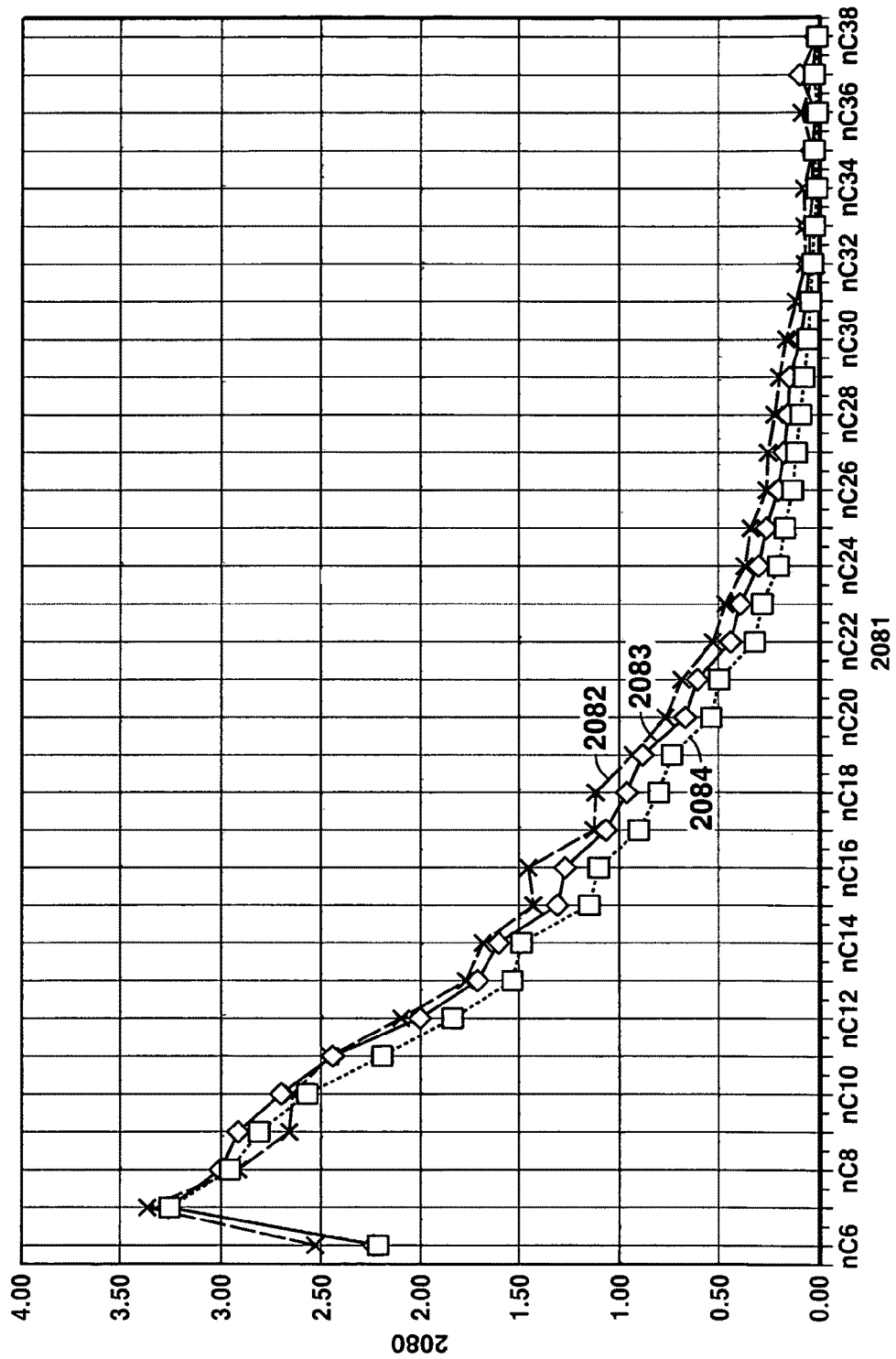
FIG. 11 is a graph of the weight percent of normal alkane hydrocarbon compounds occurring from normal-C6 to normal-C38 for laboratory experiments conducted at three different stress levels.

FIG. 11 is a graph of the weight percent of normal alkane hydrocarbon compounds occurring from the normal-C6 alkane to the normal-C38 alkane for each of the three stress levels tested and analyzed in the laboratory experiments discussed herein. The normal alkane compound weight percentages were obtained as described for FIG. 7, except that each individual normal alkane compound peak area integration was used to determine each respective normal alkane compound weight percentage. For clarity, the normal alkane hydrocarbon weight percentages are taken as a percentage of the entire C3 to pseudo C38 whole oil gas chromatography areas and calculated weights as used in the pseudo compound data presented in FIG. 7. The y-axis 2080 represents the concentration in terms of weight percent of each normal-C6 to normal-C38 compound found in the liquid phase. The x-axis 2081 contains the identity of each normal alkane hydrocarbon compound from normal-C6 to normal-C38. The data points occurring on line 2082 represent the weight percent of each normal-C6 to normal-C38 hydrocarbon compound for the unstressed experiment of Example 1. The data points occurring on line 2083 represent the weight percent of each normal-C6 to normal-C38 hydrocarbon compound for the 400 psi stressed experiment of Example 3. While the data points occurring on line 2084 represent the weight percent of each normal-C6 to normal-C38 hydrocarbon compound for the 1,000 psi stressed experiment of Example 4. From FIG. 11 it can be seen that the hydrocarbon liquid produced in the unstressed experiment, represented by data points on line 2082, contains a greater weight percentage of hydrocarbon compounds in the normal-C12 to normal-C30 compound range, both as compared to the 400 psi stress experiment hydrocarbon liquid and the 1,000 psi stress experiment hydrocarbon liquid. Looking now at the data points occurring on line 2083, it is apparent that the intermediate level 400 psi stress experiment produced a hydrocarbon liquid having normal-C12 to normal-C30 compound concentrations between the unstressed experiment represented by line 2082 and the 1,000 psi stressed experiment represented by line 2084. Lastly, it is apparent that the high level 1,000 psi stress experiment produced a hydrocarbon liquid having normal-C12 to normal-C30 compound concentrations less than both the unstressed experiment represented by line 2082 and the 400 psi stressed experiment represented by line 2083. Thus pyrolyzing oil shale under increasing levels of lithostatic stress appears to produce hydrocarbon liquids having lower concentrations of normal alkane hydrocarbons.

Figure 12:
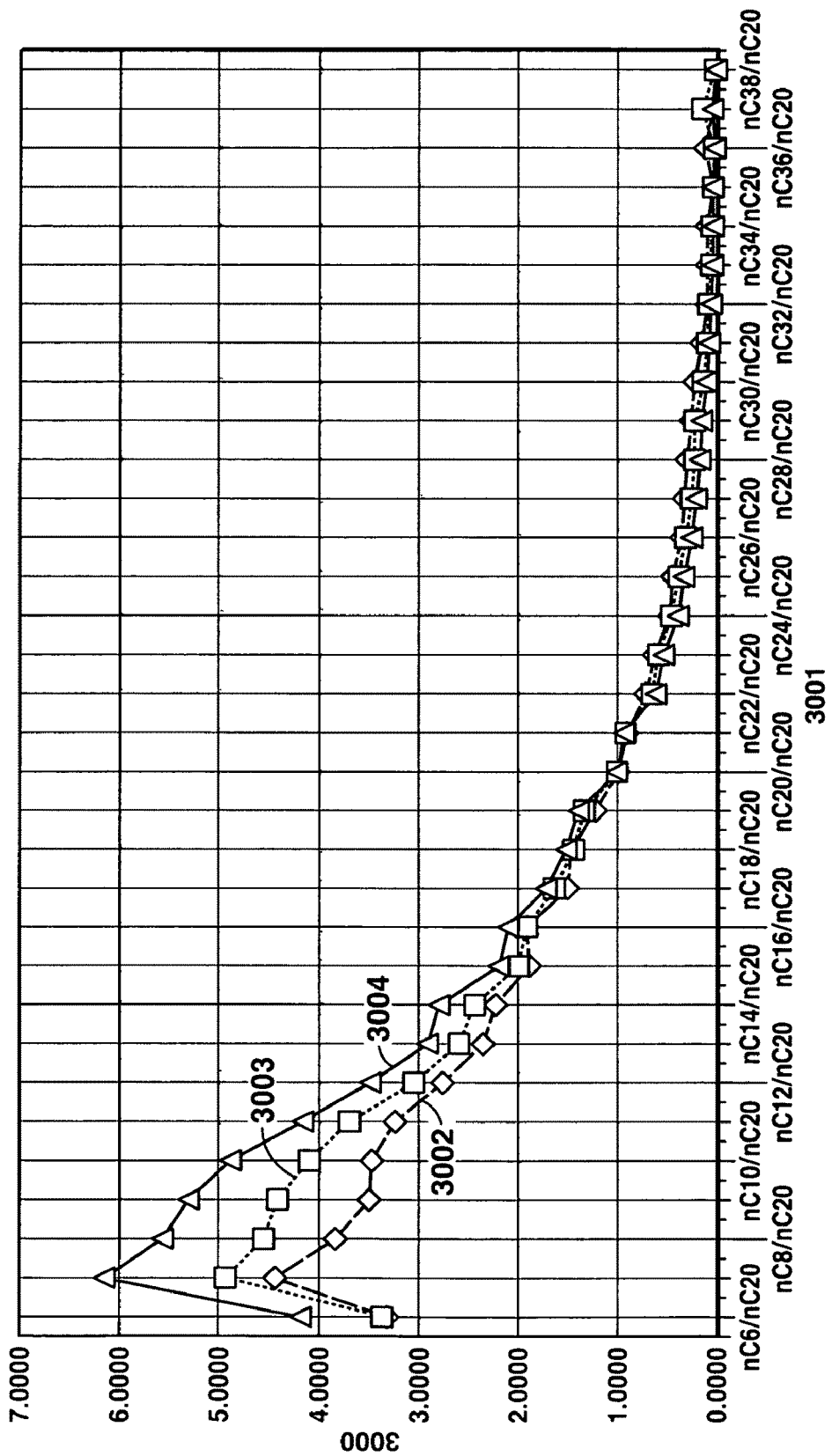
FIG. 12 is a graph of the weight percent of normal alkane hydrocarbon compounds occurring from normal-C6 to normal-C38 as compared to the normal-C20 hydrocarbon compound for laboratory experiments conducted at three different stress levels.

FIG. 12 is a graph of the weight percent of normal alkane hydrocarbon compounds occurring from normal-C6 to normal-C38 as compared to the normal-C20 hydrocarbon compound for each of the three stress levels tested and analyzed in the laboratory experiments discussed herein. The normal compound weight percentages were obtained as described for FIG. 11. The y-axis 3000 represents the concentration in terms of weight ratio of each normal-C6 to normal-C38 compound as compared to the normal-C20 compound found in the liquid phase. The x-axis 3001 contains the identity of each normal alkane hydrocarbon compound ratio from normal-C6/normal-C20 to normal-C38/normal-C20. The data points occurring on line 3002 represent the weight ratio of each normal-C6 to normal-C38 hydrocarbon compound as compared to the normal-C20 compound for the unstressed experiment of Example 1. The data points occurring on line 3003 represent the weight ratio of each normal-C6 to normal-C38 hydrocarbon compound as compared to the normal-C20 compound for the 400 psi stressed experiment of Example 3. While the data points occurring on line 3004 represent the weight ratio of each normal-C6 to normal-C38 hydrocarbon compound as compared to the normal-C20 compound for the 1,000 psi stressed experiment of Example 4. From FIG. 12 it can be seen that the hydrocarbon liquid produced in the unstressed experiment, represented by data points on line 3002, contains a lower weight percentage of lighter normal alkane hydrocarbon components in the normal-C6 to normal-C17 compound range as compared to the normal-C20 compound and a greater weight percentage of heavier hydrocarbon components in the normal-C22 to normal-C34 compound range as compared to the normal-C20 compound, both as compared to the 400 psi stress experiment hydrocarbon liquid and the 1,000 psi stress experiment hydrocarbon liquid. Looking now at the data points occurring on line 3003, it is apparent that the intermediate level 400 psi stress experiment produced a hydrocarbon liquid having normal-C6 to normal-C17 compound concentrations as compared to the normal-C20 compound between the unstressed experiment represented by line 3002 and the 1,000 psi stressed experiment represented by line 3004. Further, it is apparent that the weight percentage of heavier hydrocarbon components in the normal-C22 to normal-C34 compound range as compared to the normal-C20 compound for the intermediate stress level experiment represented by line 3003 falls between the unstressed experiment (Line 3002) hydrocarbon liquid and the 1,000 psi stress experiment (Line 3004) hydrocarbon liquid. Lastly, it is apparent that the high level 1,000 psi stress experiment produced a hydrocarbon liquid having normal-C6 to normal-C17 compound concentrations as compared to the normal-C20 compound greater than both the unstressed experiment represented by line 3002 and the 400 psi stressed experiment represented by line 3003. Further, it is apparent that the weight percentage of heavier hydrocarbon components in the normal-C22 to normal-C34 compound range as compared to the normal-C20 compound for the high level stress experiment represented by line 3004 are less than both the unstressed experiment (Line 3002) hydrocarbon liquid and the 400 psi stress experiment (Line 3003) hydrocarbon liquid. This analysis further supports the relationship that pyrolyzing oil shale under increasing levels of lithostatic stress produces hydrocarbon liquids having lower concentrations of normal alkane hydrocarbons.

Figure 13:
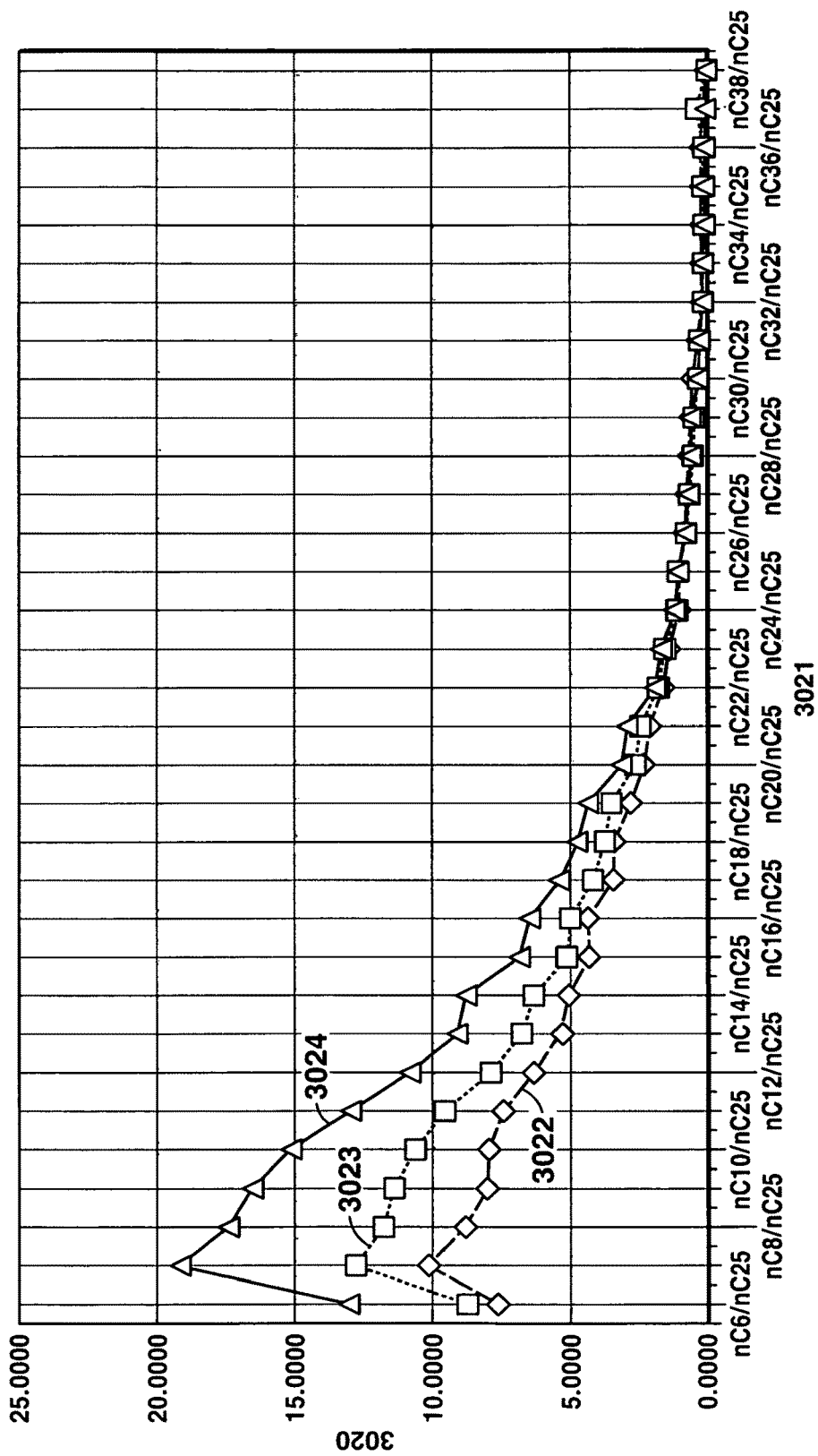
FIG. 13 is a graph of the weight percent of normal alkane hydrocarbon compounds occurring from normal-C6 to normal-C38 as compared to the normal-C25 hydrocarbon compound for laboratory experiments conducted at three different stress levels.

FIG. 13 is a graph of the weight percent of normal alkane hydrocarbon compounds occurring from normal-C6 to normal-C38 as compared to the normal-C25 hydrocarbon compound for each of the three stress levels tested and analyzed in the laboratory experiments discussed herein. The normal compound weight percentages were obtained as described for FIG. 11. The y-axis 3020 represents the concentration in terms of weight ratio of each normal-C6 to normal-C38 compound as compared to the normal-C25 compound found in the liquid phase. The x-axis 3021 contains the identity of each normal alkane hydrocarbon compound ratio from normal-C6/normal-C25 to normal-C38/normal-C25. The data points occurring on line 3022 represent the weight ratio of each normal-C6 to normal-C38 hydrocarbon compound as compared to the normal-C25 compound for the unstressed experiment of Example 1. The data points occurring on line 3023 represent the weight ratio of each normal-C6 to normal-C38 hydrocarbon compound as compared to the normal-C25 compound for the 400 psi stressed experiment of Example 3. While the data points occurring on line 3024 represent the weight ratio of each normal-C6 to normal-C38 hydrocarbon compound as compared to the normal-C25 compound for the 1,000 psi stressed experiment of Example 4. From FIG. 13 it can be seen that the hydrocarbon liquid produced in the unstressed experiment, represented by data points on line 3022, contains a lower weight percentage of lighter normal alkane hydrocarbon components in the normal-C6 to normal-C24 compound range as compared to the normal-C25 compound and a greater weight percentage of heavier hydrocarbon components in the normal-C26 to normal-C30 compound range as compared to the normal-C25 compound, both as compared to the 400 psi stress experiment hydrocarbon liquid and the 1,000 psi stress experiment hydrocarbon liquid. Looking now at the data points occurring on line 3023, it is apparent that the intermediate level 400 psi stress experiment produced a hydrocarbon liquid having normal-C6 to normal-C24 compound concentrations as compared to the normal-C25 compound between the unstressed experiment represented by line 3022 and the 1,000 psi stressed experiment represented by line 3024. Further, it is apparent that the weight percentage of heavier hydrocarbon components in the normal-C26 to normal-C30 compound range as compared to the normal-C25 compound for the intermediate stress level experiment represented by line 3023 falls between the unstressed experiment (Line 3022) hydrocarbon liquid and the 1,000 psi stress experiment (Line 3024) hydrocarbon liquid. Lastly, it is apparent that the high level 1,000 psi stress experiment produced a hydrocarbon liquid having normal-C6 to normal-C24 compound concentrations as compared to the normal-C25 compound greater than both the unstressed experiment represented by line 3022 and the 400 psi stressed experiment represented by line 3023. Further, it is apparent that the weight percentage of heavier hydrocarbon components in the normal-C26 to normal-C30 compound range as compared to the normal-C25 compound for the high level stress experiment represented by line 3024 are less than both the unstressed experiment (Line 3022) hydrocarbon liquid and the 400 psi stress experiment (Line 3023) hydrocarbon liquid. This analysis further supports the relationship that pyrolyzing oil shale under increasing levels of lithostatic stress produces hydrocarbon liquids having lower concentrations of normal alkane hydrocarbons.

Figure 14:
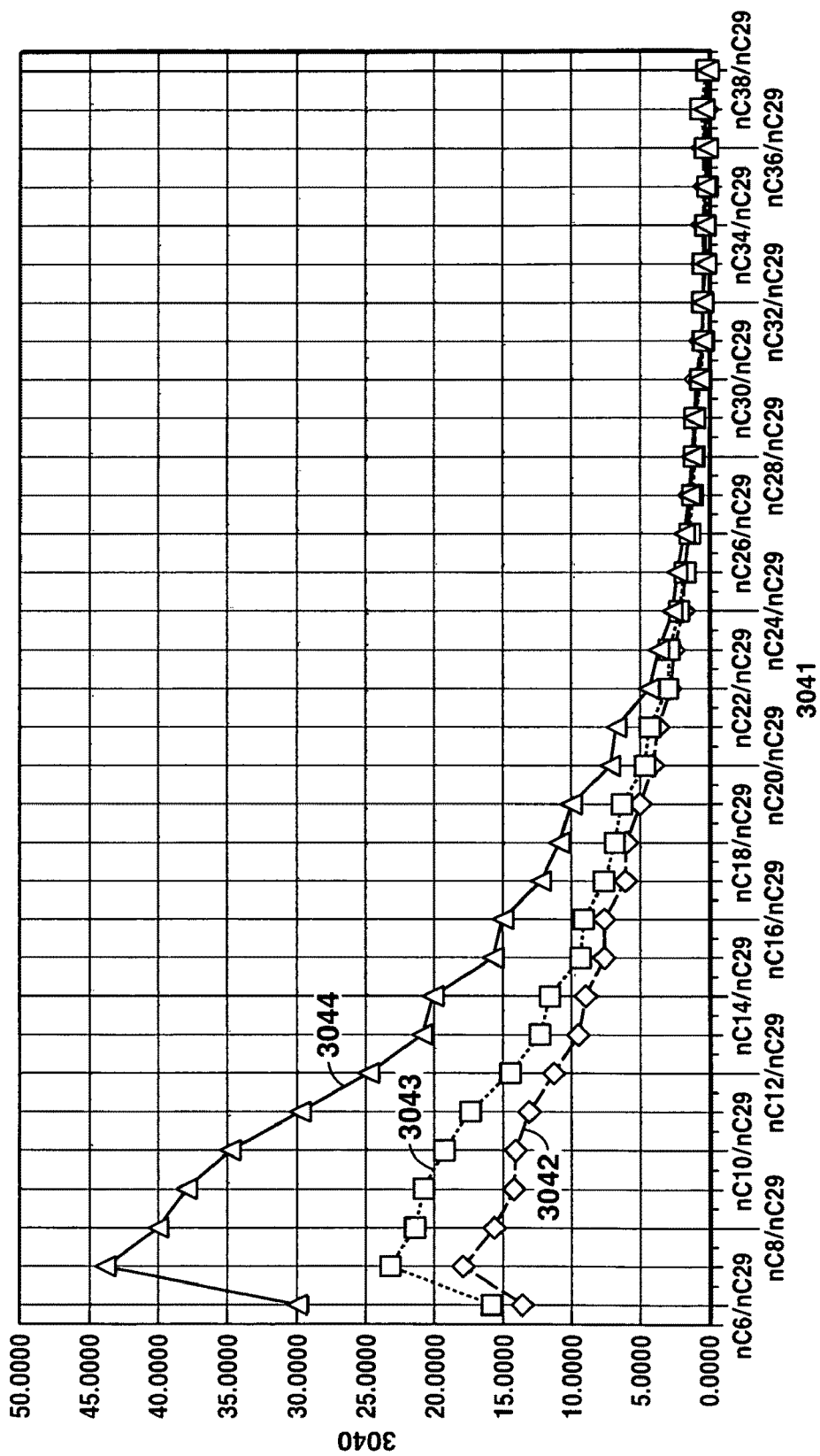
FIG. 14 is a graph of the weight percent of normal alkane hydrocarbon compounds occurring from normal-C6 to normal-C38 as compared to the normal-C29 hydrocarbon compound for laboratory experiments conducted at three different stress levels.

FIG. 14 is a graph of the weight percent of normal alkane hydrocarbon compounds occurring from normal-C6 to normal-C38 as compared to the normal-C29 hydrocarbon compound for each of the three stress levels tested and analyzed in the laboratory experiments discussed herein. The normal compound weight percentages were obtained as described for FIG. 11. The y-axis 3040 represents the concentration in terms of weight ratio of each normal-C6 to normal-C38 compound as compared to the normal-C29 compound found in the liquid phase. The x-axis 3041 contains the identity of each normal alkane hydrocarbon compound ratio from normal-C6/normal-C29 to normal-C38/normal-C29. The data points occurring on line 3042 represent the weight ratio of each normal-C6 to normal-C38 hydrocarbon compound as compared to the normal-C29 compound for the unstressed experiment of Example 1. The data points occurring on line 3043 represent the weight ratio of each normal-C6 to normal-C38 hydrocarbon compound as compared to the normal-C29 compound for the 400 psi stressed experiment of Example 3. While the data points occurring on line 3044 represent the weight ratio of each normal-C6 to normal-C38 hydrocarbon compound as compared to the normal-C29 compound for the 1,000 psi stressed experiment of Example 4. From FIG. 14 it can be seen that the hydrocarbon liquid produced in the unstressed experiment, represented by data points on line 3042, contains a lower weight percentage of lighter normal alkane hydrocarbon components in the normal-C6 to normal-C26 compound range as compared to the normal-C29 compound, both as compared to the 400 psi stress experiment hydrocarbon liquid and the 1,000 psi stress experiment hydrocarbon liquid. Looking now at the data points occurring on line 3043, it is apparent that the intermediate level 400 psi stress experiment produced a hydrocarbon liquid having normal-C6 to normal-C26 compound concentrations as compared to the normal-C29 compound between the unstressed experiment represented by line 3042 and the 1,000 psi stressed experiment represented by line 3044. Lastly, it is apparent that the high level 1,000 psi stress experiment produced a hydrocarbon liquid having normal-C6 to normal-C26 compound concentrations as compared to the normal-C29 compound greater than both the unstressed experiment represented by line 3042 and the 400 psi stressed experiment represented by line 3043. This analysis further supports the relationship that pyrolyzing oil shale under increasing levels of lithostatic stress produces hydrocarbon liquids having lower concentrations of normal alkane hydrocarbons.

Figure 15:
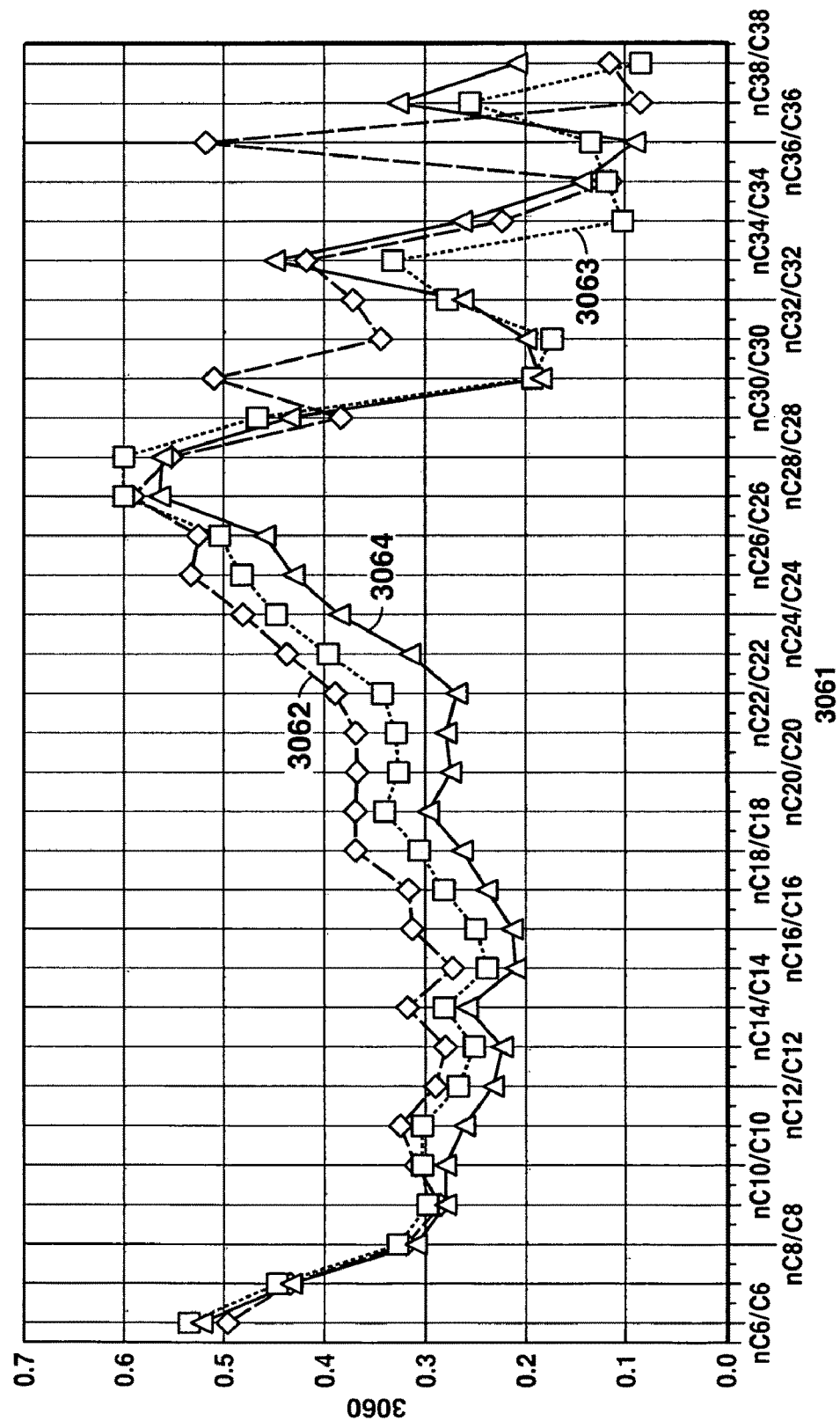
FIG. 15 is a graph of the weight ratio of normal alkane hydrocarbon compounds to pseudo components for each carbon number from C6 to C38 for laboratory experiments conducted at three different stress levels.

FIG. 15 is a graph of the weight ratio of normal alkane hydrocarbon compounds to pseudo components for each carbon number from C6 to C38 for each of the three stress levels tested and analyzed in the laboratory experiments discussed herein. The normal compound and pseudo component weight percentages were obtained as described for FIGS. 7 and 11. For clarity, the normal alkane hydrocarbon and pseudo component weight percentages are taken as a percentage of the entire C3 to pseudo C38 whole oil gas chromatography areas and calculated weights as used in the pseudo compound data presented in FIG. 7. The y-axis 3060 represents the concentration in terms of weight ratio of each normal-C6/pseudo C6 to normal-C38/pseudo C38 compound found in the liquid phase. The x-axis 3061 contains the identity of each normal alkane hydrocarbon compound to pseudo component ratio from normal-C6/pseudo C6 to normal-C38/pseudo C38. The data points occurring on line 3062 represent the weight ratio of each normal-C6/pseudo C6 to normal-C38/pseudo C38 ratio for the unstressed experiment of Example 1. The data points occurring on line 3063 represent the weight ratio of each normal-C6/pseudo C6 to normal-C38/pseudo C38 ratio for the 400 psi stressed experiment of Example 3. While the data points occurring on line 3064 represent the weight ratio of each normal-C6/pseudo C6 to normal-C38/pseudo C38 ratio for the 1,000 psi stressed experiment of Example 4. From FIG. 15 it can be seen that the hydrocarbon liquid produced in the unstressed experiment, represented by data points on line 3062, contains a greater weight percentage of normal alkane hydrocarbon compounds to pseudo components in the C10 to C26 range, both as compared to the 400 psi stress experiment hydrocarbon liquid and the 1,000 psi stress experiment hydrocarbon liquid. Looking now at the data points occurring on line 3063, it is apparent that the intermediate level 400 psi stress experiment produced a hydrocarbon liquid having normal alkane hydrocarbon compound to pseudo component ratios in the C10 to C26 range between the unstressed experiment represented by line 3062 and the 1,000 psi stressed experiment represented by line 3064. Lastly, it is apparent that the high level 1,000 psi stress experiment produced a hydrocarbon liquid having normal alkane hydrocarbon compound to pseudo component ratios in the C10 to C26 range less than both the unstressed experiment represented by line 3062 and the 400 psi stressed experiment represented by line 3063. Thus pyrolyzing oil shale under increasing levels of lithostatic stress appears to produce hydrocarbon liquids having lower concentrations of normal alkane hydrocarbons as compared to the total hydrocarbons for a given carbon number occurring between C10 and C26.

From the above-described data, it can be seen that heating and pyrolysis of oil shale under increasing levels of stress results in a condensable hydrocarbon fluid product that is lighter (i.e., greater proportion of lower carbon number compounds or components relative to higher carbon number compounds or components) and contains a lower concentration of normal alkane hydrocarbon compounds. Such a product may be suitable for refining into gasoline and distillate products. Further, such a product, either before or after further fractionation, may have utility as a feed stock for certain chemical processes.

In some embodiments, the produced hydrocarbon fluid includes a condensable hydrocarbon portion. In some embodiments the condensable hydrocarbon portion may have one or more of a total C7 to total C20 weight ratio greater than 0.8, a total C8 to total C20 weight ratio greater than 1.7, a total C9 to total C20 weight ratio greater than 2.5, a total C10 to total C20 weight ratio greater than 2.8, a total C11 to total C20 weight ratio greater than 2.3, a total C12 to total C20 weight ratio greater than 2.3, a total C13 to total C20 weight ratio greater than 2.9, a total C14 to total C20 weight ratio greater than 2.2, a total C15 to total C20 weight ratio greater than 2.2, and a total C16 to total C20 weight ratio greater than 1.6. In alternative embodiments the condensable hydrocarbon portion has one or more of a total C7 to total C20 weight ratio greater than 2.5, a total C8 to total C20 weight ratio greater than 3.0, a total C9 to total C20 weight ratio greater than 3.5, a total C10 to total C20 weight ratio greater than 3.5, a total C11 to total C20 weight ratio greater than 3.0, and a total C12 to total C20 weight ratio greater than 3.0. In alternative embodiments the condensable hydrocarbon portion has one or more of a total C7 to total C20 weight ratio greater than 3.5, a total C8 to total C20 weight ratio greater than 4.3, a total C9 to total C20 weight ratio greater than 4.5, a total C10 to total C20 weight ratio greater than 4.2, a total C11 to total C20 weight ratio greater than 3.7, and a total C12 to total C20 weight ratio greater than 3.5. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a total C7 to total C20 weight ratio greater than 0.8. Alternatively, the condensable hydrocarbon portion may have a total C7 to total C20 weight ratio greater than 1.0, greater than 1.5, greater than 2.0, greater than 2.5, greater than 3.5 or greater than 3.7. In alternative embodiments, the condensable hydrocarbon portion may have a total C7 to total C20 weight ratio less than 10.0, less than 7.0, less than 5.0 or less than 4.0. In some embodiments the condensable hydrocarbon portion has a total C8 to total C20 weight ratio greater than 1.7. Alternatively, the condensable hydrocarbon portion may have a total C8 to total C20 weight ratio greater than 2.0, greater than 2.5, greater than 3.0, greater than 4.0, greater than 4.4, or greater than 4.6. In alternative embodiments, the condensable hydrocarbon portion may have a total C8 to total C20 weight ratio less than 7.0 or less than 6.0. In some embodiments the condensable hydrocarbon portion has a total C9 to total C20 weight ratio greater than 2.5. Alternatively, the condensable hydrocarbon portion may have a total C9 to total C20 weight ratio greater than 3.0, greater than 4.0, greater than 4.5, or greater than 4.7. In alternative embodiments, the condensable hydrocarbon portion may have a total C9 to total C20 weight ratio less than 7.0 or less than 6.0. In some embodiments the condensable hydrocarbon portion has a total C10 to total C20 weight ratio greater than 2.8. Alternatively, the condensable hydrocarbon portion may have a total C10 to total C20 weight ratio greater than 3.0, greater than 3.5, greater than 4.0, or greater than 4.3. In alternative embodiments, the condensable hydrocarbon portion may have a total C10 to total C20 weight ratio less than 7.0 or less than 6.0. In some embodiments the condensable hydrocarbon portion has a total C11 to total C20 weight ratio greater than 2.3. Alternatively, the condensable hydrocarbon portion may have a total C11 to total C20 weight ratio greater than 2.5, greater than 3.5, greater than 3.7, greater than 4.0. In alternative embodiments, the condensable hydrocarbon portion may have a total C11 to total C20 weight ratio less than 7.0 or less than 6.0. In some embodiments the condensable hydrocarbon portion has a total C12 to total C20 weight ratio greater than 2.3. Alternatively, the condensable hydrocarbon portion may have a total C12 to total C20 weight ratio greater than 2.5, greater than 3.0, greater than 3.5, or greater than 3.7. In alternative embodiments, the condensable hydrocarbon portion may have a total C12 to total C20 weight ratio less than 7.0 or less than 6.0. In some embodiments the condensable hydrocarbon portion has a total C13 to total C20 weight ratio greater than 2.9. Alternatively, the condensable hydrocarbon portion may have a total C13 to total C20 weight ratio greater than 3.0, greater than 3.1, or greater than 3.2. In alternative embodiments, the condensable hydrocarbon portion may have a total C13 to total C20 weight ratio less than 6.0 or less than 5.0. In some embodiments the condensable hydrocarbon portion has a total C14 to total C20 weight ratio greater than 2.2. Alternatively, the condensable hydrocarbon portion may have a total C14 to total C20 weight ratio greater than 2.5, greater than 2.6, or greater than 2.7. In alternative embodiments, the condensable hydrocarbon portion may have a total C14 to total C20 weight ratio less than 6.0 or less than 4.0. In some embodiments the condensable hydrocarbon portion has a total C15 to total C20 weight ratio greater than 2.2. Alternatively, the condensable hydrocarbon portion may have a total C15 to total C20 weight ratio greater than 2.3, greater than 2.4, or greater than 2.6. In alternative embodiments, the condensable hydrocarbon portion may have a total C15 to total C20 weight ratio less than 6.0 or less than 4.0. In some embodiments the condensable hydrocarbon portion has a total C16 to total C20 weight ratio greater than 1.6. Alternatively, the condensable hydrocarbon portion may have a total C16 to total C20 weight ratio greater than 1.8, greater than 2.3, or greater than 2.5. In alternative embodiments, the condensable hydrocarbon portion may have a total C16 to total C20 weight ratio less than 5.0 or less than 4.0. Certain features of the present invention are described in terms of a set of numerical upper limits (e.g. "less than") and a set of numerical lower limits (e.g. "greater than") in the preceding paragraph. It should be appreciated that ranges formed by any combination of these limits are within the scope of the invention unless otherwise indicated. The embodiments described in this paragraph may be combined with any of the other aspects of the invention discussed herein.

In some embodiments the condensable hydrocarbon portion may have the one or more of a total C7 to total C25 weight ratio greater than 2.0, a total C8 to total C25 weight ratio greater than 4.5, a total C9 to total C25 weight ratio greater than 6.5, a total C10 to total C25 weight ratio greater than 7.5, a total C11 to total C25 weight ratio greater than 6.5, a total C12 to total C25 weight ratio greater than 6.5, a total C13 to total C25 weight ratio greater than 8.0, a total C14 to total C25 weight ratio greater than 6.0, a total C15 to total C25 weight ratio greater than 6.0, a total C16 to total C25 weight ratio greater than 4.5, a total C17 to total C25 weight ratio greater than 4.8, and a total C18 to total C25 weight ratio greater than 4.5. In alternative embodiments the condensable hydrocarbon portion has one or more of a total C7 to total C25 weight ratio greater than 7.0, a total C8 to total C25 weight ratio greater than 10.0, a total C9 to total C25 weight ratio greater than 10.0, a total C10 to total C25 weight ratio greater than 10.0, a total C11 to total C25 weight ratio greater than 8.0, and a total C12 to total C25 weight ratio greater than 8.0. In alternative embodiments the condensable hydrocarbon portion has one or more of a total C7 to total C25 weight ratio greater than 13.0, a total C8 to total C25 weight ratio greater than 17.0, a total C9 to total C25 weight ratio greater than 17.0, a total C10 to total C25 weight ratio greater than 15.0, a total C11 to total C25 weight ratio greater than 14.0, and a total C12 to total C25 weight ratio greater than 13.0. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a total C7 to total C25 weight ratio greater than 2.0. Alternatively, the condensable hydrocarbon portion may have a total C7 to total C25 weight ratio greater than 3.0, greater than 5.0, greater than 10.0, greater than 13.0, or greater than 15.0. In alternative embodiments, the condensable hydrocarbon portion may have a total C7 to total C25 weight ratio less than 30.0 or less than 25.0. In some embodiments the condensable hydrocarbon portion has a total C8 to total C25 weight ratio greater than 4.5. Alternatively, the condensable hydrocarbon portion may have a total C8 to total C25 weight ratio greater than 5.0, greater than 7.0, greater than 10.0, greater than 15.0, or greater than 17.0. In alternative embodiments, the condensable hydrocarbon portion may have a total C8 to total C25 weight ratio less than 35.0, or less than 30.0. In some embodiments the condensable hydrocarbon portion has a total C9 to total C25 weight ratio greater than 6.5. Alternatively, the condensable hydrocarbon portion may have a total C9 to total C25 weight ratio greater than 8.0, greater than 10.0, greater than 15.0, greater than 17.0, or greater than 19.0. In alternative embodiments, the condensable hydrocarbon portion may have a total C9 to total C25 weight ratio less than 40.0 or less than 35.0. In some embodiments the condensable hydrocarbon portion has a total C10 to total C25 weight ratio greater than 7.5. Alternatively, the condensable hydrocarbon portion may have a total C10 to total C25 weight ratio greater than 10.0, greater than 14.0, or greater than 17.0. In alternative embodiments, the condensable hydrocarbon portion may have a total C10 to total C25 weight ratio less than 35.0 or less than 30.0. In some embodiments the condensable hydrocarbon portion has a total C11 to total C25 weight ratio greater than 6.5. Alternatively, the condensable hydrocarbon portion may have a total C11 to total C25 weight ratio greater than 8.5, greater than 10.0, greater than 12.0, or greater than 14.0. In alternative embodiments, the condensable hydrocarbon portion may have a total C11 to total C25 weight ratio less than 35.0 or less than 30.0. In some embodiments the condensable hydrocarbon portion has a total C12 to total C25 weight ratio greater than 6.5. Alternatively, the condensable hydrocarbon portion may have a total C12 to total C25 weight ratio greater than 8.5, a total C12 to total C25 weight ratio greater than 10.0, greater than 12.0, or greater than 14.0. In alternative embodiments, the condensable hydrocarbon portion may have a total C12 to total C25 weight ratio less than 30.0 or less than 25.0. In some embodiments the condensable hydrocarbon portion has a total C13 to total C25 weight ratio greater than 8.0. Alternatively, the condensable hydrocarbon portion may have a total C13 to total C25 weight ratio greater than 10.0, greater than 12.0, or greater than 14.0. In alternative embodiments, the condensable hydrocarbon portion may have a total C13 to total C25 weight ratio less than 25.0 or less than 20.0. In some embodiments the condensable hydrocarbon portion has a total C14 to total C25 weight ratio greater than 6.0. Alternatively, the condensable hydrocarbon portion may have a total C14 to total C25 weight ratio greater than 8.0, greater than 10.0, or greater than 12.0. In alternative embodiments, the condensable hydrocarbon portion may have a total C14 to total C25 weight ratio less than 25.0 or less than 20.0. In some embodiments the condensable hydrocarbon portion has a total C15 to total C25 weight ratio greater than 6.0. Alternatively, the condensable hydrocarbon portion may have a total C15 to total C25 weight ratio greater than 8.0, or greater than 10.0. In alternative embodiments, the condensable hydrocarbon portion may have a total C15 to total C25 weight ratio less than 25.0 or less than 20.0. In some embodiments the condensable hydrocarbon portion has a total C16 to total C25 weight ratio greater than 4.5. Alternatively, the condensable hydrocarbon portion may have a total C16 to total C25 weight ratio greater than 6.0, greater than 8.0, or greater than 10.0. In alternative embodiments, the condensable hydrocarbon portion may have a total C16 to total C25 weight ratio less than 20.0 or less than 15.0. In some embodiments the condensable hydrocarbon portion has a total C17 to total C25 weight ratio greater than 4.8. Alternatively, the condensable hydrocarbon portion may have a total C17 to total C25 weight ratio greater than 5.5 or greater than 7.0. In alternative embodiments, the condensable hydrocarbon portion may have a total C17 to total C25 weight ratio less than 20.0. In some embodiments the condensable hydrocarbon portion has a total C18 to total C25 weight ratio greater than 4.5. Alternatively, the condensable hydrocarbon portion may have a total C18 to total C25 weight ratio greater than 5.0 or greater than 5.5. In alternative embodiments, the condensable hydrocarbon portion may have a total C18 to total C25 weight ratio less than 15.0. Certain features of the present invention are described in terms of a set of numerical upper limits (e.g. "less than") and a set of numerical lower limits (e.g. "greater than") in the preceding paragraph. It should be appreciated that ranges formed by any combination of these limits are within the scope of the invention unless otherwise indicated. The embodiments described in this paragraph may be combined with any of the other aspects of the invention discussed herein.

In some embodiments the condensable hydrocarbon portion may have the one or more of a total C7 to total C29 weight ratio greater than 3.5, a total C8 to total C29 weight ratio greater than 9.0, a total C9 to total C29 weight ratio greater than 12.0, a total C10 to total C29 weight ratio greater than 15.0, a total C11 to total C29 weight ratio greater than 13.0, a total C12 to total C29 weight ratio greater than 12.5, and a total C13 to total C29 weight ratio greater than 16.0, a total C14 to total C29 weight ratio greater than 12.0, a total C15 to total C29 weight ratio greater than 12.0, a total C16 to total C29 weight ratio greater than 9.0, a total C17 to total C29 weight ratio greater than 10.0, a total C18 to total C29 weight ratio greater than 8.8, a total C19 to total C29 weight ratio greater than 7.0, a total C20 to total C29 weight ratio greater than 6.0, a total C21 to total C29 weight ratio greater than 5.5, and a total C22 to total C29 weight ratio greater than 4.2. In alternative embodiments the condensable hydrocarbon portion has one or more of a total C7 to total C29 weight ratio greater than 16.0, a total C8 to total C29 weight ratio greater than 19.0, a total C9 to total C29 weight ratio greater than 20.0, a total C10 to total C29 weight ratio greater than 18.0, a total C11 to total C29 weight ratio greater than 16.0, a total C12 to total C29 weight ratio greater than 15.0, and a total C13 to total C29 weight ratio greater than 17.0, a total C14 to total C29 weight ratio greater than 13.0, a total C15 to total C29 weight ratio greater than 13.0, a total C16 to total C29 weight ratio greater than 10.0, a total C17 to total C29 weight ratio greater than 11.0, a total C18 to total C29 weight ratio greater than 9.0, a total C19 to total C29 weight ratio greater than 8.0, a total C20 to total C29 weight ratio greater than 6.5, and a total C21 to total C29 weight ratio greater than 6.0. In alternative embodiments the condensable hydrocarbon portion has one or more of a total C7 to total C29 weight ratio greater than 24.0, a total C8 to total C29 weight ratio greater than 30.0, a total C9 to total C29 weight ratio greater than 32.0, a total C10 to total C29 weight ratio greater than 30.0, a total C11 to total C29 weight ratio greater than 27.0, a total C12 to total C29 weight ratio greater than 25.0, and a total C13 to total C29 weight ratio greater than 22.0, a total C14 to total C29 weight ratio greater than 18.0, a total C15 to total C29 weight ratio greater than 18.0, a total C16 to total C29 weight ratio greater than 16.0, a total C17 to total C29 weight ratio greater than 13.0, a total C18 to total C29 weight ratio greater than 10.0, a total C19 to total C29 weight ratio greater than 9.0, and a total C20 to total C29 weight ratio greater than 7.0. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a total C7 to total C29 weight ratio greater than 3.5. Alternatively, the condensable hydrocarbon portion may have a total C7 to total C29 weight ratio greater than 5.0, greater than 10.0, greater than 18.0, greater than 20.0, or greater than 24.0. In alternative embodiments, the condensable hydrocarbon portion may have a total C7 to total C29 weight ratio less than 60.0 or less than 50.0. In some embodiments the condensable hydrocarbon portion has a total C8 to total C29 weight ratio greater than 9.0. Alternatively, the condensable hydrocarbon portion may have a total C8 to total C29 weight ratio greater than 10.0, greater than 18.0, greater than 20.0, greater than 25.0, or greater than 30.0. In alternative embodiments, the condensable hydrocarbon portion may have a total C8 to total C29 weight ratio less than 85.0 or less than 75.0. In some embodiments the condensable hydrocarbon portion has a total C9 to total C29 weight ratio greater than 12.0. Alternatively, the condensable hydrocarbon portion may have a total C9 to total C29 weight ratio greater than 15.0, greater than 20.0, greater than 23.0, greater than 27.0, or greater than 32.0. In alternative embodiments, the condensable hydrocarbon portion may have a total C9 to total C29 weight ratio less than 85.0 or less than 75.0. In some embodiments the condensable hydrocarbon portion has a total C10 to total C29 weight ratio greater than 15.0. Alternatively, the condensable hydrocarbon portion may have a total C10 to total C29 weight ratio greater than 18.0, greater than 22.0, or greater than 28.0. In alternative embodiments, the condensable hydrocarbon portion may have a total C10 to total C29 weight ratio less than 80.0 or less than 70.0. In some embodiments the condensable hydrocarbon portion has a total C11 to total C29 weight ratio greater than 13.0. Alternatively, the condensable hydrocarbon portion may have a total C11 to total C29 weight ratio greater than 16.0, greater than 18.0, greater than 24.0, or greater than 27.0. In alternative embodiments, the condensable hydrocarbon portion may have a total C11 to total C29 weight ratio less than 75.0 or less than 65.0. In some embodiments the condensable hydrocarbon portion has a total C12 to total C29 weight ratio greater than 12.5. Alternatively, the condensable hydrocarbon portion may have a total C12 to total C29 weight ratio greater than 14.5, greater than 18.0, greater than 22.0, or greater than 25.0. In alternative embodiments, the condensable hydrocarbon portion may have a total C12 to total C29 weight ratio less than 75.0 or less than 65.0. In some embodiments the condensable hydrocarbon portion has a total C13 to total C29 weight ratio greater than 16.0. Alternatively, the condensable hydrocarbon portion may have a total C13 to total C29 weight ratio greater than 18.0, greater than 20.0, or greater than 22.0. In alternative embodiments, the condensable hydrocarbon portion may have a total C13 to total C29 weight ratio less than 70.0 or less than 60.0. In some embodiments the condensable hydrocarbon portion has a total C14 to total C29 weight ratio greater than 12.0. Alternatively, the condensable hydrocarbon portion may have a total C14 to total C29 weight ratio greater than 14.0, greater than 16.0, or greater than 18.0. In alternative embodiments, the condensable hydrocarbon portion may have a total C14 to total C29 weight ratio less than 60.0 or less than 50.0. In some embodiments the condensable hydrocarbon portion has a total C15 to total C29 weight ratio greater than 12.0. Alternatively, the condensable hydrocarbon portion may have a total C15 to total C29 weight ratio greater than 15.0 or greater than 18.0. In alternative embodiments, the condensable hydrocarbon portion may have a total C15 to total C29 weight ratio less than 60.0 or less than 50.0. In some embodiments the condensable hydrocarbon portion has a total C16 to total C29 weight ratio greater than 9.0. Alternatively, the condensable hydrocarbon portion may have a total C16 to total C29 weight ratio greater than 10.0, greater than 13.0, or greater than 16.0. In alternative embodiments, the condensable hydrocarbon portion may have a total C16 to total C29 weight ratio less than 55.0 or less than 45.0. In some embodiments the condensable hydrocarbon portion has a total C17 to total C29 weight ratio greater than 10.0. Alternatively, the condensable hydrocarbon portion may have a total C17 to total C29 weight ratio greater than 11.0 or greater than 12.0. In alternative embodiments, the condensable hydrocarbon portion may have a total C17 to total C29 weight ratio less than 45.0. In some embodiments the condensable hydrocarbon portion has a total C18 to total C29 weight ratio greater than 8.8. Alternatively, the condensable hydrocarbon portion may have a total C18 to total C29 weight ratio greater than 9.0 or greater than 10.0. In alternative embodiments, the condensable hydrocarbon portion may have a total C18 to total C29 weight ratio less than 35.0. In some embodiments the condensable hydrocarbon portion has a total C19 to total C29 weight ratio greater than 7.0. Alternatively, the condensable hydrocarbon portion may have a total C19 to total C29 weight ratio greater than 8.0 or greater than 9.0. In alternative embodiments, the condensable hydrocarbon portion may have a total C19 to total C29 weight ratio less than 30.0. Certain features of the present invention are described in terms of a set of numerical upper limits (e.g. "less than") and a set of numerical lower limits (e.g. "greater than") in the preceding paragraph. It should be appreciated that ranges formed by any combination of these limits are within the scope of the invention unless otherwise indicated. The embodiments described in this paragraph may be combined with any of the other aspects of the invention discussed herein.

In some embodiments the condensable hydrocarbon portion may have the one or more of a total C9 to total C20 weight ratio between 2.5 and 6.0, a total C10 to total C20 weight ratio between 2.8 and 7.3, a total C11 to total C20 weight ratio between 2.6 and 6.5, a total C12 to total C20 weight ratio between 2.6 and 6.4 and a total C13 to total C20 weight ratio between 3.2 and 8.0. In alternative embodiments the condensable hydrocarbon portion has one or more of a total C9 to total C20 weight ratio between 3.0 and 5.5, a total C10 to total C20 weight ratio between 3.2 and 7.0, a total C11 to total C20 weight ratio between 3.0 and 6.0, a total C12 to total C20 weight ratio between 3.0 and 6.0, and a total C13 to total C20 weight ratio between 3.3 and 7.0. In alternative embodiments the condensable hydrocarbon portion has one or more of a total C9 to total C20 weight ratio between 4.6 and 5.5, a total C10 to total C20 weight ratio between 4.2 and 7.0, a total C11 to total C20 weight ratio between 3.7 and 6.0, a total C12 to total C20 weight ratio between 3.6 and 6.0, and a total C13 to total C20 weight ratio between 3.4 and 7.0. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a total C9 to total C20 weight ratio between 2.5 and 6.0. Alternatively, the condensable hydrocarbon portion may have a total C9 to total C20 weight ratio between 3.0 and 5.8, between 3.5 and 5.8, between 4.0 and 5.8, between 4.5 and 5.8, between 4.6 and 5.8, or between 4.7 and 5.8. In some embodiments the condensable hydrocarbon portion has a total C10 to total C20 weight ratio between 2.8 and 7.3. Alternatively, the condensable hydrocarbon portion may have a total C10 to total C20 weight ratio between 3.0 and 7.2, between 3.5 and 7.0, between 4.0 and 7.0, between 4.2 and 7.0, between 4.3 and 7.0, or between 4.4 and 7.0. In some embodiments the condensable hydrocarbon portion has a total C11 to total C20 weight ratio between 2.6 and 6.5. Alternatively, the condensable hydrocarbon portion may have a total C11 to total C20 weight ratio between 2.8 and 6.3, between 3.5 and 6.3, between 3.7 and 6.3, between 3.8 and 6.3, between 3.9 and 6.2, or between 4.0 and 6.2. In some embodiments the condensable hydrocarbon portion has a total C12 to total C20 weight ratio between 2.6 and 6.4. Alternatively, the condensable hydrocarbon portion may have a total C12 to total C20 weight ratio between 2.8 and 6.2, between 3.2 and 6.2, between 3.5 and 6.2, between 3.6 and 6.2, between 3.7 and 6.0, or between 3.8 and 6.0. In some embodiments the condensable hydrocarbon portion has a total C13 to total C20 weight ratio between 3.2 and 8.0. Alternatively, the condensable hydrocarbon portion may have a total C13 to total C20 weight ratio between 3.3 and 7.8, between 3.3 and 7.0, between 3.4 and 7.0, between 3.5 and 6.5, or between 3.6 and 6.0. The embodiments described in this paragraph may be combined with any of the other aspects of the invention discussed herein.

In some embodiments the condensable hydrocarbon portion may have one or more of a total C10 to total C25 weight ratio between 7.1 and 24.5, a total C11 to total C25 weight ratio between 6.5 and 22.0, a total C12 to total C25 weight ratio between 6.5 and 22.0, and a total C13 to total C25 weight ratio between 8.0 and 27.0. In alternative embodiments the condensable hydrocarbon portion has one or more of a total C10 to total C25 weight ratio between 10.0 and 24.0, a total C11 to total C25 weight ratio between 10.0 and 21.5, a total C12 to total C25 weight ratio between 10.0 and 21.5, and a total C13 to total C25 weight ratio between 9.0 and 25.0. In alternative embodiments the condensable hydrocarbon portion has one or more of a total C10 to total C25 weight ratio between 14.0 and 24.0, a total C11 to total C25 weight ratio between 12.5 and 21.5, a total C12 to total C25 weight ratio between 12.0 and 21.5, and a total C13 to total C25 weight ratio between 10.5 and 25.0. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a total C10 to total C25 weight ratio between 7.1 and 24.5. Alternatively, the condensable hydrocarbon portion may have a total C10 to total C25 weight ratio between 7.5 and 24.5, between 12.0 and 24.5, between 13.8 and 24.5, between 14.0 and 24.5, or between 15.0 and 24.5. In some embodiments the condensable hydrocarbon portion has a total C11 to total C25 weight ratio between 6.5 and 22.0. Alternatively, the condensable hydrocarbon portion may have a total C11 to total C25 weight ratio between 7.0 and 21.5, between 10.0 and 21.5, between 12.5 and 21.5, between 13.0 and 21.5, between 13.7 and 21.5, or between 14.5 and 21.5. In some embodiments the condensable hydrocarbon portion has a total C12 to total C25 weight ratio between 10.0 and 21.5. Alternatively, the condensable hydrocarbon portion may have a total C12 to total C25 weight ratio between 10.5 and 21.0, between 11.0 and 21.0, between 12.0 and 21.0, between 12.5 and 21.0, between 13.0 and 21.0, or between 13.5 and 21.0. In some embodiments the condensable hydrocarbon portion has a total C13 to total C25 weight ratio between 8.0 and 27.0. Alternatively, the condensable hydrocarbon portion may have a total C13 to total C25 weight ratio between 9.0 and 26.0, between 10.0 and 25.0, between 10.5 and 25.0, between 11.0 and 25.0, or between 11.5 and 25.0. The embodiments described in this paragraph may be combined with any of the other aspects of the invention discussed herein.

In some embodiments the condensable hydrocarbon portion may have one or more of a total C10 to total C29 weight ratio between 15.0 and 60.0, a total C11 to total C29 weight ratio between 13.0 and 54.0, a total C12 to total C29 weight ratio between 12.5 and 53.0, and a total C13 to total C29 weight ratio between 16.0 and 65.0. In alternative embodiments the condensable hydrocarbon portion has one or more of a total C10 to total C29 weight ratio between 17.0 and 58.0, a total C11 to total C29 weight ratio between 15.0 and 52.0, a total C12 to total C29 weight ratio between 14.0 and 50.0, and a total C13 to total C29 weight ratio between 17.0 and 60.0. In alternative embodiments the condensable hydrocarbon portion has one or more of a total C10 to total C29 weight ratio between 20.0 and 58.0, a total C11 to total C29 weight ratio between 18.0 and 52.0, a total C12 to total C29 weight ratio between 18.0 and 50.0, and a total C13 to total C29 weight ratio between 18.0 and 50.0. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a total C10 to total C29 weight ratio between 15.0 and 60.0. Alternatively, the condensable hydrocarbon portion may have a total C10 to total C29 weight ratio between 18.0 and 58.0, between 20.0 and 58.0, between 24.0 and 58.0, between 27.0 and 58.0, or between 30.0 and 58.0. In some embodiments the condensable hydrocarbon portion has a total C11 to total C29 weight ratio between 13.0 and 54.0. Alternatively, the condensable hydrocarbon portion may have a total C11 to total C29 weight ratio between 15.0 and 53.0, between 18.0 and 53.0, between 20.0 and 53.0, between 22.0 and 53.0, between 25.0 and 53.0, or between 27.0 and 53.0. In some embodiments the condensable hydrocarbon portion has a total C12 to total C29 weight ratio between 12.5 and 53.0. Alternatively, the condensable hydrocarbon portion may have a total C12 to total C29 weight ratio between 14.5 and 51.0, between 16.0 and 51.0, between 18.0 and 51.0, between 20.0 and 51.0, between 23.0 and 51.0, or between 25.0 and 51.0. In some embodiments the condensable hydrocarbon portion has a total C13 to total C29 weight ratio between 16.0 and 65.0. Alternatively, the condensable hydrocarbon portion may have a total C13 to total C29 weight ratio between 17.0 and 60.0, between 18.0 and 60.0, between 20.0 and 60.0, between 22.0 and 60.0, or between 25.0 and 60.0. The embodiments described in this paragraph may be combined with any of the other aspects of the invention discussed herein.

In some embodiments the condensable hydrocarbon portion may have one or more of a normal-C7 to normal-C20 weight ratio greater than 0.9, a normal-C8 to normal-C20 weight ratio greater than 2.0, a normal-C9 to normal-C20 weight ratio greater than 1.9, a normal-C10 to normal-C20 weight ratio greater than 2.2, a normal-C11 to normal-C20 weight ratio greater than 1.9, a normal-C12 to normal-C20 weight ratio greater than 1.9, a normal-C13 to normal-C20 weight ratio greater than 2.3, a normal-C14 to normal-C20 weight ratio greater than 1.8, a normal-C15 to normal-C20 weight ratio greater than 1.8, and normal-C16 to normal-C20 weight ratio greater than 1.3. In alternative embodiments the condensable hydrocarbon portion has one or more of a normal-C7 to normal-C20 weight ratio greater than 4.4, a normal-C8 to normal-C20 weight ratio greater than 3.7, a normal-C9 to normal-C20 weight ratio greater than 3.5, a normal-C10 to normal-C20 weight ratio greater than 3.4, a normal-C11 to normal-C20 weight ratio greater than 3.0, and a normal-C12 to normal-C20 weight ratio greater than 2.7. In alternative embodiments the condensable hydrocarbon portion has one or more of a normal-C7 to normal-C20 weight ratio greater than 4.9, a normal-C8 to normal-C20 weight ratio greater than 4.5, a normal-C9 to normal-C20 weight ratio greater than 4.4, a normal-C10 to normal-C20 weight ratio greater than 4.1, a normal-C11 to normal-C20 weight ratio greater than 3.7, and a normal-C12 to normal-C20 weight ratio greater than 3.0. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a normal-C7 to normal-C20 weight ratio greater than 0.9. Alternatively, the condensable hydrocarbon portion may have a normal-C7 to normal-C20 weight ratio greater than 1.0, than 2.0, greater than 3.0, greater than 4.0, greater than 4.5, or greater than 5.0. In alternative embodiments, the condensable hydrocarbon portion may have a normal-C7 to normal-C20 weight ratio less than 8.0 or less than 7.0. In some embodiments the condensable hydrocarbon portion has a normal-C8 to normal-C20 weight ratio greater than 1.7. Alternatively, the condensable hydrocarbon portion may have a normal-C8 to normal-C20 weight ratio greater than 2.0, greater than 2.5, greater than 3.0, greater than 3.5, greater than 4.0, or greater than 4.4. In alternative embodiments, the condensable hydrocarbon portion may have a normal-C8 to normal-C20 weight ratio less than 8.0 or less than 7.0. In some embodiments the condensable hydrocarbon portion has a normal-C9 to normal-C20 weight ratio greater than 1.9. Alternatively, the condensable hydrocarbon portion may have a normal-C9 to normal-C20 weight ratio greater than 2.0, greater than 3.0, greater than 4.0, or greater than 4.5. In alternative embodiments, the condensable hydrocarbon portion may have a normal-C9 to normal-C20 weight ratio less than 7.0 or less than 6.0. In some embodiments the condensable hydrocarbon portion has a normal-C10 to normal-C20 weight ratio greater than 2.2. Alternatively, the condensable hydrocarbon portion may have a normal-C10 to normal-C20 weight ratio greater than 2.8, greater than 3.3, greater than 3.5, or greater than 4.0. In alternative embodiments, the condensable hydrocarbon portion may have a normal-C10 to normal-C20 weight ratio less than 7.0 or less than 6.0. In some embodiments the condensable hydrocarbon portion has a normal-C11 to normal-C20 weight ratio greater than 1.9. Alternatively, the condensable hydrocarbon portion may have a normal-C11 to normal-C20 weight ratio greater than 2.5, greater than 3.0, greater than 3.5, or greater than 3.7. In alternative embodiments, the condensable hydrocarbon portion may have a normal-C11 to normal-C20 weight ratio less than 7.0 or less than 6.0. In some embodiments the condensable hydrocarbon portion has a normal-C12 to normal-C20 weight ratio greater than 1.9. Alternatively, the condensable hydrocarbon portion may have a normal-C12 to normal-C20 weight ratio greater than 2.0, greater than 2.2, greater than 2.6, or greater than 3.0. In alternative embodiments, the condensable hydrocarbon portion may have a normal-C12 to normal-C20 weight ratio less than 7.0 or less than 6.0. In some embodiments the condensable hydrocarbon portion has a normal-C13 to normal-C20 weight ratio greater than 2.3. Alternatively, the condensable hydrocarbon portion may have a normal-C13 to normal-C20 weight ratio greater than 2.5, greater than 2.7, or greater than 3.0. In alternative embodiments, the condensable hydrocarbon portion may have a normal-C13 to normal-C20 weight ratio less than 6.0 or less than 5.0. In some embodiments the condensable hydrocarbon portion has a normal-C14 to normal-C20 weight ratio greater than 1.8. Alternatively, the condensable hydrocarbon portion may have a normal-C14 to normal-C20 weight ratio greater than 2.0, greater than 2.2, or greater than 2.5. In alternative embodiments, the condensable hydrocarbon portion may have a normal-C14 to normal-C20 weight ratio less than 6.0 or less than 4.0. In some embodiments the condensable hydrocarbon portion has a normal-C15 to normal-C20 weight ratio greater than 1.8. Alternatively, the condensable hydrocarbon portion may have a normal-C15 to normal-C20 weight ratio greater than 2.0, greater than 2.2, or greater than 2.4. In alternative embodiments, the condensable hydrocarbon portion may have a normal-C15 to normal-C20 weight ratio less than 6.0 or less than 4.0. In some embodiments the condensable hydrocarbon portion has a normal-C16 to normal-C20 weight ratio greater than 1.3. Alternatively, the condensable hydrocarbon portion may have a normal-C16 to normal-C20 weight ratio greater than 1.5, greater than 1.7, or greater than 2.0. In alternative embodiments, the condensable hydrocarbon portion may have a normal-C16 to normal-C20 weight ratio less than 5.0 or less than 4.0. Certain features of the present invention are described in terms of a set of numerical upper limits (e.g. "less than") and a set of numerical lower limits (e.g. "greater than") in the preceding paragraph. It should be appreciated that ranges formed by any combination of these limits are within the scope of the invention unless otherwise indicated. The embodiments described in this paragraph may be combined with any of the other aspects of the invention discussed herein.

In some embodiments the condensable hydrocarbon portion may have one or more of a normal-C7 to normal-C25 weight ratio greater than 1.9, a normal-C8 to normal-C25 weight ratio greater than 3.9, a normal-C9 to normal-C25 weight ratio greater than 3.7, a normal-C10 to normal-C25 weight ratio greater than 4.4, a normal-C11 to normal-C25 weight ratio greater than 3.8, a normal-C12 to normal-C25 weight ratio greater than 3.7, a normal-C13 to normal-C25 weight ratio greater than 4.7, a normal-C14 to normal-C25 weight ratio greater than 3.7, a normal-C15 to normal-C25 weight ratio greater than 3.7, a normal-C16 to normal-C25 weight ratio greater than 2.5, a normal-C17 to normal-C25 weight ratio greater than 3.0, and a normal-C18 to normal-C25 weight ratio greater than 3.4. In alternative embodiments the condensable hydrocarbon portion has one or more of a normal-C7 to normal-C25 weight ratio greater than 10, a normal-C8 to normal-C25 weight ratio greater than 8.0, a normal-C9 to normal-C25 weight ratio greater than 7.0, a normal-C10 to normal-C25 weight ratio greater than 7.0, a normal-C11 to normal-C25 weight ratio greater than 7.0, and a normal-C12 to normal-C25 weight ratio greater than 6.0. In alternative embodiments the condensable hydrocarbon portion has one or more of a normal-C7 to normal-C25 weight ratio greater than 10.0, a normal-C8 to normal-C25 weight ratio greater than 12.0, a normal-C9 to normal-C25 weight ratio greater than 11.0, a normal-C10 to normal-C25 weight ratio greater than 11.0, a normal-C11 to normal-C25 weight ratio greater than 9.0, and a normal-C12 to normal-C25 weight ratio greater than 8.0. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a normal-C7 to normal-C25 weight ratio greater than 1.9. Alternatively, the condensable hydrocarbon portion may have a normal-C7 to normal-C25 weight ratio greater than 3.0, greater than 5.0, greater than 8.0, greater than 10.0, or greater than 13.0. In alternative embodiments, the condensable hydrocarbon portion may have a normal-C7 to normal-C25 weight ratio less than 35.0 or less than 25.0. In some embodiments the condensable hydrocarbon portion has a normal-C8 to normal-C25 weight ratio greater than 3.9. Alternatively, the condensable hydrocarbon portion may have a normal-C8 to normal-C25 weight ratio greater than 4.5, greater than 6.0, greater than 8.0, greater than 10.0, or greater than 13.0. In alternative embodiments, the condensable hydrocarbon portion may have a normal-C8 to normal-C25 weight ratio less than 35.0 or less than 25.0. In some embodiments the condensable hydrocarbon portion has a normal-C9 to normal-C25 weight ratio greater than 3.7. Alternatively, the condensable hydrocarbon portion may have a normal-C9 to normal-C25 weight ratio greater than 4.5, greater than 7.0, greater than 10.0, greater than 12.0, or greater than 13.0. In alternative embodiments, the condensable hydrocarbon portion may have a normal-C9 to normal-C25 weight ratio less than 35.0 or less than 25.0. In some embodiments the condensable hydrocarbon portion has a normal-C10 to normal-C25 weight ratio greater than 4.4. Alternatively, the condensable hydrocarbon portion may have a normal-C10 to normal-C25 weight ratio greater than 6.0, greater than 8.0, or greater than 11.0. In alternative embodiments, the condensable hydrocarbon portion may have a normal-C10 to normal-C25 weight ratio less than 35.0 or less than 25.0. In some embodiments the condensable hydrocarbon portion has a normal-C11 to normal-C25 weight ratio greater than 3.8. Alternatively, the condensable hydrocarbon portion may have a normal-C11 to normal-C25 weight ratio greater than 4.5, greater than 7.0, greater than 8.0, or greater than 10.0. In alternative embodiments, the condensable hydrocarbon portion may have a normal-C11 to normal-C25 weight ratio less than 35.0 or less than 25.0. In some embodiments the condensable hydrocarbon portion has a normal-C12 to normal-C25 weight ratio greater than 3.7. Alternatively, the condensable hydrocarbon portion may have a normal-C12 to normal-C25 weight ratio greater than 4.5, greater than 6.0, greater than 7.0, or greater than 8.0. In alternative embodiments, the condensable hydrocarbon portion may have a normal-C12 to normal-C25 weight ratio less than 30.0 or less than 20.0. In some embodiments the condensable hydrocarbon portion has a normal-C13 to normal-C25 weight ratio greater than 4.7. Alternatively, the condensable hydrocarbon portion may have a normal-C13 to normal-C25 weight ratio greater than 5.0, greater than 6.0, or greater than 7.5. In alternative embodiments, the condensable hydrocarbon portion may have a normal-C13 to normal-C25 weight ratio less than 25.0 or less than 20.0. In some embodiments the condensable hydrocarbon portion has a normal-C14 to normal-C25 weight ratio greater than 3.7. Alternatively, the condensable hydrocarbon portion may have a normal-C14 to normal-C25 weight ratio greater than 4.5, greater than 5.5, or greater than 7.0. In alternative embodiments, the condensable hydrocarbon portion may have a normal-C14 to normal-C25 weight ratio less than 25.0 or less than 20.0. In some embodiments the condensable hydrocarbon portion has a normal-C15 to normal-C25 weight ratio greater than 3.7. Alternatively, the condensable hydrocarbon portion may have a normal-C15 to normal-C25 weight ratio greater than 4.2 or greater than 5.0. In alternative embodiments, the condensable hydrocarbon portion may have a normal-C15 to normal-C25 weight ratio less than 25.0 or less than 20.0. In some embodiments the condensable hydrocarbon portion has a normal-C16 to normal-C25 weight ratio greater than 2.5. Alternatively, the condensable hydrocarbon portion may have a normal-C16 to normal-C25 weight ratio greater than 3.0, greater than 4.0, or greater than 5.0. In alternative embodiments, the condensable hydrocarbon portion may have a normal-C16 to normal-C25 weight ratio less than 20.0 or less than 15.0. In some embodiments the condensable hydrocarbon portion has a normal-C17 to normal-C25 weight ratio greater than 3.0. Alternatively, the condensable hydrocarbon portion may have a normal-C17 to normal-C25 weight ratio greater than 3.5 or greater than 4.0. In alternative embodiments, the condensable hydrocarbon portion may have a normal-C17 to normal-C25 weight ratio less than 20.0. In some embodiments the condensable hydrocarbon portion has a normal-C18 to normal-C25 weight ratio greater than 3.4. Alternatively, the condensable hydrocarbon portion may have a normal-C18 to normal-C25 weight ratio greater than 3.6 or greater than 4.0. In alternative embodiments, the condensable hydrocarbon portion may have a normal-C18 to normal-C25 weight ratio less than 15.0. Certain features of the present invention are described in terms of a set of numerical upper limits (e.g. "less than") and a set of numerical lower limits (e.g. "greater than") in the preceding paragraph. It should be appreciated that ranges formed by any combination of these limits are within the scope of the invention unless otherwise indicated. The embodiments described in this paragraph may be combined with any of the other aspects of the invention discussed herein.

In some embodiments the condensable hydrocarbon portion may have one or more of a normal-C7 to normal-C29 weight ratio greater than 18.0, a normal-C8 to normal-C29 weight ratio greater than 16.0, a normal-C9 to normal-C29 weight ratio greater than 14.0, a normal-C10 to normal-C29 weight ratio greater than 14.0, a normal-C11 to normal-C29 weight ratio greater than 13.0, a normal-C12 to normal-C29 weight ratio greater than 11.0, a normal-C13 to normal-C29 weight ratio greater than 10.0, a normal-C14 to normal-C29 weight ratio greater than 9.0, a normal-C15 to normal-C29 weight ratio greater than 8.0, a normal-C16 to normal-C29 weight ratio greater than 8.0, a normal-C17 to normal-C29 weight ratio greater than 6.0, a normal-C18 to normal-C29 weight ratio greater than 6.0, a normal-C19 to normal-C29 weight ratio greater than 5.0, a normal-C20 to normal-C29 weight ratio greater than 4.0, a normal-C21 to normal-C29 weight ratio greater than 3.6, and a normal-C22 to normal-C29 weight ratio greater than 2.8. In alternative embodiments the condensable hydrocarbon portion has one or more of a normal-C7 to normal-C29 weight ratio greater than 20.0, a normal-C8 to normal-C29 weight ratio greater than 18.0, a normal-C9 to normal-C29 weight ratio greater than 17.0, a normal-C10 to normal-C29 weight ratio greater than 16.0, a normal-C11 to normal-C29 weight ratio greater than 15.0, a normal-C12 to normal-C29 weight ratio greater than 12.5, a normal-C13 to normal-C29 weight ratio greater than 11.0, a normal-C14 to normal-C29 weight ratio greater than 10.0, a normal-C15 to normal-C29 weight ratio greater than 8.0, a normal-C16 to normal-C29 weight ratio greater than 8.0, a normal-C17 to normal-C29 weight ratio greater than 7.0, a normal-C18 to normal-C29 weight ratio greater than 6.5, a normal-C19 to normal-C29 weight ratio greater than 5.5, a normal-C20 to normal-C29 weight ratio greater than 4.5, and a normal-C21 to normal-C29 weight ratio greater than 4.0. In alternative embodiments the condensable hydrocarbon portion has one or more of a normal-C7 to normal-C29 weight ratio greater than 23.0, a normal-C8 to normal-C29 weight ratio greater than 21.0, a normal-C9 to normal-C29 weight ratio greater than 20.0, a normal-C10 to normal-C29 weight ratio greater than 19.0, a normal-C11 to normal-C29 weight ratio greater than 17.0, a normal-C12 to normal-C29 weight ratio greater than 14.0, a normal-C13 to normal-C29 weight ratio greater than 12.0, a normal-C14 to normal-C29 weight ratio greater than 11.0, a normal-C15 to normal-C29 weight ratio greater than 9.0, a normal-C16 to normal-C29 weight ratio greater than 9.0, a normal-C17 to normal-C29 weight ratio greater than 7.5, a normal-C18 to normal-C29 weight ratio greater than 7.0, a normal-C19 to normal-C29 weight ratio greater than 6.5, a normal-C20 to normal-C29 weight ratio greater than 4.8, and a normal-C21 to normal-C29 weight ratio greater than 4.5. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a normal-C7 to normal-C29 weight ratio greater than 18.0. Alternatively, the condensable hydrocarbon portion may have a normal-C7 to normal-C29 weight ratio greater than 20.0, greater than 22.0, greater than 25.0, greater than 30.0, or greater than 35.0. In alternative embodiments, the condensable hydrocarbon portion may have a normal-C7 to normal-C29 weight ratio less than 70.0 or less than 60.0. In some embodiments the condensable hydrocarbon portion has a normal-C8 to normal-C29 weight ratio greater than 16.0. Alternatively, the condensable hydrocarbon portion may have a normal-C8 to normal-C29 weight ratio greater than 18.0, greater than 22.0, greater than 25.0, greater than 27.0, or greater than 30.0. In alternative embodiments, the condensable hydrocarbon portion may have a normal-C8 to normal-C29 weight ratio less than 85.0 or less than 75.0. In some embodiments the condensable hydrocarbon portion has a normal-C9 to normal-C29 weight ratio greater than 14.0. Alternatively, the condensable hydrocarbon portion may have a normal-C9 to normal-C29 weight ratio greater than 18.0, greater than 20.0, greater than 23.0, greater than 27.0, or greater than 30.0. In alternative embodiments, the condensable hydrocarbon portion may have a normal-C9 to normal-C29 weight ratio less than 85.0 or less than 75.0. In some embodiments the condensable hydrocarbon portion has a normal-C10 to normal-C29 weight ratio greater than 14.0. Alternatively, the condensable hydrocarbon portion may have a normal-C10 to normal-C29 weight ratio greater than 20.0, greater than 25.0, or greater than 30.0. In alternative embodiments, the condensable hydrocarbon portion may have a normal-C10 to normal-C29 weight ratio less than 80.0 or less than 70.0. In some embodiments the condensable hydrocarbon portion has a normal-C11 to normal-C29 weight ratio greater than 13.0. Alternatively, the condensable hydrocarbon portion may have a normal-C11 to normal-C29 weight ratio greater than 16.0, greater than 18.0, greater than 24.0, or greater than 27.0. In alternative embodiments, the condensable hydrocarbon portion may have a normal-C11 to normal-C29 weight ratio less than 75.0 or less than 65.0. In some embodiments the condensable hydrocarbon portion has a normal-C12 to normal-C29 weight ratio greater than 11.0. Alternatively, the condensable hydrocarbon portion may have a normal-C12 to normal-C29 weight ratio greater than 14.5, greater than 18.0, greater than 22.0, or greater than 25.0. In alternative embodiments, the condensable hydrocarbon portion may have a normal-C12 to normal-C29 weight ratio less than 75.0 or less than 65.0. In some embodiments the condensable hydrocarbon portion has a normal-C13 to normal-C29 weight ratio greater than 10.0. Alternatively, the condensable hydrocarbon portion may have a normal-C13 to normal-C29 weight ratio greater than 18.0, greater than 20.0, or greater than 22.0. In alternative embodiments, the condensable hydrocarbon portion may have a normal-C13 to normal-C29 weight ratio less than 70.0 or less than 60.0. In some embodiments the condensable hydrocarbon portion has a normal-C14 to normal-C29 weight ratio greater than 9.0. Alternatively, the condensable hydrocarbon portion may have a normal-C14 to normal-C29 weight ratio greater than 14.0, greater than 16.0, or greater than 18.0. In alternative embodiments, the condensable hydrocarbon portion may have a normal-C14 to normal-C29 weight ratio less than 60.0 or less than 50.0. In some embodiments the condensable hydrocarbon portion has a normal-C15 to normal-C29 weight ratio greater than 8.0. Alternatively, the condensable hydrocarbon portion may have a normal-C15 to normal-C29 weight ratio greater than 12.0 or greater than 16.0. In alternative embodiments, the condensable hydrocarbon portion may have a normal-C15 to normal-C29 weight ratio less than 60.0 or less than 50.0. In some embodiments the condensable hydrocarbon portion has a normal-C16 to normal-C29 weight ratio greater than 8.0. Alternatively, the condensable hydrocarbon portion may have a normal-C16 to normal-C29 weight ratio greater than 10.0, greater than 13.0, or greater than 15.0. In alternative embodiments, the condensable hydrocarbon portion may have a normal-C16 to normal-C29 weight ratio less than 55.0 or less than 45.0. In some embodiments the condensable hydrocarbon portion has a normal-C17 to normal-C29 weight ratio greater than 6.0. Alternatively, the condensable hydrocarbon portion may have a normal-C17 to normal-C29 weight ratio greater than 8.0 or greater than 12.0. In alternative embodiments, the condensable hydrocarbon portion may have a normal-C17 to normal-C29 weight ratio less than 45.0. In some embodiments the condensable hydrocarbon portion has a normal-C18 to normal-C29 weight ratio greater than 6.0. Alternatively, the condensable hydrocarbon portion may have a normal-C18 to normal-C29 weight ratio greater than 8.0 or greater than 10.0. In alternative embodiments, the condensable hydrocarbon portion may have a normal-C18 to normal-C29 weight ratio less than 35.0. In some embodiments the condensable hydrocarbon portion has a normal-C19 to normal-C29 weight ratio greater than 5.0. Alternatively, the condensable hydrocarbon portion may have a normal-C19 to normal-C29 weight ratio greater than 7.0 or greater than 9.0. In alternative embodiments, the condensable hydrocarbon portion may have a normal-C19 to normal-C29 weight ratio less than 30.0. In some embodiments the condensable hydrocarbon portion has a normal-C20 to normal-C29 weight ratio greater than 4.0. Alternatively, the condensable hydrocarbon portion may have a normal-C20 to normal-C29 weight ratio greater than 6.0 or greater than 8.0. In alternative embodiments, the condensable hydrocarbon portion may have a normal-C20 to normal-C29 weight ratio less than 30.0. In some embodiments the condensable hydrocarbon portion has a normal-C21 to normal-C29 weight ratio greater than 3.6. Alternatively, the condensable hydrocarbon portion may have a normal-C21 to normal-C29 weight ratio greater than 4.0 or greater than 6.0. In alternative embodiments, the condensable hydrocarbon portion may have a normal-C21 to normal-C29 weight ratio less than 30.0. In some embodiments the condensable hydrocarbon portion has a normal-C22 to normal-C29 weight ratio greater than 2.8. Alternatively, the condensable hydrocarbon portion may have a normal-C22 to normal-C29 weight ratio greater than 3.0. In alternative embodiments, the condensable hydrocarbon portion may have a normal-C22 to normal-C29 weight ratio less than 30.0. Certain features of the present invention are described in terms of a set of numerical upper limits (e.g. "less than") and a set of numerical lower limits (e.g. "greater than") in the preceding paragraph. It should be appreciated that ranges formed by any combination of these limits are within the scope of the invention unless otherwise indicated. The embodiments described in this paragraph may be combined with any of the other aspects of the invention discussed herein.

In some embodiments the condensable hydrocarbon portion may have one or more of a normal-C10 to total C10 weight ratio less than 0.31, a normal-C11 to total C11 weight ratio less than 0.32, a normal-C12 to total C12 weight ratio less than 0.29, a normal-C13 to total C13 weight ratio less than 0.28, a normal-C14 to total C14 weight ratio less than 0.31, a normal-C15 to total C15 weight ratio less than 0.27, a normal-C16 to total C16 weight ratio less than 0.31, a normal-C17 to total C17 weight ratio less than 0.31, a normal-C18 to total C18 weight ratio less than 0.37, normal-C19 to total C19 weight ratio less than 0.37, a normal-C20 to total C20 weight ratio less than 0.37, a normal-C21 to total C21 weight ratio less than 0.37, a normal-C22 to total C22 weight ratio less than 0.38, normal-C23 to total C23 weight ratio less than 0.43, a normal-C24 to total C24 weight ratio less than 0.48, and a normal-C25 to total C25 weight ratio less than 0.53. In alternative embodiments the condensable hydrocarbon portion has one or more of a normal-C11 to total C11 weight ratio less than 0.30, a normal-C12 to total C12 weight ratio less than 0.27, a normal-C13 to total C13 weight ratio less than 0.26, a normal-C14 to total C14 weight ratio less than 0.29, a normal-C15 to total C15 weight ratio less than 0.24, a normal-C16 to total C16 weight ratio less than 0.25, a normal-C17 to total C17 weight ratio less than 0.29, a normal-C18 to total C18 weight ratio less than 0.31, normal-C19 to total C19 weight ratio less than 0.35, a normal-C20 to total C20 weight ratio less than 0.33, a normal-C21 to total C21 weight ratio less than 0.33, a normal-C22 to total C22 weight ratio less than 0.35, normal-C23 to total C23 weight ratio less than 0.40, a normal-C24 to total C24 weight ratio less than 0.45, and a normal-C25 to total C25 weight ratio less than 0.49. In alternative embodiments the condensable hydrocarbon portion has one or more of a normal-C11 to total C11 weight ratio less than 0.28, a normal-C12 to total C12 weight ratio less than 0.25, a normal-C13 to total C13 weight ratio less than 0.24, a normal-C14 to total C14 weight ratio less than 0.27, a normal-C15 to total C15 weight ratio less than 0.22, a normal-C16 to total C16 weight ratio less than 0.23, a normal-C17 to total C17 weight ratio less than 0.25, a normal-C18 to total C18 weight ratio less than 0.28, normal-C19 to total C19 weight ratio less than 0.31, a normal-C20 to total C20 weight ratio less than 0.29, a normal-C21 to total C21 weight ratio less than 0.30, a normal-C22 to total C22 weight ratio less than 0.28, normal-C23 to total C23 weight ratio less than 0.33, a normal-C24 to total C24 weight ratio less than 0.40, and a normal-C25 to total C25 weight ratio less than 0.45. As used in this paragraph and in the claims, the phrase "one or more" followed by a listing of different compound or component ratios with the last ratio introduced by the conjunction "and" is meant to include a condensable hydrocarbon portion that has at least one of the listed ratios or that has two or more, or three or more, or four or more, etc., or all of the listed ratios. Further, a particular condensable hydrocarbon portion may also have additional ratios of different compounds or components that are not included in a particular sentence or claim and still fall within the scope of such a sentence or claim. The embodiments described in this paragraph may be combined with any of the other aspects of the invention discussed herein.

In some embodiments the condensable hydrocarbon portion has a normal-C10 to total C10 weight ratio less than 0.31. Alternatively, the condensable hydrocarbon portion may have a normal-C10 to total C10 weight ratio less than 0.30 or less than 0.29. In alternative embodiments, the condensable hydrocarbon portion may have a normal-C10 to total C10 weight ratio greater than 0.15 or greater than 0.20. In some embodiments the condensable hydrocarbon portion has a normal-C11 to total C11 weight ratio less than 0.32. Alternatively, the condensable hydrocarbon portion may have a normal-C11 to total C11 weight ratio less than 0.31, less than 0.30, or less than 0.29. In alternative embodiments, the condensable hydrocarbon portion may have a normal-C11 to total C11 weight ratio greater than 0.15 or greater than 0.20. In some embodiments the condensable hydrocarbon portion has a normal-C12 to total C12 weight ratio less than 0.29. Alternatively, the condensable hydrocarbon portion may have a normal-C12 to total C12 weight ratio less than 0.26, or less than 0.24. In alternative embodiments, the condensable hydrocarbon portion may have a normal-C12 to total C12 weight ratio greater than 0.10 or greater than 0.15. In some embodiments the condensable hydrocarbon portion has a normal-C13 to total C13 weight ratio less than 0.28. Alternatively, the condensable hydrocarbon portion may have a normal-C13 to total C13 weight ratio less than 0.27, less than 0.25, or less than 0.23. In alternative embodiments, the condensable hydrocarbon portion may have a normal-C13 to total C13 weight ratio greater than 0.10 or greater than 0.15. In some embodiments the condensable hydrocarbon portion has a normal-C14 to total C14 weight ratio less than 0.31. Alternatively, the condensable hydrocarbon portion may have a normal-C14 to total C14 weight ratio less than 0.30, less than 0.28, or less than 0.26. In alternative embodiments, the condensable hydrocarbon portion may have a normal-C14 to total C14 weight ratio greater than 0.10 or greater than 0.15. In some embodiments the condensable hydrocarbon portion has a normal-C15 to total C15 weight ratio less than 0.27. Alternatively, the condensable hydrocarbon portion may have a normal-CIS to total C15 weight ratio less than 0.26, less than 0.24, or less than 0.22. In alternative embodiments, the condensable hydrocarbon portion may have a normal-C15 to total C15 weight ratio greater than 0.10 or greater than 0.15. In some embodiments the condensable hydrocarbon portion has a normal-C16 to total C16 weight ratio less than 0.31. Alternatively, the condensable hydrocarbon portion may have a normal-C16 to total C16 weight ratio less than 0.29, less than 0.26, or less than 0.24. In alternative embodiments, the condensable hydrocarbon portion may have a normal-C16 to total C16 weight ratio greater than 0.10 or greater than 0.15. In some embodiments the condensable hydrocarbon portion has a normal-C17 to total C17 weight ratio less than 0.31. Alternatively, the condensable hydrocarbon portion may have a normal-C17 to total C17 weight ratio less than 0.29, less than 0.27, or less than 0.25. In alternative embodiments, the condensable hydrocarbon portion may have a normal-C17 to total C17 weight ratio greater than 0.10 or greater than 0.15. In some embodiments the condensable hydrocarbon portion has a normal-C18 to total C18 weight ratio less than 0.37. Alternatively, the condensable hydrocarbon portion may have a normal-C18 to total C18 weight ratio less than 0.35, less than 0.31, or less than 0.28. In alternative embodiments, the condensable hydrocarbon portion may have a normal-C18 to total C18 weight ratio greater than 0.10 or greater than 0.15. In some embodiments the condensable hydrocarbon portion has a normal-C19 to total C19 weight ratio less than 0.37. Alternatively, the condensable hydrocarbon portion may have a normal-C19 to total C19 weight ratio less than 0.36, less than 0.34, or less than 0.31. In alternative embodiments, the condensable hydrocarbon portion may have a normal-C19 to total C19 weight ratio greater than 0.10 or greater than 0.15. In some embodiments the condensable hydrocarbon portion has a normal-C20 to total C20 weight ratio less than 0.37. Alternatively, the condensable hydrocarbon portion may have a normal-C20 to total C20 weight ratio less than 0.35, less than 0.32, or less than 0.29. In alternative embodiments, the condensable hydrocarbon portion may have a normal-C20 to total C20 weight ratio greater than 0.10 or greater than 0.15. In some embodiments the condensable hydrocarbon portion has a normal-C21 to total C21 weight ratio less than 0.37. Alternatively, the condensable hydrocarbon portion may have a normal-C21 to total C21 weight ratio less than 0.35, less than 0.32, or less than 0.30. In alternative embodiments, the condensable hydrocarbon portion may have a normal-C21 to total C21 weight ratio greater than 0.10 or greater than 0.15. In some embodiments the condensable hydrocarbon portion has a normal-C22 to total C22 weight ratio less than 0.38. Alternatively, the condensable hydrocarbon portion may have a normal-C22 to total C22 weight ratio less than 0.36, less than 0.34, or less than 0.30. In alternative embodiments, the condensable hydrocarbon portion may have a normal-C22 to total C22 weight ratio greater than 0.10 or greater than 0.15. In some embodiments the condensable hydrocarbon portion has a normal-C23 to total C23 weight ratio less than 0.43. Alternatively, the condensable hydrocarbon portion may have a normal-C23 to total C23 weight ratio less than 0.40, less than 0.35, or less than 0.29. In alternative embodiments, the condensable hydrocarbon portion may have a normal-C23 to total C23 weight ratio greater than 0.15 or greater than 0.20. In some embodiments the condensable hydrocarbon portion has a normal-C24 to total C24 weight ratio less than 0.48. Alternatively, the condensable hydrocarbon portion may have a normal-C24 to total C24 weight ratio less than 0.46, less than 0.42, or less than 0.40. In alternative embodiments, the condensable hydrocarbon portion may have a normal-C24 to total C24 weight ratio greater than 0.15 or greater than 0.20. In some embodiments the condensable hydrocarbon portion has a normal-C25 to total C25 weight ratio less than 0.48. Alternatively, the condensable hydrocarbon portion may have a normal-C25 to total C25 weight ratio less than 0.46, less than 0.42, or less than 0.40. In alternative embodiments, the condensable hydrocarbon portion may have a normal-C25 to total C25 weight ratio greater than 0.20 or greater than 0.25. Certain features of the present invention are described in terms of a set of numerical upper limits (e.g. "less than") and a set of numerical lower limits (e.g. "greater than") in the preceding paragraph. It should be appreciated that ranges formed by any combination of these limits are within the scope of the invention unless otherwise indicated. The embodiments described in this paragraph may be combined with any of the other aspects of the invention discussed herein.

The use of "total C_" (e.g., total C10) herein and in the claims is meant to refer to the amount of a particular pseudo component found in a condensable hydrocarbon fluid determined as described herein, particularly as described in the section labeled "Experiments" herein. That is "total C_" is determined using the whole oil gas chromatography (WOGC) analysis methodology according to the procedure described in the Experiments section of this application. Further, "total C_" is determined from the whole oil gas chromatography (WOGC) peak integration methodology and peak identification methodology used for identifying and quantifying each pseudo-component as described in the Experiments section herein. Further, "total C_" weight percent and mole percent values for the pseudo components were obtained using the pseudo component analysis methodology involving correlations developed by Katz and Firoozabadi (Katz, D. L., and A. Firoozabadi, 1978. Predicting phase behavior of condensate/crude-oil systems using methane interaction coefficients, J. Petroleum Technology (November 1978), 1649-1655) as described in the Experiments section, including the exemplary molar and weight percentage determinations.

The use of "normal-C_" (e.g., normal-C10) herein and in the claims is meant to refer to the amount of a particular normal alkane hydrocarbon compound found in a condensable hydrocarbon fluid determined as described herein, particularly in the section labeled "Experiments" herein. That is "normal-C_" is determined from the GC peak areas determined using the whole oil gas chromatography (WOGC) analysis methodology according to the procedure described in the Experiments section of this application. Further, "total C_" is determined from the whole oil gas chromatography (WOGC) peak identification and integration methodology used for identifying and quantifying individual compound peaks as described in the Experiments section herein. Further, "normal-C_" weight percent and mole percent values for the normal alkane compounds were obtained using methodology analogous to the pseudo component exemplary molar and weight percentage determinations explained in the Experiments section, except that the densities and molecular weights for the particular normal alkane compound of interest were used and then compared to the totals obtained in the pseudo component methodology to obtain weight and molar percentages.

Figure 16:
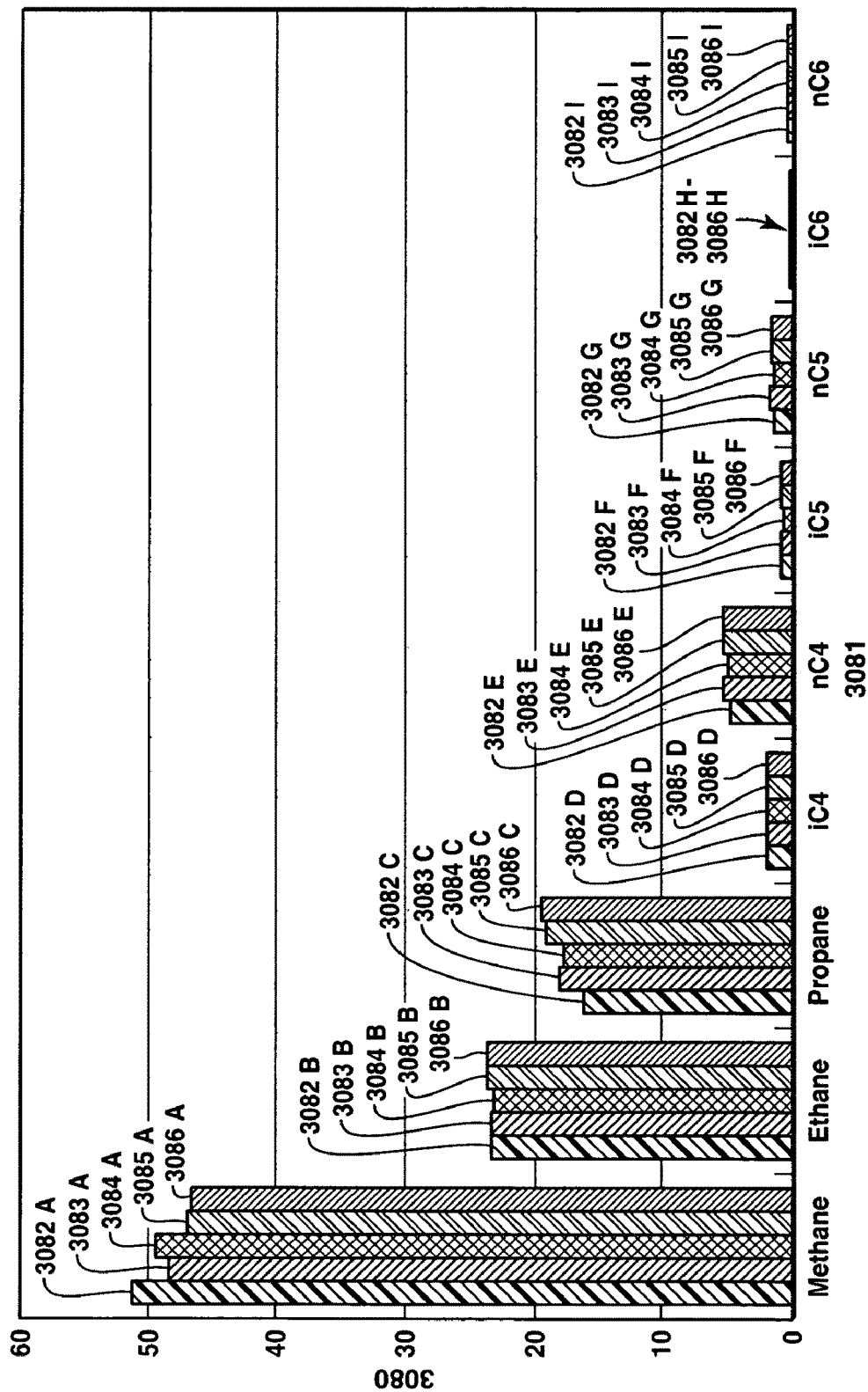
FIG. 16 is a bar graph showing the concentration, in molar percentage, of the hydrocarbon species present in the gas samples taken from duplicate laboratory experiments conducted at three different stress levels.

The following discussion of FIG. 16 concerns data obtained in Examples 1-5 which are discussed in the section labeled "Experiments". The data was obtained through the experimental procedures, gas sample collection procedures, hydrocarbon gas sample gas chromatography (GC) analysis methodology, and gas sample GC peak identification and integration methodology discussed in the Experiments section. For clarity, when referring to gas chromatograms of gaseous hydrocarbon samples, graphical data is provided for one unstressed experiment through Example 1, two 400 psi stressed experiments through Examples 2 and 3, and two 1,000 psi stressed experiments through Examples 4 and 5.

FIG. 16 is a bar graph showing the concentration, in molar percentage, of the hydrocarbon species present in the gas samples taken from each of the three stress levels tested and analyzed in the laboratory experiments discussed herein. The gas compound molar percentages were obtained through the experimental procedures, gas sample collection procedures, hydrocarbon gas sample gas chromatography (GC) analysis methodology, gas sample GC peak integration methodology and molar concentration determination procedures described herein. For clarity, the hydrocarbon molar percentages are taken as a percentage of the total of all identified hydrocarbon gas GC areas (i.e., methane, ethane, propane, iso-butane, n-butane, iso-pentane, n-pentane, 2-methyl pentane, and n-hexane) and calculated molar concentrations. Thus the graphed methane to normal C6 molar percentages for all of the experiments do not include the molar contribution of any associated non-hydrocarbon gas phase product (e.g., hydrogen, $CO_2$ or $H_2S$), any of the unidentified hydrocarbon gas species listed in Tables 2, 4, 5, 7, or 9 (e.g., peak numbers 2, 6, 8-11, 13, 15-22, 24-26, and 28-78 in Table 2) or any of the gas species dissolved in the liquid phase which were separately treated in the liquid GC's. The y-axis 3080 represents the concentration in terms of molar percent of each gaseous compound in the gas phase. The x-axis 3081 contains the identity of each hydrocarbon compound from methane to normal hexane. The bars 3082A-I represent the molar percentage of each gaseous compound for the unstressed experiment of Example 1. That is 3082A represents methane, 3082B represents ethane, 3082C represents propane, 3082D represents iso-butane, 3082E represents normal butane, 3082F represents iso-pentane, 3082G represents normal pentane, 3082H represents 2-methyl pentane, and 3082I represents normal hexane. The bars 3083A-I and 3084A-I represent the molar percent of each gaseous compound for samples from the duplicate 400 psi stressed experiments of Examples 2 and 3, with the letters assigned in the manner described for the unstressed experiment. While the bars 3085A-I and 3086A-I represent the molar percent of each gaseous compound for the duplicate 1,000 psi stressed experiments of Examples 4 and 5, with the letters assigned in the manner described for the unstressed experiment. From FIG. 16 it can be seen that the hydrocarbon gas produced in all the experiments is primarily methane, ethane and propane on a molar basis. It is further apparent that the unstressed experiment, represented by bars 3082A-I, contains the most methane 3082A and least propane 3082C, both as compared to the 400 psi stress experiments hydrocarbon gases and the 1,000 psi stress experiments hydrocarbon gases. Looking now at bars 3083A-I and 3084A-I, it is apparent that the intermediate level 400 psi stress experiments produced a hydrocarbon gas having methane 3083A and 3084A and propane 3083C and 3084C concentrations between the unstressed experiment represented by bars 3082A and 3082C and the 1,000 psi stressed experiment represented by bars 3085A and 3085C and 3086A and 3086C. Lastly, it is apparent that the high level 1,000 psi stress experiments produced hydrocarbon gases having the lowest methane 3085A and 3086A concentration and the highest propane concentrations 3085C and 3086C, as compared to both the unstressed experiments represented by bars 3082A and 3082C and the 400 psi stressed experiment represented by bars 3083A and 3084A and 3083C and 3084C. Thus pyrolyzing oil shale under increasing levels of lithostatic stress appears to produce hydrocarbon gases having decreasing concentrations of methane and increasing concentrations of propane.

The hydrocarbon fluid produced from the organic-rich rock formation may include both a condensable hydrocarbon portion (e.g. liquid) and a non-condensable hydrocarbon portion (e.g. gas). In some embodiments the non-condensable hydrocarbon portion includes methane and propane. In some embodiments the molar ratio of propane to methane in the non-condensable hydrocarbon portion is greater than 0.32. In alternative embodiments, the molar ratio of propane to methane in the non-condensable hydrocarbon portion is greater than 0.34, 0.36 or 0.38. As used herein "molar ratio of propane to methane" is the molar ratio that may be determined as described herein, particularly as described in the section labeled "Experiments" herein. That is "molar ratio of propane to methane" is determined using the hydrocarbon gas sample gas chromatography (GC) analysis methodology, gas sample GC peak identification and integration methodology and molar concentration determination procedures described in the Experiments section of this application.

In some embodiments the condensable hydrocarbon portion of the hydrocarbon fluid includes benzene. In some embodiments the condensable hydrocarbon portion has a benzene content between 0.1 and 0.8 weight percent. Alternatively, the condensable hydrocarbon portion may have a benzene content between 0.15 and 0.6 weight percent, a benzene content between 0.15 and 0.5, or a benzene content between 0.15 and 0.5.

In some embodiments the condensable hydrocarbon portion of the hydrocarbon fluid includes cyclohexane. In some embodiments the condensable hydrocarbon portion has a cyclohexane content less than 0.8 weight percent. Alternatively, the condensable hydrocarbon portion may have a cyclohexane content less than 0.6 weight percent or less than 0.43 weight percent. Alternatively, the condensable hydrocarbon portion may have a cyclohexane content greater than 0.1 weight percent or greater than 0.2 weight percent.

In some embodiments the condensable hydrocarbon portion of the hydrocarbon fluid includes methyl-cyclohexane. In some embodiments the condensable hydrocarbon portion has a methyl-cyclohexane content greater than 0.5 weight percent. Alternatively, the condensable hydrocarbon portion may have a methyl-cyclohexane content greater than 0.7 weight percent or greater than 0.75 weight percent. Alternatively, the condensable hydrocarbon portion may have a methyl-cyclohexane content less than 1.2 or 1.0 weight percent.

The use of weight percentage contents of benzene, cyclohexane, and methyl-cyclohexane herein and in the claims is meant to refer to the amount of benzene, cyclohexane, and methyl-cyclohexane found in a condensable hydrocarbon fluid determined as described herein, particularly as described in the section labeled "Experiments" herein. That is, respective compound weight percentages are determined from the whole oil gas chromatography (WOGC) analysis methodology and whole oil gas chromatography (WOGC) peak identification and integration methodology discussed in the Experiments section herein. Further, the respective compound weight percentages were obtained as described for FIG. 11, except that each individual respective compound peak area integration was used to determine each respective compound weight percentage. For clarity, the compound weight percentages are taken as a percentage of the entire C3 to pseudo C38 whole oil gas chromatography areas and calculated weights as used in the pseudo compound data presented in FIG. 7.

In some embodiments the condensable hydrocarbon portion of the hydrocarbon fluid has an API gravity greater than 30. Alternatively, the condensable hydrocarbon portion may have an API gravity greater than 30, 32, 34, 36, 40, 42 or 44. As used herein and in the claims, API gravity may be determined by any generally accepted method for determining API gravity.

In some embodiments the condensable hydrocarbon portion of the hydrocarbon fluid has a basic nitrogen to total nitrogen ratio between 0.1 and 0.50. Alternatively, the condensable hydrocarbon portion may have a basic nitrogen to total nitrogen ratio between 0.15 and 0.40. As used herein and in the claims, basic nitrogen and total nitrogen may be determined by any generally accepted method for determining basic nitrogen and total nitrogen. Where results conflict, the generally accepted more accurate methodology shall control.

The discovery that lithostatic stress can affect the composition of produced fluids generated within an organic-rich rock via heating and pyrolysis implies that the composition of the produced hydrocarbon fluid can also be influenced by altering the lithostatic stress of the organic-rich rock formation. For example, the lithostatic stress of the organic-rich rock formation may be altered by choice of pillar geometries and/or locations and/or by choice of heating and pyrolysis formation region thickness and/or heating sequencing.

Pillars are regions within the organic-rich rock formation left unpyrolyzed at a given time to lessen or mitigate surface subsidence. Pillars may be regions within a formation surrounded by pyrolysis regions within the same formation. Alternatively, pillars may be part of or connected to the unheated regions outside the general development area. Certain regions that act as pillars early in the life of a producing field may be converted to producing regions later in the life of the field.

Typically in its natural state, the weight of a formation's overburden is fairly uniformly distributed over the formation. In this state the lithostatic stress existing at particular point within a formation is largely controlled by the thickness and density of the overburden. A desired lithostatic stress may be selected by analyzing overburden geology and choosing a position with an appropriate depth and position.

Although lithostatic stresses are commonly assumed to be set by nature and not changeable short of removing all or part of the overburden, lithostatic stress at a specific location within a formation can be adjusted by redistributing the overburden weight so it is not uniformly supported by the formation. For example, this redistribution of overburden weight may be accomplished by two exemplary methods. One or both of these methods may be used within a single formation. In certain cases, one method may be primarily used earlier in time whereas the other may be primarily used at a later time. Favorably altering the lithostatic stress experienced by a formation region may be performed prior to instigating significant pyrolysis within the formation region and also before generating significant hydrocarbon fluids. Alternately, favorably altering the lithostatic stress may be performed simultaneously with the pyrolysis.

A first method of altering lithostatic stress involves making a region of a subsurface formation less stiff than its neighboring regions. Neighboring regions thus increasingly act as pillars supporting the overburden as a particular region becomes less stiff. These pillar regions experience increased lithostatic stress whereas the less stiff region experience reduced lithostatic stress. The amount of change in lithostatic stress depends upon a number of factors including, for example, the change in stiffness of the treated region, the size of the treated region, the pillar size, the pillar spacing, the rock compressibility, and the rock strength. In an organic-rich rock formation, a region within a formation may be made to experience mechanical weakening by pyrolyzing the region and creating void space within the region by removing produced fluids. In this way a region within a formation may be made less stiff than neighboring regions that have not experienced pyrolysis or have experienced a lesser degree of pyrolysis or production.

A second method of altering lithostatic stress involves causing a region of a subsurface formation to expand and push against the overburden with greater force than neighboring regions. This expansion may remove a portion of the overburden weight from the neighboring regions thus increasing the lithostatic stress experienced by the heated region and reducing the lithostatic stress experienced by neighboring regions. If the expansion is sufficient, horizontal fractures will form in the neighboring regions and the contribution of these regions to supporting the overburden will decrease. The amount of change in lithostatic stress depends upon a number of factors including, for example, the amount of expansion in the treated region, the size of the treated region, the pillar size, the pillar spacing, the rock compressibility, and the rock strength. A region within a formation may be made to expand by heating it so to cause thermal expansion of the rock. Fluid expansion or fluid generation can also contribute to expansion if the fluids are largely trapped within the region. The total expansion amount may be proportional to the thickness of the heated region. It is noted that if pyrolysis occurs in the heated region and sufficient fluids are removed, the heated region may mechanically weaken and thus may alter the lithostatic stresses experienced by the neighboring regions as described in the first exemplary method.

Embodiments of the method may include controlling the composition of produced hydrocarbon fluids generated by heating and pyrolysis from a first region within an organic-rich rock formation by increasing the lithostatic stresses within the first region by first heating and pyrolyzing formation hydrocarbons present in the organic-rich rock formation and producing fluids from a second neighboring region within the organic-rich rock formation such that the Young's modulus (i.e., stiffness) of the second region is reduced.

Embodiments of the method may include controlling the composition of produced hydrocarbon fluids generated by heating and pyrolysis from a first region within an organic-rich rock formation by increasing the lithostatic stresses within the first region by heating the first region prior to or to a greater degree than neighboring regions within the organic-rich rock formation such that the thermal expansion within the first region is greater than that within the neighboring regions of the organic-rich rock formation.

Embodiments of the method may include controlling the composition of produced hydrocarbon fluids generated by heating and pyrolysis from a first region within an organic-rich rock formation by decreasing the lithostatic stresses within the first region by heating one or more neighboring regions of the organic-rich rock formation prior to or to a greater degree than the first region such that the thermal expansion within the neighboring regions is greater than that within the first region.

Embodiments of the method may include locating, sizing, and/or timing the heating of heated regions within an organic-rich rock formation so as to alter the in situ lithostatic stresses of current or future heating and pyrolysis regions within the organic-rich rock formation so as to control the composition of produced hydrocarbon fluids.

Some production procedures include in situ heating of an organic-rich rock formation that contains both formation hydrocarbons and formation water-soluble minerals prior to substantial removal of the formation water-soluble minerals from the organic-rich rock formation. In some embodiments of the invention there is no need to partially, substantially or completely remove the water-soluble minerals prior to in situ heating. For example, in an oil shale formation that contains naturally occurring nahcolite, the oil shale may be heated prior to substantial removal of the nahcolite by solution mining. Substantial removal of a water-soluble mineral may represent the degree of removal of a water-soluble mineral that occurs from any commercial solution mining operation as known in the art. Substantial removal of a water-soluble mineral may be approximated as removal of greater than 5 weight percent of the total amount of a particular water-soluble mineral present in the zone targeted for hydrocarbon fluid production in the organic-rich rock formation. In alternative embodiments, in situ heating of the organic-rich rock formation to pyrolyze formation hydrocarbons may be commenced prior to removal of greater than 3 weight percent, alternatively 7 weight percent, 10 weight percent or 13 weight percent of the formation water-soluble minerals from the organic-rich rock formation.

The impact of heating oil shale to produce oil and gas prior to producing nahcolite is to convert the nahcolite to a more recoverable form (soda ash), and provide permeability facilitating its subsequent recovery. Water-soluble mineral recovery may take place as soon as the retorted oil is produced, or it may be left for a period of years for later recovery. If desired, the soda ash can be readily converted back to nahcolite on the surface. The ease with which this conversion can be accomplished makes the two minerals effectively interchangeable.

In some production processes, heating the organic-rich rock formation includes generating soda ash by decomposition of nahcolite. The method may include processing an aqueous solution containing water-soluble minerals in a surface facility to remove a portion of the water-soluble minerals. The processing step may include removing the water-soluble minerals by precipitation caused by altering the temperature of the aqueous solution.

The water-soluble minerals may include sodium. The water-soluble minerals may also include nahcolite (sodium bicarbonate), soda ash (sodium carbonate), dawsonite ($NaAl(CO_3)(OH)_2$), or combinations thereof. The surface processing may further include converting the soda ash back to sodium bicarbonate (nahcolite) in the surface facility by reaction with $CO_2$. After partial or complete removal of the water-soluble minerals, the aqueous solution may be re-injected into a subsurface formation where it may be sequestered. The subsurface formation may be the same as or different from the original organic-rich rock formation.

In some production processes, heating of the organic-rich rock formation both pyrolyzes at least a portion of the formation hydrocarbons to create hydrocarbon fluids and makes available migratory contaminant species previously bound in the organic-rich rock formation. The migratory contaminant species may be formed through pyrolysis of the formation hydrocarbons, may be liberated from the formation itself upon heating, or may be made accessible through the creation of increased permeability upon heating of the formation. The migratory contaminant species may be soluble in water or other aqueous fluids present in or injected into the organic-rich rock formation.

Producing hydrocarbons from pyrolyzed oil shale will generally leave behind some migratory contaminant species which are at least partially water-soluble. Depending on the hydrological connectivity of the pyrolyzed shale oil to shallower zones, these components may eventually migrate into ground water in concentrations which are environmentally unacceptable. The types of potential migratory contaminant species depend on the nature of the oil shale pyrolysis and the composition of the oil shale being converted. If the pyrolysis is performed in the absence of oxygen or air, the contaminant species may include aromatic hydrocarbons (e.g. benzene, toluene, ethylbenzene, xylenes), polyaromatic hydrocarbons (e.g. anthracene, pyrene, naphthalene, chrysene), metal contaminants (e.g. As, Co, Pb, Mo, Ni, and Zn), and other species such as sulfates, ammonia, Al, K, Mg, chlorides, fluorides and phenols. If oxygen or air is employed, contaminant species may also include ketones, alcohols, and cyanides. Further, the specific migratory contaminant species present may include any subset or combination of the above-described species.

It may be desirable for a field developer to assess the connectivity of the organic-rich rock formation to aquifers. This may be done to determine if, or to what extent, in situ pyrolysis of formation hydrocarbons in the organic-rich rock formation may create migratory species with the propensity to migrate into an aquifer. If the organic-rich rock formation is hydrologically connected to an aquifer, precautions may be taken to reduce or prevent species generated or liberated during pyrolysis from entering the aquifer. Alternatively, the organic-rich rock formation may be flushed with water or an aqueous fluid after pyrolysis as described herein to remove water-soluble minerals and/or migratory contaminant species. In other embodiments, the organic-rich rock formation may be substantially hydrologically unconnected to any source of ground water. In such a case, flushing the organic-rich rock formation may not be desirable for removal of migratory contaminant species but may nevertheless be desirable for recovery of water-soluble minerals.

Following production of hydrocarbons from an organic-rich formation, some migratory contaminant species may remain in the rock formation. In such case, it may be desirable to inject an aqueous fluid into the organic-rich rock formation and have the injected aqueous fluid dissolve at least a portion of the water-soluble minerals and/or the migratory contaminant species to form an aqueous solution. The aqueous solution may then be produced from the organic-rich rock formation through, for example, solution production wells. The aqueous fluid may be adjusted to increase the solubility of the migratory contaminant species and/or the water-soluble minerals. The adjustment may include the addition of an acid or base to adjust the pH of the solution. The resulting aqueous solution may then be produced from the organic-rich rock formation to the surface for processing.

After initial aqueous fluid production, it may further be desirable to flush the matured organic-rich rock zone and the unmatured organic-rich rock zone with an aqueous fluid. The aqueous fluid may be used to further dissolve water-soluble minerals and migratory contaminant species. The flushing may optionally be completed after a substantial portion of the hydrocarbon fluids have been produced from the matured organic-rich rock zone. In some embodiments, the flushing step may be delayed after the hydrocarbon fluid production step. The flushing may be delayed to allow heat generated from the heating step to migrate deeper into surrounding unmatured organic-rich rock zones to convert nahcolite within the surrounding unmatured organic-rich rock zones to soda ash. Alternatively, the flushing may be delayed to allow heat generated from the heating step to generate permeability within the surrounding unmatured organic-rich rock zones. Further, the flushing may be delayed based on current and/or forecast market prices of sodium bicarbonate, soda ash, or both as further discussed herein. This method may be combined with any of the other aspects of the invention as discussed herein Upon flushing of an aqueous solution, it may be desirable to process the aqueous solution in a surface facility to remove at least some of the migratory contaminant species. The migratory contaminant species may be removed through use of, for example, an adsorbent material, reverse osmosis, chemical oxidation, bio-oxidation, and/or ion exchange. Examples of these processes are individually known in the art. Exemplary adsorbent materials may include activated carbon, clay, or fuller's earth.

In certain areas with oil shale resources, additional oil shale resources or other hydrocarbon resources may exist at lower depths. Other hydrocarbon resources may include natural gas in low permeability formations (so-called "tight gas") or natural gas trapped in and adsorbed on coal (so called "coalbed methane"). In some embodiments with multiple oil shale resources it may be advantageous to develop deeper zones first and then sequentially shallower zones. In this way, wells need not cross hot zones or zones of weakened rock. In other embodiments in may be advantageous to develop deeper zones by drilling wells through regions being utilized as pillars for shale oil development at a shallower depth.

Simultaneous development of shale oil resources and natural gas resources in the same area can synergistically utilize certain facility and logistic operations. For example, gas treating may be performed at a single plant. Likewise personnel may be shared among the developments.

Figure 6:
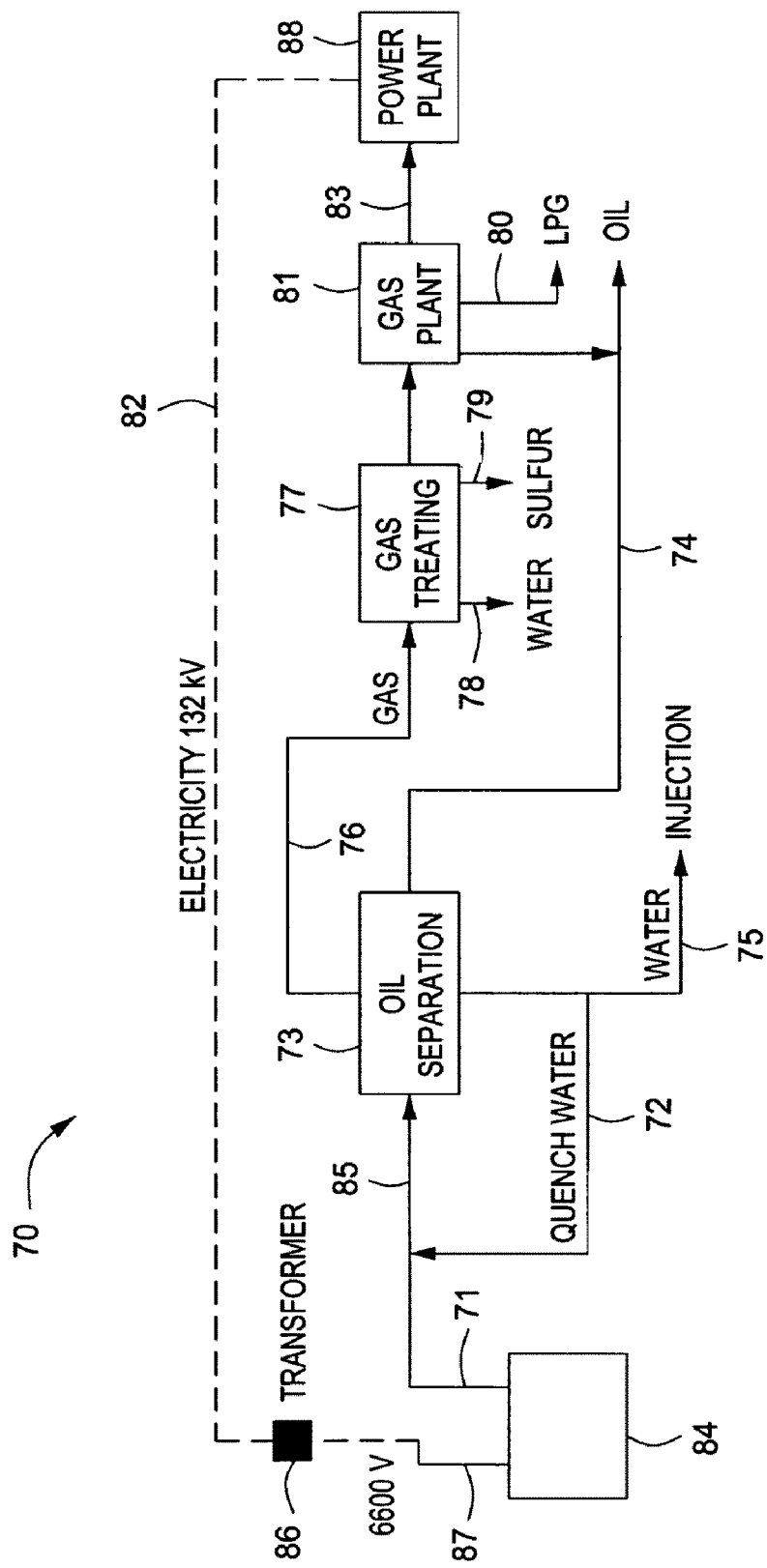
FIG. 6 is a process flow diagram of exemplary surface processing facilities for a subsurface formation development.

FIG. 6 illustrates a schematic diagram of an embodiment of surface facilities 70 that may be configured to treat a produced fluid. The produced fluid 85 may be produced from the subsurface formation 84 though a production well 71 as described herein. The produced fluid may include any of the produced fluids produced by any of the methods as described herein. The subsurface formation 84 may be any subsurface formation, including, for example, an organic-rich rock formation containing any of oil shale, coal, or tar sands for example. A production scheme may involve quenching 72 produced fluids to a temperature below 300° F., 200° F., or even 100° F., separating out condensable components (i.e., oil 74 and water 75) in an oil separator 73, treating the noncondensable components 76 (i.e. gas) in a gas treating unit 77 to remove water 78 and sulfur species 79, removing the heavier components from the gas (e.g., propane and butanes) in a gas plant 81 to form liquid petroleum gas (LPG) 80 for sale, and generating electrical power 82 in a power plant 88 from the remaining gas 83. The electrical power 82 may be used as an energy source for heating the subsurface formation 84 through any of the methods described herein. For example, the electrical power 82 may be feed at a high voltage, for example 132 kV, to a transformer 86 and let down to a lower voltage, for example 6600 V, before being fed to an electrical resistance heater element located in a heater well 87 located in the subsurface formation 84. In this way all or a portion of the power required to heat the subsurface formation 84 may be generated from the non-condensable portion of the produced fluids 85. Excess gas, if available, may be exported for sale.

Produced fluids from in situ oil shale production contain a number of components which may be separated in surface facilities. The produced fluids typically contain water, non-condensable hydrocarbon alkane species (e.g., methane, ethane, propane, n-butane, isobutane), noncondensable hydrocarbon alkene species (e.g., ethene, propene), condensable hydrocarbon species composed of (alkanes, olefins, aromatics, and polyaromatics among others), $CO_2$, CO, $H_2$, $H_2S$, and $NH_3$.

In a surface facility, condensable components may be separated from non-condensable components by reducing temperature and/or increasing pressure. Temperature reduction may be accomplished using heat exchangers cooled by ambient air or available water. Alternatively, the hot produced fluids may be cooled via heat exchange with produced hydrocarbon fluids previously cooled. The pressure may be increased via centrifugal or reciprocating compressors. Alternatively, or in conjunction, a diffuser-expander apparatus may be used to condense out liquids from gaseous flows. Separations may involve several stages of cooling and/or pressure changes.

Water in addition to condensable hydrocarbons may be dropped out of the gas when reducing temperature or increasing pressure. Liquid water may be separated from condensable hydrocarbons via gravity settling vessels or centrifugal separators. Demulsifiers may be used to aid in water separation.

Methods to remove $CO_2$, as well as other so-called acid gases (such as $H_2S$), from produced hydrocarbon gas include the use of chemical reaction processes and of physical solvent processes. Chemical reaction processes typically involve contacting the gas stream with an aqueous amine solution at high pressure and/or low temperature. This causes the acid gas species to chemically react with the amines and go into solution. By raising the temperature and/or lowering the pressure, the chemical reaction can be reversed and a concentrated stream of acid gases can be recovered. An alternative chemical reaction process involves hot carbonate solutions, typically potassium carbonate. The hot carbonate solution is regenerated and the concentrated stream of acid gases is recovered by contacting the solution with steam. Physical solvent processes typically involve contacting the gas stream with a glycol at high pressure and/or low temperature. Like the amine processes, reducing the pressure or raising the temperature allows regeneration of the solvent and recovery of the acid gases. Certain amines or glycols may be more or less selective in the types of acid gas species removed. Sizing of any of these processes requires determining the amount of chemical to circulate, the rate of circulation, the energy input for regeneration, and the size and type of gas-chemical contacting equipment. Contacting equipment may include packed or multi-tray countercurrent towers. Optimal sizing for each of these aspects is highly dependent on the rate at which gas is being produced from the formation and the concentration of the acid gases in the gas stream.

Acid gas removal may also be effectuated through the use of distillation towers. Such towers may include an intermediate freezing section wherein frozen $CO_2$ and $H_2S$ particles are allowed to form. A mixture of frozen particles and liquids fall downward into a stripping section, where the lighter hydrocarbon gasses break out and rise within the tower. A rectification section may be provided at an upper end of the tower to further facilitate the cleaning of the overhead gas stream.

The hydrogen content of a gas stream may be adjusted by either removing all or a portion of the hydrogen or by removing all or a portion of the non-hydrogen species (e.g., $CO_2$, $CH_4$, etc.) Separations may be accomplished using cryogenic condensation, pressure-swing or temperature-swing adsorption, or selective diffusion membranes. If additional hydrogen is needed, hydrogen may be made by reforming methane via the classic water-shift reaction.

EXPERIMENTS

Figure 18:
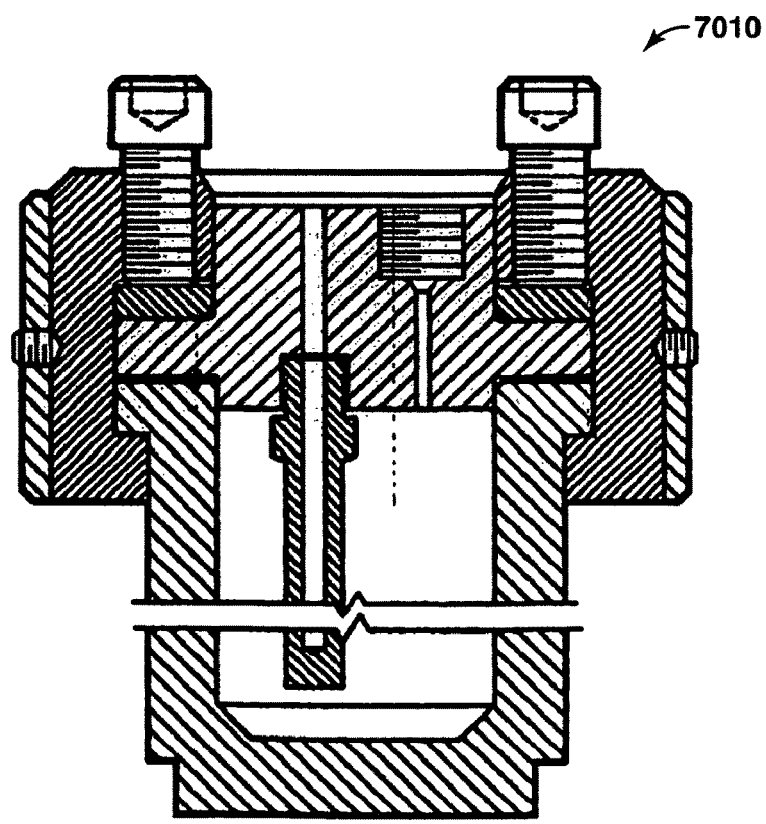
FIG. 18 is a cross-sectional view of the Parr vessel used in Examples 1-5, described below.

Heating experiments were conducted on several different oil shale specimens and the liquids and gases released from the heated oil shale examined in detail. An oil shale sample from the Mahogany formation in the Piceance Basin in Colorado was collected. A solid, continuous block of the oil shale formation, approximately 1 cubic foot in size, was collected from the pilot mine at the Colony mine site on the eastern side of Parachute Creek. The oil shale block was designated CM-1B. The core specimens taken from this block, as described in the following examples, were all taken from the same stratigraphic interval. The heating tests were conducted using a Parr vessel, model number 243HC5, which is shown in FIG. 18 and is available from Parr Instrument Company.

Example 1

Figure 17:
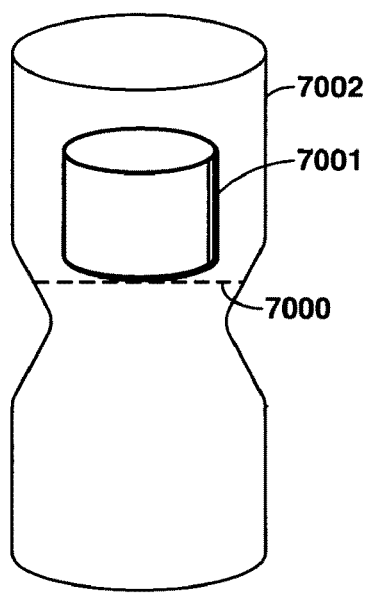
FIG. 17 is an exemplary view of the gold tube apparatus used in the unstressed Parr heating test described below in Example 1.

Oil shale block CM-1B was cored across the bedding planes to produce a cylinder 1.391 inches in diameter and approximately 2 inches long. A gold tube 7002 approximately 2 inches in diameter and 5 inches long was crimped and a screen 7000 inserted to serve as a support for the core specimen 7001 (FIG. 17). The oil shale core specimen 7001, 82.46 grams in weight, was placed on the screen 7000 in the gold tube 7002 and the entire assembly placed into a Parr heating vessel. The Parr vessel 7010, shown in FIG. 18, had an internal volume of 565 milliliters. Argon was used to flush the Parr vessel 7010 several times to remove air present in the chamber and the vessel pressurized to 500 psi with argon. The Parr vessel was then placed in a furnace which was designed to fit the Parr vessel. The furnace was initially at room temperature and was heated to 400° C. after the Parr vessel was placed in the furnace. The temperature of the Parr vessel achieved 400° C. after about 3 hours and remained in the 400° C. furnace for 24 hours. The Parr vessel was then removed from the furnace and allowed to cool to room temperature over a period of approximately 16 hours.

Figure 19:
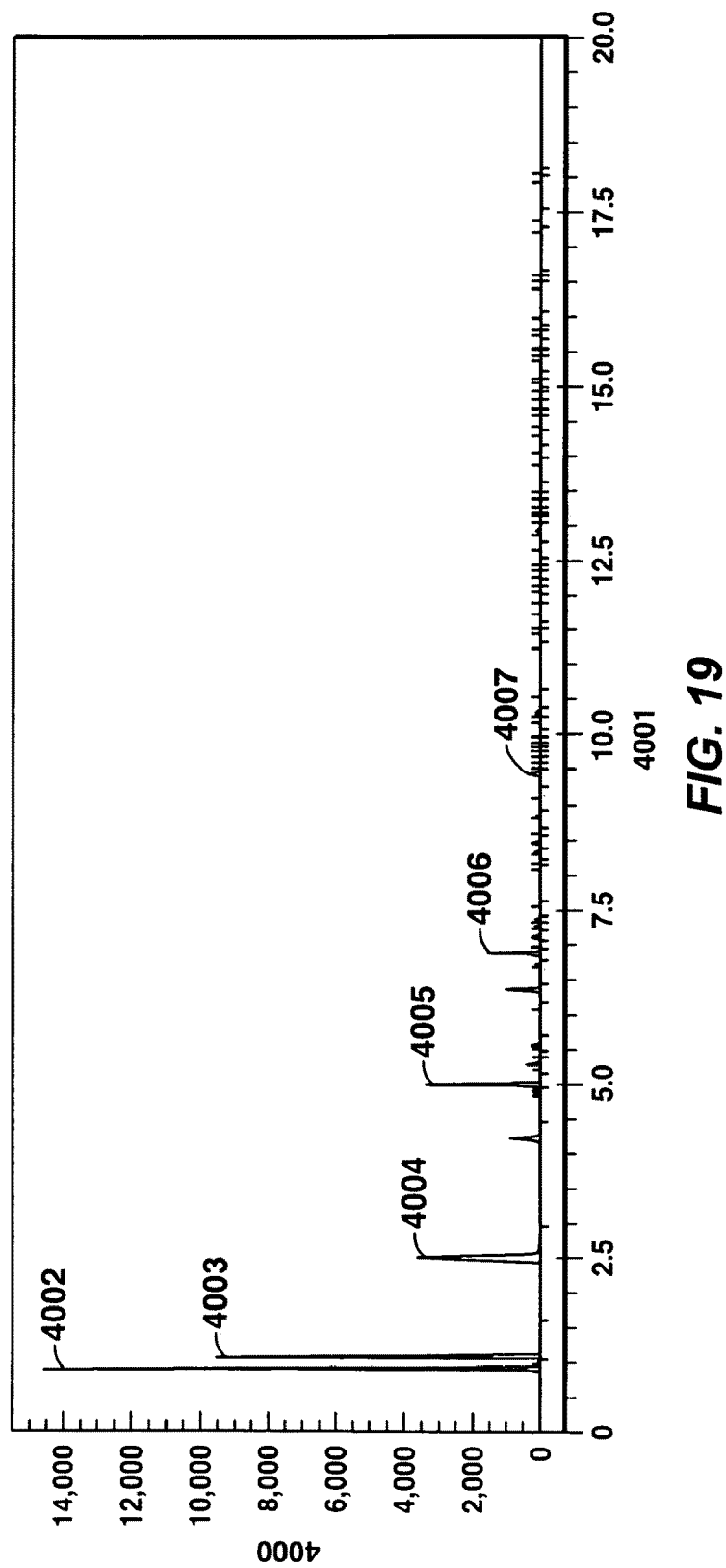
FIG. 19 is gas chromatogram of gas sampled from Example 1.

The room temperature Parr vessel was sampled to obtain a representative portion of the gas remaining in the vessel following the heating experiment. A small gas sampling cylinder 150 milliliters in volume was evacuated, attached to the Parr vessel and the pressure allowed to equilibrate. Gas chromatography (GC) analysis testing and non-hydrocarbon gas sample gas chromatography (GC) (GC not shown) of this gas sample yielded the results shown in FIG. 19, Table 2 and Table 1. In FIG. 19 the y-axis 4000 represents the detector response in pico-amperes (pA) while the x-axis 4001 represents the retention time in minutes. In FIG. 19 peak 4002 represents the response for methane, peak 4003 represents the response for ethane, peak 4004 represents the response for propane, peak 4005 represents the response for butane, peak 4006 represents the response for pentane and peak 4007 represents the response for hexane. From the GC results and the known volumes and pressures involved the total hydrocarbon content of the gas (2.09 grams), $CO_2$ content of the gas (3.35 grams), and H2S content of the gas (0.06 gram) were obtained.

TABLE 2

Peak and Area Details for FIG. 19 - Example 1 - 0 stress - Gas GC

| Peak Number | Ret Time [min] | Area [pA*s] | Compound Name |
|---|---|---|---|
| 1 | 0.910 | 1.46868e4 | Methane |
| 2 | 0.999 | 148.12119 | ? |
| 3 | 1.077 | 1.26473e4 | Ethane |
| 4 | 2.528 | 1.29459e4 | Propane |
| 5 | 4.243 | 2162.93066 | iC4 |
| 6 | 4.922 | 563.11804 | ? |
| 7 | 5.022 | 5090.54150 | n-Butane |
| 8 | 5.301 | 437.92255 | ? |
| 9 | 5.446 | 4.67394 | ? |
| 10 | 5.582 | 283.92194 | ? |
| 11 | 6.135 | 15.47334 | ? |
| 12 | 6.375 | 1159.83130 | iC5 |
| 13 | 6.742 | 114.83960 | ? |
| 14 | 6.899 | 1922.98450 | n-Pentane |
| 15 | 7.023 | 2.44915 | ? |
| 16 | 7.136 | 264.34424 | ? |
| 17 | 7.296 | 127.60601 | ? |
| 18 | 7.383 | 118.79453 | ? |
| 19 | 7.603 | 3.99227 | ? |
| 20 | 8.138 | 13.15432 | ? |
| 21 | 8.223 | 13.01887 | ? |
| 22 | 8.345 | 103.15615 | ? |
| 23 | 8.495 | 291.26767 | 2-methyl pentane |
| 24 | 8.651 | 15.64066 | |
| 25 | 8.884 | 91.85989 | ? |
| 26 | 9.165 | 40.09448 | ? |
| 27 | 9.444 | 534.44507 | ? |
| 28 | 9.557 | 2.64731 | n-Hexane |
| 29 | 9.650 | 32.28295 | ? |
| 30 | 9.714 | 52.42796 | ? |
| 31 | 9.793 | 42.05001 | ? |
| 32 | 9.852 | 8.93775 | ? |
| 33 | 9.914 | 4.43648 | ? |
| 34 | 10.013 | 24.74299 | ? |
| 35 | 10.229 | 13.34387 | ? |
| 36 | 10.302 | 133.95892 | ? |
| 37 | 10.577 | 2.67224 | ? |
| 38 | 11.252 | 27.57400 | ? |
| 39 | 11.490 | 23.41665 | ? |
| 40 | 11.567 | 8.13992 | ? |
| 41 | 11.820 | 32.80781 | ? |
| 42 | 11.945 | 4.61821 | ? |
| 43 | 12.107 | 30.67044 | ? |
| 44 | 12.178 | 2.58269 | ? |
| 45 | 12.308 | 13.57769 | ? |
| 46 | 12.403 | 12.43018 | ? |
| 47 | 12.492 | 34.29918 | ? |
| 48 | 12.685 | 4.71311 | ? |
| 49 | 12.937 | 183.31729 | ? |
| 50 | 13.071 | 7.18510 | ? |
| 51 | 13.155 | 2.01699 | ? |
| 52 | 13.204 | 7.77467 | ? |
| 53 | 13.317 | 7.21400 | ? |
| 54 | 13.443 | 4.22721 | ? |
| 55 | 13.525 | 35.08374 | ? |
| 56 | 13.903 | 18.48654 | ? |
| 57 | 14.095 | 6.39745 | ? |
| 58 | 14.322 | 3.19935 | ? |
| 59 | 14.553 | 8.48772 | ? |
| 60 | 14.613 | 3.34738 | ? |
| 61 | 14.730 | 5.44062 | ? |
| 62 | 14.874 | 40.17010 | ? |
| 63 | 14.955 | 3.41596 | ? |
| 64 | 15.082 | 3.04766 | ? |
| 65 | 15.138 | 7.33028 | ? |
| 66 | 15.428 | 2.71734 | ? |
| 67 | 15.518 | 11.00256 | ? |
| 68 | 15.644 | 5.16752 | ? |
| 69 | 15.778 | 45.12025 | ? |
| 70 | 15.855 | 3.26920 | ? |
| 71 | 16.018 | 3.77424 | ? |
| 72 | 16.484 | 4.66657 | ? |
| 73 | 16.559 | 5.54783 | ? |
| 74 | 16.643 | 10.57255 | ? |
| 75 | 17.261 | 2.19534 | ? |
| 76 | 17.439 | 10.26123 | ? |
| 77 | 17.971 | 1.85618 | ? |
| 78 | 18.097 | 11.42077 | ? |

Figure 20:
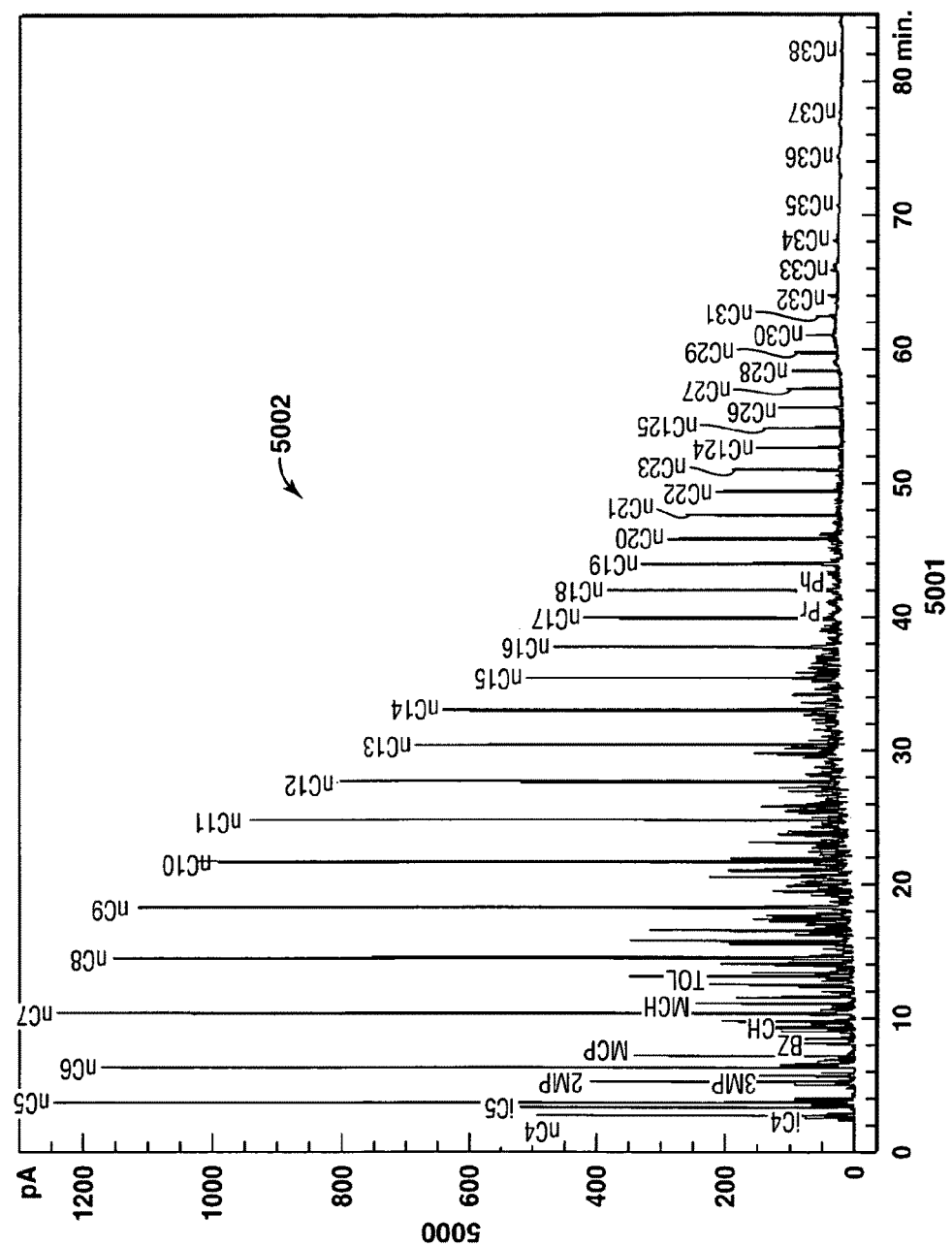
FIG. 20 is a whole oil gas chromatogram of liquid sampled from Example 1.

The Parr vessel was then vented to achieve atmospheric pressure, the vessel opened, and liquids collected from both inside the gold tube and in the bottom of the Parr vessel. Water was separated from the hydrocarbon layer and weighed. The amount collected is noted in Table 1. The collected hydrocarbon liquids were placed in a small vial, sealed and stored in the absence of light. No solids were observed on the walls of the gold tube or the walls of the Parr vessel. The solid core specimen was weighed and determined to have lost 19.21 grams as a result of heating. Whole oil gas chromatography (WOGC) testing of the liquid yielded the results shown in FIG. 20, Table 3, and Table 1. In FIG. 20 the y-axis 5000 represents the detector response in pico-amperes (pA) while the x-axis 5001 represents the retention time in minutes. The GC chromatogram is shown generally by label 5002 with individual identified peaks labeled with abbreviations.

TABLE 3

Peak and Area Details for FIG. 20 - Example 1 - 0 stress - Liquid GC

| Peak Number | Ret. Time [min] | Peak Area [pA*s] | Compound Name |
|---|---|---|---|
| 1 | 2.660 | 119.95327 | iC4 |
| 2 | 2.819 | 803.25989 | nC4 |
| 3 | 3.433 | 1091.80298 | iC5 |
| 4 | 3.788 | 2799.32520 | nC5 |
| 5 | 5.363 | 1332.67871 | 2-methyl pentane (2MP) |
| 6 | 5.798 | 466.35703 | 3-methyl pentane (3MP) |
| 7 | 6.413 | 3666.46240 | nC6 |
| 8 | 7.314 | 1161.70435 | Methyl cyclopentane (MCP) |
| 9 | 8.577 | 287.05969 | Benzene (BZ) |
| 10 | 9.072 | 530.19781 | Cyclohexane (CH) |
| 11 | 10.488 | 4700.48291 | nC7 |
| 12 | 11.174 | 937.38757 | Methyl cyclohexane (MCH) |
| 13 | 12.616 | 882.17358 | Toluene (TOL) |
| 14 | 14.621 | 3954.29687 | nC8 |
| 15 | 18.379 | 3544.52905 | nC9 |
| 16 | 21.793 | 3452.04199 | nC10 |
| 17 | 24.929 | 3179.11841 | nC11 |
| 18 | 27.843 | 2680.95459 | nC12 |
| 19 | 30.571 | 2238.89600 | nC13 |
| 20 | 33.138 | 2122.53540 | nC14 |
| 21 | 35.561 | 1773.59973 | nC15 |
| 22 | 37.852 | 1792.89526 | nC16 |
| 23 | 40.027 | 1394.61707 | nC17 |
| 24 | 40.252 | 116.81663 | Pristane (Pr) |
| 25 | 42.099 | 1368.02734 | nC18 |
| 26 | 42.322 | 146.96437 | Phytane (Ph) |
| 27 | 44.071 | 1130.63342 | nC19 |
| 28 | 45.956 | 920.52136 | nC20 |
| 29 | 47.759 | 819.92810 | nC21 |
| 30 | 49.483 | 635.42065 | nC22 |
| 31 | 51.141 | 563.24316 | nC23 |
| 32 | 52.731 | 432.74606 | nC24 |
| 33 | 54.261 | 397.36270 | nC25 |
| 34 | 55.738 | 307.56073 | nC26 |
| 35 | 57.161 | 298.70926 | nC27 |
| 36 | 58.536 | 252.60083 | nC28 |
| 37 | 59.867 | 221.84540 | nC29 |
| 38 | 61.154 | 190.29596 | nC30 |
| 39 | 62.539 | 123.65781 | nC31 |
| 40 | 64.133 | 72.47668 | nC32 |
| 41 | 66.003 | 76.84142 | nC33 |
| 42 | 68.208 | 84.35004 | nC34 |
| 43 | 70.847 | 36.68131 | nC35 |
| 44 | 74.567 | 87.62341 | nC36 |
| 45 | 77.798 | 33.30892 | nC37 |
| 46 | 82.361 | 21.99784 | nC38 |
| Totals: | | 5.32519e4 | |

Example 2

Figure 21:
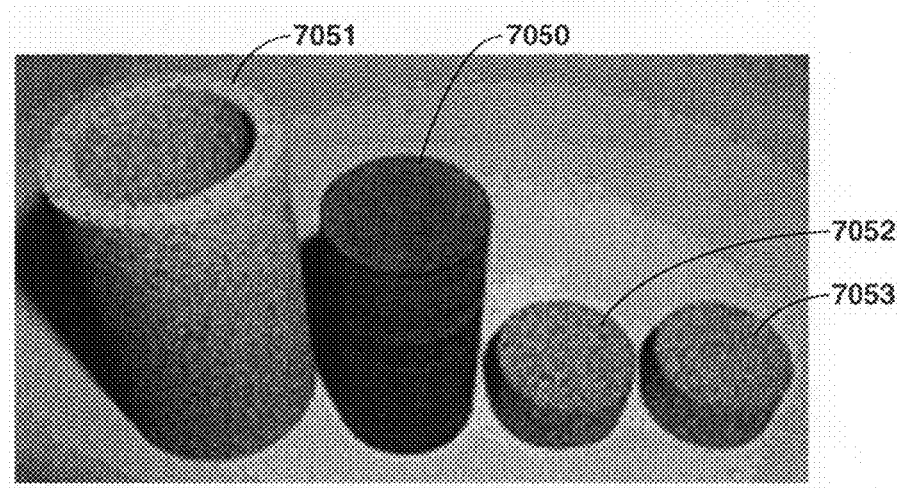
FIG. 21 is an exemplary view of a Berea cylinder, Berea plugs, and an oil shale core specimen as used in Examples 2-5.
Figure 22:
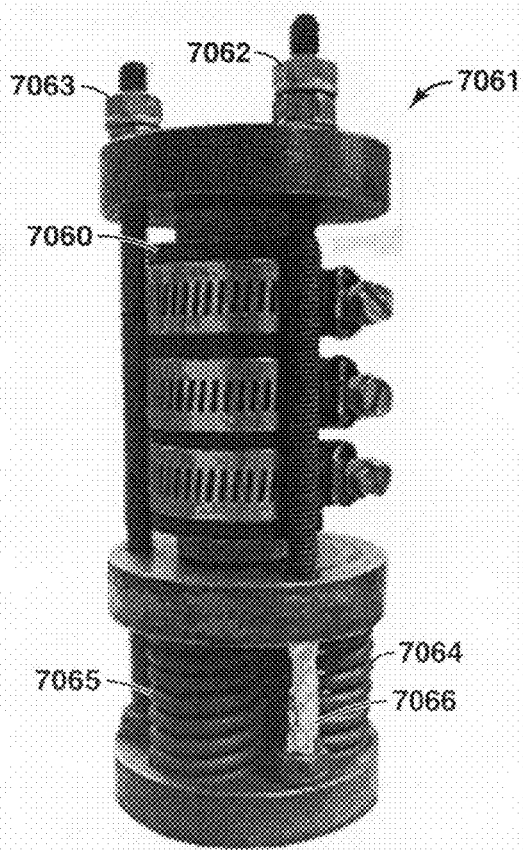
FIG. 22 is an exemplary view of the mini load frame and sample assembly used in Examples 2-5.

Oil shale block CM-1B was cored in a manner similar to that of Example 1 except that a 1 inch diameter core was created. With reference to FIG. 21, the core specimen 7050 was approximately 2 inches in length and weighed 42.47 grams. This core specimen 7050 was placed in a Berea sandstone cylinder 7051 with a 1-inch inner diameter and a 1.39 inch outer diameter. Berea plugs 7052 and 7053 were placed at each end of this assembly, so that the core specimen was completely surrounded by Berea. The Berea cylinder 7051 along with the core specimen 7050 and the Berea end plugs 7052 and 7053 were placed in a slotted stainless steel sleeve and clamped into place. The sample assembly 7060 was placed in a spring-loaded mini-load-frame 7061 as shown in FIG. 22. Load was applied by tightening the nuts 7062 and 7063 at the top of the load frame 7061 to compress the springs 7064 and 7065. The springs 7064 and 7065 were high temperature, Inconel springs, which delivered 400 psi effective stress to the oil shale specimen 7060 when compressed. Sufficient travel of the springs 7064 and 7065 remained in order to accommodate any expansion of the core specimen 7060 during the course of heating. In order to ensure that this was the case, gold foil 7066 was placed on one of the legs of the apparatus to gauge the extent of travel. The entire spring loaded apparatus 7061 was placed in the Parr vessel (FIG. 18) and the heating experiment conducted as described in Example 1.

Figure 23:
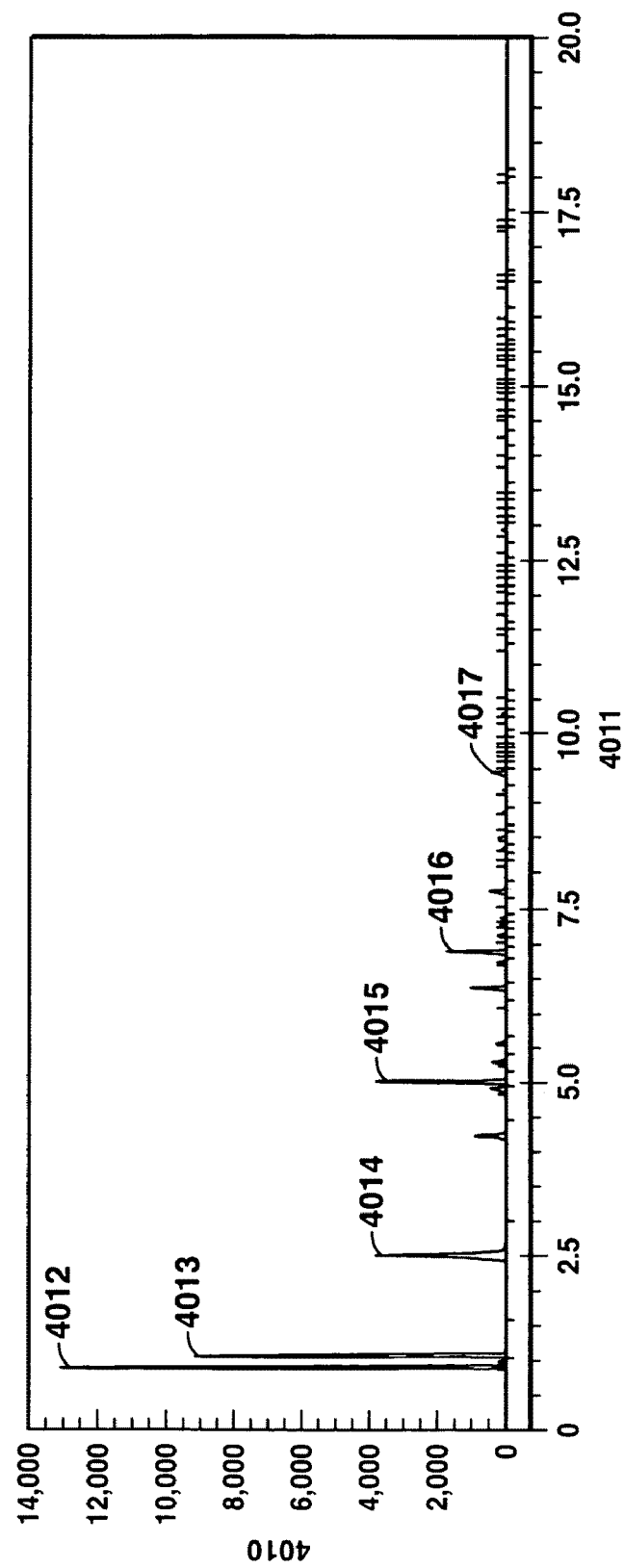
FIG. 23 is gas chromatogram of gas sampled from Example 2.

As described in Example 1, the room temperature Parr vessel was then sampled to obtain a representative portion of the gas remaining in the vessel following the heating experiment. Gas sampling, hydrocarbon gas sample gas chromatography (GC) testing, and non-hydrocarbon gas sample gas chromatography (GC) was conducted as in Example 1. Results are shown in FIG. 23, Table 4 and Table 1. In FIG. 23 the y-axis 4010 represents the detector response in pico-amperes (pA) while the x-axis 4011 represents the retention time in minutes. In FIG. 23 peak 4012 represents the response for methane, peak 4013 represents the response for ethane, peak 4014 represents the response for propane, peak 4015 represents the response for butane, peak 4016 represents the response for pentane and peak 4017 represents the response for hexane. From the gas chromatographic results and the known volumes and pressures involved the total hydrocarbon content of the gas was determined to be 1.33 grams and $CO_2$ content of the gas was 1.70 grams.

TABLE 4

Peak and Area Details for FIG. 23 - Example 2 - 400 psi stress - Gas GC

| Peak Number | Ret. Time [min] | Area [pA*s] | Compound Name |
|---|---|---|---|
| 1 | 0.910 | 1.36178e4 | Methane |
| 2 | 0.999 | 309.65613 | ? |
| 3 | 1.077 | 1.24143e4 | Ethane |
| 4 | 2.528 | 1.41685e4 | Propane |
| 5 | 4.240 | 2103.01929 | iC4 |
| 6 | 4.917 | 1035.25513 | ? |
| 7 | 5.022 | 5689.08887 | n-Butane |
| 8 | 5.298 | 450.26572 | ? |
| 9 | 5.578 | 302.56229 | ? |
| 10 | 6.125 | 33.82201 | ? |
| 11 | 6.372 | 1136.37097 | iC5 |
| 12 | 6.736 | 263.35754 | ? |
| 13 | 6.898 | 2254.86621 | n-Pentane |
| 14 | 7.066 | 7.12101 | ? |
| 15 | 7.133 | 258.31876 | ? |
| 16 | 7.293 | 126.54671 | ? |
| 17 | 7.378 | 155.60977 | ? |
| 18 | 7.598 | 6.73467 | ? |
| 19 | 7.758 | 679.95312 | ? |
| 20 | 8.133 | 27.13466 | ? |
| 21 | 8.216 | 24.77329 | ? |
| 22 | 8.339 | 124.70064 | ? |
| 23 | 8.489 | 289.12952 | 2-methyl pentane |
| 24 | 8.644 | 19.83309 | ? |
| 25 | 8.878 | 92.18938 | ? |
| 26 | 9.184 | 102.25701 | ? |
| 27 | 9.438 | 664.42584 | n-Hexane |
| 28 | 9.549 | 2.91525 | ? |
| 29 | 9.642 | 26.86672 | ? |
| 30 | 9.705 | 49.83235 | ? |
| 31 | 9.784 | 52.11239 | ? |
| 32 | 9.843 | 9.03158 | ? |
| 33 | 9.904 | 6.18217 | ? |
| 34 | 10.004 | 24.84150 | ? |

TABLE 4-continued

Peak and Area Details for FIG. 23 - Example 2 - 400 psi stress - Gas GC

| Peak Number | Ret. Time [min] | Area [pA*s] | Compound Name |
|---|---|---|---|
| 35 | 10.219 | 13.21182 | ? |
| 36 | 10.292 | 158.67511 | ? |
| 37 | 10.411 | 2.49094 | ? |
| 38 | 10.566 | 3.25252 | ? |
| 39 | 11.240 | 46.79988 | ? |
| 40 | 11.478 | 29.59438 | ? |
| 41 | 11.555 | 12.84377 | ? |
| 42 | 11.809 | 38.67433 | ? |
| 43 | 11.935 | 5.68525 | ? |
| 44 | 12.096 | 31.29068 | ? |
| 45 | 12.167 | 5.84513 | ? |
| 46 | 12.297 | 15.52042 | ? |
| 47 | 12.393 | 13.54158 | ? |
| 48 | 12.483 | 30.95983 | ? |
| 49 | 12.669 | 20.21915 | ? |
| 50 | 12.929 | 229.00655 | ? |
| 51 | 13.063 | 6.38678 | ? |
| 52 | 13.196 | 10.89876 | ? |
| 47 | 13.306 | 7.91553 | ? |
| 48 | 13.435 | 5.05444 | ? |
| 49 | 13.516 | 44.42806 | ? |
| 50 | 13.894 | 20.61910 | ? |
| 51 | 14.086 | 8.32365 | ? |
| 52 | 14.313 | 2.80677 | ? |
| 53 | 14.545 | 9.18198 | ? |
| 54 | 14.605 | 4.93703 | ? |
| 55 | 14.722 | 5.06628 | ? |
| 56 | 14.865 | 46.53282 | ? |
| 57 | 14.946 | 6.55945 | ? |
| 58 | 15.010 | 2.85594 | ? |
| 59 | 15.075 | 4.05371 | ? |
| 60 | 15.131 | 9.15954 | ? |
| 61 | 15.331 | 2.16523 | ? |
| 62 | 15.421 | 3.03294 | ? |
| 63 | 15.511 | 9.73797 | ? |
| 64 | 15.562 | 5.22962 | ? |
| 65 | 15.636 | 3.73105 | ? |
| 66 | 15.771 | 54.64651 | ? |
| 67 | 15.848 | 3.95764 | ? |
| 68 | 16.010 | 3.39639 | ? |
| 69 | 16.477 | 5.49586 | ? |
| 70 | 16.552 | 6.21470 | ? |
| 71 | 16.635 | 11.08140 | ? |
| 72 | 17.257 | 2.28673 | ? |
| 73 | 17.318 | 2.82284 | ? |
| 74 | 17.433 | 11.11376 | ? |
| 75 | 17.966 | 2.54065 | ? |
| 76 | 18.090 | 14.28333 | ? |
| 77 | | | |
| 78 | | | |
| 79 | | | |
| 80 | | | |
| 81 | | | |
| 82 | | | |

At this point, the Parr vessel was vented to achieve atmospheric pressure, the vessel opened, and liquids collected from inside the Parr vessel. Water was separated from the hydrocarbon layer and weighed. The amount collected is noted in Table 1. The collected hydrocarbon liquids were placed in a small vial, sealed and stored in the absence of light. Any additional liquid coating the surface of the apparatus or sides of the Parr vessel was collected with a paper towel and the weight of this collected liquid added to the total liquid collected. Any liquid remaining in the Berea sandstone was extracted with methylene chloride and the weight accounted for in the liquid total reported in Table 1. The Berea sandstone cylinder and end caps were clearly blackened with organic material as a result of the heating. The organic material in the Berea was not extractable with either toluene or methylene chloride, and was therefore determined to be coke formed from the cracking of hydrocarbon liquids. After the heating experiment, the Berea was crushed and its total organic carbon (TOC) was measured. This measurement was used to estimate the amount of coke in the Berea and subsequently how much liquid must have cracked in the Berea. A constant factor of 2.283 was used to convert the TOC measured to an estimate of the amount of liquid, which must have been present to produce the carbon found in the Berea. This liquid estimated is the "inferred oil" value shown in Table 1. The solid core specimen was weighed and determined to have lost 10.29 grams as a result of heating.

Example 3

Figure 24:
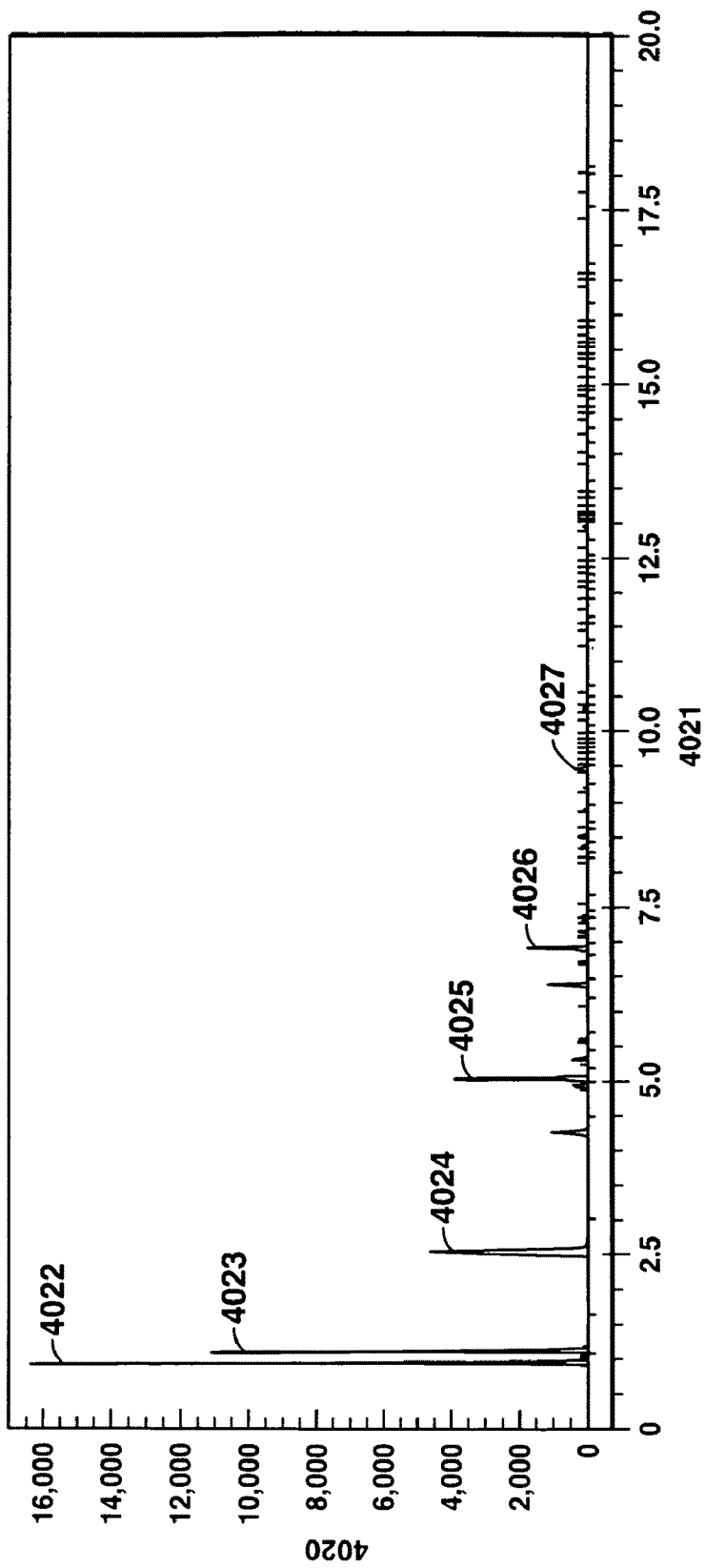
FIG. 24 is gas chromatogram of gas sampled from Example 3.
Figure 25:
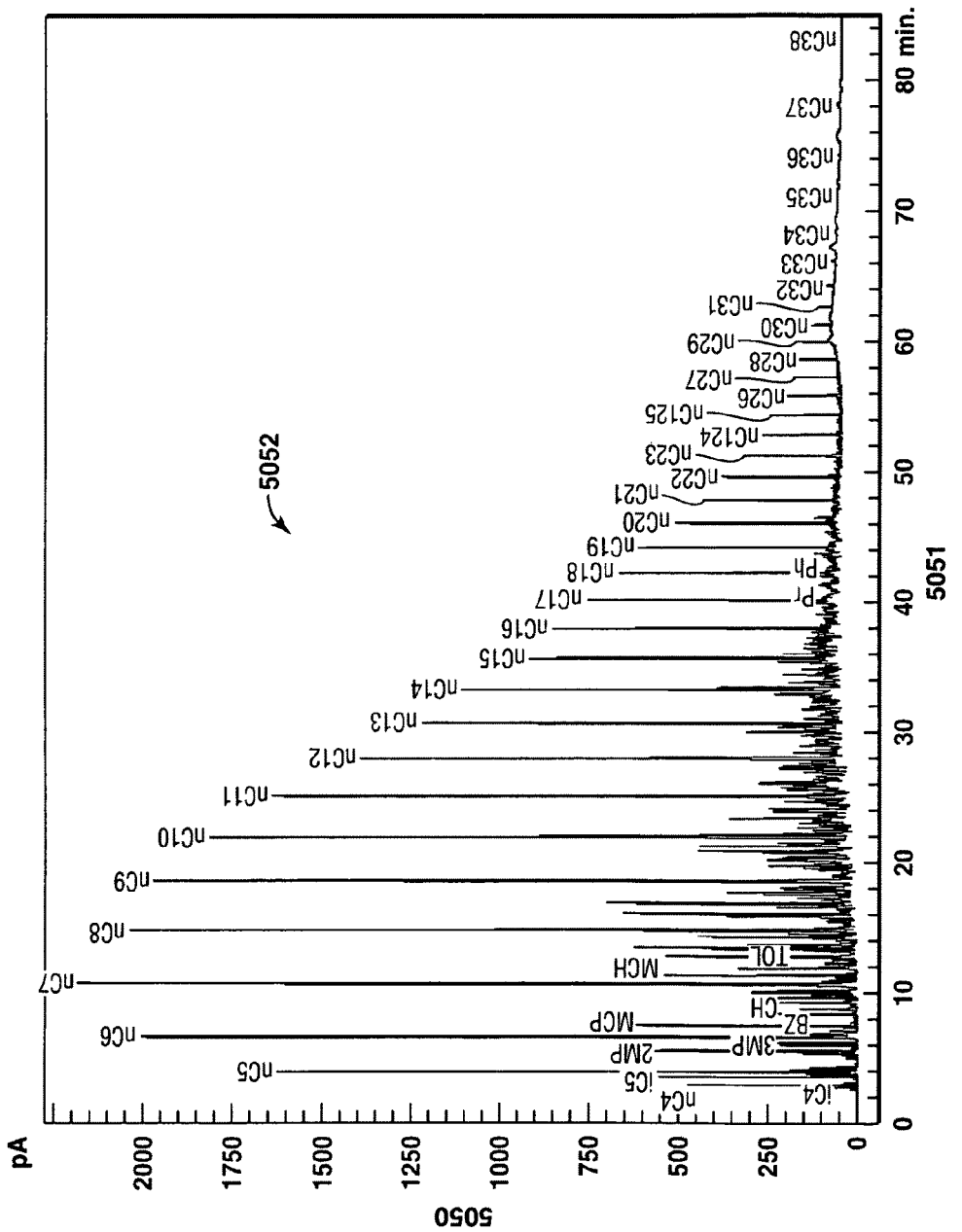
FIG. 25 is a whole oil gas chromatogram of liquid sampled from Example 3.

Conducted in a manner similar to that of Example 2 on a core specimen from oil shale block CM-1B, where the effective stress applied was 400 psi. Results for the gas sample collected and analyzed by hydrocarbon gas sample gas chromatography (GC) and non-hydrocarbon gas sample gas chromatography (GC) (GC not shown) are shown in FIG. 24, Table 5 and Table 1. In FIG. 24 the y-axis 4020 represents the detector response in pico-amperes (pA) while the x-axis 4021 represents the retention time in minutes. In FIG. 24 peak 4022 represents the response for methane, peak 4023 represents the response for ethane, peak 4024 represents the response for propane, peak 4025 represents the response for butane, peak 4026 represents the response for pentane and peak 4027 represents the response for hexane. Results for the liquid collected and analyzed by whole oil gas chromatography (WOGC) analysis are shown in FIG. 25, Table 6 and Table 1. In FIG. 25 the y-axis 5050 represents the detector response in pico-amperes (pA) while the x-axis 5051 represents the retention time in minutes. The GC chromatogram is shown generally by label 5052 with individual identified peaks labeled with abbreviations.

TABLE 5

Peak and Area Details for FIG. 24 - Example 3 - 400 psi stress - Gas GC

| Peak Number | Ret Time [min] | Area [pA*s] | Compound Name |
|---|---|---|---|
| 1 | 0.910 | 1.71356e4 | Methane |
| 2 | 0.998 | 341.71646 | ? |
| 3 | 1.076 | 1.52621e4 | Ethane |
| 4 | 2.534 | 1.72319e4 | Propane |
| 5 | 4.242 | 2564.04077 | iC4 |
| 6 | 4.919 | 1066.90942 | ? |
| 7 | 5.026 | 6553.25244 | n-Butane |
| 8 | 5.299 | 467.88803 | ? |
| 9 | 5.579 | 311.65158 | ? |
| 10 | 6.126 | 33.61063 | ? |
| 11 | 6.374 | 1280.77869 | iC5 |
| 12 | 6.737 | 250.05510 | ? |
| 13 | 6.900 | 2412.40918 | n-Pentane |
| 14 | 7.134 | 249.80679 | ? |
| 15 | 7.294 | 122.60424 | ? |
| 16 | 7.379 | 154.40988 | ? |
| 17 | 7.599 | 6.87471 | ? |
| 18 | 8.132 | 25.50270 | ? |
| 19 | 8.216 | 22.33015 | ? |
| 20 | 8.339 | 129.17023 | ? |
| 21 | 8.490 | 304.97903 | 2-methyl pentane |
| 22 | 8.645 | 18.48411 | ? |
| 23 | 8.879 | 98.23043 | ? |
| 24 | 9.187 | 89.71329 | ? |
| 25 | 9.440 | 656.02161 | n-Hexane |
| 26 | 9.551 | 3.05892 | ? |
| 27 | 9.645 | 25.34058 | ? |
| 28 | 9.708 | 45.14915 | ? |
| 29 | 9.786 | 48.62077 | ? |
| 30 | 9.845 | 10.03335 | ? |

TABLE 5-continued

Peak and Area Details for FIG. 24 - Example 3 - 400 psi stress - Gas GC

| Peak Number | Ret Time [min] | Area [pA*s] | Compound Name |
|---|---|---|---|
| 31 | 9.906 | 5.43165 | ? |
| 32 | 10.007 | 22.33582 | ? |
| 33 | 10.219 | 16.02756 | ? |
| 34 | 10.295 | 196.43715 | ? |
| 35 | 10.413 | 2.98115 | ? |
| 36 | 10.569 | 3.88067 | ? |
| 37 | 11.243 | 41.63386 | ? |
| 38 | 11.482 | 28.44063 | ? |
| 39 | 11.558 | 12.05196 | ? |
| 40 | 11.812 | 37.83630 | ? |
| 41 | 11.938 | 5.45990 | ? |
| 42 | 12.100 | 31.03111 | ? |
| 43 | 12.170 | 4.91053 | ? |
| 44 | 12.301 | 15.75041 | ? |
| 45 | 12.397 | 13.75454 | ? |
| 46 | 12.486 | 1.62203 | ? |
| 47 | 12.672 | 7.97665 | ? |
| 48 | 12.931 | 7.49605 | ? |
| 49 | 13.064 | 4.64921 | ? |
| 50 | 13.103 | 41.82572 | ? |
| 51 | 13.149 | 19.01739 | ? |
| 52 | 13.198 | 7.34498 | ? |
| 53 | 13.310 | 2.68912 | ? |
| 54 | 13.437 | 8.29593 | ? |
| 55 | 13.519 | 3.93147 | ? |
| 56 | 13.898 | 4.75483 | ? |
| 57 | 14.089 | 40.93447 | ? |
| 58 | 14.316 | 5.30140 | ? |
| 59 | 14.548 | 5.79979 | ? |
| 60 | 14.608 | 7.95179 | ? |
| 61 | 14.725 | 1.91589 | ? |
| 62 | 14.869 | 2.75893 | ? |
| 63 | 14.949 | 8.64343 | ? |
| 64 | 15.078 | 3.76481 | ? |
| 65 | 15.134 | 3.41854 | ? |
| 66 | 15.335 | 45.59035 | ? |
| 67 | 15.423 | 3.73501 | ? |
| 68 | 15.515 | 5.84199 | ? |
| 69 | 15.565 | 4.87036 | ? |
| 70 | 15.639 | 5.12607 | ? |
| 71 | 15.774 | 9.97469 | ? |
| 72 | 15.850 | 8.00434 | ? |
| 73 | 16.014 | 3.86749 | ? |
| 74 | 16.480 | 9.71661 | ? |
| 75 | 16.555 | 30.26099 | ? |
| 76 | 16.639 | 15.14775 | ? |
| 77 | 17.436 | 207.50433 | ? |
| 78 | 17.969 | 3.35393 | ? |
| 79 | 18.093 | 3.04880 | ? |

TABLE 6

Peak and Area Details from FIG. 25 - Example 3 - 400 psi stress - Liquid GC.

| Peak Number | Ret Time [min] | Peak Area [pA*s] | Compound Name |
|---|---|---|---|
| 1 | 2.744 | 102.90978 | iC4 |
| 2 | 2.907 | 817.57861 | nC4 |
| 3 | 3.538 | 1187.01831 | iC5 |
| 4 | 3.903 | 3752.84326 | nC5 |
| 5 | 5.512 | 1866.25342 | 2MP |
| 6 | 5.950 | 692.18964 | 3MP |
| 7 | 6.580 | 6646.48242 | nC6 |
| 8 | 7.475 | 2117.66919 | MCP |
| 9 | 8.739 | 603.21204 | BZ |
| 10 | 9.230 | 1049.96240 | CH |
| 11 | 10.668 | 9354.29590 | nC7 |
| 12 | 11.340 | 2059.10303 | MCH |
| 13 | 12.669 | 689.82861 | TOL |
| 14 | 14.788 | 8378.59375 | nC8 |

TABLE 6-continued

Peak and Area Details from FIG. 25 - Example 3 - 400 psi stress - Liquid GC.

| Peak Number | Ret Time [min] | Peak Area [pA*s] | Compound Name |
|---|---|---|---|
| 15 | 18.534 | 7974.54883 | nC9 |
| 16 | 21.938 | 7276.47705 | nC10 |
| 17 | 25.063 | 6486.47998 | nC11 |
| 18 | 27.970 | 5279.17187 | nC12 |
| 19 | 30.690 | 4451.49902 | nC13 |
| 20 | 33.254 | 4156.73389 | nC14 |
| 21 | 35.672 | 3345.80273 | nC15 |
| 22 | 37.959 | 3219.63745 | nC16 |
| 23 | 40.137 | 2708.28003 | nC17 |
| 24 | 40.227 | 219.38252 | Pr |
| 25 | 42.203 | 2413.01929 | nC18 |
| 26 | 42.455 | 317.17825 | Ph |
| 27 | 44.173 | 2206.65405 | nC19 |
| 28 | 46.056 | 1646.56616 | nC20 |
| 29 | 47.858 | 1504.49097 | nC21 |
| 30 | 49.579 | 1069.23608 | nC22 |
| 31 | 51.234 | 949.49316 | nC23 |
| 32 | 52.823 | 719.34735 | nC24 |
| 33 | 54.355 | 627.46436 | nC25 |
| 34 | 55.829 | 483.81885 | nC26 |
| 35 | 57.253 | 407.86371 | nC27 |
| 36 | 58.628 | 358.52216 | nC28 |
| 37 | 59.956 | 341.01791 | nC29 |
| 38 | 61.245 | 214.87863 | nC30 |
| 39 | 62.647 | 146.06461 | nC31 |
| 40 | 64.259 | 127.66831 | nC32 |
| 41 | 66.155 | 85.17574 | nC33 |
| 42 | 68.403 | 64.29253 | nC34 |
| 43 | 71.066 | 56.55088 | nC35 |
| 44 | 74.282 | 28.61854 | nC36 |
| 45 | 78.140 | 220.95929 | nC37 |
| 46 | 83.075 | 26.95426 | nC38 |
| Totals: | | 9.84518e4 | |

Example 4

Figure 26:
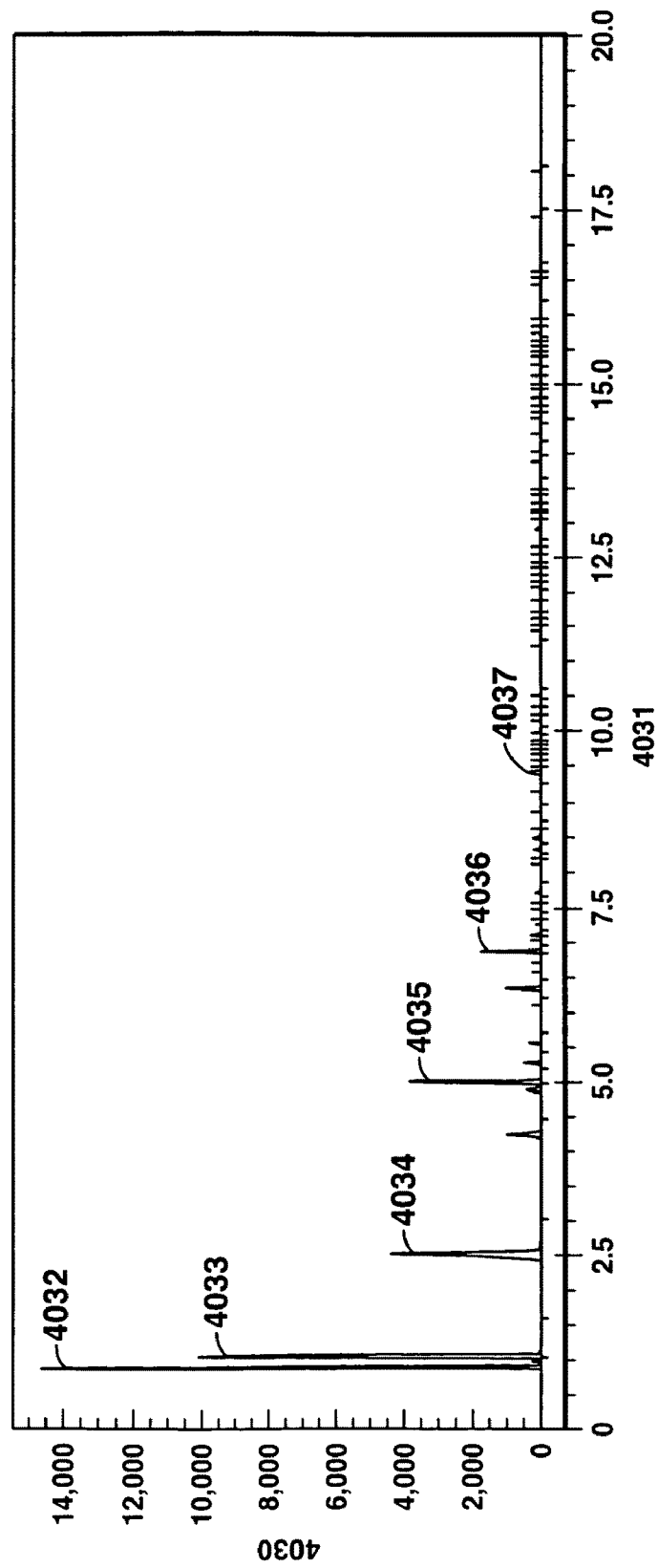
FIG. 26 is gas chromatogram of gas sampled from Example 4.
Figure 27:
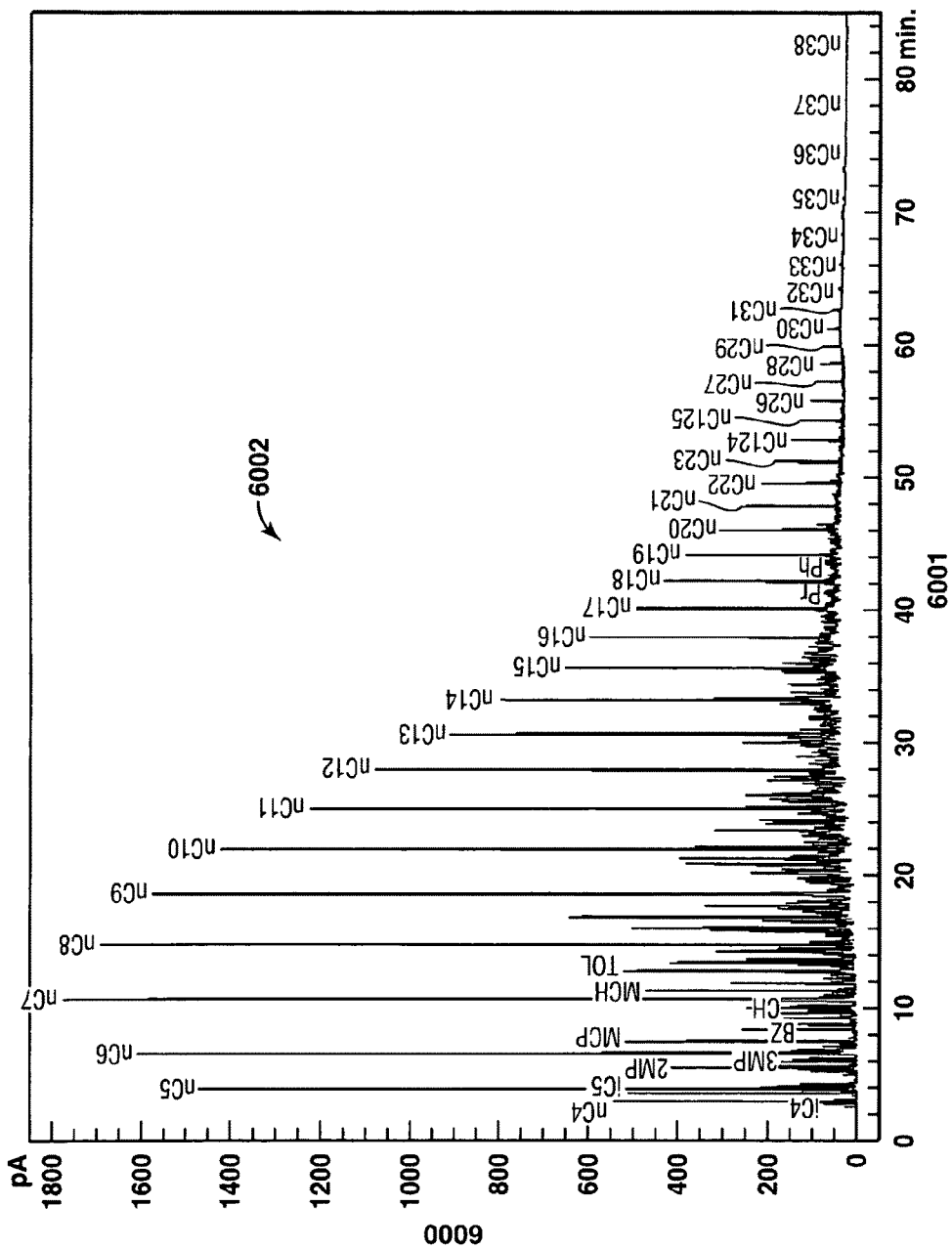
FIG. 27 is a whole oil gas chromatogram of liquid sampled from Example 4.

Conducted in a manner similar to that of Example 2 on a core specimen from oil shale block CM-1B; however, in this example the applied effective stress was 1,000 psi. Results for the gas collected and analyzed by hydrocarbon gas sample gas chromatography (GC) and non-hydrocarbon gas sample gas chromatography (GC) (GC not shown) are shown in FIG. 26, Table 7 and Table 1. In FIG. 26 the y-axis 4030 represents the detector response in pico-amperes (pA) while the x-axis 4031 represents the retention time in minutes. In FIG. 26 peak 4032 represents the response for methane, peak 4033 represents the response for ethane, peak 4034 represents the response for propane, peak 4035 represents the response for butane, peak 4036 represents the response for pentane and peak 4037 represents the response for hexane. Results for the liquid collected and analyzed by whole oil gas chromatography (WOGC) are shown in FIG. 27, Table 8 and Table 1. In FIG. 27 the y-axis 6000 represents the detector response in pico-amperes (pA) while the x-axis 6001 represents the retention time in minutes. The GC chromatogram is shown generally by label 6002 with individual identified peaks labeled with abbreviations.

TABLE 7

Peak and Area Details for FIG. 26 - Example 4 - 1000 psi stress - Gas GC

| Peak Number | Ret Time [min] | Area [pA*s] | Compound Name |
|---|---|---|---|
| 1 | 0.910 | 1.43817e4 | Methane |
| 2 | 1.000 | 301.69287 | ? |
| 3 | 1.078 | 1.37821e4 | Ethane |
| 4 | 2.541 | 1.64047e4 | Propane |
| 5 | 4.249 | 2286.08032 | iC4 |
| 6 | 4.924 | 992.04395 | ? |
| 7 | 5.030 | 6167.50000 | n-Butane |
| 8 | 5.303 | 534.37000 | ? |
| 9 | 5.583 | 358.96567 | ? |
| 10 | 6.131 | 27.44937 | ? |
| 11 | 6.376 | 1174.68872 | iC5 |
| 12 | 6.740 | 223.61662 | ? |
| 13 | 6.902 | 2340.79248 | n-Pentane |
| 14 | 7.071 | 5.29245 | ? |
| 15 | 7.136 | 309.94775 | ? |
| 16 | 7.295 | 154.59171 | ? |
| 17 | 7.381 | 169.53279 | ? |
| 18 | 7.555 | 2.80458 | ? |
| 19 | 7.601 | 5.22327 | ? |
| 20 | 7.751 | 117.69164 | ? |
| 21 | 8.134 | 29.41086 | ? |
| 22 | 8.219 | 19.39338 | ? |
| 23 | 8.342 | 133.52739 | ? |
| 24 | 8.492 | 281.61343 | 2-methyl pentane |
| 25 | 8.647 | 22.19704 | ? |
| 26 | 8.882 | 99.56919 | ? |
| 27 | 9.190 | 86.65676 | ? |
| 28 | 9.443 | 657.28754 | n-Hexane |
| 29 | 9.552 | 4.12572 | ? |
| 30 | 9.646 | 34.33701 | ? |
| 31 | 9.710 | 59.12064 | ? |
| 32 | 9.788 | 62.97972 | ? |
| 33 | 9.847 | 15.13559 | ? |
| 34 | 9.909 | 6.88310 | ? |
| 35 | 10.009 | 29.11555 | ? |
| 36 | 10.223 | 23.65434 | ? |
| 37 | 10.298 | 173.95422 | ? |
| 38 | 10.416 | 3.37255 | ? |
| 39 | 10.569 | 7.64592 | ? |
| 40 | 11.246 | 47.30062 | ? |
| 41 | 11.485 | 32.04262 | ? |
| 42 | 11.560 | 13.74583 | ? |
| 43 | 11.702 | 2.68917 | ? |
| 44 | 11.815 | 36.51670 | ? |
| 45 | 11.941 | 6.45255 | ? |
| 46 | 12.103 | 28.44484 | ? |
| 47 | 12.172 | 5.96475 | ? |
| 48 | 12.304 | 17.59856 | ? |
| 49 | 12.399 | 15.17446 | ? |
| 50 | 12.490 | 31.96492 | ? |
| 51 | 12.584 | 3.27834 | ? |
| 52 | 12.675 | 14.08259 | ? |
| 53 | 12.934 | 207.21574 | ? |
| 54 | 13.105 | 8.29743 | ? |
| 55 | 13.151 | 2.25476 | ? |
| 56 | 13.201 | 8.36965 | ? |
| 57 | 13.312 | 9.49917 | ? |
| 58 | 13.436 | 6.09893 | ? |
| 59 | 13.521 | 46.34579 | ? |
| 60 | 13.900 | 20.53506 | ? |
| 61 | 14.090 | 8.41120 | ? |
| 62 | 14.318 | 4.36870 | ? |
| 63 | 14.550 | 8.68951 | ? |
| 64 | 14.610 | 4.39150 | ? |
| 65 | 14.727 | 4.35713 | ? |
| 66 | 14.870 | 37.17881 | ? |
| 67 | 14.951 | 5.78219 | ? |
| 68 | 15.080 | 5.54470 | ? |
| 69 | 15.136 | 8.07308 | ? |
| 70 | 15.336 | 2.07075 | ? |
| 71 | 15.425 | 2.67118 | ? |
| 72 | 15.516 | 8.47004 | ? |
| 73 | 15.569 | 3.89987 | ? |
| 74 | 15.641 | 3.96979 | ? |
| 75 | 15.776 | 40.75155 | ? |
| 76 | 16.558 | 5.06379 | ? |
| 77 | 16.641 | 8.43767 | ? |
| 78 | 17.437 | 6.00180 | ? |
| 79 | 18.095 | 7.66881 | ? |
| 80 | 15.853 | 3.97375 | ? |
| 81 | 16.016 | 5.68997 | ? |
| 82 | 16.482 | 3.27234 | ? |

TABLE 8

Peak and Area Details from FIG. 27 - Example 4 - 1000 psi stress - Liquid GC.

| Peak Number | Ret Time [min] | Peak Area [pA*s] | Compound Name |
|---|---|---|---|
| 1 | 2.737 | 117.78948 | iC4 |
| 2 | 2.901 | 923.40125 | nC4 |
| 3 | 3.528 | 1079.83325 | iC5 |
| 4 | 3.891 | 3341.44604 | nC5 |
| 5 | 5.493 | 1364.53186 | 2MP |
| 6 | 5.930 | 533.68530 | 3MP |
| 7 | 6.552 | 5160.12207 | nC6 |
| 8 | 7.452 | 1770.29932 | MCP |
| 9 | 8.717 | 487.04718 | BZ |
| 10 | 9.206 | 712.61566 | CH |
| 11 | 10.634 | 7302.51123 | nC7 |
| 12 | 11. | 1755.92236 | MCH |
| 13 | 12.760 | 2145.57666 | TOL |
| 14 | 14.755 | 6434.40430 | nC8 |
| 15 | 18.503 | 6007.12891 | nC9 |
| 16 | 21.906 | 5417.67480 | nC10 |
| 17 | 25.030 | 4565.11084 | nC11 |
| 18 | 27.936 | 3773.91943 | nC12 |
| 19 | 30.656 | 3112.23950 | nC13 |
| 20 | 33.220 | 2998.37720 | nC14 |
| 21 | 35.639 | 2304.97632 | nC15 |
| 22 | 37.927 | 2197.88892 | nC16 |
| 23 | 40.102 | 1791.11877 | nC17 |
| 24 | 40.257 | 278.39423 | Pr |
| 25 | 42.171 | 1589.64233 | nC18 |
| 26 | 42.428 | 241.65131 | Ph |
| 27 | 44.141 | 1442.51843 | nC19 |
| 28 | 46.025 | 1031.68481 | nC20 |
| 29 | 47.825 | 957.65479 | nC21 |
| 30 | 49.551 | 609.59943 | nC22 |
| 31 | 51.208 | 526.53339 | nC23 |
| 32 | 52.798 | 383.01022 | nC24 |
| 33 | 54.329 | 325.93640 | nC25 |
| 34 | 55.806 | 248.12935 | nC26 |
| 35 | 57.230 | 203.21725 | nC27 |
| 36 | 58.603 | 168.78055 | nC28 |
| 37 | 59.934 | 140.40034 | nC29 |
| 38 | 61.222 | 95.47594 | nC30 |
| 39 | 62.622 | 77.49546 | nC31 |
| 40 | 64.234 | 49.08135 | nC32 |
| 41 | 66.114 | 33.61663 | nC33 |
| 42 | 68.350 | 27.46170 | nC34 |
| 43 | 71.030 | 35.89277 | nC35 |
| 44 | 74.162 | 16.87499 | nC36 |
| 45 | 78.055 | 29.21477 | nC37 |
| 46 | 82.653 | 9.88631 | nC38 |
| Totals: | | 7.38198e4 | |

Example 5

Figure 28:
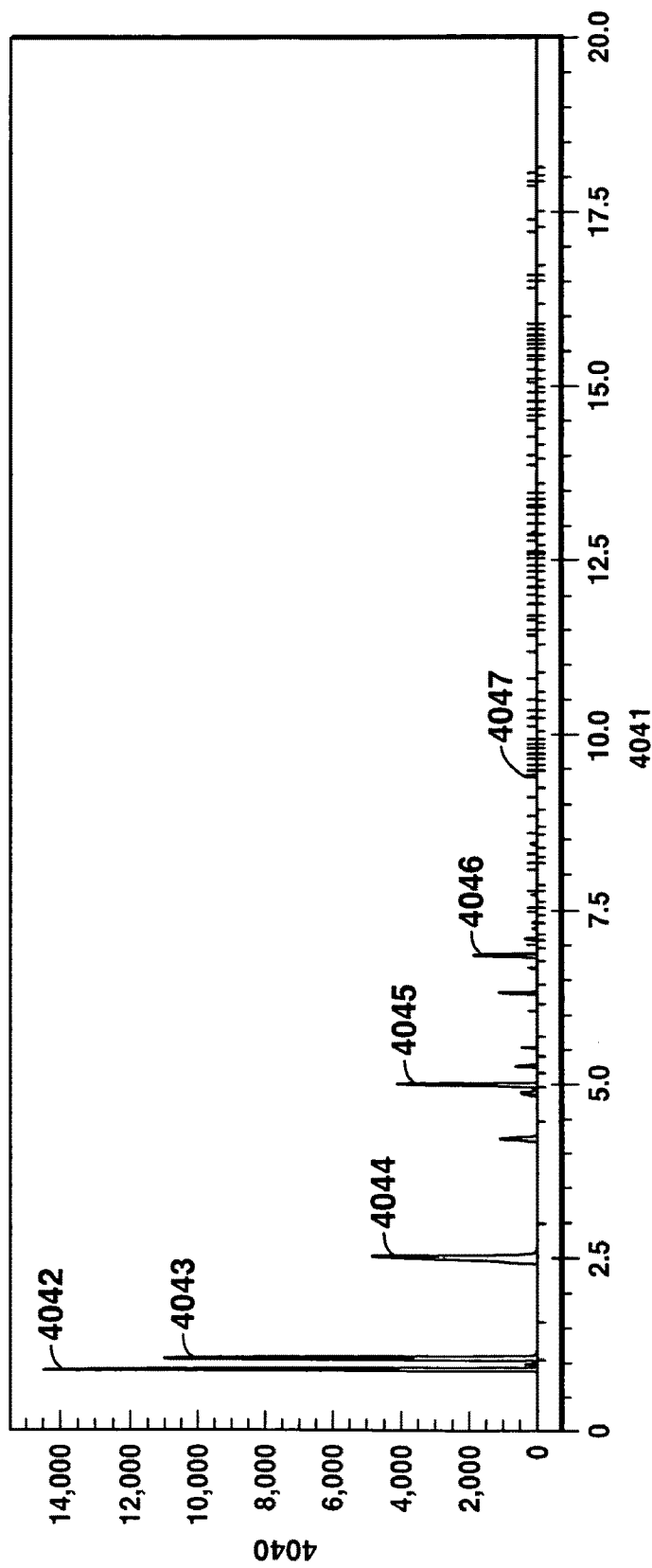
FIG. 28 is gas chromatogram of gas sampled from Example 5.

Conducted in a manner similar to that of Example 2 on a core specimen from oil shale block CM-1B; however, in this example the applied effective stress was 1,000 psi. Results for the gas collected and analyzed by hydrocarbon gas sample gas chromatography (GC) and non-hydrocarbon gas sample gas chromatography (GC) (GC not shown) are shown in FIG. 28, Table 9 and Table 1. In FIG. 28 the y-axis 4040 represents the detector response in pico-amperes (pA) while the x-axis 4041 represents the retention time in minutes. In FIG. 28 peak 4042 represents the response for methane, peak 4043 represents the response for ethane, peak 4044 represents the response for propane, peak 4045 represents the response for butane, peak 4046 represents the response for pentane and peak 4047 represents the response for hexane.

TABLE 9

Peak and Area Details for FIG. 28 - Example 5 - 1000 psi stress - Gas GC

| Peak Number | Ret Time [min] | Area [pA*s] | Compound Name |
|---|---|---|---|
| 1 | 0.910 | 1.59035e4 | Methane |
| 2 | 0.999 | 434.21375 | ? |
| 3 | 1.077 | 1.53391e4 | Ethane |
| 4 | 2.537 | 1.86530e4 | Propane |
| 5 | 4.235 | 2545.45850 | iC4 |
| 6 | 4.907 | 1192.68970 | ? |
| 7 | 5.015 | 6814.44678 | n-Butane |
| 8 | 5.285 | 687.83679 | ? |
| 9 | 5.564 | 463.25885 | ? |
| 10 | 6.106 | 30.02624 | ? |
| 11 | 6.351 | 1295.13477 | iC5 |
| 12 | 6.712 | 245.26985 | ? |
| 13 | 6.876 | 2561.11792 | n-Pentane |
| 14 | 7.039 | 4.50998 | ? |
| 15 | 7.109 | 408.32999 | ? |
| 16 | 7.268 | 204.45311 | ? |
| 17 | 7.354 | 207.92183 | ? |
| 18 | 7.527 | 4.02397 | ? |
| 19 | 7.574 | 5.65699 | ? |
| 20 | 7.755 | 2.35952 | ? |
| 21 | 7.818 | 2.00382 | ? |
| 22 | 8.107 | 38.23093 | ? |
| 23 | 8.193 | 20.54333 | ? |
| 24 | 8.317 | 148.54445 | ? |
| 25 | 8.468 | 300.31586 | 2-methyl pentane |
| 26 | 8.622 | 26.06131 | ? |
| 27 | 8.858 | 113.70123 | ? |
| 28 | 9.168 | 90.37163 | ? |
| 29 | 9.422 | 694.74438 | n-Hexane |
| 30 | 9.531 | 4.88823 | ? |
| 31 | 9.625 | 45.91505 | ? |
| 32 | 9.689 | 76.32931 | ? |
| 33 | 9.767 | 77.63214 | ? |
| 34 | 9.826 | 19.23768 | ? |
| 35 | 9.889 | 8.54605 | ? |
| 36 | 9.989 | 37.74959 | ? |
| 37 | 10.204 | 30.83943 | ? |
| 38 | 10.280 | 184.58420 | ? |
| 39 | 10.397 | 4.43609 | ? |
| 40 | 10.551 | 10.59880 | ? |
| 41 | 10.843 | 2.30370 | ? |
| 42 | 11.231 | 55.64666 | ? |
| 43 | 11.472 | 35.46931 | ? |
| 44 | 11.547 | 17.16440 | ? |
| 45 | 11.691 | 3.30460 | ? |
| 46 | 11.804 | 39.46368 | ? |
| 47 | 11.931 | 7.32969 | ? |
| 48 | 12.094 | 30.59748 | ? |
| 49 | 12.163 | 6.93754 | ? |
| 50 | 12.295 | 18.69523 | ? |
| 51 | 12.391 | 15.96837 | ? |
| 52 | 12.482 | 33.66422 | ? |
| 53 | 12.577 | 2.02121 | ? |
| 54 | 12.618 | 2.32440 | ? |
| 55 | 12.670 | 12.83803 | ? |
| 56 | 12.851 | 2.22731 | ? |
| 57 | 12.929 | 218.23195 | ? |
| 58 | 13.100 | 14.33166 | ? |
| 59 | 13.198 | 10.20244 | ? |
| 60 | 13.310 | 12.02551 | ? |
| 61 | 13.432 | 8.23884 | ? |
| 62 | 13.519 | 47.64641 | ? |
| 63 | 13.898 | 22.63760 | ? |
| 64 | 14.090 | 9.29738 | ? |
| 65 | 14.319 | 3.88012 | ? |
| 66 | 14.551 | 9.26884 | ? |
| 67 | 14.612 | 4.34914 | ? |
| 68 | 14.729 | 4.07543 | ? |
| 69 | 14.872 | 46.24465 | ? |
| 70 | 14.954 | 6.62461 | ? |
| 71 | 15.084 | 3.92423 | ? |
| 72 | 15.139 | 8.60328 | ? |
| 73 | 15.340 | 2.17899 | ? |
| 74 | 15.430 | 2.96646 | ? |
| 75 | 15.521 | 9.66407 | ? |
| 76 | 15.578 | 4.27190 | ? |
| 77 | 15.645 | 4.37904 | ? |
| 78 | 15.703 | 2.68909 | ? |
| 79 | 15.782 | 46.97895 | ? |
| 80 | 15.859 | 4.69475 | ? |
| 81 | 16.022 | 7.36509 | ? |
| 82 | 16.489 | 3.91073 | ? |
| 83 | 16.564 | 6.22445 | ? |
| 84 | 16.648 | 10.24660 | ? |
| 85 | 17.269 | 2.69753 | ? |
| 86 | 17.445 | 10.16989 | ? |
| 87 | 17.925 | 2.28341 | ? |
| 88 | 17.979 | 2.71101 | ? |
| 89 | 18.104 | 11.19730 | ? |

TABLE 1

Summary data for Examples 1-5.

| | Example 1 | Example 2 | Example 3 | Example 4 | Example 5 |
|---|---|---|---|---|---|
| Effective Stress (psi) | 0 | 400 | 400 | 1000 | 1000 |
| Sample weight (g) | 82.46 | 42.57 | 48.34 | 43.61 | 43.73 |
| Sample weight loss (g) | 19.21 | 10.29 | 11.41 | 10.20 | 9.17 |
| Fluids Recovered: | | | | | |
| Oil (g) | 10.91 | 3.63 | 3.77 | 3.02 | 2.10 |
| | 36.2 gal/ton | 23.4 gal/ton | 21.0 gal/ton | 19.3 gal/ton | 13/1 gal/ton |
| Water (g) | 0.90 | 0.30 | 0.34 | 0.39 | 0.28 |
| | 2.6 gal/ton | 1.7 gal/ton | 1.7 gal/ton | 2.1 gal/ton | 1.5 gal/ton |

TABLE 1-continued

Summary data for Examples 1-5.

|  | Example 1 | Example 2 | Example 3 | Example 4 | Example 5 |
|---|---|---|---|---|---|
| HC gas (g) | 2.09 | 1.33 | 1.58 | 1.53 | 1.66 |
|  | 683 scf/ton | 811 scf/ton | 862 scf/ton | 905 scf/ton | 974 scf/ton |
| $CO_2$ (g) | 3.35 | 1.70 | 1.64 | 1.74 | 1.71 |
|  | 700 scf/ton | 690 scf/ton | 586 scf/ton | 690 scf/ton | 673 scf/ton |
| $H_2S$ (g) | 0.06 | 0.0 | 0.0 | 0.0 | 0.0 |
| Coke Recovered: | 0.0 | 0.73 | 0.79 | .47 | 0.53 |
| Inferred Oil (g) | 0.0 | 1.67 | 1.81 | 1.07 | 1.21 |
|  | 0 gal/ton | 10.8 gal/ton | 10.0 gal/ton | 6.8 gal/ton | 7.6 gal/ton |
| Total Oil (g) | 10.91 | 5.31 | 5.58 | 4.09 | 3.30 |
|  | 36.2 gal/ton | 34.1 gal/ton | 31.0 gal/ton | 26.1 gal/ton | 20.7 gal/ton |
| Balance (g) | 1.91 | 2.59 | 3.29 | 3.05 | 2.91 |

Analysis

The gas and liquid samples obtained through the experimental procedures and gas and liquid sample collection procedures described for Examples 1-5, were analyzed by the following hydrocarbon gas sample gas chromatography (GC) analysis methodology, non-hydrocarbon gas sample gas chromatography (GC) analysis methodology, gas sample GC peak identification and integration methodology, whole oil gas chromatography (WOGC) analysis methodology, and whole oil gas chromatography (WOGC) peak identification and integration methodology.

Gas samples collected during the heating tests as described in Examples 1-5 were analyzed for both hydrocarbon and non-hydrocarbon gases, using an Agilent Model 6890 Gas Chromatograph coupled to an Agilent Model 5973 quadrapole mass selective detector. The 6890 GC was configured with two inlets (front and back) and two detectors (front and back) with two fixed volume sample loops for sample introduction. Peak identifications and integrations were performed using the Chemstation software (Revision A.03.01) supplied with the GC instrument. For hydrocarbon gases, the GC configuration consisted of the following:

a) split/splitless inlet (back position of the GC)
b) FID (Flame ionization detector) back position of the GC
c) HP Ultra-2 (5% Phenyl Methyl Siloxane) capillary columns (two) (25 meters×200 μm ID) one directed to the FID detector, the other to an Agilent 5973 Mass Selective Detector
d) 500 μl fixed volume sample loop
e) six-port gas sampling valve
f) cryogenic (liquid nitrogen) oven cooling capability
g) Oven program –80° C. for 2 mins., 20° C./min. to 0° C., then 4° C./min to 20° C., then 10° C./min. to 100° C., hold for 1 min.
h) Helium carrier gas flow rate of 2.2 ml/min
i) Inlet temperature 100° C.
j) Inlet pressure 19.35 psi
k) Split ratio 25:1
l) FID temperature 310° C.

For non-hydrocarbon gases (e.g., argon, carbon dioxide and hydrogen sulfide) the GC configuration consisted of the following:

a) PTV (programmable temperature vaporization) inlet (front position of the GC)
b) TCD (Thermal conductivity detector) front position of the GC
c) GS-GasPro capillary column (30 meters×0.32 mm ID)
d) 100 μl fixed volume sample loop
e) six port gas sampling valve
f) Oven program: 25° C. hold for 2 min., then 10° C./min to 200° C., hold 1 min.
g) Helium carrier gas flow rate of 4.1 ml/min.
h) Inlet temperature 200° C.
i) Inlet pressure 14.9 psi
j) Splitless mode
k) TCD temperature 250° C.

For Examples 1-5, a stainless steel sample cylinder containing gas collected from the Parr vessel (FIG. 18) was fitted with a two stage gas regulator (designed for lecture bottle use) to reduce gas pressure to approximately twenty pounds per square inch. A septum fitting was positioned at the outlet port of the regulator to allow withdrawal of gas by means of a Hamilton model 1005 gas-tight syringe. Both the septum fitting and the syringe were purged with gas from the stainless steel sample cylinder to ensure that a representative gas sample was collected. The gas sample was then transferred to a stainless steel cell (septum cell) equipped with a pressure transducer and a septum fitting. The septum cell was connected to the fixed volume sample loop mounted on the GC by stainless steel capillary tubing. The septum cell and sample loop were evacuated for approximately 5 minutes. The evacuated septum cell was then isolated from the evacuated sample loop by closure of a needle valve positioned at the outlet of the septum cell. The gas sample was introduced into the septum cell from the gas-tight syringe through the septum fitting and a pressure recorded. The evacuated sample loop was then opened to the pressurized septum cell and the gas sample allowed to equilibrate between the sample loop and the septum cell for one minute. The equilibrium pressure was then recorded, to allow calculation of the total moles of gas present in the sample loop before injection into the GC inlet. The sample loop contents were then swept into the inlet by Helium carrier gas and components separated by retention time in the capillary column, based upon the GC oven temperature program and carrier gas flow rates.

Calibration curves, correlating integrated peak areas with concentration, were generated for quantification of gas compositions using certified gas standards. For hydrocarbon gases, standards containing a mixture of methane, ethane, propane, butane, pentane and hexane in a helium matrix in varying concentrations (parts per million, mole basis) were injected into the GC through the fixed volume sample loop at atmospheric pressure. For non-hydrocarbon gases, standards containing individual components, i.e., carbon dioxide in helium and hydrogen sulfide in natural gas, were injected into the GC at varying pressures in the sample loop to generate calibration curves.

The hydrocarbon gas sample molar percentages reported in FIG. 16 were obtained using the following procedure. Gas standards for methane, ethane, propane, butane, pentane and hexane of at least three varying concentrations were run on the gas chromatograph to obtain peak area responses for such standard concentrations. The known concentrations were then correlated to the respective peak area responses within the Chemstation software to generate calibration curves for methane, ethane, propane, butane, pentane and hexane. The calibration curves were plotted in Chemstation to ensure good linearity (R2>0.98) between concentration and peak intensity. A linear fit was used for each calibrated compound, so that the response factor between peak area and molar concentration was a function of the slope of the line as determined by the Chemstation software. The Chemstation software program then determined a response factor relating GC peak area intensity to the amount of moles for each calibrated compound. The software then determined the number of moles of each calibrated compound from the response factor and the peak area. The peak areas used in Examples 1-5 are reported in Tables 2, 4, 5, 7, and 9. The number of moles of each identified compound for which a calibration curve was not determined (i.e., iso-butane, iso-pentane, and 2-methyl pentane) was then estimated using the response factor for the closest calibrated compound (i.e., butane for iso-butane; pentane for iso-pentane; and hexane for 2-methyl pentane) multiplied by the ratio of the peak area for the identified compound for which a calibration curve was not determined to the peak area of the calibrated compound. The values reported in FIG. 16 were then taken as a percentage of the total of all identified hydrocarbon gas GC areas (i.e., methane, ethane, propane, iso-butane, n-butane, iso-pentane, n-pentane, 2-methyl pentane, and n-hexane) and calculated molar concentrations. Thus the graphed methane to normal C6 molar percentages for all of the experiments do not include the molar contribution of the unidentified hydrocarbon gas species listed in Tables 2, 4, 5, 7, or 9 (e.g., peak numbers 2, 6, 8-11, 13, 15-22, 24-26, and 28-78 in Table 2).

Liquid samples collected during the heating tests as described in Examples 1, 3 and 4 were analyzed by whole oil gas chromatography (WOGC) according to the following procedure. Samples, QA/QC standards and blanks (carbon disulfide) were analyzed using an Ultra 1 Methyl Siloxane column (25 m length, 0.32 μm diameter, 0.52 μm film thickness) in an Agilent 6890 GC equipped with a split/splitless injector, autosampler and flame ionization detector (FID). Samples were injected onto the capillary column in split mode with a split ratio of 80:1. The GC oven temperature was kept constant at 20° C. for 5 min, programmed from 20° C. to 300° C. at a rate of 5° C.min$^{-1}$, and then maintained at 300° C. for 30 min (total run time=90 min.). The injector temperature was maintained at 300° C. and the FID temperature set at 310° C. Helium was used as carrier gas at a flow of 2.1 mL min$^{-1}$. Peak identifications and integrations were performed using Chemstation software Rev.A.10.02 [1757] (Agilent Tech. 1990-2003) supplied with the Agilent instrument.

Standard mixtures of hydrocarbons were analyzed in parallel by the WOGC method described above and by an Agilent 6890 GC equipped with a split/splitless injector, auto sampler and mass selective detector (MS) under the same conditions. Identification of the hydrocarbon compounds was conducted by analysis of the mass spectrum of each peak from the GC-MS. Since conditions were identical for both instruments, peak identification conducted on the GC-MS could be transferred to the peaks obtained on the GC-FID. Using these data, a compound table relating retention time and peak identification was set up in the GC-FID Chemstation. This table was used for peak identification.

The gas chromatograms obtained on the liquid samples (FIGS. 4, 9 and 11) were analyzed using a pseudo-component technique. The convention used for identifying each pseudo-component was to integrate all contributions from normal alkane to next occurring normal alkane with the pseudo-component being named by the late eluting n-alkane. For example, the C-10 pseudo-component would be obtained from integration beginning just past normal-C9 and continue just through normal-C10. The carbon number weight % and mole % values for the pseudo-components obtained in this manner were assigned using correlations developed by Katz and Firoozabadi (Katz, D. L., and A. Firoozabadi, 1978. Predicting phase behavior of condensate/crude-oil systems using methane interaction coefficients, J. Petroleum Technology (November 1978), 1649-1655). Results of the pseudo-component analyses for Examples 1, 3 and 4 are shown in Tables 10, 11 and 12.

An exemplary pseudo component weight percent calculation is presented below with reference to Table 10 for the C10 pseudo component for Example 1 in order to illustrate the technique. First, the C-10 pseudo-component total area is obtained from integration of the area beginning just past normal-C9 and continued just through normal-C10 as described above. The total integration area for the C10 pseudo component is 10551.700 pico-ampere-seconds (pAs). The total C10 pseudo component integration area (10551.700 pAs) is then multiplied by the C10 pseudo component density (0.7780 g/ml) to yield an "area×density" of 8209.22 pAs g/ml. Similarly, the peak integration areas for each pseudo component and all lighter listed compounds (i.e., nC3, iC4, nC4, iC5 & nC5) are determined and multiplied by their respective densities to yield "area×density" numbers for each respective pseudo component and listed compound. The respective determined "area×density" numbers for each pseudo component and listed compound is then summed to determine a "total area×density" number. The "total area X density" number for Example 1 is 96266.96 pAs g/ml. The C10 pseudo component weight percentage is then obtained by dividing the C10 pseudo component "area×density" number (8209.22 pAs g/ml) by the "total area×density" number (96266.96 pAs g/ml) to obtain the C10 pseudo component weight percentage of 8.53 weight percent.

An exemplary pseudo component molar percent calculation is presented below with reference to Table 10 for the C10 pseudo component for Example 1 in order to further illustrate the pseudo component technique. First, the C-10 pseudo-component total area is obtained from integration of the area beginning just past normal-C9 and continued just through normal-C10 as described above. The total integration area for the C10 pseudo component is 10551.700 pico-ampere-seconds (pAs). The total C10 pseudo component integration area (10551.700 pAs) is then multiplied by the C10 pseudo component density (0.7780 g/ml) to yield an "area×density" of 8209.22 pAs g/ml. Similarly, the integration areas for each pseudo component and all lighter listed compounds (i.e., nC3, iC4, nC4, iC5 & nC5) are determined and multiplied by their respective densities to yield "area×density" numbers for each respective pseudo component and listed compound. The C10 pseudo component "area×density" number (8209.22 pAs g/ml) is then divided by the C10 pseudo component molecular weight (134.00 g/mol) to yield a C10 pseudo component "area×density/molecular weight" number of 61.26 pAs mol/ml. Similarly, the "area×density" number for each pseudo component and listed compound is then divided by such components or compounds respective molecular weight to yield an "area×density/molecular weight" number for each respective pseudo component and listed compound. The respective determined "area×density/molecular weight" numbers for each pseudo component and listed compound is then summed to determine a "total area×density/molecular weight" number. The total "total area×density/molecular weight" number for Example 1 is 665.28 pAs mol/ml. The C10 pseudo component molar percentage is then obtained by dividing the C10 pseudo component "area×density/molecular weight" number (61.26 pAs mol/ml) by the "total area×density/molecular weight" number (665.28 pAs mol/ml) to obtain the C10 pseudo component molar percentage of 9.21 molar percent.

TABLE 10

Pseudo-components for Example 1 - GC of liquid - 0 stress

| Component | Area (cts.) | Area % | Avg. Boiling Pt. (° F.) | Density (g/ml) | Molecular Wt. (g/mol) | Wt. % | Mol % |
|---|---|---|---|---|---|---|---|
| $nC_3$ | 41.881 | 0.03 | −43.73 | 0.5069 | 44.10 | 0.02 | 0.07 |
| $iC_4$ | 120.873 | 0.10 | 10.94 | 0.5628 | 58.12 | 0.07 | 0.18 |
| $nC_4$ | 805.690 | 0.66 | 31.10 | 0.5840 | 58.12 | 0.49 | 1.22 |
| $iC_5$ | 1092.699 | 0.89 | 82.13 | 0.6244 | 72.15 | 0.71 | 1.42 |
| $nC_5$ | 2801.815 | 2.29 | 96.93 | 0.6311 | 72.15 | 1.84 | 3.68 |
| Pseudo $C_6$ | 7150.533 | 5.84 | 147.00 | 0.6850 | 84.00 | 5.09 | 8.76 |
| Pseudo $C_7$ | 10372.800 | 8.47 | 197.50 | 0.7220 | 96.00 | 7.78 | 11.73 |
| Pseudo $C_8$ | 11703.500 | 9.56 | 242.00 | 0.7450 | 107.00 | 9.06 | 12.25 |
| Pseudo $C_9$ | 11776.200 | 9.61 | 288.00 | 0.7640 | 121.00 | 9.35 | 11.18 |
| Pseudo $C_{10}$ | 10551.700 | 8.61 | 330.50 | 0.7780 | 134.00 | 8.53 | 9.21 |
| Pseudo $C_{11}$ | 9274.333 | 7.57 | 369.00 | 0.7890 | 147.00 | 7.60 | 7.48 |
| Pseudo $C_{12}$ | 8709.231 | 7.11 | 407.00 | 0.8000 | 161.00 | 7.24 | 6.50 |
| Pseudo $C_{13}$ | 7494.549 | 6.12 | 441.00 | 0.8110 | 175.00 | 6.31 | 5.22 |
| Pseudo $C_{14}$ | 6223.394 | 5.08 | 475.50 | 0.8220 | 190.00 | 5.31 | 4.05 |
| Pseudo $C_{15}$ | 6000.179 | 4.90 | 511.00 | 0.8320 | 206.00 | 5.19 | 3.64 |
| Pseudo $C_{16}$ | 5345.791 | 4.36 | 542.00 | 0.8390 | 222.00 | 4.66 | 3.04 |
| Pseudo $C_{17}$ | 4051.886 | 3.31 | 572.00 | 0.8470 | 237.00 | 3.57 | 2.18 |
| Pseudo $C_{18}$ | 3398.586 | 2.77 | 595.00 | 0.8520 | 251.00 | 3.01 | 1.73 |
| Pseudo $C_{19}$ | 2812.101 | 2.30 | 617.00 | 0.8570 | 263.00 | 2.50 | 1.38 |
| Pseudo $C_{20}$ | 2304.651 | 1.88 | 640.50 | 0.8620 | 275.00 | 2.06 | 1.09 |
| Pseudo $C_{21}$ | 2038.925 | 1.66 | 664.00 | 0.8670 | 291.00 | 1.84 | 0.91 |
| Pseudo $C_{22}$ | 1497.726 | 1.22 | 686.00 | 0.8720 | 305.00 | 1.36 | 0.64 |
| Pseudo $C_{23}$ | 1173.834 | 0.96 | 707.00 | 0.8770 | 318.00 | 1.07 | 0.49 |
| Pseudo $C_{24}$ | 822.762 | 0.67 | 727.00 | 0.8810 | 331.00 | 0.75 | 0.33 |
| Pseudo $C_{25}$ | 677.938 | 0.55 | 747.00 | 0.8850 | 345.00 | 0.62 | 0.26 |
| Pseudo $C_{26}$ | 532.788 | 0.43 | 766.00 | 0.8890 | 359.00 | 0.49 | 0.20 |
| Pseudo $C_{27}$ | 459.465 | 0.38 | 784.00 | 0.8930 | 374.00 | 0.43 | 0.16 |
| Pseudo $C_{28}$ | 413.397 | 0.34 | 802.00 | 0.8960 | 388.00 | 0.38 | 0.14 |
| Pseudo $C_{29}$ | 522.898 | 0.43 | 817.00 | 0.8990 | 402.00 | 0.49 | 0.18 |
| Pseudo $C_{30}$ | 336.968 | 0.28 | 834.00 | 0.9020 | 416.00 | 0.32 | 0.11 |
| Pseudo $C_{31}$ | 322.495 | 0.26 | 850.00 | 0.9060 | 430.00 | 0.30 | 0.10 |
| Pseudo $C_{32}$ | 175.615 | 0.14 | 866.00 | 0.9090 | 444.00 | 0.17 | 0.05 |
| Pseudo $C_{33}$ | 165.912 | 0.14 | 881.00 | 0.9120 | 458.00 | 0.16 | 0.05 |
| Pseudo $C_{34}$ | 341.051 | 0.28 | 895.00 | 0.9140 | 472.00 | 0.32 | 0.10 |
| Pseudo $C_{35}$ | 286.861 | 0.23 | 908.00 | 0.9170 | 486.00 | 0.27 | 0.08 |
| Pseudo $C_{36}$ | 152.814 | 0.12 | 922.00 | 0.9190 | 500.00 | 0.15 | 0.04 |
| Pseudo $C_{37}$ | 356.947 | 0.29 | 934.00 | 0.9220 | 514.00 | 0.34 | 0.10 |
| Pseudo $C_{38}$ | 173.428 | 0.14 | 947.00 | 0.9240 | 528.00 | 0.17 | 0.05 |
| Totals | 122484.217 | 100.00 | | | | 100.00 | 100.00 |

TABLE 11

Pseudo-components for Example 3 - GC of liquid - 400 psi stress

| Component | Area | Area % | Avg. Boiling Pt. (° F.) | Density (g/ml) | Molecular Wt. (g/mol) | Wt. % | Mol % |
|---|---|---|---|---|---|---|---|
| $nC_3$ | 35.845 | 0.014 | −43.730 | 0.5069 | 44.10 | 0.01 | 0.03 |
| $iC_4$ | 103.065 | 0.041 | 10.940 | 0.5628 | 58.12 | 0.03 | 0.07 |
| $nC_4$ | 821.863 | 0.328 | 31.100 | 0.5840 | 58.12 | 0.24 | 0.62 |
| $iC_5$ | 1187.912 | 0.474 | 82.130 | 0.6244 | 72.15 | 0.37 | 0.77 |
| $nC_5$ | 3752.655 | 1.498 | 96.930 | 0.6311 | 72.15 | 1.20 | 2.45 |
| Pseudo $C_6$ | 12040.900 | 4.805 | 147.000 | 0.6850 | 84.00 | 4.17 | 7.34 |
| Pseudo $C_7$ | 20038.600 | 7.997 | 197.500 | 0.7220 | 96.00 | 7.31 | 11.26 |
| Pseudo $C_8$ | 24531.500 | 9.790 | 242.000 | 0.7450 | 107.00 | 9.23 | 12.76 |
| Pseudo $C_9$ | 25315.000 | 10.103 | 288.000 | 0.7640 | 121.00 | 9.77 | 11.94 |
| Pseudo $C_{10}$ | 22640.400 | 9.035 | 330.500 | 0.7780 | 134.00 | 8.90 | 9.82 |
| Pseudo $C_{11}$ | 20268.100 | 8.089 | 369.000 | 0.7890 | 147.00 | 8.08 | 8.13 |
| Pseudo $C_{12}$ | 18675.600 | 7.453 | 407.000 | 0.8000 | 161.00 | 7.55 | 6.93 |
| Pseudo $C_{13}$ | 16591.100 | 6.621 | 441.000 | 0.8110 | 175.00 | 6.80 | 5.74 |
| Pseudo $C_{14}$ | 13654.000 | 5.449 | 475.500 | 0.8220 | 190.00 | 5.67 | 4.41 |
| Pseudo $C_{15}$ | 13006.300 | 5.191 | 511.000 | 0.8320 | 206.00 | 5.47 | 3.92 |

TABLE 11-continued

Pseudo-components for Example 3 - GC of liquid - 400 psi stress

| Component | Area | Area % | Avg. Boiling Pt. (° F.) | Density (g/ml) | Molecular Wt. (g/mol) | Wt. % | Mol % |
|---|---|---|---|---|---|---|---|
| Pseudo $C_{16}$ | 11962.200 | 4.774 | 542.000 | 0.8390 | 222.00 | 5.07 | 3.38 |
| Pseudo $C_{17}$ | 8851.622 | 3.533 | 572.000 | 0.8470 | 237.00 | 3.79 | 2.36 |
| Pseudo $C_{18}$ | 7251.438 | 2.894 | 595.000 | 0.8520 | 251.00 | 3.12 | 1.84 |
| Pseudo $C_{19}$ | 5946.166 | 2.373 | 617.000 | 0.8570 | 263.00 | 2.57 | 1.45 |
| Pseudo $C_{20}$ | 4645.178 | 1.854 | 640.500 | 0.8620 | 275.00 | 2.02 | 1.09 |
| Pseudo $C_{21}$ | 4188.168 | 1.671 | 664.000 | 0.8670 | 291.00 | 1.83 | 0.93 |
| Pseudo $C_{22}$ | 2868.636 | 1.145 | 686.000 | 0.8720 | 305.00 | 1.26 | 0.61 |
| Pseudo $C_{23}$ | 2188.895 | 0.874 | 707.000 | 0.8770 | 318.00 | 0.97 | 0.45 |
| Pseudo $C_{24}$ | 1466.162 | 0.585 | 727.000 | 0.8810 | 331.00 | 0.65 | 0.29 |
| Pseudo $C_{25}$ | 1181.133 | 0.471 | 747.000 | 0.8850 | 345.00 | 0.53 | 0.23 |
| Pseudo $C_{26}$ | 875.812 | 0.350 | 766.000 | 0.8890 | 359.00 | 0.39 | 0.16 |
| Pseudo $C_{27}$ | 617.103 | 0.246 | 784.000 | 0.8930 | 374.00 | 0.28 | 0.11 |
| Pseudo $C_{28}$ | 538.147 | 0.215 | 802.000 | 0.8960 | 388.00 | 0.24 | 0.09 |
| Pseudo $C_{29}$ | 659.027 | 0.263 | 817.000 | 0.8990 | 402.00 | 0.30 | 0.11 |
| Pseudo $C_{30}$ | 1013.942 | 0.405 | 834.000 | 0.9020 | 416.00 | 0.46 | 0.16 |
| Pseudo $C_{31}$ | 761.259 | 0.304 | 850.000 | 0.9060 | 430.00 | 0.35 | 0.12 |
| Pseudo $C_{32}$ | 416.031 | 0.166 | 866.000 | 0.9090 | 444.00 | 0.19 | 0.06 |
| Pseudo $C_{33}$ | 231.207 | 0.092 | 881.000 | 0.9120 | 458.00 | 0.11 | 0.03 |
| Pseudo $C_{34}$ | 566.926 | 0.226 | 895.000 | 0.9140 | 472.00 | 0.26 | 0.08 |
| Pseudo $C_{35}$ | 426.697 | 0.170 | 908.000 | 0.9170 | 486.00 | 0.20 | 0.06 |
| Pseudo $C_{36}$ | 191.626 | 0.076 | 922.000 | 0.9190 | 500.00 | 0.09 | 0.03 |
| Pseudo $C_{37}$ | 778.713 | 0.311 | 934.000 | 0.9220 | 514.00 | 0.36 | 0.10 |
| Pseudo $C_{38}$ | 285.217 | 0.114 | 947.000 | 0.9240 | 528.00 | 0.13 | 0.04 |
| Totals | 250574.144 | 100.000 | | | | 100.00 | 100.00 |

TABLE 12

Pseudo-Components for Example 4 - GC of Liquid - 1000 psi stress

| Component | Area | Area % | Avg. Boiling Pt. (° F.) | Density (g/ml) | Molecular Wt. (g/mol) | Wt. % | Mol % |
|---|---|---|---|---|---|---|---|
| $nC_3$ | 44.761 | 0.023 | −43.730 | 0.5069 | 44.10 | 0.01 | 0.05 |
| $iC_4$ | 117.876 | 0.060 | 10.940 | 0.5628 | 58.12 | 0.04 | 0.11 |
| $nC_4$ | 927.866 | 0.472 | 31.100 | 0.5840 | 58.12 | 0.35 | 0.87 |
| $iC_5$ | 1082.570 | 0.550 | 82.130 | 0.6244 | 72.15 | 0.44 | 0.88 |
| $nC_5$ | 3346.533 | 1.701 | 96.930 | 0.6311 | 72.15 | 1.37 | 2.74 |
| Pseudo $C_6$ | 9579.443 | 4.870 | 147.000 | 0.6850 | 84.00 | 4.24 | 7.31 |
| Pseudo $C_7$ | 16046.200 | 8.158 | 197.500 | 0.7220 | 96.00 | 7.49 | 11.29 |
| Pseudo $C_8$ | 19693.300 | 10.012 | 242.000 | 0.7450 | 107.00 | 9.48 | 12.83 |
| Pseudo $C_9$ | 20326.300 | 10.334 | 288.000 | 0.7640 | 121.00 | 10.04 | 12.01 |
| Pseudo $C_{10}$ | 18297.600 | 9.302 | 330.500 | 0.7780 | 134.00 | 9.20 | 9.94 |
| Pseudo $C_{11}$ | 16385.600 | 8.330 | 369.000 | 0.7890 | 147.00 | 8.36 | 8.23 |
| Pseudo $C_{12}$ | 15349.000 | 7.803 | 407.000 | 0.8000 | 161.00 | 7.94 | 7.14 |
| Pseudo $C_{13}$ | 13116.500 | 6.668 | 441.000 | 0.8110 | 175.00 | 6.88 | 5.69 |
| Pseudo $C_{14}$ | 10816.100 | 5.499 | 475.500 | 0.8220 | 190.00 | 5.75 | 4.38 |
| Pseudo $C_{15}$ | 10276.900 | 5.225 | 511.000 | 0.8320 | 206.00 | 5.53 | 3.88 |
| Pseudo $C_{16}$ | 9537.818 | 4.849 | 542.000 | 0.8390 | 222.00 | 5.17 | 3.37 |
| Pseudo $C_{17}$ | 6930.611 | 3.523 | 572.000 | 0.8470 | 237.00 | 3.79 | 2.32 |
| Pseudo $C_{18}$ | 5549.802 | 2.821 | 595.000 | 0.8520 | 251.00 | 3.06 | 1.76 |
| Pseudo $C_{19}$ | 4440.457 | 2.257 | 617.000 | 0.8570 | 263.00 | 2.46 | 1.35 |
| Pseudo $C_{20}$ | 3451.250 | 1.755 | 640.500 | 0.8620 | 275.00 | 1.92 | 1.01 |
| Pseudo $C_{21}$ | 3133.251 | 1.593 | 664.000 | 0.8670 | 291.00 | 1.76 | 0.87 |
| Pseudo $C_{22}$ | 2088.036 | 1.062 | 686.000 | 0.8720 | 305.00 | 1.18 | 0.56 |
| Pseudo $C_{23}$ | 1519.460 | 0.772 | 707.000 | 0.8770 | 318.00 | 0.86 | 0.39 |
| Pseudo $C_{24}$ | 907.473 | 0.461 | 727.000 | 0.8810 | 331.00 | 0.52 | 0.23 |
| Pseudo $C_{25}$ | 683.205 | 0.347 | 747.000 | 0.8850 | 345.00 | 0.39 | 0.16 |
| Pseudo $C_{26}$ | 493.413 | 0.251 | 766.000 | 0.8890 | 359.00 | 0.28 | 0.11 |
| Pseudo $C_{27}$ | 326.831 | 0.166 | 784.000 | 0.8930 | 374.00 | 0.19 | 0.07 |
| Pseudo $C_{28}$ | 272.527 | 0.139 | 802.000 | 0.8960 | 388.00 | 0.16 | 0.06 |
| Pseudo $C_{29}$ | 291.862 | 0.148 | 817.000 | 0.8990 | 402.00 | 0.17 | 0.06 |
| Pseudo $C_{30}$ | 462.840 | 0.235 | 834.000 | 0.9020 | 416.00 | 0.27 | 0.09 |
| Pseudo $C_{31}$ | 352.886 | 0.179 | 850.000 | 0.9060 | 430.00 | 0.21 | 0.07 |
| Pseudo $C_{32}$ | 168.635 | 0.086 | 866.000 | 0.9090 | 444.00 | 0.10 | 0.03 |
| Pseudo $C_{33}$ | 67.575 | 0.034 | 881.000 | 0.9120 | 458.00 | 0.04 | 0.01 |
| Pseudo $C_{34}$ | 95.207 | 0.048 | 895.000 | 0.9140 | 472.00 | 0.06 | 0.02 |
| Pseudo $C_{35}$ | 226.660 | 0.115 | 908.000 | 0.9170 | 486.00 | 0.13 | 0.04 |
| Pseudo $C_{36}$ | 169.729 | 0.086 | 922.000 | 0.9190 | 500.00 | 0.10 | 0.03 |

TABLE 12-continued

Pseudo-Components for Example 4 - GC of Liquid - 1000 psi stress

| Component | Area | Area % | Avg. Boiling Pt. (° F.) | Density (g/ml) | Molecular Wt. (g/mol) | Wt. % | Mol % |
|---|---|---|---|---|---|---|---|
| Pseudo $C_{37}$ | 80.976 | 0.041 | 934.000 | 0.9220 | 514.00 | 0.05 | 0.01 |
| Pseudo $C_{38}$ | 42.940 | 0.022 | 947.000 | 0.9240 | 528.00 | 0.03 | 0.01 |
| Totals | 196699.994 | 100.000 | | | | 100.00 | 100.00 |

TOC and Rock-eval tests were performed on specimens from oil shale block CM-1B taken at the same stratigraphic interval as the specimens tested by the Parr heating method described in Examples 1-5. These tests resulted in a TOC of 21% and a Rock-eval Hydrogen Index of 872 mg/g-toc.

The TOC and rock-eval procedures described below were performed on the oil shale specimens remaining after the Parr heating tests described in Examples 1-5. Results are shown in Table 13.

The Rock-Eval pyrolysis analyses described above were performed using the following procedures. Rock-Eval pyrolysis analyses were performed on calibration rock standards (IFP standard #55000), blanks, and samples using a Delsi Rock-Eval II instrument. Rock samples were crushed, micronized, and air-dried before loading into Rock-Eval crucibles. Between 25 and 100 mg of powdered-rock samples were loaded into the crucibles depending on the total organic carbon (TOC) content of the sample. Two or three blanks were run at the beginning of each day to purge the system and stabilize the temperature. Two or three samples of IFP calibration standard #55000 with weight of 100+/−1 mg were run to calibrate the system. If the Rock-Eval $T_{max}$ parameter was 419° C.+/−2° C. on these standards, analyses proceeded with samples. The standard was also run before and after every 10 samples to monitor the instrument's performance.

The Rock-Eval pyrolysis technique involves the rate-programmed heating of a powdered rock sample to a high temperature in an inert (helium) atmosphere and the characterization of products generated from the thermal breakdown of chemical bonds. After introduction of the sample the pyrolysis oven was held isothermally at 300° C. for three minutes. Hydrocarbons generated during this stage are detected by a flame-ionization detector (FID) yielding the $S_1$ peak. The pyrolysis-oven temperature was then increased at a gradient of 25° C./minute up to 550° C., where the oven was held isothermally for one minute. Hydrocarbons generated during this step were detected by the FID and yielded the $S_2$ peak.

Hydrogen Index (HI) is calculated by normalizing the $S_2$ peak (expressed as $mg_{hydrocarbons}/g_{rock}$) to weight % TOC (Total Organic Carbon determined independently) as follows:

HI=($S_2$/TOC)*100 where HI is expressed as $mg_{hydrocarbons}/g_{TOC}$

Total Organic Carbon (TOC) was determined by well known methods suitable for geological samples—i.e., any carbonate rock present was removed by acid treatment followed by combustion of the remaining material to produce and measure organic based carbon in the form of CO2.

TABLE 13

TOC and Rock Eval Results on Oil Shale Specimens after the Parr Heating Tests.

| | Example 1 | Example 2 | Example 3 | Example 4 | Example 5 |
|---|---|---|---|---|---|
| TOC (%) | 12.07 | 10.83 | 10.62 | 11.22 | 11.63 |
| HI (mg/g-toc) | 77 | 83 | 81 | 62 | 77 |

The API gravity of Examples 1-5 was estimated by estimating the room temperature specific gravity (SG) of the liquids collected and the results are reported in Table 14. The API gravity was estimated from the determined specific gravity by applying the following formula:

API gravity=(141.5/SG)−131.5

The specific gravity of each liquid sample was estimated using the following procedure. An empty 50 μl Hamilton Model 1705 gastight syringe was weighed on a Mettler AE 163 digital balance to determine the empty syringe weight. The syringe was then loaded by filling the syringe with a volume of liquid. The volume of liquid in the syringe was noted. The loaded syringe was then weighed. The liquid sample weight was then estimated by subtracting the loaded syringe measured weight from the measured empty syringe weight. The specific gravity was then estimated by dividing the liquid sample weight by the syringe volume occupied by the liquid sample.

TABLE 14

Estimated API Gravity of liquid samples from Examples 1-5

| | Example | | | | |
|---|---|---|---|---|---|
| | Example 1 | Example 2 | Example 3 | Example 4 | Example 5 |
| API Gravity | 29.92 | 30.00 | 27.13 | 32.70 | 30.00 |

The above-described processes may be of merit in connection with the recovery of hydrocarbons in the Piceance Basin of Colorado. Some have estimated that in some oil shale deposits of the Western United States, up to 1 million barrels of oil may be recoverable per surface acre. One study has estimated the oil shale resource within the nahcolite-bearing portions of the oil shale formations of the Piceance Basin to be 400 billion barrels of shale oil in place. Overall, up to 1 trillion barrels of shale oil may exist in the Piceance Basin alone.

Certain features of the present inventions are described in terms of a set of numerical upper limits and a set of numerical lower limits. It should be appreciated that ranges formed by any combination of these limits are within the scope of the invention unless otherwise indicated. Although some of the dependent claims have single dependencies in accordance with U.S. practice, each of the features in any of such dependent claims can be combined with each of the features of one or more of the other dependent claims dependent upon the same independent claim or claims.

While it will be apparent that the invention herein described is well calculated to achieve the benefits and advantages set forth above, it will be appreciated that the invention is susceptible to modification, variation and change without departing from the spirit thereof.

What is claimed is:

1. A method for in situ heating of an organic-rich rock formation, comprising:
   providing a first wellbore extending at least to a depth of the organic-rich rock formation, wherein the first wellbore comprises a first approximately vertical section;
   providing a second wellbore intersecting the first wellbore, wherein the second wellbore comprises a second approximately vertical section, the first wellbore and the second wellbore together forming a first heater well;
   injecting an oxidant and a first combustible fuel into the first wellbore;
   providing hardware in the approximately vertical section of the first wellbore so as to cause the oxidant and the first combustible fuel to mix and to combust at substantially a single depth, which is substantially the depth of the organic-rich rock formation, thereby forming combustion products; and
   flowing the combustion products into and up the second wellbore such that a first heat profile is created from the first approximately vertical section and a second heat profile is created from the second approximately vertical section, the first heat profile mating with the second heat profile after flowing the combustion products for a period of time so as to form a substantially continuous pyrolysis zone of formation hydrocarbons within a substantial portion of the organic-rich rock formation between the first and second wellbores.

2. The method of claim 1, wherein the formation hydrocarbons comprise heavy hydrocarbons.

3. The method of claim 1, wherein the organic-rich rock formation is an oil shale formation and the formation hydrocarbons comprise oil shale.

4. The method of claim 3, wherein the combustion products are above a pyrolysis temperature in the second wellbore at or just below the approximate depth of the hardware in the first wellbore.

5. The method of claim 3, wherein the combustion products fall below a pyrolysis temperature in the approximately vertical section of the second wellbore at or just above the approximate depth of the hardware in the approximately vertical section of the first wellbore.

6. The method of claim 3, wherein, at or near the end of flowing, the combustion products in the second wellbore are at a temperature of between 270° C. and 360° C. at a depth proximate to that of an upper depth of the hardware in the first wellbore.

7. The method of claim 3, further comprising:
   providing a casing string within the first wellbore; and
   providing a casing string within the second wellbore.

8. The method of claim 7, wherein:
   the first wellbore and the second wellbore are spaced apart from about 20 feet to 100 feet; and
   the pyrolysis zone has a temperature of greater than 270° C. across a substantial portion of the organic-rich rock formation between the first and second wellbores.

9. The method of claim 8, wherein the pyrolysis zone has a temperature between about 300° C. and 700° C.

10. The method of claim 7, wherein the hardware comprises:
    a tubular member residing within the casing string within the first wellbore and extending to a selected portion of the organic-rich rock formation and forming an annular region within the casing; and
    a first burner connected to the tubular member at a first depth within the organic-rich rock formation.

11. The method of claim 10, wherein:
    injecting the first combustible fuel comprises injecting the first combustible fuel into the tubing; and
    injecting the oxidant comprises injecting the oxidant into the annular space.

12. The method of claim 10, wherein:
    injecting the oxidant comprises injecting the oxidant into the tubing; and
    injecting the first combustible fuel comprises injecting the first combustible fuel into the annular space.

13. The method claim 10, wherein the hardware further comprises a tubular cowl located immediately below the burner.

14. The method of claim 10, wherein the mating of the first heat profile and the second heat profile is accomplished by selecting a specific first burner intensity, a first combustible fuel composition, an oxidant injection rate, a first combustible fuel injection rate, a spacing between the first wellbore and the second wellbore, or combinations thereof.

15. The method of claim 10, wherein the first burner is placed near the top of a targeted zone within the organic-rich rock formation.

16. The method of claim 10, wherein the first burner is ignited using electric resistive heating elements.

17. The method of claim 10, wherein the first burner is ignited by injecting a pyrophoric substance into the first and second tubular members.

18. The method of claim 10, wherein the hardware further comprises at least one fuel line for delivering the injected combustible fuel to the burners.

19. The method of claim 10, further comprising:
    monitoring the temperature of the combustion products in the second wellbore.

20. The method of claim 10, further comprising:
    collecting the combustion products from the second wellbore at a surface;
    separating the combustion products in order to reclaim at least a part of the first combustible fuel; and
    reinjecting the first combustible fuel along with other combustion products as a second combustible fuel.

21. The method of claim 10, further comprising:
    collecting the combustion products from the second wellbore at a surface, the collected combustion products comprising available oxygen;
    compressing the collected combustion products;
    mixing compressed air with the collected combustion products to form an oxidant mixture; and
    delivering the oxidant mixture into the first wellbore, the oxidant mixture forming at least a portion of the injected oxidant.

22. The method of claim 10, further comprising:
    collecting the combustion products from the second wellbore at a surface, the collected combustion products having available fuel;
    compressing the collected combustion products;
    mixing compressed fuel with the combustion products to form a second combustible fuel; and delivering at least a portion of the second combustible fuel back into the first wellbore.

23. The method of claim 22, further comprising:
delivering at least a portion of the second combustible fuel into a first wellbore of a second heater well.

24. The method of claim 10, further comprising:
collecting the combustion products from the second wellbore at a surface; and
monitoring the collected combustion products for the presence of combustible species, thereby assessing whether the burner is firing properly.

25. The method of claim 24, wherein the combustible species comprise at least one of methane, ethane, hydrogen ($H_2$), and carbon monoxide.

26. The method of claim 24, further comprising:
treating the combustion products at the surface to remove $NO_x$ components; and
venting the treated combustion products to the atmosphere.

27. The method of claim 10, further comprising:
monitoring a temperature of the combustion products at a point in the casing string within the second wellbore at approximately the depth of the first burner.

28. The method of claim 10, wherein the oxidant is injected in excess at a mass rate of 1.25 to 6.0 times the stoichiometric combustion amount.

29. The method of claim 28, wherein the oxidant is $O_2$-enriched air.

30. The method of claim 10, wherein the burner provides 0.5 to 3.0 kW per meter of well length in a zone within the organic-rich rock formation targeted for pyrolysis.

31. The method of claim 10, wherein the oxidant is injected at a rate of about 10,000 to 50,000 kg/day.

32. The method of claim 10, wherein the oxidant is injected under a pressure of about 50 to 250 psia.

33. The method of claim 10, wherein the first combustible fuel is injected under a pressure of greater than about 600 psia.

34. The method of claim 10, wherein the burner supplies about 50 to 250 kW of thermal energy.

35. The method of claim 10, wherein:
the first combustible fuel is a fuel gas; and
the intensity of the burner is controlled by adjusting the composition of the fuel gas.

36. The method of claim 10, wherein the first combustible fuel is natural gas that has been diluted with added inert components.

37. The method of claim 36, wherein the added inert components comprise at least one of carbon dioxide ($CO_2$) or nitrogen ($N_2$).

38. The method of claim 10, wherein the tubular member terminates proximate the first burner and no burners are in the second wellbore.

39. The method of claim 10, wherein the first burner is the only burner within the first wellbore and no burners are in the second wellbore.

40. The method of claim 3, further comprising:
heating the oil shale in order to pyrolyze at least a portion of the oil shale into hydrocarbon fluids, the hydrocarbon fluids comprising gas;
producing the gas; and
wherein at least a portion of the first combustible fuel comprises the gas produced from the hydrocarbon fluids.

41. The method of claim 1, wherein the temperature variance in a plane between the first and second wellbore after mating of the first and second heat profiles is less than 350° C.

42. A method for in situ heating of a targeted oil shale formation, comprising:
providing a first wellbore extending at least to a depth of the targeted oil shale formation, the first wellbore having an approximately vertical first section and a lower end;
providing a second wellbore also having an approximately vertical second section and a lower end, the lower end of the second wellbore intersecting with the lower end of the first wellbore to create fluid communication therebetween;
selecting a distance between the first wellbore and the second wellbore;
providing a burner in only the first wellbore at substantially a single depth;
injecting an oxidant and a combustible fuel into the first wellbore and to the burner so as to combust the combustible fuel; and
circulating flue gas generated from the burner through the second wellbore and to the surface so as to form a first pyrolysis zone around the vertical first section and a second pyrolysis zone around the vertical second section, with the first pyrolysis zone mating with the second pyrolysis zone upon circulating the flue gas for a period of time so as to form a substantially continuous pyrolysis zone of formation hydrocarbons within a substantial portion of the oil shale formation between the first and second wellbores.

43. The method of claim 42, wherein, at or near the end of flowing, the flue gas falls below a pyrolysis temperature in the second wellbore at or just above the proximate depth of the hardware in the first wellbore.

44. The method of claim 43, wherein the first wellbore is completed substantially horizontally, thereby defining a heel and a toe.

45. The method of claim 44, wherein the second wellbore is completed substantially vertically.

46. The method of claim 44, wherein the burner is disposed above the heel of the first wellbore.

47. The method of claim 43, wherein the targeted oil shale formation is heated to between about 280° C. and 800° C. between the heel and the toe.

48. The method of claim 47, further comprising:
collecting the flue gas from the second wellbore; and
separating the flue gas in order to reclaim at least a part of the combustible fuel.

49. The method of claim 47, further comprising:
providing a burner and tubular member in the second wellbore; and
after the targeted oil shale formation has been heated adjacent the first wellbore above the heel and towards the toe of the first wellbore but before the first and second pyrolysis zones mate,
(1) injecting the oxidant and the combustible fuel into the second wellbore and to the burner therein so as to combust the combustible fuel, and (2) circulating flue gas generated from the burner through the first wellbore and to the surface;
(1) injecting the oxidant and the combustible fuel into the second wellbore and through the burner therein so as to combust the combustible fuel and to further heat the targeted oil shale formation adjacent the second wellbore and towards the heel of the first wellbore; and
(2) circulating flue gas generated from the burner in the second wellbore through the first wellbore and to the surface.

50. The method of claim 43, wherein the mating of the first pyrolysis zone and the second pyrolysis zone is further accomplished by selecting a specific burner intensity, a combustible fuel composition, an oxidant injection rate, a combustible fuel injection rate, or combinations thereof.

51. The method of claim 43, further comprising:
heating the oil shale in order to pyrolyze at least a portion of the oil shale into hydrocarbon fluids, the hydrocarbon fluids comprising gas;
producing the gas; and
using at least a portion of the produced gas as the combustible fuel.

52. The method of claim 51, further comprising:
treating the gas in order to substantially remove $H_2S$ from the gas.

53. The method of claim 43, wherein the first wellbore, the second wellbore, and the burner define a first heater well, and further comprising:
providing a plurality of additional heater wells each of which also comprises a first wellbore, a second wellbore, and a burner within the first wellbore;
arranging the first heater well and the plurality of additional heater wells such that the respective first wellbores and the respective second wellbores are in alternating relation;
injecting an oxidant and a combustible fuel into the first wellbore and through the burner of each of the respective plurality of additional heater wells so as to combust the combustible fuel within the plurality of additional heater wells; and
circulating flue gas generated from each of the burners through the respective second wellbores of the plurality of additional heater wells and to the surface.

54. A heater well for in situ heating of a targeted organic-rich rock formation, comprising:
a first wellbore extending at least to a depth of the targeted organic-rich rock formation having a substantially vertical portion and a deviated portion defining a heel and a toe;
a substantially vertical second wellbore having a lower end, the lower end of the second wellbore intersecting with the toe of the first wellbore to create fluid communication therebetween;
a single downhole combustion burner within the first wellbore and no burners in the second wellbore; and
wherein a spacing between the first wellbore and the second wellbore is selected so that following the circulation of heated flue gas through the heater well for a period of time, a first pyrolysis zone from the substantially vertical portion of the first wellbore mates with a second pyrolysis zone from the substantially vertical portion of the second wellbore in such a manner that (i) a substantially continuous pyrolysis zone of formation hydrocarbons is formed within a substantial portion of the organic-rich rock formation between the first and second wellbores, and (ii) the combustion products are above a pyrolysis temperature in the second wellbore at or just below the approximate depth of the single combustion burner in the first wellbore, and fall below a pyrolysis temperature in the second wellbore at or just above the approximate depth of the single combustion burner in the first wellbore.

55. A method of producing a hydrocarbon fluid, comprising:
heating an organic-rich rock formation in situ using a heater well; and
producing a hydrocarbon fluid from the organic-rich rock formation, the hydrocarbon fluid having been at least partially generated as a result of pyrolysis of formation hydrocarbons located in the organic-rich rock formation, wherein the heater well includes:
a first wellbore extending at least to a depth of the targeted organic-rich rock formation having a substantially vertical portion and a deviated portion defining a heel and a toe;
a substantially vertical second wellbore having a lower end, the lower end of the second wellbore intersecting with the toe of the first wellbore to create fluid communication therebetween; and
a single downhole combustion burner within either the first or the second wellbore; and
wherein a spacing between the first wellbore and the second wellbore is selected so that following the circulation of heated flue gas through the heater well for a period of time, a first pyrolysis zone from the substantially vertical portion of the first wellbore mates with a second pyrolysis zone from the substantially vertical portion of the second wellbore in such a manner that (i) a substantially continuous pyrolysis zone of formation hydrocarbons is formed within a substantial portion of the organic-rich rock formation between the first and second wellbores, and (ii) the combustion products are above a pyrolysis temperature in the second wellbore at or just below the approximate depth of the single combustion burner in the first wellbore, and fall below a pyrolysis temperature in the second wellbore at or just above the approximate depth of the single combustion burner in the first wellbore.

56. The method of claim 55, further comprising:
producing a hydrocarbon fluid from the organic-rich rock formation, the hydrocarbon fluid having been at least partially generated as a result of pyrolysis of formation hydrocarbons located in the organic-rich rock formation.

57. A method for producing a hydrocarbon fluid from a targeted organic-rich formation comprising a plurality of heater wells, each heater well comprising:
a first wellbore extending at least to a depth of the targeted organic-rich rock formation and having a substantially vertical portion and a deviated portion defining a heel and a toe;
a substantially vertical second wellbore having a lower end, the lower end of the second wellbore intersecting with the toe of the first wellbore to create fluid communication therebetween; and
a single downhole combustion burner at substantially a single depth within either the first or the second wellbore;
wherein a spacing between each of the first and second wellbores is selected so that following the circulation of heated flue gas through the heater well for a period of time, a first pyrolysis zone from the substantially vertical portion of the first wellbore mates with a second pyrolysis zone from the substantially vertical second wellbore in such a manner that (i) a substantially continuous pyrolysis zone of formation hydrocarbons is formed within a substantial portion of the organic-rich rock formation between the first and second wellbores; and
wherein the plurality of heater wells is arranged in an array comprised of rows and columns so that along each row and along each column the first wellbores and the second wellbores alternate.

58. The method of claim 57, wherein, as a result of circulation, (ii) the combustion products are above a pyrolysis temperature in each of the respective second wellbores at or just below the approximate depth of the at least one combustion burner in corresponding first wellbores, and fall below a pyrolysis temperature in each of the respective second wellbores at or just above the approximate depth of the at least one combustion burner in the corresponding first wellbores.

* * * * *